US007115726B2

(12) United States Patent
Cox et al.

(10) Patent No.: US 7,115,726 B2
(45) Date of Patent: Oct. 3, 2006

(54) HAPLOTYPE STRUCTURES OF CHROMOSOME 21

(75) Inventors: David R. Cox, Belmont, CA (US); Deana A. Arnold, Los Gatos, CA (US)

(73) Assignee: Perlegen Sciences, Inc., Mountain View, CA (US)

( * ) Notice: Subject to any disclaimer, the term of this patent is extended or adjusted under 35 U.S.C. 154(b) by 310 days.

(21) Appl. No.: 10/227,195

(22) Filed: Aug. 22, 2002

(65) Prior Publication Data

US 2003/0077633 A1 Apr. 24, 2003

Related U.S. Application Data

(63) Continuation-in-part of application No. 10/166,341, filed on Sep. 18, 2001, now abandoned, and a continuation-in-part of application No. 10/106,097, filed on Mar. 26, 2002, now Pat. No. 6,969,589.

(60) Provisional application No. 60/332,550, filed on Nov. 26, 2001, provisional application No. 60/327,006, filed on Oct. 5, 2001, provisional application No. 60/313,264, filed on Aug. 17, 2001, provisional application No. 60/280,530, filed on Mar. 30, 2001.

(51) Int. Cl.
C07H 21/04 (2006.01)
(52) U.S. Cl. .................................... 536/23.1
(58) Field of Classification Search ............... 536/23.1, 536/24.3
See application file for complete search history.

(56) References Cited

U.S. PATENT DOCUMENTS

| 4,683,202 | A |   | 7/1987  | Mullis           |
|-----------|---|---|---------|------------------|
| 5,143,854 | A |   | 9/1992  | Pirrung et al.   |
| 5,412,087 | A |   | 5/1995  | McGall et al.    |
| 5,445,934 | A |   | 8/1995  | Fodor et al.     |
| 5,459,325 | A |   | 10/1995 | Hueton et al.    |
| 5,474,796 | A | * | 12/1995 | Brennan ........ 427/2.13 |
| 5,578,832 | A |   | 11/1996 | Trulson et al.   |
| 5,744,305 | A |   | 4/1998  | Fodor et al.     |
| 5,800,992 | A |   | 9/1998  | Fodor et al.     |
| 5,837,832 | A |   | 11/1998 | Chee et al.      |
| 5,953,727 | A |   | 9/1999  | Maslyn et al.    |
| 5,981,956 | A |   | 11/1999 | Stern            |
| 6,040,138 | A |   | 3/2000  | Lockhart et al.  |
| 6,040,193 | A |   | 3/2000  | Winkler et al.   |
| 6,262,838 | B1 |  | 7/2001  | Montagu          |
| 6,274,332 | B1 |  | 8/2001  | Keating et al.   |
| 6,300,063 | B1 |  | 10/2001 | Lipshutz et al.  |
| 6,323,026 | B1 |  | 11/2001 | Keating et al.   |
| 2004/0086886 | A1 | | 5/2004 | Goldstein        |

FOREIGN PATENT DOCUMENTS

| EP | 0717113 | 6/1996 |
| EP | 0950720 | 10/1999 |
| WO | 9511995 | 5/1995 |
| WO | 9523225 | 8/1995 |
| WO | 9710365 | 3/1997 |
| WO | 9727317 | 7/1997 |
| WO | 9856954 | 12/1998 |
| WO | WO 99/52942 | * 10/1999 |
| WO | 0180156 | 10/2001 |

OTHER PUBLICATIONS

Pennisi, Science, 281 (5384):1787-1789.*
Hacker et al. Gut, 1997, vol. 40, pp. 623-627.*
dbSNP record ss4013642, entry date Sep. 26, 2001.*
GenBank Record having Accession A24697 (GI: 833430), dated Jan. 24, 1995.*
GenBank Record having Accession Z30080 (GI: 454996), dated Feb. 15, 1994.*
Altshuler, D., Daly, M., Kruglyak, L. "Guilt by Association" *Nature Genetics* 26, 135-137 (2000).
Priori, S.G., Barhanin, J., Hauer, R.N.W., Haverkamp, W., Jongsma, H.J., Kleber, A.G., McKenna, W.J., Roden, D.M., Rudy, Y., Schwartz, K., Schwartz, P.J., Towbln, J.A., Wilde, A.M. "Genetic and Molecular Basis of Cardiac Arrhythmias: Impact on Clinical Management Parts I and II" *Circulation* 99:518-28 (1999).
Kruglyak, L., Nickerson, D.A. "Variation is the spice of life" *Nature Genetics* 27, 234-236 (2001).
Daly, M.J., Rioux, J.D., Schaffner, S.F., Hudson, T.J., Lander, E.S. "High-resolution haplotype structure in the human genome" *Nature Genetics* 29, 229-232, (2001).
Agarwal, P. et al. "Comparison study for identifying promoter allelic polymorphism in interleukin 10 and tumor necrosis factor alpha genes" Diagn Mol Pathol 9, 158-64(2000).
Moss, A.J., Zareba, W., Hall, W.J., Schwartz, P.J., Crampton, R.S., Benhorin, J., Vincent, M., Locati, E.H., Priori, S.G., Napolitano, C., Medina, A., Zhang, L., Robinson, J.L., Timothy, K., Towbin, J.A., Andrews, M.L. "Effectiveness and Limitations of beta-Blocker Therapy in Congenital Long-QT Syndrome" *Circulation* 101:616-23 (2000).
Fullerton, S.M. et al. "Apolipoprotein E Variation at the Sequence Haplotype Level: Implications for the Origin and Maintenance of a Major Human Polymorphism" *The American Society of Human Genetics* 67, 881-900 (2000).

(Continued)

*Primary Examiner*—Juliet C. Switzer
(74) *Attorney, Agent, or Firm*—Deana A. Arnold; Gulshan U. Shaver, Esq.

(57) ABSTRACT

The present invention includes the use of any of the polymorphisms, SNP haplotype blocks or SNP haplotype patterns. In one embodiment, susceptibility to a phenotype resulting from an allele or marker in linkage disequilibrium with such polymorphic forms is evaluated. Novel therapeutic and diagnostic compounds and methods are also disclosed.

1 Claim, 3 Drawing Sheets

OTHER PUBLICATIONS

Marth, G. et al. "Single-nucleotide polymorphisms in the public domain: how useful are they?" *Nature Genetics* 27, 371-372 (2001).

Yang, Z. et al. "Sampling SNPs" *Nature Genetics* 26, 13-14 (2000).

Atlshuler, D., et al. "The common PPAR Pro12Ala polymorphism is associated with decreased risk of type 2 diabetes" *Nature Genetics* 26, 76-80 (2000).

Douglas, J.A. et al. "Experimentally-derived haplotypes substantially increase the efficiency of linkage disequilibrium studies" *Nature Genetics* 28, 361-364 (2001).

Roses, A.D. "Pharmacogenetics" *Human Molecular Genetics* 10, 2261-2267 (2001).

Splawski, I., et al. "Spectrum of Mutations in Long-QT Syndrome Genes *KVLQT1, HERG, SCN5A, KCNE1*, and *KCNE2*" *Circulation* 102:1178-85 (2000).

Evans, W.E., Relling, M.V. "Pharacogenetics: Translating Functional Genomics into Rational Therapeutics" *Science Magazine* 286, 487-491 (1999).

Lizardi, P.M. et al. "Mutation detection and single-molecule counting using isothermal rolling-circle amplification" *Nature Genetics* 19, 225-232 (1998).

Chee, M. et al. "Accessing Genetic Information with High-Density DNA Arrays" *Science Magazine* 274, 610-614 (1996).

Sambrook, J., et al., *Molecular Cloning A Laboratory Manual*, Third Edition, Cold Spring Harbor Laboratory Press (2001), table of contents & p. 11.98-11.105 only.

Atlshuler, D., et al. "An SNP map of the human genome generated by reduced representation shotgun sequencing" *Nature* 407, 513-516 (2000).

Reich, D.E. et al. "Linkage disequilibrium in the human genome" *Nature* 411, 199-204 (2001).

Stephens, J.C. et al. "Haplotype Variation and Linkage Disequilibrium in 313 Human Genes" *Science Magazine* 293, 489-493 (2001).

Doll, J.J. "The Patenting of DNA" *Science Magazine* 280, 689-690 (1998).

Pennacchio, L.A., Rubin, E.M. "Genomic Strategies to Identify Mammalian Regulatory Sequences" *Nature* 2, 100-109 (2001).

Lockhart, D.J., Winzeler, E.A., "Genomics, gene expression and DNA arrays" *Nature* 405, 827-836 (2000).

Lander, E.S. "The New Genomics: Global Views of Biology" *Science Magazine* 274, 536-539 (1996).

McCarthy, J.J., Hilfiker, R. "The use of single-nucleotide polymorphism maps in pharmacogenomics" *Nature Biotechnology* 18, 505-508 (2000).

Rothberg, B.E., "Mapping a role for SNPs in drug development" *Nature Biotechnology* 19, 209-211 (2001).

Riley, J.H. et al. "The use of single nucleotide polymorphisms in the isolation of common disease genes" *Pharmacogenomics*. 1(1):39-47, (2000).

Cardon, L.R., Bell, J.I. "Association Study Designs for Complex Diseases" *Nature* 2, 91-99 (2001).

Wang, D.G., "Large-Scale Identification, Mapping, and Genotyping of Single-Nucleotide Polymorphisms in the Human Genome" *Science Magazine* 280, 1077-1082 (1998).

Cargill, M., Daley, G.Q., "Mining for SNPs: putting the common variants-common disease hypothesis to the test" *Pharamacogenomics*. 1(1):27-37, (2000).

Karet, G. et al. "Unraveling Human Diversity" *Drug Discovery & Development Magazine* Nov./Dec. S5-S14 (2000).

Lai, E. "Application of SNP Technologies in Medicine: Lessons Learned and Future Challenges" *Genome Research* 1, 927-929 (2001).

Jorde, L.B., "Linkage Disequilibrium and the Search for Complex Disease Genes" *Genome Research* 10, 1435-1444 (2000).

Cormen, T.H., et al., "Introduction to Algorithms" Fourteenth printing, 1994, table of contents only.

Fu, Y.X., Li, W.H. "Statistical Tests of Neutrality of Mutations" *Genetics* 133: 693-709 (1993).

Risch, N., Merikangas, K. "The Future of Genetic Studies of Complex Human Diseases" *Science Magazine* 273, 1516-1517 (1996).

Kota, R. "Application of denaturing high-performance liquid chromatography for mapping of single nucleotide polymorphisms in barley (Hordeum vulgare L.)" *Genome* 44: 523-528, (2001).

Shapero, M.H. "SNP Genotyping by Multiplexed Solid-Phase Amplification and Flourescent Minisequencing" *Genome Research* 11, 1926-1934 (2001).

Shoemaker,D.D. "Experimental annotation of the human genome using microarray technology" *Nature* 409, 922-927 (2001).

Cutler, D.J. et al. "High-Throughput Variation Detection and Genotyping Using Microarrays" *Genome Research* 11, 1913-1925 (2001).

Waterston, R.H. et al. "A map of human genome sequence variation containing 1.42 million single nucleotide polymorphisms" *Nature* 409, 928-933 (2001).

Judson R, Stephens JC. "The predictive power of haplotypes in clinical response" *Pharmacogenomics*. 1(1):15-26, (2000).

Patil, N., et al. "Blocks of Limited Haplotype Diversity Revealed by High-Resolution Scanning of Human Chromosome 21" *Science* 294:1719-23 (2001).

Judson, R., Stephens, J.C., "Notes from the SNP vs. haplotype front" *Pharmacogenomics*. 2 (1):1-7 (2001).

Oestreicher, P., "4th Annual Pharmacogenomics and Medicine Lectures" *Pharmacogenomics*. 2 (3):291-296 (2001).

Hartl, D.L., Clark, A.G., "Principles of Population Genetics", Oct. 1, 1997, 3rd Edition, Sinauer Associates, Sunderland, MA.

NCBI Entrez database nucleotide sequences, NIH (Bethesda, MD, USA) Acc #NT_002836, GI: 8134249, (2000).

* cited by examiner

Figure 1: Common SNPs

| HAPLOTYPE BLOCK | POSITION IN GENBANK SEQUENCE | POSITION IN SEQ ID NO: 1 | REFERENCE BASE | ALTERNATE BASE |
|---|---|---|---|---|
| B137313 | 21302875 | 924 | G | T |
|  | 21303403 | 1452 | C | T |
|  | 21303667 | 1716 | T | C |
|  | 21305929 | 3978 | A | G |
|  | 21306344 | 4393 | G | T |
|  | 21308169 | 6218 | C | A |
|  | 21309105 | 7154 | A | G |
|  | 21309126 | 7175 | G | C |
|  | 21340269 | 38318 | A | G |
| B137314 | 21352474 | 50523 | T | C |
|  | 21352768 | 50817 | T | C |
|  | 21353310 | 51359 | C | A |
|  | 21353340 | 51389 | G | T |
|  | 21354257 | 52306 | T | A |
|  | 21359868 | 57917 | T | C |
|  | 21369636 | 67685 | A | T |
|  | 21372019 | 70068 | C | T |
| B137315 | 21378872 | 76921 | C | G |
|  | 21391468 | 89517 | C | T |
|  | 21393590 | 91639 | T | G |
|  | 21395663 | 93712 | G | A |
|  | 21399221 | 97270 | A | G |

Figure 2: Rare SNPs

| POSITION IN GENBANK SEQUENCE | POSITION IN SEQ ID NO: 1 | REFERENCE BASE | ALTERNATE BASE |
|---|---|---|---|
| 21305873 | 3922 | T | G |
| 21306057 | 4106 | T | G |
| 21307885 | 5934 | C | T |
| 21308171 | 6220 | A | C |
| 21309046 | 7095 | G | A |
| 21309155 | 7204 | C | G |
| 21309317 | 7366 | G | A |
| 21310937 | 8986 | T | G |
| 21311496 | 9545 | C | T |
| 21312110 | 10159 | T | A |
| 21313033 | 11082 | G | A |
| 21327890 | 25939 | C | T |
| 21331062 | 29111 | G | A |
| 21331488 | 29537 | G | A |
| 21331894 | 29943 | A | G |
| 21333167 | 31216 | C | T |
| 21334436 | 32485 | C | T |
| 21338924 | 36973 | G | C |
| 21339196 | 37245 | A | T |
| 21349786 | 47835 | C | T |
| 21350580 | 48629 | C | A |
| 21351582 | 49631 | C | T |
| 21352572 | 50621 | A | G |
| 21356604 | 54653 | G | A |
| 21358682 | 56731 | G | T |
| 21368043 | 66092 | C | A |
| 21368323 | 66372 | G | C |
| 21368414 | 66463 | G | A |
| 21368602 | 66651 | A | C |
| 21375373 | 73422 | A | G |
| 21376403 | 74452 | C | A |
| 21376529 | 74578 | G | A |
| 21376783 | 74832 | G | A |
| 21383463 | 81512 | C | G |
| 21390468 | 88517 | C | A |
| 21390597 | 88646 | C | T |
| 21390678 | 88727 | G | C |
| 21392840 | 90889 | T | C |
| 21395607 | 93656 | C | A |
| 21395712 | 93761 | T | C |
| 21395731 | 93780 | T | C |
| 21397614 | 95663 | A | G |
| 21400398 | 98447 | G | A |
| 21401251 | 99300 | T | C |
| 21415497 | 113546 | C | A |

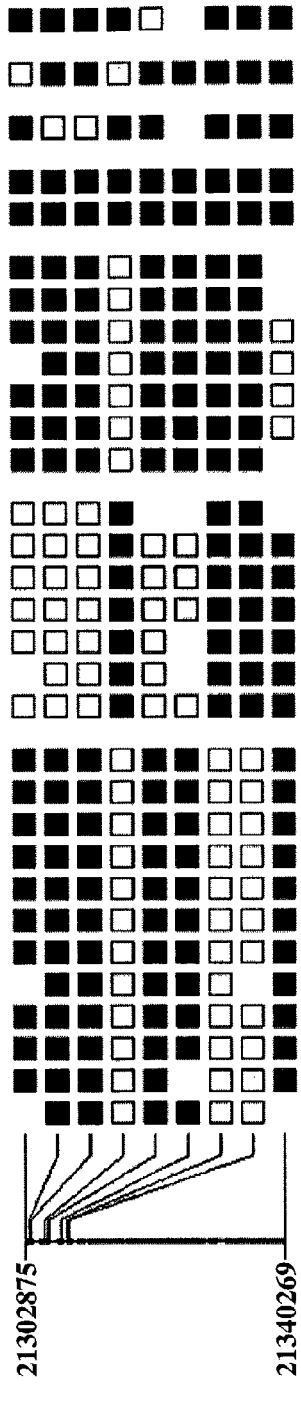
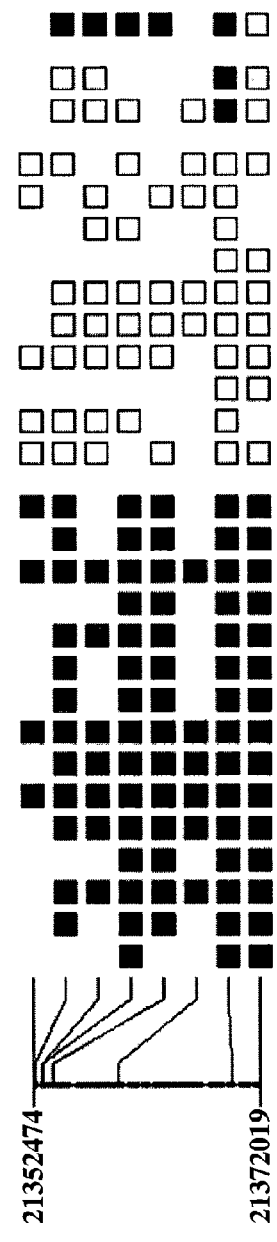
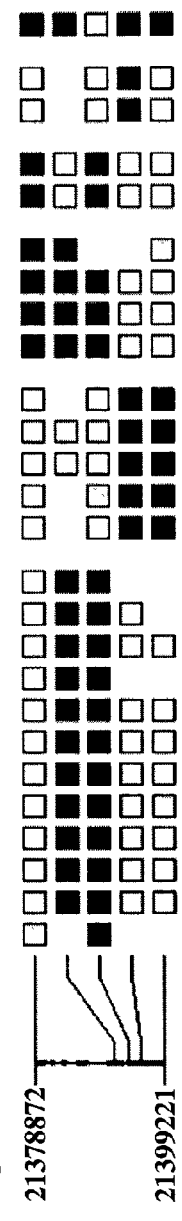
FIGURE 3
A. Haplotype block B137313  21302875 – 21340269
B. Haplotype block B137314  21352474 – 21372019
C. Haplotype block B137315  21378872 – 21399221

HAPLOTYPE STRUCTURES OF CHROMOSOME 21

CROSS REFERENCE TO RELATED APPLICATIONS

The present application is continuation-in-part of U.S. application Ser. No. 10/166,341, filed Sep. 18, 2001, now abandoned, which was originally filed as U.S. Provisional Application No. 60/323,059, and was subsequently converted to the cited utility application: and is a continuation-in-part of U.S. patent application Ser. No. 10/106,097, filed Mar. 26, 2002, now Pat. No. 6,969,589, which claims the benefit of U.S. Provisional Application No. 60/332,550, filed Nov. 26, 2001, now expired, U.S. Provisional Application No. 60/327,006, filed Oct. 5, 2001, now expired, U.S. Provisional Application No. 60/313,264, filed Aug. 17, 2001, now expired, and U.S. Provisional Application No. 60/280,530, filed Mar. 30, 2001, now expired, all of which are incorporated by reference in their entirety for all purposes.

BRIEF DESCRIPTION OF THE SEQUENCE LISTING

The Sequence Listing, which is incorporated herein by reference in its entirety, provides two sequences, each of which is identified by a sequence identification number (SEQ ID NO). SEQ ID NO: 2 is a DNA sequence that extends from position 21301952 to position 21415555 of the genomic DNA sequence identified by the GenBank accession number NT_002836. SEQ ID NO: 1 is based on SEQ ID NO: 2, but further comprises nucleotide positions, each designated by an "s", "r", "y", "m", "k", or "w" in the sequence listing in accordance with MPEP 2422 and WIPO Standard ST.25, Appendix 2, Table 1, that may contain an alternate base.

BACKGROUND OF THE INVENTION

Variations or mutations in DNA are directly related to almost all human phenotypic traits and diseases, including infectious disease, cancer, inherited disorders, and autoimmune disorders. The most common type of DNA variation is a single nucleotide polymorphism (SNP), which is a base pair substitution at a single position in the genome. It has been estimated that SNPs account for the bulk of the DNA sequence difference between humans (Patil, N. et al., *Science*, 294:1719 (2001)). Blocks of such SNPs in close physical proximity in the genome are often genetically linked, resulting in reduced genetic variability and defining a limited number of "SNP haplotypes", each of which reflects descent from a single, ancient chromosome (Fullerton, S. M., et al., *Am. J. Hum. Genet.* 67: 881 (2000)).

Patterns of human DNA sequence variation (haplotypes) defined by SNPs have important implications for identifying associations between phenotypic traits and genetic loci. However, the complexity of local haplotype structure in the human genome and the distance over which individual haplotype blocks extend is poorly defined, with some haplotype blocks extending for only a few kilobases and others extending for more than 100 kilobases (Patil, N. et al., *Science*, 294:1719 (2001)). These findings suggest that any comprehensive description of the haplotype structure of the human genome, defined by common SNPs, will require empirical analysis of a dense set of SNPs in many independent copies of the human genome. As a first step toward achieving this goal, high-density oligonucleotide arrays were used to identify a large fraction of all human chromosome 21 SNPs and to analyze the haplotype structure they define (Patil, N. et al., *Science*, 294:1719 (2001)).

The haplotype structure of the human genome is of great value for various applications. For example, specific regions of interest may be further analyzed to associate SNPs in haplotype blocks with phenotypic traits—for example, disease susceptibility or resistance, a predisposition to a genetic disorder, or drug response—and this information may be invaluable in understanding the biological basis for the trait as well as identifying candidate genes useful in the development of therapeutics and diagnostics. The haplotype structure may also be used to identify individuals from biological samples, for example, in paternity testing or criminal investigations.

One such region of interest is found on the long arm of chromosome 21. This region contains two genes, KCNE1 and KCNE2, both of which code for proteins that are subunits of cardiac potassium channels, key components of the electrical system of the heart. Malfunction of these channels can cause abnormalities in the repolarization of the heart resulting in less efficient pumping of oxygenated blood through the body. Long QT Syndrome (LQTS), a familial and potentially fatal disorder of the electrical system of the heart, is also caused by malfunction of the cardiac potassium ion channels, which can lead to cardiac arrhythmia that may degenerate into ventricular tachycardia and even result in death. Currently, there is no quick and reliable method of identifying individuals with malfunctions of these potassium ion channels or a predisposition to LQTS.

SUMMARY OF THE INVENTION

The present invention provides an isolated nucleic acid molecule comprising SEQ ID NO: 1 and fragments thereof. The present invention also provides sequences that are complementary to SEQ ID NO: 1, as well as isolated nucleic acid molecules that hybridize to SEQ ID NO: 1 under stringent conditions. The present invention also provides a database, which is on a computer-readable medium, comprising at least one SNP allele of SEQ ID NO: 1 that was derived from the analysis of at least one genome. In a preferred embodiment, the SNP allele of SEQ ID NO: 1 is associated with a phenotypic trait.

In some embodiments of the present invention, a method for identifying a genetic locus associated with a phenotypic trait of interest is provided. The method includes the following steps: obtaining a biological sample from a control population that does not possess the phenotypic trait of interest and a biological sample from a clinical population that possesses the phenotypic trait of interest, determining an allelic frequency for at least one single nucleotide polymorphism listed in FIG. 1 or FIG. 2 in the control population and the clinical population, and comparing the allelic frequencies from the two populations to identify those that indicate the presence of a genetic locus associated with the phenotypic trait of interest.

In some aspects, the present invention provides a method of screening an individual for a predisposition, susceptibility, or resistance to a phenotypic trait of interest. The method includes the following steps: obtaining a biological sample from an individual, analyzing the biological sample for the presence of a nucleic acid molecule that comprises at least 10 nucleotides of SEQ ID NO: 1 and at least one alternate base as listed in FIG. 1 or FIG. 2, or a complementary sequence thereto, and determining the predisposition, susceptibility, or resistance of the individual to the phenotypic trait of interest based on the presence or absence of the nucleic acid molecule. In preferred embodiments, the presence or absence of the nucleic acid molecule indicates a predisposition, susceptibility, or resistance to a cardiovascular disorder, a response to a drug, a hearing disability, or a potassium ion channel disorder.

In further embodiments, the present invention provides a method for selecting a therapeutic for an individual that has or is predisposed to a phenotypic trait of interest that is associated with an isolated nucleic acid molecule that comprises at least 10 nucleotides of SEQ ID NO: 1 and at least one alternate base as listed in FIG. 1 or FIG. 2, or a complementary sequence thereto. The method includes the following steps: detecting whether the individual possesses the isolated nucleic acid molecule, and selecting a therapeutic that compensates for a causative functional mutation that is in linkage disequilibrium with the isolated nucleic acid molecule.

The present invention further provides a kit for diagnosing a disease, disease susceptibility, or therapy response associated with an isolated nucleic acid molecule that comprises at least 10 nucleotides of SEQ ID NO: 1 and at least one alternate base as listed in FIG. 1 or FIG. 2, or a complementary sequence thereto. The kit includes a means for detecting a presence or absence of the isolated nucleic acid molecule in a DNA sample from a patient, as well as a data set of associations of the nucleic acid molecule with the disease, disease susceptibility, or therapy response. In preferred embodiments, the data set of associations is on a computer-readable medium.

BRIEF DESCRIPTION OF THE FIGURES

The following figures and drawings form part of the present specification and are included to further demonstrate certain aspects of the patent invention. The invention may be better understood by reference to one or more of these drawings in combination with the detailed description of the specific embodiments presented herein. All publications mentioned herein are cited for the purpose of describing and disclosing reagents, methodologies and concepts that may be used in connection with the present invention. Nothing herein is to be construed as an admission that these references are prior art in relation to the inventions described.

FIG. 1 shows common SNPs in the region of interest.

FIG. 2 shows rare SNPs in the region of interest.

FIG. 3 shows haplotype blocks B137313, B137314, and B137315.

DETAILED DESCRIPTION OF PREFERRED EMBODIMENTS

I. Glossary
II. General
III. Polymorphisms, Haplotype Blocks and Haplotype Patterns
IV. Detection of Haplotype Structure of the Invention in Target DNA
V. Methods of Use
   A. Identification of genetic loci associated with phenotypic traits
   B. Production and use of peptides
   C. Diagnostics
   D. Pharmacogenomics
   E. Therapeutics
   F. Other uses and aspects of the invention
VI. Conclusion I. Glossary As used in the specification, "a" or "an" means one or more. As used in the claim(s), when used in conjunction with the word "comprising", the words "a" or "an" mean one or more. As used herein, "another" means at least a second or more.

"Gene" is intended to mean the ORF (open reading frame) encoding an RNA or polypeptide, intronic regions, and the adjacent 5' and 3' non-coding nucleotide sequences, which may extend up to about 10 kb beyond the coding region, but possibly further in either direction. The adjacent and intronic sequences may be involved in the regulation of expression of the encoded RNA or polypeptide.

"Haplotype structure" refers to the combination of polymorphisms, haplotype patterns and haplotype blocks in a nucleic acid sequence of interest.

"Hybridization probes" or "probes" are oligonucleotides capable of binding in a base-specific manner to a partially or completely complementary strand of nucleic acid. Such probes include peptide nucleic acids, as described in Nielsen et al., *Science* 254: 1497–1500 (1991), as well as all other kinds of oligonucleotides, as described supra.

Hybridizations are usually performed under stringent conditions. Stringent conditions are sequence-dependent and are different in different circumstances. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. As the target sequences are generally present in excess, at Tm, 50% of the probes are occupied at equilibrium. Typically, stringent conditions include a salt concentration of at least about 0.01 to 1.0 M Na ion concentration (or other salts) at pH 7.0 to 8.3 and the temperature is at least about 25° C. for short probes (e.g., 10 to 50 nucleotides). Stringent conditions can also be achieved with the addition of destabilizing agents such as formamide. For example, conditions of 5× SSPE (750 mM NaCl, 50 mM NaPhosphate, 5 mM EDTA, pH 7.4) and a temperature of 25–30° C. are suitable for allele-specific probe hybridizations.

"Informative SNP" refers to a SNP (or plurality of SNPs) which has been selected from the set of all SNPs in a SNP haplotype pattern and that tends to distinguish one SNP haplotype pattern from other SNP haplotype patterns within a SNP haplotype block. Thus, once SNP haplotype patterns for a particular SNP haplotype block are known, one can select one or more informative SNPs from each SNP haplotype pattern to 1) identify the genotype of all other SNPs in that SNP haplotype pattern, and 2) distinguish the SNP haplotype pattern from other SNP haplotype patterns that belong to a particular SNP haplotype block.

An "isolated nucleic acid" means an object species invention that is the predominant species present (e.g., on a molar basis it is more abundant than any other individual species in the composition). Preferably, an isolated nucleic acid comprises at least about 50, 80, or 90 percent (on a molar basis) of all macromolecular species present. Most preferably, the object species is purified to essential homogeneity (contaminant species cannot be detected in the composition by conventional detection methods).

"Linkage" or "linked" describes or relates to the tendency of genes, alleles, loci or genetic markers to be inherited together from generation to generation as a result of the proximity of their locations on the same chromosome; e.g., genetic loci that are inherited non-randomly.

"Linkage disequilibrium" or "allelic association" means the preferential association of a particular allele or genetic marker with a specific allele or genetic marker at a nearby chromosomal location more frequently than expected by chance for any particular allele frequency in the population. For example, if locus X has alleles a and b, which occur equally frequently, and linked locus Y has alleles c and d, which occur equally frequently, one would expect the combination ac to occur with a frequency of 0.25. If ac occurs more frequently, then alleles a and c are in linkage disequilibrium. Linkage disequilibrium may result from natural selection of certain combination of alleles or because an allele has been introduced into a population too recently to have reached equilibrium with linked alleles. A marker in linkage disequilibrium can be particularly useful in detecting susceptibility to disease (or other phenotype) notwithstanding that the marker does not cause the disease. For example, a marker (X) that is not itself a causative element of a disease, but which is in linkage disequilibrium with a gene (including regulatory sequences) (Y) that is a causative element of a phenotype, can be used detected to indicate susceptibility to the disease in circumstances in which the gene Y may not have been identified or may not be readily detectable.

"Nucleic acids" include but are not limited to DNA, RNA, single- or double-stranded, genomic, cloned, naturally occurring or synthetic molecules and may be polynucleotides, amplicons, RNA transcripts, protein nucleic acids, nucleic acid mimetics, and the like.

"Oligonucleotides" are nucleic acids that are usually between 5 and 100 contiguous bases, and often between 5–10, 5–20, 10–20, 10–50, 15–50, 15–100, 20–50, or 20–100 contiguous bases. An oligonucleotide that is longer than about 20 contiguous bases may be referred to as a polynucleotide. A polymorphic site (polymorphism) can occur at any position within an oligonucleotide. An oligonucleotide may include any of the allelic forms of the polymorphic sites (polymorphisms) shown in FIG. 1 or FIG. 2.

A "polymorphic site" refers the position in a nucleic acid sequence at which a polymorphism occurs. A polymorphic site may be as small as one base pair. A "SNP location" or "SNP locus" is a polymorphic site at which a SNP occurs.

"Polymorphism" refers to a genetic variation, or the occurrence of two or more genetically determined alternative sequences or alleles at a single genetic locus in a population. Preferred polymorphisms have two alleles, with the minor allele occurring at a frequency of greater than 1%, and more preferably greater than 10% or 20% of a selected population. The allelic form occurring most frequently in a selected population is sometimes referenced as the "wild-type" form. Diploid organisms may be homozygous or heterozygous for allelic forms. A biallelic polymorphism has two forms. A triallelic polymorphism has three forms. Examples of polymorphisms include restriction fragment length polymorphisms (RFLPs), variable number of tandem repeats (VNTRs), single nucleotide polymorphisms (SNPs), dinucleotide repeats, trinucleotide repeats, tetranucleotide repeats, simple sequence repeats, and insertion elements such as Alu.

A "SNP" or "single nucleotide polymorphism" is a polymorphism that occurs at a polymorphic site occupied by a single nucleotide. The site of the SNP is usually preceded by and followed by highly conserved sequences (e.g., sequences that vary in less that $1/100$ or $1/1000$ members of a population). As used herein, "SNPs" is the plural of SNP. SNPs are most frequently diallelic. A most common allele of a SNP is called a "major allele" and an alternative allele of said SNP is called a "minor allele". A SNP usually arises due to substitution of one nucleotide for another at the polymorphic site. A transition is the replacement of one purine by another purine or one pyrimidine by another pyrimidine. A transversion is the replacement of a purine by a pyrimidine or vice versa. SNPs can also arise from a deletion of a nucleotide or an insertion of a nucleotide relative to a reference allele.

A "SNP haplotype block" or "haplotype block" is a nucleic acid sequence containing a group of SNPs or polymorphisms that do not appear to recombine independently but are passed from generation to generation in variable-length blocks.

A "SNP haplotype pattern" or "haplotype pattern" refers to the set of genotypes for SNPs or other polymorphisms in a haplotype block in a single strand of nucleic acid, preferably a single strand of genomic DNA.

II. General

Throughout the disclosure various patents, patent applications and publications are referenced. Unless otherwise indicated, each is incorporated by reference in its entirety for all purposes.

It readily should be apparent to one skilled in the art that various embodiments and modifications may be made to the invention disclosed in this application without departing from the scope and spirit of the invention.

The present invention includes the use of any of the polymorphisms, SNP haplotype blocks or SNP haplotype patterns shown in FIG. 1, FIG. 2 and FIG. 3, as well as polymorphisms, alleles, or markers in linkage disequilibrium with them, as a means to study a phenotype for a variety of purposes including drug target identification, diagnostics, and therapeutics. In the present invention, the DNA composition of a plurality of biological samples was analyzed to reveal novel polymorphisms (e.g., SNPs) and SNP haplotype patterns. In one embodiment they, or polymorphisms in linkage disequilibrium with them, may be predictive of or used to study cardiovascular disorders (e.g., LQTS or ventricular fibrillation), drug response (e.g., clarithromycin-induced arrhythmia) and other phenotypes related to cardiovascular disorders, drug response, or the LQTS1 and LQTS2 genes. The approach of the present invention has tremendous advantages in conducting genetic association studies over other whole genome or genotyping methods known in the art. Instead of reading all bases of each individual's DNA, or even reading the common SNPs that may be found, only informative SNPs from the sample population need to be determined and scanned.

Polymorphisms of the present invention are shown in FIG. 1 and FIG. 2 and were identified by, e.g., the methods described in the earlier patent applications U.S. Ser. No. 10/106,097, filed Mar. 26, 2002, and U.S. Ser. No. 10/134,510, filed Mar. 29, 2002, both entitled "Methods for Genomic Analysis" and incorporated herein in their entirety by reference. These polymorphisms occur in a region of chromosome 21 that contains genes that code for subunits of potassium ion channels known to be involved in several disorders including Long QT Syndrome (LQTS), ventricular fibrillation, clarithromycin-induced arrhythmia, and deafness. Polymorphisms of the present invention also include those in haplotype blocks with one or more of the polymorphisms shown in FIG. 1 or FIG. 2.

LQTS is a familial and potentially fatal disorder of the electrical system of the heart characterized by an abnormally prolonged "QT interval" and is one phenotype measure of the time it takes for the heart to undergo ventricular depolarization (contraction) and repolarization (recharging/rest) between each heart beat. When this interval is prolonged, patients may develop an extremely rapid, abnormal heart rhythm (arrhythmia) that can degenerate into a severe ventricular tachycardia known as "torsade de pointes". When this occurs, the heart can no longer effectively pump blood through the body and the resulting decrease of bloodflow to the brain can cause loss of consciousness (syncope). If treatment is not immediate, this tachycardia can lead to ventricular fibrillation and, eventually, cardiac arrest and sudden death.

The symptoms of LQTS are caused by abnormalities of protein structures, called "ion channels", which regulate the flow of ions, such as potassium, in and out of heart cells, thereby controlling the electrical activity of the heart. When the ion channels are dysfunctional, as in the case of LQTS, the depolarization and repolarization of the heart takes longer, and the result is a prolonged QT interval. These abnormalities can be passed on from parent to child when a mutation is present in a gene that codes for one of the ion channel proteins. Since a variety of mutations can cause the disorder, several forms of LQTS exist. To date, mutations causing LQTS have been identified in genes encoding both potassium channels and sodium channels (Splawski, et al., *Circulation* 102: 1178 (2000)). At least two of these genes, KCNE1 and KCNE2, are located on chromosome 21 in the 21q22.1–22.2 region. These genes code for proteins in potassium ($K^+$) channels: the "slowly activating delayed rectifier $K^+$ ($I_{ks}$) channel" and the "rapidly activating delayed rectifier $K^+$ ($I_{kr}$) channel", respectively. In addition to the cardiac phenotype, complete loss of the $I_{ks}$ channel also causes hearing disability (partial hearing loss to complete deafness) in the LQTS subtype known as Jervell and Lange-Nielsen syndrome (Schulze-Bahr, et al., *Nature Genetics* 17:267 (1997)).

LQTS-related deaths are largely preventable with treatment, but unfortunately, individuals with LQTS often remain undiagnosed until it is too late. Many carriers are asymptomatic until under some kind of physical or emotional stress, and even at that time the severity of the symptoms varies widely depending on the length of time the arrhythmia persists. For a short episode, the individual may experience only a few seconds of extreme dizziness or syncope, which may not prompt them to seek medical attention. As such, a diagnosis is often not made until after a serious cardiac incident, such as ventricular tachycardia or cardiac arrest, or after the LQTS-related death of a family member.

Currently, individuals suspected of having LQTS are tested by electrocardiogram (ECG), which measures and records the electrical activity of the heart and can thereby detect a clearly prolonged QT interval. However, this symptom is not apparent in all affected persons; some patients have normal or borderline-prolonged QT intervals based on their resting ECG. In fact, in a study of nine families with "sporadic" cases of LQTS, 33% of family members who were considered on clinical grounds to be non-affected were found to be carriers (Priori, et al., *Circulation* 99:518 (1999)). This, along with the day to day variability of an individual's QT intervals, makes ECG diagnosis of LQTS unreliable. As a result, some LQTS carriers are not identified as such, and others are misclassified as having the disorder when they do not; both of these misdiagnoses lead to inappropriate treatment of the individual. Since this is a hereditary disease, proper diagnosis of both symptomatic and asymptomatic individuals is needed to allow informed decisions regarding the risk of LQTS to their offspring. Therefore, improved diagnosis of LQTS is desperately needed to properly identify and treat those individuals at risk to prevent the potentially lethal LQTS-related syncope and ventricular tachycardia, as well as to predict the risk of LQTS to their offspring.

Another aspect of LQTS is that affected individuals are sensitive to certain drugs and can experience ventricular tachycardia if these drugs are administered to them (Priori, et al., *Circulation*, 99:518 (1999)). Ironically, many of these drugs are antiarrhythmia drugs, but they also include certain antidepressants, antihistamines, and the antibiotic erythromycin. Clearly, if an individual is not properly diagnosed with LQTS or is an otherwise asymptomatic carrier, they may unnecessarily be put at risk by being prescribed these medications, especially since their symptoms in the absence of a clearly prolonged QT interval may suggest a need for antiarrhythmia drugs, so improved diagnosis of LQTS would protect LQTS patients from drugs dangerous to their condition.

The most common treatment for LQTS patients is beta-blocker drug therapy, which blunts the surges of adrenaline that trigger episodes of ventricular tachycardia. However, current research suggests that while beta-blockers can be quite effective for individuals carrying certain LQTS genotypes, patients with other forms of LQTS seem to respond better to the administration of potassium or a sodium channel blocker, and still others require the implantation of an artificial pacemaker or an implantable cardioverter defibrillator (ICD) (Moss, et al., *Circulation*, 101:616–623 (2000); Priori, et al., *Circulation*, 99:518 (1999)). So although several treatments are available, their efficacy is dependent on the genotype of the LQTS patient. As such, the most effective treatment could be more quickly and correctly determined if tailored to the specific LQTS subtype carried by the affected individual. specific LQTS subtype carried by the affected individual.

In addition, potassium channels not only control repolarization, but also affect other aspects of normal heart function, such as resting membrane potential. As such, it is likely that identifying the genotypes involved in the function of ion channels would not only facilitate the understanding and treatment of LQTS, but also other more general disorders that involve ion channel function. For example, individuals with inefficient ion channels may have a greater risk of developing heart disease. Another example is the involvement of these ion channels in normal hearing as evidenced by the loss of hearing or complete deafness that affects some LQTS patients.

III. Polymorphisms, Haplotype Blocks and Haplotype Patterns

SEQ ID NO: 1 extends from position 21301951 to position 21415555 of the genomic DNA sequence identified by the GenBank accession number NT_002836. More specifically, this region contains the KCNE1 and KCNE2 genes, both of which are known to be involved in LQTS. This region may also contain additional genes as evidenced by a RefSeq gene prediction, C21or f51, several GenScan and Acembly gene predictions, and multiple sites that align with human mRNAs and other ESTs in GenBank. The present invention provides nucleic acids containing polymorphisms, haplotype blocks and haplotype patterns based on SEQ ID NO: 2, including SEQ ID NO: 1 or fragments thereof with at least one single nucleotide polymorphism listed in FIG. 1 or FIG. 2, as well as nucleic acid derivatives of these SEQ ID NO: 1 variants or fragments thereof, such as but not limited to RNA, cDNA and nucleic acid mimetics, provided that the sequence is not a fragment of SEQ ID NO: 2. These nucleic acids may further comprise genic or nongenic regions. Genic regions further comprise coding regions (exons) and intronic regions. In addition, genic regions also comprise regulatory regions that may be found hundreds, and possibly thousands of kilobases upstream from the transcriptional start site or downstream of the most distal base pair transcribed. These nucleic acids may be studied substantially free of other nucleic acid sequences, and may be amplified prior to evaluation, as discussed infra.

Polymorphisms of the present invention were identified within SEQ ID NO: 1 by scanning the genomes of a plurality of individuals from a diverse population spanning multiple ethnic and geographic backgrounds. In a preferred embodiment, the polymorphisms identified were SNPs, or "single nucleotide polymorphisms". The location of these polymorphisms was mapped onto the human genome and analyzed to determine the haplotype structure of this genomic region. The analysis involves the determination of each allele (e.g., A, C, T or G) of a polymorphism. The allele that is present in the reference sequence (SEQ ID NO: 2) is referred to as the "reference base", and the alternate allele is referred to as the "alternate base".

The analysis also involves the determination of the frequency of each allele for each polymorphism. "Common SNPs" are those SNPs whose less common form (minor allele) is present at or above a certain minimum frequency in a given population. For example, common SNPs are those SNPs that are found in at least about 2% to 25% of the population. Preferably, common SNPs are those SNPs that are found in at least about 5% to 15% of the population. More preferably, common SNPs are those that are found in at least about 10% of the population. Common SNPs are listed in FIG. 1 in order of their location (nucleotide position) (column 2) relative to the genomic DNA sequence identified by the GenBank accession number NT_002836; also included are the reference (column 3) and alternate (column 4) bases for each SNP, as well as a haplotype block (column 1) to which each SNP may be assigned according to one embodiment of the invention (discussed infra).

Common SNPs likely result from mutations that occurred early in the evolution of a species. Focusing on common SNPs decreases the false positives that result from recent population anomalies; i.e., allele or variant differences between control and experimental populations that appear as disease or drug-response associated, yet are result of migratory history or mating practices. Moreover, common SNPs are relevant to a larger proportion of the human population, making the present methods more broadly applicable to disease and drug response studies. However, the present invention also includes "rare SNPs" (FIG. 2) since certain analyses may be performed including some or all rare SNPs, particularly when looking at individuals in a population, specific sub-populations, the migratory history of populations, the environmental effect on the genetic makeup of a population, investigation of rare phenotypic traits and the like. Rare SNPs are listed in FIG. 2 in order of their location (nucleotide position) (column 1) relative to the genomic DNA sequence identified by the GenBank accession number NT_002836; also included are the reference (column 2) and alternate (column 3) bases for each SNP.

Sequences from different origins were compared, SNPs were scored, and a SNP map was constructed. Once the individual SNPs were identified and mapped to the genome, the SNP haplotype blocks and SNP haplotype patterns within the SNP haplotype blocks were defined. SNP haplotype blocks are sequences containing a set of one or more SNPs that do not recombine independently but are passed from generation to generation in variable-length blocks. The set of genotypes for all the SNPs in a SNP haplotype block on a single chromosome of an individual is a SNP haplotype pattern. It is important to note that blocks are defined based on their genetic information content and not on knowledge of how this information originated or why it exists. As such, blocks do not have absolute boundaries, and may be defined in different ways, depending on the specific application. The algorithm in this embodiment provides only one of many possible approaches. Those with skill in the art recognize a variety of algorithms can be used to define a set of haplotype blocks for a given region, including but not limited to greedy algorithms and shortest path algorithms. Further, parameters within an algorithm may be adjusted so to attain more or less stringent criteria for grouping SNPs into a haplotype block. For more detailed methods useful for defining the boundaries of haplotype blocks, see the U.S. patent application Ser. No. 10/134,510 filed Apr. 29, 2002 entitled "Methods for Genomic Analysis", incorporated herein in its entirety for all purposes.

According to one embodiment of the invention, SNP haplotype blocks and SNP haplotype patterns within each SNP haplotype block were constructed using common SNPs and are shown in FIG. 3. Three haplotype blocks, B137313, B137314, and B137315, were constructed for the region comprising SEQ ID NO: 1. Each row of boxes represents a single common SNP within the haplotype block. As in FIG. 1, these SNPs are ordered based on their position within SEQ ID NO: 1; the position numbers are shown for only the most proximal and most distal common SNP in each haplotype block. For example, for haplotype block B137313 containing nine common SNPs, the common SNP at position 21302875 is shown in the top row, the common SNP at position 21303403 is shown in the second row, and so forth. Each column of boxes in a haplotype block represents a haplotype pattern. For example, for haplotype block B137313 containing seven haplotype patterns, the first twelve columns represent twelve individual chromosomes, each containing the same haplotype pattern. For each haplotype block, the dark boxes represent the reference base and the light boxes represent the alternate base, both of which are listed in FIG. 1 for each common SNP position. In summary, FIG. 3 illustrates that SNPs occur in haplotype blocks in a genome, and that more than one haplotype pattern can occur within each haplotype block.

The boundaries between haplotype blocks may be defined in several different ways, including, but not limited to the following examples. One method of defining the boundaries of haplotype blocks is to extend them only to the most distal SNP in each block as shown in FIG. 3. In this case, there would most often be gaps between adjacent blocks. Another method of defining the boundaries of haplotype blocks is to extend them up to (but not including) the most proximal SNP of the adjacent block. In this case, the blocks would overlap. Yet another way is to extend the blocks to the nucleotide position that is halfway in between the most distal SNP in the block and the most proximal SNP in the next block. In this case there would be no gaps nor overlap between adjacent blocks. As mentioned above, the boundaries of the haplotype blocks shown in FIG. 3 are the outermost common SNPs in each block. It is expected that the boundaries between haplotype blocks will be adjusted accordingly if additional common SNPs are identified in this genomic region.

An informative SNP is a SNP, which has been selected from the set of all SNPs in a haplotype pattern, that, either alone or in combination with other informative haplotype block. Thus, once haplotype patterns for a particular haplotype block are known, one can select one or more informative SNPs from each haplotype pattern to 1) identify the genotype of all other SNPs in that haplotype pattern, and 2) distinguish the haplotype pattern from other haplotype patterns that belong to a particular haplotype block. Informative SNPs are selected so that the genotype of an informative SNP predicts the genotype of other, preferably all remaining, SNPs in that haplotype pattern. Knowing the informative SNPs for all patterns in all haplotype blocks allows for the design of less expensive genotyping assays that retain most of the power of an assay constructed using all SNPs.

The number of informative SNPs required for each block is the number of SNPs necessary to distinguish between the common SNP haplotype patterns in each SNP haplotype block. The number of informative SNPs required for haplotype blocks B137313, B137314 and B137315 is 2, 1 and 2, respectively. However, more than one SNP in a haplotype pattern may serve as an informative SNP. For example, if there exist only two haplotype patterns in a haplotype block, then any SNP that has a different genotype in one versus the other may be used to distinguish between them. If there are three or four haplotype patterns, then at least two SNPs are required. Given a sufficient number of informative SNPs to distinguish between all haplotype patterns, the existence of a particular haplotype pattern in an unknown sample may be inferred with accuracy. For example, for haplotype block B137314 any of the seven SNPs in the block can distinguish greater than 89% of the haplotype patterns, and two SNPs can distinguish greater than 96% of the haplotype patterns. In one embodiment, an algorithm was used to identify informative SNPs for each haplotype block.

IV. Detection of Haplotype Structure of the Invention in Target DNA

Detecting polymorphisms involves comparing DNA sequences in different individuals to identify points of variation, i.e., polymorphic sites or polymorphisms. By analyzing groups of individuals, haplotype structure comprising the frequencies of variation at each SNP locus (allelic frequency) and haplotype patterns in a population can be determined. Once a baseline of allelic or haplotype pattern frequencies is determined for a population, allelic or haplotype pattern frequencies can be determined for sub-populations characterized by many different criteria including, but not limited to geography, race, gender, disease susceptibility or resistance, and response to therapeutics.

The polymorphisms, haplotype patterns, and haplotype blocks of the invention may be detected in sample nucleic acids ("target DNA") from an individual being screened, and this target DNA may be obtained from virtually any biological sample (other than pure red blood cells). For example, convenient tissue samples include whole blood, semen, saliva, tears, fecal matter, urine, sweat, buccal, skin and hair. For assays of cDNA or mRNA, the tissue should be obtained from an organ in which the target nucleic acid is expressed. For example, if the target nucleic acid is KCNE1 or KCNE2 mRNA, the heart is a suitable source.

Sample nucleic acids may be prepared for analysis using any technique known to those skilled in the art. Preferably, such techniques result in the production of a nucleic acid molecule sufficiently pure to determine the presence or absence of one or more polymorphisms at one or more locations in the nucleic acid molecule. Such techniques may be found, for example, in Sambrook, et al., *Molecular Cloning: A Laboratory Manual* (Cold Spring Harbor Laboratory, New York) (2001), incorporated herein by reference. In addition, the methods disclosed in pending U.S. patent application U.S. Ser. No. 10/134,510, filed Apr. 29, 2002 entitled "Methods for Genomic Analysis" are particularly suitable for preparing nucleic acids for use in the methods of the present invention and are incorporated herein in their entirety.

It may be desirable to amplify and/or label one or more nucleic acids of interest before determining the presence or absence of one or more polymorphisms in the nucleic acid. Any amplification technique known to those of skill in the art may be used in conjunction with the present invention including, but not limited to, polymerase chain reaction (PCR) techniques. PCR may be carried out using materials and methods known to those of skill in the art. See generally PCR Technology: *Principals and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Matilla et al., *Nucleic Acids Res.* 19: 4967 (1991); Eckert et al., *PCR Methods and Applications* 1: 17 (1991); *PCR* (eds. McPherson et al., IRL Press, Oxford); and U.S. Pat. No. 4,683,202 (each of which is incorporated by reference for all purposes). Other suitable amplification methods include the ligase chain reaction (LCR) (see Wu and Wallace, *Genomics* 4: 560 (1989) and Landegren et al., *Science* 241: 1077 (1988)), transcription amplification (Kwoh et al., *Proc. Natl. Acad. Sci. USA* 86: 1173 (1989)), self-sustained sequence replication (Guatelli et al., *Proc. Nat. Acad. Sci. USA*, 87: 1874 (1990)) and nucleic acid-based sequence amplification (NASBA). Further, the methods disclosed in pending U.S. patent applications U.S. Ser. No. 10/134,510, filed Apr. 29, 2002 entitled "Methods for Genomic Analysis"; U.S. Ser. No. 10/042,492, filed Jan. 9, 2002 entitled "Methods for Amplification of Nucleic Acids"; and U.S. Ser. No. [unassigned], attorney docket number 1027U-1, filed Jun. 17, 2002 entitled "Methods for Storage of Reaction Cocktails" particularly suitable for amplifying, labeling, or further manipulating (i.e. fragmentation) nucleic acids for use in the methods of the present invention (incorporated by reference in their entirety for all purposes).

Determination of the presence or absence of one or more polymorphisms in a nucleic acid may be made using any technique known to those of skill in the art. Any technique that permits the accurate determination of a variation can be used. Preferred techniques permit rapid, accurate determination of multiple variations with a minimum of sample handling. Some examples of suitable techniques involve but are not limited to direct DNA sequencing, capillary electrophoresis, hybridization, allele-specific probes or primers, single-strand conformation polymorphism analysis, nucleic acid arrays and other techniques well known in the art. Several methods for DNA sequencing are well known and generally available in the art and may be used to determine the location of SNPs in a genome. See, for example, Sambrook, et al., *Molecular Cloning: A Laboratory Manual* (Cold Spring Harbor Laboratory, New York) (2001), and Ausubel, et al., *Current Protocols in Molecular Biology* (John Wiley and Sons, New York) (1997), incorporated herein by reference. Descriptions of the use of these methodologies are also detailed in provisional patent application serial No. 60/323,059, filed Sep. 18, 2001, entitled "Human Genomic Polymorphisms", incorporated by reference in its entirety for all purposes. Some examples of these are described by WO 95/11995 (incorporated by reference in its entirety for all purposes). WO 95/11995 also describes subarrays that are optimized for detection of different allelic forms of precharacterized polymorphisms, such as those of the present invention. For details on the use of nucleic acid arrays (DNA chips) for the detection of, for example, SNPs, see U.S. Pat. No. 6,300,063 issued to Lipshultz, et al., and U.S. Pat. No. 5,837,832 to Chee, et al., HuSNP Mapping Assay, reagent kit and user manual, Affymetrix Part No. 90094 (Affymetrix, Santa Clara, Calif.), all incorporated by reference herein.

V. Methods of Use

The invention has utility for identifying polymorphisms, haplotype patterns, and haplotype blocks in biological samples. This information may then be used in any number of ways including, but not limited to association studies, forensics, paternity testing, genetic mapping of phenotypic traits (e.g., disease resistance or susceptibility, drug response, etc.), diagnostics, identification of candidate drug targets, drug (or other treatment) efficacy trials, development of protein, small molecule, antisense, antibody, or other therapeutics, and to reveal the biological basis for a phenotypic trait. More details of these various utilities are provided infra.

The nucleic acids of the invention may be used in Southern or Northern analysis, dot blot, or other membrane based technologies, in PCR technologies, in dipstick assays, and in microarrays utilizing fluids or tissue extracts from patients. The polynucleotide sequences of the present invention, and longer or shorter sequences derived therefrom, also may be used as targets in a microarray, or other genotyping system. These systems can be used to detect the presence or absence of a large number of particular allelic SNP forms or to monitor the expression of a large number of gene products simultaneously.

In a preferred embodiment, it is possible to use allele-specific probes to determine the genotype of the polymorphisms (e.g., the haplotype structure) in a target DNA molecule. The design and use of allele-specific probes for analyzing polymorphisms is described by e.g., U.S. Pat. No. 6,361,947 issued to Dong, et al. Allele-specific probes can be designed that hybridize to a segment of target DNA from one individual but do not hybridize to the corresponding segment from another individual due to the presence of different polymorphic forms (alleles) in the respective segments from the two individuals. Hybridization conditions should be sufficiently stringent such that there is a significant difference in hybridization intensity between alleles, and preferably an essentially binary response, whereby a probe hybridizes to only one of the alleles. Some probes are designed to hybridize to a segment of target DNA such that the polymorphic site aligns with a central position (e.g., in a 15-mer at the $7^{th}$ position; in a 25-mer at the $13^{th}$ position) of the probe. This design of probe achieves good discrimination in hybridization between different allelic forms. In a preferred embodiment, a nucleic acid of the invention is specifically hybridized to a target nucleic acid as a means of detecting a polymorphism in the target nucleic acid. These allele-specific probes can also be immobilized on a nucleic acid array, some examples of which are described by WO 95/11995 (incorporated by reference in its entirety for all purposes). An example of hybridization to a nucleic acid array involves the use of DNA chips (oligonucleotide arrays), for example, those available from Affymetrix, Inc. Santa Clara, Calif. In a preferred embodiment, nucleic acid arrays are used to detect the polymorphisms of the invention in a target DNA sample.

A. Identification of Genetic Loci Associated with Phenotypic Traits

The polymorphisms, haplotype patterns, and haplotype blocks are useful for the identification of genetic components associated with phenotypic traits, whether causative or predictive, whether at one specific locus in the genome or at multiple loci on the same or different chromosomes. Association (or "correlation") studies may be performed for this purpose by determining the genotype of a set of at least one polymorphism for two populations of individuals, one of which exhibits a particular phenotypic trait, and one of which lacks the trait. In another embodiment, the genotypes of more than two populations may be compared, for example, by age, ethnicity, or geographic location. The characteristics of the set of polymorphisms that are compared between the populations include, but are not limited to, the frequency of each genotype of each polymorphism, haplotype patterns that include at least one of the polymorphisms, and haplotype blocks that include at least one haplotype pattern. For example, sets of polymorphisms that occur at a higher or lower frequency in one population than in another indicate areas in the genome where phenotypic trait-related loci may be located. In preferred embodiments, an analysis may be performed by comparing the haplotype structure of a region of interest present in two populations to identify those polymorphisms or haplotype patterns that associate (or "correlate") with a phenotypic trait of interest. For example, the haplotype structure of the genomic region corresponding to SEQ ID NO: 1 may be used to identify polymorphisms or haplotype patterns that associate with such phenotypic traits as LQTS susceptibility, LQTS-related drug sensitivity, $I_{ks}$ channel-related hearing loss, or other phenotypic traits that are in linkage disequilibrium with the polymorphisms or haplotype patterns of the invention, such as those that may be related to the gene predictions discussed supra.

An association between a polymorphism or haplotype pattern and a phenotypic trait can be determined by standard statistical methods and statistically significant associations between the haplotype structure and the phenotypic trait are then noted. For example, it may be found that a G at position 21393590 (haplotype block B137315) correlates with hearing impairment. As a further example, it might be found that the combined presence of a G at position 21393590 (haplotype block B137315) and a G at position 21340269 (haplotype block B137313) correlates with increased risk for heart disease. In some aspects, polymorphisms used in an association study constitute at least one SNP haplotype block and its constituent haplotype patterns. In yet another aspect, only informative SNPs are screened for association with a phenotypic trait of interest.

The haplotype blocks and haplotype patterns of the present invention also are useful for identifying a genetic locus, preferably a gene, within SEQ ID NO: 1 associated with a phenotypic trait of interest that is not associated with LQTS. See Lander et al., Proc. Natl. Acad. Sci. USA 84: 2363–2367 (1987) (incorporated by reference in its entirety for all purposes). Prime candidates for such a genetic locus include the gene predictions discussed supra. This can be accomplished as long as the polymorphisms, haplotype blocks or haplotype patterns of the present invention co-segregate with the genetic locus responsible for the trait; they need not be causally related to the trait. In some embodiments, a polymorphism of the invention is directly responsible for a phenotypic trait by changing the expression, function, or activity of a gene encoded by SEQ ID NO: 1. Several putative genes have already been identified in this genomic region as described supra. Such analysis is useful not only for defining associations, but also for elucidating the function of a new gene or regulatory locus, or for defining new functions of known genes, such as KCNE1 and KCNE2. Genes localized in an association study can be cloned by a process known as directional cloning and can be used to study the biological basis of the trait of interest. Further, if the trait of interest is a disease or disorder, this information could be used to develop preventative treatments or to find potential drug targets. See Collins, *Nature Genetics* 1: 3–6 (1992) (incorporated by reference in its entirety for all purposes).

Associations also may identify a genetic locus that could reveal information about the normal expression and function of biological molecules and complexes (e.g., the $I_{Ks}$ and $I_{Kr}$ ion channels), as well as the biological basis of their related disorders (e.g., LQTS). For example, heart disease is a multifactorial trait caused by both environmental and genetic factors, many of which remain unknown. By identifying the genetic factors, an individual's risk of developing heart disease could be much more accurately calculated. However, this is no small task as many of these genetic factors have very small effects on the overall phenotype. For example, a small change in the activity or function of the KCNE1 or KCNE2 proteins may not appear to have a phenotypic effect unless combined with changes in the activity or function of other proteins in a related biological pathway, such as other components of ion channels. So, even though the combination of these factors may be predictive of a susceptibility to general cardiovascular disease, their small contributions are difficult to detect when these loci are examined individually. However, by identifying these loci through the methods of the invention, their biological basis can be studied and potentially used for the development of, for example, diagnostics to identify, or therapeutics to treat, individuals at a high risk of developing heart disease. Scanning multiple regions of a genome is a powerful tool for identifying loci involved in complex phenotypic traits, especially those that result from the action of many loci that have only a small or weak individual effect. In preferred embodiments, the polymorphisms of the invention are scanned in combination with polymorphisms elsewhere in the genome to identify additional loci associated with a phenotypic trait, such as risk of LQTS-related sudden death. In more preferred embodiments, loci from all chromosomes are scanned (whole genome scanning). For example, whole genome scanning that utilizes the haplotype structure of the invention may be used in a broad screen to examine factors involved in cardiovascular disease, other disorders related to ion channel dysfunction, or other phenotypic traits in linkage disequilibrium with the polymorphisms and haplotype patterns provided herein.

B. Production and Use of Peptides

The nucleic acids of the invention may be employed for producing all or portions of an encoded RNA or polypeptide, for example, a KCNE1 or KCNE2 variant protein or the product of a gene identified in an association study as described supra. The nucleic acids of the invention may also alter the expression of a protein, which may be encoded within SEQ ID NO: 1 or in other regions of the genome, and so may be used to study the biological effect of the altered expression as well as the structure-function and regulatory characteristics of the protein. To express an RNA or protein product, an expression cassette incorporating the corresponding nucleic acid may be employed. The expression cassette or vector generally provides a transcriptional and translational initiation region, which may be inducible or constitutive, where the coding region is operably linked under the transcriptional control of the transcriptional initiation region, and a transcriptional and translational termination region. These control regions may be native to the identified gene, or may be derived from exogenous sources.

The peptide may be expressed in prokaryotes or eukaryotes in accordance with conventional methods, depending on the purpose for expression. For large scale production of a protein, such as a KCNE1 or KCNE2 variant, a unicellular organism, such as *E. coli, B. subtilis, S. cerevisiae*, insect cells in combination with baculovirus vectors, or cells of a higher organism such as vertebrates, particularly mammals, e.g. COS 7 cells, may be used as the expression host cells. In many situations, it may be desirable to express a gene, such as a KCNE1 or KCNE2 variant, or the gene predictions discussed supra, in eukaryotic cells where the gene will benefit from native folding and post-translational modifications. Peptides also may be synthesized in the laboratory.

The modified cells or animals are useful in the study of protein function and regulation. For example, a polymorphism that correlates with the expression of a dysfunctional protein or altered expression of a normal protein would provide insight into the biological basis for the normal function and expression of that protein. In addition, mutations may be made in one or more haplotype blocks in various ways known in the art to generate targeted changes in expression level, or changes in the sequence of the encoded RNA or protein, etc. to determine the biological role of different regions of the haplotype block and to study the expression and function of encoded genes, such as KCNE1 and KCNE2. The mutations may be substitutions, insertions, translocations or deletions. Deletions may include large changes, such as deletions of an entire domain or exon. Techniques for in vitro mutagenesis of cloned genes are known. Examples of protocols for site specific mutagenesis may be found in Sambrook, et al., *Molecular Cloning: A Laboratory Manual* (Cold Spring Harbor Laboratory, New York) (2001). Specific constructs of interest include, but are not limited to, antisense constructs to block gene expression, polymorphisms that reduce or prevent transcription, and polymorphisms that cause over-expression of the encoded gene. For example, a polymorphism may associate with increased expression of KCNE1. Further investigation of the biological basis of this correlation could reveal ways to produce large amounts of KCNE1 protein for further study. One may also provide for expression of a gene or variants thereof in cells or tissues where it is not normally expressed or at abnormal times of development. For example, one of the polymorphisms or a targeted mutation of a haplotype block may correlate with aberrant expression of KCNE2 in skeletal muscle. The phenotype associated with this expression pattern may provide insight into the normal function of the protein.

Variant proteins encoded by the nucleic acids of the present invention are also provided. With the availability of the protein or fragments thereof in large amounts, the protein may be isolated and purified in accordance with conventional ways. A lysate may be prepared of the expression host and the RNA or protein purified using HPLC, exclusion chromatography, gel electrophoresis, affinity chromatography, or other purification techniques. An expressed protein variant may be used for the production of antibodies, where short fragments induce the expression of antibodies specific for the particular polypeptide (monoclonal antibodies), and larger fragments or the entire protein allow for the production of antibodies over the length of the polypeptide (polyclonal antibodies). Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized are by cell fusion and screened for high affinity antibody binding. The immortalized cells, i.e., hybridomas, producing the desired antibodies may then be expanded. For further description, see *Monoclonal Antibodies: A Laboratory Manual*, Harlow and Lane, eds. (Cold Spring Harbor Laboratories, Cold Spring Harbor, N.Y.) (1988). If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation. The antibodies may be used with or without modification, and may be labeled by covalent or non-covalent attachment of a reporter molecule.

C. Diagnostics

Preventative measures are very successful in preventing LQTS-related ventricular fibrillation and sudden death, but many individuals with this disorder remain unidentified due to the variable phenotype and unreliable testing methods. Associations may be utilized to assess risk or susceptibility to a disease or other condition (diagnostics). For example, detection of the polymorphisms, haplotype patterns, and haplotype blocks of the invention in a target DNA sample may be used to determine whether an individual has an increased risk of LQTS or LQTS-related drug sensitivity, or other phenotypic trait in linkage disequilibrium with the polymorphisms, haplotype patterns, and haplotype blocks of the invention. In the case of an association between a set of one or more polymorphisms and an increased risk of LQTS, detection of the set of polymorphisms in an individual may justify the institution of preventative measures (e.g., avoidance of extreme physical exertion) or immediate administration of a treatment regimen (e.g., beta-blocker drug therapy). Alternatively, they may also be used to identify individuals who are resistant to a disease, infection, or other condition. For example, some individuals who display a lengthened QT interval never experience ventricular tachycardia and so are at a very low risk of sudden death. This knowledge could preclude more drastic treatments, such as the use of an implantable cardioverter defibrillator (ICD) in these individuals. Associations may also be used to identify individuals with increased risk of adverse, non-disease conditions and to motivate life-style changes to prevent onset of the condition. For example, an association between a haplotype pattern and obesity could provide strong incentive to exercise and eat a healthy diet. Further, an association between a haplotype pattern and an LQTS-related drug sensitivity would disallow administration of that drug to an individual.

An association may or may not be due to direct effects of the polymorphisms on the phenotypic trait of interest. For example, a polymorphism that is found to associate with a high risk of LQTS-related sudden death may affect the expression or function of the KCNE1 or KCNE2 protein directly, or may be in linkage disequilibrium with (and so predictive of) another locus that affects the expression or function of one or both of these proteins. As such, a polymorphism within a nucleic acid may be used for diagnosis of a disorder that is associated with a genetic locus that is linked to the polymorphism, but not necessarily within the nucleic acid. Examples of direct effects to the expression or function of a protein include, but are not limited to, a polymorphism that alters the polypeptide sequence of the protein, and a polymorphism that occurs in a regulatory region (i.e., promoter, enhancer, etc.) resulting in the increased or decreased expression of the protein. However, the polymorphisms themselves need not be directly involved in the manifestation of the phenotypic trait of interest in order to serve as a means to identify genomic regions that are involved; they need only be correlated with that trait and genetically linked to the genomic region. In preferred embodiments, the set of polymorphisms used in the association studies would be chosen based on the genomic haplotype structure of an organism. In more preferred embodiments, the polymorphisms would be SNPs in identifiable haplotype patterns. In more preferred embodiments, at least one of the polymorphisms would be an informative SNP.

The nucleic acids and haplotype structure of the invention may also be used to detect or quantify expression of an encoded gene, such as KCNE1 or KCNE2, or other genes in linkage disequilibrium with the nucleic acids and haplotype structure in a biological specimen for use as a diagnostic marker, e.g., to predict a phenotypic characteristic such as disease susceptibility or drug responsiveness by using nucleic acids of the invention as probes to determine whether a particular polymorphism or a set of polymorphisms is present in the genome of an organism being tested. For example, the nucleic acids may be used as oligonucleotide probes to monitor RNA or mRNA levels within the organism to be tested or a part thereof, such as a specific tissue or organ, so as to determine the expression level of the gene encoding the RNA or mRNA, where the expression level can be correlated to a particular phenotypic characteristic of the organism. Likewise, the expression of the gene may be assayed at the protein level using any customary technique such as immunological methods (e.g., Western blots, radioimmune precipitation and the like) or activity based assays measuring an activity associated with the gene product. The manner in which cells are probed for the presence of particular nucleotide or polypeptide sequences is well established in the literature and does not require further elaboration here, however, see, e.g., Sambrook, et al., *Molecular Cloning: A Laboratory Manual* (Cold Spring Harbor Laboratory, New York) (2001).

Antibodies which bind specifically to the gene products of the present invention (i.e., KCNE1 or KCNE2 variants) also may be used for the diagnosis of disorders characterized by their expression, or in assays to monitor patients being treated with the gene products or with agonists, antagonists or inhibitors of the gene products. Diagnostic assays for the gene products of the present invention include methods which utilize an antibody and a label to detect the gene product in human body fluids or in extract of cells or tissues, such as heart muscle.

D. Pharmacogenomics

Associations may be used for pharmacogenomic studies and drug development. For example, since the response of individuals with LQTS to different treatments varies, identifying sets of polymorphisms that associate with positive (or negative) response or side-effects to an administered drug or other treatment would be useful for stratifying patient populations and individualizing treatment regimens. In addition, associations may be used to develop clinical trials for new treatments for LQTS and other disorders or diseases by allowing stratification of the patient population. For example, if an antiarrythmia drug were to be tested for efficacy and safety, it would be valuable to identify and remove individuals with LQTS from the population to be tested, since these individuals are at a higher risk of ventricular fibrillation when these types of drugs are administered. Further, if a new drug for treatment of potassium channel-related LQTS were being tested, then a population of individuals with LQTS could be stratified based on the type of LQTS that they possess. For example, individuals with a sodium channel-related LQTS would likely be non-responders and could be excluded while individuals with a potassium channel-related LQTS would be more likely to be responders and could be included in the study. Even a population of individuals with potassium channel-related LQTS may be further stratified based on polymorphisms that associate with responses to different classes of drugs and thereby distinguish probable responders from nonresponders from individuals likely to have toxic side effects.

E. Therapeutics

The nucleic acids, or the encoded protein variant or fragments thereof may be useful in gene therapy to treat potassium ion channel-related disorders, such as LQTS, and other disorders found to be in linkage disequilibrium with the polymorphisms and haplotype structure of the invention. For example, expression vectors may be used to introduce an identified gene (e.g., a beneficial variant of KCNE1) into a cell. Such vectors generally have convenient restriction sites located near the promoter sequence to provide for the insertion of nucleic acid sequences in a recipient genome. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to be transiently or stably maintained in the cells. The gene or protein product may be introduced directly into tissues or host cells by any number of routes, including viral infection, microinjection, or fusion of vesicles. Jet injection may also be used for intramuscular administration, as described by Furth, et al., *Anal. Biochem,* 205: 365–68 (1992). Alternatively, the DNA may be coated onto gold microparticles, and delivered intradermally by a particle bombardment device or "gene gun" as described in the literature (see, for example, Tang, et al., *Nature,* 356: 152–54 (1992)).

Antibodies which bind specifically to the gene products of the present invention (i.e., KCNE1 or KCNE2 variants) may be used as therapeutics. For example, such antibodies may be administered to a patient as a means to inhibit the activity of a detrimental variant of KCNE1, KCNE2, or another variant protein encoded by SEQ ID NO: 1.

Antisense molecules may be used to down-regulate expression of an identified gene (e.g., a detrimental variant of KCNE2) in cells. An antisense molecule forms a duplex with the mRNA of a gene whose expression is to be down-regulated, blocking translation of the corresponding protein. For example, if a KCNE2 variant is found to be correlated with an increased risk of LQTS in a patient who is heterozygous for the wildtype (normal) version of KCNE2, then an antisense reagent may be developed based on the sequence of the mRNA of the KCNE2 variant. This antisense agent may then be administered to the patient to decrease the expression of the detrimental KCNE2 variant, allowing the expression of the wildtype KCNE2 to predominate. The antisense reagent may be antisense oligonucleotides, particularly synthetic antisense oligonucleotides having chemical modifications, or nucleic acid constructs that express such antisense molecules as RNA. A combination of antisense molecules may be administered, where a combination may comprise multiple different sequences.

As an alternative to antisense inhibitors, catalytic nucleic acid compounds, e.g., ribozymes, anti-sense conjugates, etc., may be used to inhibit expression of detrimental gene variants. Ribozymes may be synthesized in vitro and administered to the patient, or may be encoded on an expression vector, from which the ribozyme is synthesized in the targeted cell (for example, see International patent application WO 9523225, and Beigelman, et al., *Nucl. Acids Res.* 23: 4434–42 (1995)). Examples of oligonucleotides with catalytic activity are described in WO 9506764. Conjugates of antisense oligonucleotides with a metal complex, e.g. terpyridylCu(II), capable of mediating mRNA hydrolysis are described in Bashkin, et al., *Appl. Biochem. Biotechnol.* 54: 43–56 (1995).

An expressed protein encoded by a nucleic acid of the invention also may be used in drug screening assays to identify ligands or substrates that bind to, modulate or mimic the action of that protein product, and thereby identify therapeutic agents to provide, for example, a replacement or enhancement for protein function in affected cells, or an agent that modulates or negates protein function. A wide variety of assays may be used for this purpose, including labeled in vitro protein-protein binding assays, protein-DNA binding assays, electrophoretic mobility shift assays, immunoassays for protein binding, and the like. The term "agent" as used herein describes any molecule, e.g., a protein or small molecule, with the capability of altering, mimicking or masking, either directly or indirectly, the physiological function of an identified gene or gene product. Generally pluralities of assays are run in parallel with different concentrations of the agent to obtain a differential response to the various concentrations. Typically, one of these concentrations serves as a negative control, e.g., at zero concentration or below the level of detection. Also, all or a fragment of a purified protein variant may be used for determination of three-dimensional crystal structure, which can be used for determining the biological function of the protein or a part thereof, modeling intermolecular interactions, membrane fusion, etc.

Candidate agents encompass numerous chemical classes, though typically they are organic molecules or complexes, preferably small organic compounds, having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, and frequently at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs.

Where the screening assay is a binding assay, one or more of the molecules may be coupled to a label, where the label can directly or indirectly provide a detectable signal. Various labels include radioisotopes, fluorescers, chemiluminescers, enzymes, specific binding molecules, particles, e.g., magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures. A variety of other reagents may be included in the screening assay. These include reagents like salts, neutral proteins, e.g., albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc., may be used.

Agents may be combined with a pharmaceutically acceptable carrier or diluent, including any and all solvents, dispersion media, coatings, anti-oxidant, isotonic and absorption delaying agents and the like. The agent may be combined with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with buffering agents, moistening agents, preservatives and flavoring agents. The use of such media and agents for pharmaceutically active substances is well known in the art and are readily available to the public. Moreover, pharmaceutically acceptable auxiliary substances, such as pH adjusting and buffering agents, tonicity adjusting agents, stabilizers, wetting agents and the like, are readily available to the public. Except insofar as any conventional media or agent is incompatible with the active ingredient, its use in the therapeutic compositions and methods described herein is contemplated. Supplementary active ingredients can also be incorporated into the compositions.

The following methods and excipients are merely exemplary and are in no way limiting. Identified agents of the invention can be incorporated into a variety of formulations for therapeutic administration. More particularly, the complexes can be formulated into pharmaceutical compositions by combination with appropriate, pharmaceutically acceptable carriers or diluents as discussed supra, and may be formulated into preparations in solid, semi-solid, liquid or gaseous forms, such as tablets, capsules, powders, granules, ointments, solutions, gels, microspheres, and aerosols. Additionally, agents may be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Further, agents may be utilized in aerosol formulation to be administered via inhalation. The agents identified by the present invention can be formulated into pressurized acceptable propellants such as dichlorodifluoromethane, propane, nitrogen and the like. Alternatively, agents may be made into suppositories for rectal administration by mixing with a variety of bases such as emulsifying bases or water-soluble bases and can include vehicles such as cocoa butter, carbowaxes and polyethylene glycols, which melt at body temperature, yet are solid at room temperature.

Implants for sustained release formulations are well known in the art. Implants are formulated as microspheres, slabs, etc. with biodegradable or non-biodegradable polymers. For example, polymers of lactic acid and/or glycolic acid form an erodible polymer that is well-tolerated by the host. The implant containing identified agents of the present invention may be placed in proximity to the site of action, so that the local concentration of active agent is increased relative to the rest of the body. Unit dosage forms for oral or rectal administration such as syrups, elixirs, and suspensions may be provided wherein each dosage unit, for example, teaspoonful, tablespoonful, gel capsule, tablet or suppository, contains a predetermined amount of the compositions of the present invention. Similarly, unit dosage forms for injection or intravenous administration may comprise the compound of the present invention in a composition as a solution in sterile water, normal saline or another pharmaceutically acceptable carrier. The specifications for the novel unit dosage forms of the present invention depend on the particular compound employed and the effect to be achieved, and the pharmacodynamics associated with each active agent in the host.

Administration of the agents can be achieved in various ways. The formulation may be given orally, by inhalation, or may be injected, e.g. intravascular, intratumor, subcutaneous, intraperitoneal, intramuscular, etc. Agents may be topical, systemic, or may be localized by the use of an implant that acts to retain the active dose at the site of implantation. The dosage of the therapeutic formulation will vary, depending on the specific agent and formulation utilized, the nature of the disease, the frequency of administration, the manner of administration, the clearance of the agent from the host, and the like, such that it is sufficient to address the disease or symptoms thereof, while minimizing side effects. In some cases, oral administration will require a different dose than if administered intravenously. The compounds will be administered at an effective dosage such that over a suitable period of time the disease progression may be substantially arrested. The initial dose may be larger, followed by smaller maintenance doses. The dose may be administered as infrequently as once, weekly or biweekly, or fractionated into smaller doses and administered daily, semi-weekly, etc., to maintain an effective dosage level. Treatment may be for short periods of time, e.g., after ventricular fibrillation, or for extended periods of time, e.g., in the prevention of further episodes of ventricular fibrillation. It is contemplated that the composition will be obtained and used under the guidance of a physician for in vivo use.

F. Other Uses and Aspects of the Invention

It should be apparent that the methods of the present invention can be used on organisms aside from humans. For example, when the organism is an animal, the methods of the invention may be used to identify loci associated, e.g., with disease resistance or susceptibility, environmental tolerance, drug response or the like, and when the organism is a plant, the method of the invention may be used to identify loci associated with disease resistance or susceptibility, environmental tolerance and or herbicide resistance. The nucleic acids of the invention may be used to generate genetically modified non-human animals to create animal models of LQTS or other ion channel-related disorders, or to generate site-specific gene modifications in cell lines for the study of protein function or regulation. Transgenic animals may be made through homologous recombination, where the endogenous gene locus is altered, replaced or otherwise disrupted. Alternatively, a nucleic acid construct may be randomly integrated into the genome. Vectors for stable integration include plasmids, retroviruses and other animal viruses, YACs, and the like. Of interest are transgenic mammals including, but not limited to: cows, pigs, goats, horses, etc., and, particularly, rodents, e.g., rats, mice, etc. Investigation of genetic function may also utilize non-mammalian models, particularly using those organisms that are biologically and genetically well-characterized, such as *C. elegans, D. melanogaster* and *S. cerevisiae*. The nucleic acid construct may be used to knock-out corresponding gene function or to complement defined genetic lesions in order to determine the physiological and biochemical pathways involved in protein function. Drug screening may be performed in combination with complementation or knock-out studies, e.g., to study LQTS-related phenotypic traits, to test therapies, or for drug discovery. test therapies, or for drug discovery.

The invention further provides kits comprising at least one nucleic acid of the invention, preferably an oligonucleotide, more preferably an oligonucleotide primer or probe that may be used to detect a polymorphism or haplotype pattern of the invention. Often, the kits contain one or more pairs of oligonucleotide primers that hybridize to a target nucleic acid to allow amplification of one or more regions of the target that contain or are a portion of one or more haplotype blocks of the invention. In preferred embodiments, the amplification product could be analyzed to determine the genotype of the polymorphisms and/or haplotype patterns contained within the target nucleic acid. In some kits, oligonucleotide probes are provided immobilized to a substrate. In preferred embodiments, an oligonucleotide probe immobilized to a substrate hybridizes to a specific allele of a given polymorphism of the invention. For example, the same substrate can comprise oligonucleotide probes for detecting multiple or all of the polymorphisms listed in FIGS. 1 and 2. Optional additional components of the kit include, for example, restriction enzymes, reverse-transcriptase or polymerase, the substrate nucleoside triphosphates, means used to label (for example, an avidin-enzyme conjugate and enzyme substrate and chromogen if the label is biotin), and the appropriate buffers for reverse transcription, PCR, or hybridization reactions. Usually, the kit also contains instructions for carrying out the methods.

These kits may facilitate both identifying those at risk of LQTS, those sensitive to the drugs that exacerbate LQTS symptoms, individuals with other phenotypic traits in linkage disequilibrium with the polymorphisms and haplotype patterns of the invention, and could also be useful for genetic counseling.

In addition, the polymorphisms, haplotype patterns and haplotype blocks of biological matter. Rare SNPs may be particularly useful for this application. This biological matter may be collected at a crime scene or from the victim of a crime, and could be used to construct a genetic profile of the perpetrator of the crime. This technology could provide a genetic profile to match a given sample to a specific individual, and may both provide stronger evidence for convicting the guilty and definitive evidence to clear many who have been wrongly convicted, some of whom may be awaiting a death sentence. Further, associations also may be used to help couples make informed reproductive decisions based on the genetic makeup and haplotype structure of their own genomes.

A database is also provided for use in recording and cataloging the polymorphisms, haplotype blocks, and haplotype patterns of the invention. The database may also contain data obtained from association studies, drug screening studies, and other utilities of the invention. The database may also contain information on LQTS or other disorders in linkage disequilibrium with the polymorphisms of the invention including, but not limited to, environmental factors, genetic factors from genomic regions outside of SEQ ID NO: 1, biochemical or genetic markers, behaviors, other polymorphisms such as insertions, deletions, inversions, translocations, RFLPs, and the like. The database may be stored on a computer-readable medium.

VI. Conclusion

The present inventions provide nucleic acids comprising polymorphisms, haplotype patterns and haplotype blocks, as well as greatly improved methods for developing diagnostics and therapeutics, and discovering the biological basis underlying a plethora of phenotypic traits. It is to be understood that the above description is intended to be illustrative and not restrictive, and that the invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention. One skilled in the art will readily recognize that the polymorphisms, haplotype blocks, haplotype patterns, and nucleic acids of the invention may be used in many different applications in addition to the examples described herein. The scope of the invention should, therefore, be determined not with reference to the above description, but should instead be determined with reference to the appended claims, along with the full scope of equivalents to which such claims are entitled.

What is claimed is:

1. An isolated nucleic acid molecule comprising at least one nucleic acid segment of SEQ ID NO: 1, wherein said segment comprises nucleotide positions 924 to 38318 of SEQ ID NO: 1, and wherein said segment further comprises the following nucleotides at the indicated positions: 924=T; 1452=T; 1716=C; 3978=A; 4393=T; 6218=A; 7154=A; 7175=G; and 38318=A.

* * * * *

SEQUENCE LISTING

<160> NUMBER OF SEQ ID NOS: 2

<210> SEQ ID NO 1
<211> LENGTH: 113604
<212> TYPE: DNA
<213> ORGANISM: Human
<220> FEATURE:
<221> NAME/KEY: misc_feature
<222> LOCATION: 7175, 7204, 36973, 66372, 76921, 81512, 88727
<223> OTHER INFORMATION: n = G or C

<400> SEQUENCE: 1

| | | | | | |
|---|---|---|---|---|---|
| tgtcagaaaa | agatacaaca | tttaataacg | atggaatgta | aatatcaaat | attttatt   60 |
| acaaacaaat | aaaagttttt | atatagaact | aaaatgattt | ctataacacc | tgttttcact  120 |
| gttcttcaat | atttctcttt | taacttttca | aagattttct | ttttaaaatt | ttttttttgta  180 |
| gagatgggat | ctcactatgt | taacccagtc | tggtctcgaa | ctcctggcat | gtgatcctcc  240 |
| ctccttggcc | tcccaaaatg | ctgggattac | aggcaaaagc | caccacgccc | agccaagatt  300 |
| ttcttttttt | attgtctgta | tttaagatat | gcaacaagat | gttctgacgt | acatatgtgg  360 |
| agtgattacc | acagacaagc | aaattaacat | accgttaaca | tattcacaca | accattaaca  420 |
| tgtccatgtt | cgtgtgtgtt | ttggggggggg | gtatgtgtgg | taagagcacc | taaaacctac  480 |
| tctcttggca | gatttccagt | atgcaatgtg | tacaatgctt | ataaacattt | ttcttatta  540 |
| aaacaaaaca | aaaaccgcc | acatatatgg | aaagagctgt | gctggatgcc | taaggaggaa  600 |
| gcttgatggt | tctaagcaaa | ggccaaaaag | tggtctgatc | tatggaaaaa | ctggaaagcc  660 |
| ggcaaaattt | gctgtgagag | ccctttctct | gctcccatct | gtgctgatct | gctttttcc  720 |
| tacaagagcc | cattggcctt | ttatagttcc | tggggaaaat | gaagccccca | cggttgtgcc  780 |
| tccttgagtt | ccaggacttc | cccctctcct | tcccatccag | ttttaacccc | cacacacctg  840 |
| tggcctgcac | gctggggggtt | cttttctgtt | tcttttgatc | ctcttcctct | ttgaaaatca  900 |
| tctttgtaaa | acaaacctaa | tackgcacca | tttccgtcca | gattcatgct | ccaggaagaa  960 |
| agggtgctgg | aggctacagg | ggggcctcac | agcccatgtg | atctctgtgt | tacattcatt  1020 |
| ttccactaac | agaaatcaaa | gaacatacc | tgccattcgg | cctgtgacag | gggtctttgt  1080 |
| taactttggg | tcttgctaaa | gttcagtaat | gtcagggcaa | acagaacaca | aggaagctga  1140 |
| gacgttctct | ggctttccgt | tgcaaactag | gcctgttgat | gatggtgaca | agcttctcaa  1200 |
| tcccagaagc | atgaagccag | caaggctggg | aaagcacctt | gggggaaggc | tccatcagaa  1260 |
| gagaatcaac | tttatcaaaa | cttggttttgc | tctatcacag | cagcggcatt | tcagaagcat  1320 |
| cctaccaagt | tgcttgtttc | attgataaac | taaagaaacc | ctacatgttt | ggagagttct  1380 |
| tggtgaggcc | tgttcattgg | aagtcgtcat | gcttgtgtgt | atcttagaga | agaagaaaat  1440 |
| tccagtagtt | cytcagtcaa | atggtgtaat | ccactccaga | atcattgcca | tctcttctaa  1500 |
| tattctgaac | caggcacaga | gaaagtagaa | gctcagtgca | tagctaaatg | aaattaccag  1560 |
| agattctcaa | tgcccccatt | tccagctttt | cacaaaacca | ttgtgctcac | attaatagca  1620 |
| tcaaggaaag | cttcctactc | tgtgagctca | attagaaacg | tcatgtattg | ttaatggttt  1680 |
| tgaaaggtg | aaaactttct | tttccagagt | cttttycatc | ggaatgataa | tcttagtacc  1740 |
| ttgtaaatag | atgaggtggt | tgatttcatc | acagccagaa | tctagaatta | tcaccattct  1800 |
| tttgggatac | agtgagagct | tttttccagc | cagacacaga | atgggcaata | caggtaaggt  1860 |
| ccctgttgtc | atggagctca | agttctgtta | gagacaggaa | agaaaaaaac | aatcaataaa  1920 |

-continued

```
acaggaaaac ttcataattc aaagaagcca cgcacagctg tgagactatg cacaggcacc      1980
attcacactg tagactaagt gacagctgcc cccgggttaa gccctgcctt gcctgggcaa      2040
cagtacatgg catccccaca caattcagat aatacaaagt gctatcaggg aaatgtgaag      2100
aaggaagaag ctgtgccaag attgggggaa aagcattaga ggcagagaga gcagcgtatg      2160
caaagatgct gaggcagtcc gtataattgc accatgaaga ggtccctgtc ctaatctctg      2220
gaagctgtga atatgttacc ttacctggta aaatggactt tgcaggtgtg attattaagt      2280
taaggatctt gagatgggaa gatgatcttg gattatccag atgggacaaa tgcaatcaca      2340
aggctcctta taagaagcag gcagggggct cagggagtgg gagaagatgt gatcacaaaa      2400
gcagaggctg ggccgggtgc ggtggctcat gcctgtaatc ccagcacttt gggaggttga      2460
ggcggacaga tcatttgagg tcacgaattt gagaccagcc tggccaacat agtgaaaccc      2520
catctctact aaaaatatac aaaaattagc ctggcatggt ggcaggcatc tgtagttcca      2580
gctactaggg aggctgaggc aggaggatca cttggaccca ggaggcggag gttgccgtga      2640
gtcaagatcg tgccgctgcg ctccagcctg ggtgacagaa tgagactctg aaaaaaaaaa      2700
agaagaaaga gaaagaagga aagaaagaaa gaaagaagga aggaaggaaa gaaagaagga      2760
aagaaagaaa gaaagagaaa aagaaagaaa aagaaagag aaagaaagaa aaagaaagaa      2820
aagcagaggc tggagggatg ccaggatgcc agggagaggg ccaagagcca aagaatgtgg      2880
gtggcctctg gaagctgcaa aaggtaaaga aatggattca cactccctcc tcaaccccca      2940
gagcatccaa aagaaactgg ctctgctgcc atcttgatgt taacccagtg aaatccactt      3000
tggacttctg accccagaa ctttaagata atattataaa tttgtgttgt ttaagtcact      3060
aagtttgtgg tcatttgtta taacagcaat gggaagctaa tacagattca aagacaaaaa      3120
caaaacaaaa agcagagaag caggatcaga ctatgtgaga agatgagctc gcagaaagga      3180
ccagcggcca gttttttccat ggcctggcca gctgcactaa gcattccggg ttttatttc      3240 agggtgaaag gaacccaatg gagagtttca agcaggggaa ttgcgggctg tggtttgtgt      3300
ttccaaaaga tccccactggt ccctcttaga aatatgtgaa tagggacaga gtgcaaagcc      3360
agaggcgtga gcggccagca gtccaggtgt gagctgagaa gtagctgtgc ggggacgtgt      3420
ttggagagtc aaattattac tataataata attattatta tttagagatg gtgtcttgct      3480
ctgtggccca ggctggaatg cagcggcatg atcccggttc acggcaatct ctgcctcccg      3540
ggttcaagcg attctcctgc ctcagccacc caagtagctg ggattacagg cacctgccac      3600
cacacctggc taattttgt attttggta gaaacggggt ttcaccatgt tggccaggct      3660
ggtctcgagc tcctgacctc aggtgatcca ccctcctcag cctcccaaag tgctgggact      3720
acaggtggga gccactgtgc ccagcctgga gcgtcaaatc aaaacaaaaa aaccaacaga      3780
gcagtaagaa acatatttca atttattacc ttcggggcta ggggaagaga gacaagttct      3840
aagaggcttt tcgtgcaaaa atggaaagaa ctaggtttaa ggcaacagtg agaaatgaca      3900
atgaaaaagg caagcttctg akaacagctg tctgtttggc tggtgagacg gattgtgact      3960
cttctttgca attggccrtt gtactagttt atggcacaaa acccaggca cagttttcaa      4020 agaagttgag atgggtatt aagggtctgg tgggttcgat gtcacccagc acaaactcat      4080
acacccacgt tcaacctgtg cagagkcttt tctttaacag gatgcagagt caacagtatt      4140
tgctagtgaa ttgggggtgt ggcagggtga ccaaaaaaaa aaaaaaaaaa aagaaatcta      4200
agttaattct ttggtttttt ggcttacaca actagaaaga aagtggagtc actttactgt      4260
```

```
gataggatag gagtaggttt ggtaggagaa ttgagttatg tttggacatc tgaggttgag    4320
atgcctatta gacatctgag tgaaaatgtc aagtgagcat cttgacattt gattctgaaa    4380
ttcagagaag agkactggac tggagataca catttgcaag tccccctacaa atacatggat   4440 tttaaagaaa tcaactttat tgtggtatag tttacataaa attatacaca cccattttaa    4500
gtgcatggtt caatgagttt tactcaggta accacctaca acaaccaaga tatagaacaa    4560
ttctatcacc ctccaaaatt gtctcttaat cctttgcagt caatcttccc ctcatctggt    4620
catagaaaac tactaatctg ctttctgtca cgagggatgg cttttgtctt tctggaattt    4680
ctagaaatgg aatcaaacag tacaacttct ttgtgtctga cttcttttgc tcatataatc    4740
tttgtgggat tcatccctgt tggtgcatgt atcatttatt tgttcttttt tattgttgag    4800
caatatttca ttgtgtgaat aaaacacaat ttgtttaccc acttatctgt tgagggatat    4860
ttggcttatt tccagttttt agctattttg aataaagctg ctataaacat tcatgagttt    4920
ttgtgtggca tattttgaaa atttctctag gtaaatacct agaagggggca ttgttgggaa    4980 cttttgatct agttaccaaa ctgtttacaa gtggctgtat cattttacat tcctaaggca    5040
atgtatgaaa atccacttag cccacatcct caccaacact tggtgttgtc agtctttta    5100 aatgtagcca ttctggccag gtatggcggc tcatgcctgt aatcccagca ctttggaagg    5160
ctgaggtggg cagatcaccc tgaggtcagg agtttgagat gagcctggcc aacatggcaa    5220
aaccccgtct ctactaaaaa tacaaaaatt agctgggtat ggtggtgtgc actgtaattc    5280
cagctactct tgttgaggca ggagaatcac ttgaaccctg gcagggagg ttgcagtgag     5340 ccgagatctc accactgcac ttcagtctgg gggacagtga gagattccat ctcaaaaaaa    5400 aaaaaaagt agtcattctg gtgagtgcgt agtggtatct cattgtaatt acaagttata     5460
tttccaatga cgttgagcat ttatgtgctt attgtatata ttttttggta gtgtctgcat    5520
aaacctactg tccattatta ttgagtcaat ttttttttcaa atgatgagtt ctttatgtat   5580
tctagatgca aatctgttgt atattctaga tacaaattca tggtggttat tttttttcagt  5640 atattacttg ccttttttatt ttcttaatta tgttcttcaa ggagtaaaag actttaataa   5700
tgatgaggcc caatatatca atattttcct tttatgatcc atgtgtttca gtctttgttt    5760
cctccatctg cttttaagat tttctcattg cttttgattt taagcatttt atgcaaaggt    5820
gtgactttct ttgaaataat tctctttgag cttttagtt cttgaactca tggcttgatt     5880
tttttaaaaa gcagttttgg aaaaaatctc attcactatt tcttcaaata ttgyttcagc    5940
ttcagccact ttctcctctc tttctgggac tccaactgta cttctgttag tccttttcc     6000 tgtatctctc atactttctt gggtgtatcc tattattttg ttctgtgctt cactgtagat    6060
attttctgct gactagattt ctaattcact aatcctctct tcagctttgc ctatgctgct    6120
ggtaaatcca tccactaaat tgatacattt aaaaaataga tttctgcgga gattctattt    6180
attcttgggc tgactctgga aatttatatt tttctggmam attatatatt tcatccaaaa    6240
cttcaaattg tatttccaga gtgacttttt atttagttga ttctatattt atttgttttc    6300
tcttttgttc ctttctgttt ttgttctaaa gtttcattta ttctacattt ttagtttatt    6360
ttttggttct tttgcttttt gagtttaatg agttcctatt attttccttt tatttatttt    6420
tattttttag agacagggtt tcactctatc acccagactg gagtgcagtg gcaccataat    6480
agctcagtct aacctagaac tcctgggctc aagcctcttc ccacctcagc ctcctgagta    6540
gctagggcta cagctatgca ccaccattcc cagataattt taaacaattt cttttttata    6600
gagatagagt ctcagtgtct cactatgtca cccaagctgt tctcaaactc ctggcctcaa    6660
```

-continued

```
gtgatcctcc tgcctcagcc tcccaaagca gtgggattac aggtataagc caccatgccc    6720
agcctctttt cctttagtg aattcattta ctgtataaat ttgcctctaa ggttcacatt    6780
gtctgcatcc cagaagtttt caaatatatg gcagttcctt tgtaatttaa tatcttatta    6840
tttatgtgtt ttcctcttta tccatatgtt acgtgatgat atacttattt tttggttttc    6900
agatatatca aggtgtacag actatatttt tgctgattta taattcaact gcattgtagt    6960
aatggaaccc agtctacata aagctgatat ttaaaaattt ggttggactt cttttgtgac    7020
ccagcacatg gtgagttttt aaaaccgttt tatggacact tataaagaat gcacatcatt    7080
tgttggttag gtgtrggttc tctccatcta ttttataaag gtaattaatt ctattactca    7140
attctatatg tttrctttt aaaaaaatct atcantttct gaaacctaat tcctaccatt    7200
gtgnatgcct caatttcttg taaatctgcc tgtttcactt tgaatatttt gagtccatat    7260
acaagcccat gattttacta tcttcttcgc aggttgtttc ttttatcaaa ttgtagtgac    7320
atttaatatc ctatggatca cctgaaattt cagttttct tagatrctg catttagcc    7380 ttagcttgat atgttttttc atcaccttat tttcaacttt ttatttgttt ttatttaga    7440 tgtgcatctt tattttgtat tttatttttt gagacagagt cttgctgttt cacccaggct    7500
ggagtgtagc agcgtgatct tggctcactg caacctctgc ctcccaggtt caagtgattc    7560
ttatgcctca gcctcccaag tagctgggat tacaggcata tgccaccatg cctggctgat    7620
ttttatattt ttagtagaga tgaggtttcg ccatgttggc cagggtggtc tcgaactctt    7680
gggttcaagt gatccgcccg tctcgccctc ccgaagtgct gggattacag gtgtgagcca    7740
ccagccccag cctagatgtt tatcttttaa gaagcatata gctagatttt attttgttat    7800
tcagtttaat aatacttctt ttaataggta cttattttaa aggatattgt gattatagat    7860
atattcagat attatcttag tcattggggc agttatagta aaaattataa actggatgac    7920
ttataaataa caaaagtta ttgctcatag tttggaggct ggcaggtcca agaccaaggc    7980
actggcagat gcggtgtctg gtgaggtctc cctctttgat tcatagaccg tgccttctag    8040
ctgcgacctc acatggtgga aaggggaagg caacctccct gtagcctctt ttaaagggc    8100 attaatcgca ttcacggggt ctccatcctc ttggcctaac cacctcccaa aagccctacc    8160
ttttagtaat atcacatggg gagttagaat ttcactatat gaattttggg gggacacaaa    8220
catttatgcc acagcagata tctttctacc accttatttg gtgatttctg ggttttgttt    8280
gtttgtttaa gacagagtct cgctctgtcg gccaggctgg agtgcagtgg caccatctcg    8340
gctcaatgca accttcgcct ccccggttca agcgattctc ctgcctcagc ctcccaagta    8400
gctgggatta cggacgtgtg ccaccacgcc tggctaattt ttgtattttt agtagagact    8460
gggtttcacc attttggcca ggctggtccc gaactgctga gttcaggtga tccacccgcc    8520
tcggcctccc aaagtctgg gattacaggc gtgagccacc atgtccggct ggtgatttct    8580
gtttaaaagt tttttcttaa agtgtttttt cccacctagt ttttcattga atgggtaaaa    8640
cattctacat ttgcttttat taaacaagaa atgaatttt gctgcatttc aatttataga    8700
ttttactatc ctacctcgtg ccaggttctg tgctaagtgc tgtatatatc tgtgatcaca    8760
tttaactttt ataacaagcc aaatgagcag gaactcttat ctctatctta cagacgaaga    8820
atccaaagac cagggacagt aagtaatttg ctcacctggt ttgccagcct ccatgacaca    8880
tcgccgtcca gttctgcctt taattaccaa agcacaacac gctgctttga ttcccctctc    8940
ctcggcgcca gaattcaaga gtgaagttaa accgcaaggg ctgagktaga agattggcct    9000
```

-continued

```
cagttccctg ttcccaccag caggtggcac cgtctcctag cggaattctt acttgaacgt    9060
tttgcttcca tttctgcaga ggcatggtga acacagttac accaccaaag tgttcctcct    9120
ggctgagttt gcctatcttg ttcagtgaag acaacccatg aggacaaatg gtgttaatga    9180
gaagcttttg cggagttaca gagatcctcg tatttcttta aaatacacct aataacgtta    9240
actctgcaat aatttgtaga tcatgttaaa tcttagctat cttcctcttg ccacccagtg    9300
tgcttcaagc cacatggttc agagcaccat ttaatgtgaa actccaattt taaaacaaag    9360
tgaaccttcc ttttacaaaa ccatgagaca agttacagag taatgaccac ccacatgacc    9420
ttgaagtgat tttgagtgag tgagtgtaac ttccgtggct gccatttaaa ttggattcaa    9480
atccaaatgg ctccacctcc atgtcatcag acctcttgtg ccctgattcc cttggctaag    9540
ttcayagtac cttccacatc aggttgtggc aatgattacc tgaggttaat acgataaaag    9600
cacatggtaa gcactcctaa atgatagcca atataaagac tcagttctcc caattccaag    9660
ggtccccacc atgatagaaa aggatctttt ggtaaataga gtatgtttag ctcttgctag    9720
gtctttaaat actttgctgg gggccaggca ccatggctca cacctgtaat cccaccgcct    9780
taggagactg aggctggagg atcctttgcg gccaagagtt tgagaccagc ctgggcaaca    9840
cagcaagacc ctatttctac aaaaataaaa ataaaaatta accaggcttt gtacacactt    9900
gtagtcccat tacttgggag gctgaggcag gaggatccct caagcccaag agttcaaagc    9960
tgtagtgagc tatgattgcg ccactgcact ccagcctggg tgacagagta agactctgtt   10020
tcaaaacaac aacaacaaac aaaaacctca aaacctcttt gttggactta acttccagct   10080
cctccatgta gtaccttagt acccttgcag cccgtttctc ttttacaaga caacaatgtt   10140
gttataaact catttggawg tggtcccgtg gaggagtatt taccagaatc tagcttattt   10200
agcgtcttca gaacacggca cttgcctgga attatactga cccctcaac ccataccaac   10260 cacccagaga tggctgttct tggctcctct ccctggggcc ctgtccttcc cacatcgtct   10320
tcttcttctt tcttcttctt tcttcttcct tcttcttcct tcttcttcct tcttcttcct   10380
tcttcttcct tcttcctctt cctcttcctc ttcttctttc ttctttcatt gagacagagt   10440
ctcactctgt cacccagcct ggagtgccgt ggtatgattt cagctcactg taacttctgc   10500
cttgtggatt caagtgattc tcctgcctca gcctccagag tagcagggac tacaggtgtg   10560
tgccaccaca cctggctaat ttttacattt ttaagtagag acggggtttc accatgttgg   10620
caaggctggt cttgaactcc tgatctcagg tgatctgccc gcctcagcct cccaaagtgc   10680
tgggattaca ggcgtgagcc accccaccca gcccttccca cgtattctgg cagggaatgc   10740
tgttgtcccc caagcctacc ctaagaggaa gacttcttct ggggaaagat gttcactgta   10800 cccaggcccct gccctggctg gagctggcag gaagggtccc agagcaggaa cttgtgccac   10860
tctgcccaaa gccagagtcc ctgaggcaca caccccatca ggcaccaagg tgaattccaa   10920
ctgccagtta gtatttaact ttccacatac gattagatta aacatgtggg ttcataaaag   10980
cataggattg cagactgcag ttgcaagggc ttagatggtt gtaaggtgaa ggtgcccagc   11040 aggctgagge ttgtgtgcaa cccagaagag agctcgctaa crccagcaag aaggttcaga   11100
acagcctggc tttggaaagg aatttcatcc tgcccacaca ctgcataggt aagtcttagc   11160
acacattctt tatttttga ggaattaagt aacaaagtta tctatgtgcc ttttccagaa    11220
aatgataaaa ggaatgattt tcctggtaca tggcctggct cctcatccac tcttccttct   11280
ttccttcttg tgttttcctt actcatttct ttgttaattg cctagaatg aaaatttga    11340 gagttttttaa aatggaggat tcatggtaaa cgtaggtaat catattgttt tctcttcttg   11400
```

```
atataaaaat gaaagactttt gctgcctttt ataggcccag gtgatgtgag cgatctacca  11460
tgtttcaaga aaagaaaact ttggggctgg gcgcggtggc tcacgcctgt aatcccagca  11520
ctttgagagg ctgaggcagg cggatcacct gaggtcagga gatcgagacc agcctggcca  11580
acatagtgaa accccatctc tactaaaaat acaaaaaaaa ttagcctggc gtggtggctg  11640
gcgcctgtag tcccagctac tcaggaagct gaggcaggag aacggcatga acccgggagg  11700
tggagcttgc agtgagccga gatcacgcca ctgcactcca gcctgggcga cagagtgaga  11760
ctccatctca aaaaaaaaaa aaagaaagaa aagaaaactc tggactttgg ggtcaaatga  11820
gtgttacttt cctaatagtg tcctgattgc tgttgtcatg aataacacac attcatgaca  11880
ggaatggctg gaattagggg atcattctgt agcctggaga cagggcacaa ctaatgacat  11940
gtgtaagctc aaatcatggt cttgatctta tgtcttgtac ccagttgagc caactggtca  12000
cagcaatgaa acagtgagt tattggaatg tgtgacctct gctaggacag tcagtgctgg  12060
acactggctt gggtgatgtg agttctagtc caggcactgt ggccaacttg agaggcttgt  12120
gatcttggac aggtgactta agccctctag gctatagtta ttccacctat cagagagcaa  12180
accagcctaa atgatctcca ggggcccagc ctgtgctagg actcagcaag aagcattcac  12240
tggaaatgta ggtcctccta ggttgataca catgaattgc ccatatttga ccatttctaa  12300
cctatataaa tggctatttc atataattcc agagaacata aatggtagtt gtcttagcat  12360
tactaaagta aatgcctatt atgatattct acttaggggt aggataagta tgtataccaa  12420
atatggtttg tttcgatttg atttttgaga cagggtctca ctgtcactgc tgagtgcagt  12480
ggtgtgatca tggcttactg cagccttgac ctcccaggtt caagctatcc tcccacctca  12540
gcctcctgag tagctgggac tataggagtg tgccatcaca tccagctatt tttttatgtt  12600
ttgtagaggt ggtgtctcgc tatgttgtcc aggctgatct cgaactcctg ggttcaagcg  12660
atcctcccac ctcggcctcc cgaagtgctg ggattacagg tgtgaaccac tgtgcctggc  12720
ctccaaatat ggttgatgtc tatcagtcag ttaaacagta attctgggaa taaaaaattg  12780
aaatcaaccc acttataatt ggaatgtctt agcataatgt ccttcaacga agctgctttc  12840
acacactgtg atttgttttt ttcctgtggt catggagcag gcatgggcca ctcggccaca  12900
tctcatgcat ccgtattcaa aagccaaatc ccttttggat cctgtttatt tggcctggcc  12960
acgggtgagc acttagacat ttaatcccta taggcccttt catccctgtg attaagtctt  13020
atcaaaaagc acctcctgac cggcttagca gtggggcctt tgttcacatt agaagggttg  13080
aacaaataat gggcagttgg ggctgcttag ctctaaaagg ctggtgaacg ctgccatgcc  13140
tgcacctgga acaaaccca aatgactcca gtggaattca gcactgaagt ccctcatctc  13200
aaagaccttt tgtggcagag actcttggat gggccttagg ggtcccagga gtcccctgaa  13260
attgaatgta gagcttccta cgtgcatagg tatactttct tggggaaaaa ttaagtcaca  13320
tcattttatt ttacttttcg agggatcttt aacaccgccc ctcccccacc cccaattccc  13380
acccccctta agaataaatt aagaatcact gttctggtag tttccagttg aattccacag  13440
aggaactgtc attcattcac accttcattc aacagatttt tagtaaagat ttgctacgta  13500
cccatcgctg tgtagggtcc cgggattcag agatgagtaa agcaatccct gccttccggg  13560
ggctcaagct ctcctgtcat cgggactcag ttactgaatc tcactaaaca tcctgaaggt  13620
aggagtttat agagtggttt tgaggatcac atgaataagc acacaataca tgggtaattc  13680
aaaaacgaaa acaaggccgg gcacggtggc tcacgcctgt aatcccagca ctttgggagg  13740
```

```
ccaaggtggg cggatcacga ggtcaggaga tcgagaccat cctggctaac atggtgaaac    13800
cccgtctgta ctaaaaatac aaaaaattag ccgggcttcg tggcgggtgc ctgtagaccc    13860
agctactcag gaggctgagg caggagaatg gcgtaaaccc gggaggcaga gcttgcagta    13920
agccgagatc gcgccactgc actccagcct gggcaaaaga gactccatct caaaaaaaaa    13980
aaaaaaaaaa aaaaaaaagg aaaaaaacaa aactaacatg gtcatttgca gaaggggcag    14040
aaaaagggtc tctgcctaga cctggggagg tcagggaaag tactatgat tggtaacaac     14100 cggctgggct tcctacaaga gaaaagact atactcacag agccagaccc catctcaaaa     14160
aaaaaaaaaa aaaaaagtct ggcatggtgg ctcaaacctg taatcccagc accttgggag    14220
gctgaagcag ggggatcact tgagcctagg agtttaacaa catagtgaga cctcatcact    14280 actttttat tttaaaaaag agttaataaa aaataaaatg aaaataaaag ggtaaaagag      14340
ccagtggcaa agtcttgagt ggattaaagc cagctcagct aactttcaca gcagactata    14400
tcattttaaa ggggaaaaag cacatctctg ttacattgct taggaaatat gcttggtata    14460
taccctgggg caatcttatc tatttgttaa gtttccttcc aacccactag cctgtgtggc    14520
caggagaggg agacaaagat cttagagctc tctaaataat agaacttaaa acatcagaca    14580
gagaagagta tattatcttg gtgatggtaa ttctcaatga ggaaaatcct ggggagggat    14640
gttctgtggg agaatgcctg caagtttatt tgtttagtag gtttgattat tcagctgatt    14700
gaaattcctt tcccagatgg ggagatctga ttctcttttc atgaaggaaa gaaaagtcac    14760
atgctaaaga gacgggcatg tctttagaac ggcagcaggc aaacccactg ctgggatcct    14820 ggggcttta ctagtggcta gtcacaggtt tacctcctgc ctgtgctcct tctagctgtg      14880
ttgaaaccca cttgccccat ctatgaaccg tgttcagctc cattttctga gccccttat     14940 cttttttgtcc atacctgttg caactctttg cacgttgcat tgtcattgat ttggtctctc    15000
ccattcaact gagcctctca cagagttcct gtcacctctg cagtttcatc gcctagcata    15060
gtacctggca cttttaattca tgcatcaaat gtccattgag tgccttctat gtgttagaca    15120
tctgctatac cgagctagac aaagttggca gacatgacag ccgagtggaa aagatgagcc    15180
cctaaaccaa taatcacaca cacacacaca cacacacaca cacacaatat atatatatat    15240
atatatatat atatatatgt atgttatata tatgtatgtt atatatatgt atgtatgtat    15300
gtattaaaaa atcttggccg ggagcggtgg ctcacacctg taatctcagc actttgggag    15360
gccgaggcag gtggatcacg aggtcacgag atcgagacca tcctggctaa catggcgaaa    15420
ccccgtctct actaaaaata caaaacatta gccaggcgta gtggcggttg cctgtagtcc    15480
cagctacttg ggaggctgag acaggagaat cacttgaacc tgggaggcag aggttgcagt    15540
gagccaagat cgcgccactg cactccagcc tgggtgacag agcgagactc cgtctcaaaa    15600
aaacaaaaaa ttttttgcctt gcaatcgttt gccttgatgt tatgtctaaa gccccacaat    15660
tctctaaaaa cagagatgta taaaaaagca cacgtatata attctctgaa aacagaatat    15720
aaatgagtca ttgctccatt taactgacat ttgttgagtg cttgttataa atatggcatt    15780
attctagctg gtgtgaggtt accaattttt tttaaacaaa agtaatatga atatatacac    15840
acacatttag tgactgcata tgtgatgtgt gcttttgaag aaaaaggaga tgctgttgga    15900
ggaaaatggt ggtggtggtg ggaagtgatt tagagtagaa ccaggaagt ctcagaagtg      15960 acaactagct ggaacctaaa gaacgaggag gtagcaggtg gaagagaaag gcaaaggcat    16020
tctaggttga gagaatagga tgtgataatg tcccgaggaa agagagctta ctgacaggga    16080
gggaagatgt caggtgtgac cgaactgtag tgagcaaagg gtaactgagg aggtggtcag    16140
```

```
gagcctgctc agccaatggg gtaaatactg ttaaggaatt aggacttgat tttaagaaca    16200
accatcgcat cattttaaaa gcaaacaaat tgcactataa tttccctctt caaaaaggca    16260
cattggctgt gcacggtggc tgacacatgt aatcccagca ctttgggagg ctgaggcggg    16320
tggatcacct gaagtcagga gttcgagacc agcctggcca atgtgttgaa acccgtctc    16380 taccaaaaat acaaaagtta gccaggcgtg gtgacatgtg cctgtaatcc cagctacttg    16440
ggaggctgag gcatgagaat tgcttgaact ggggaggcgg aggtttcagt gagcagagat    16500
cgtgccaccc cactccagcc tggacgacag agcaagattc cgtcttaaga aaaaaaaag    16560 ggcacattga tggctattca aggcagagag gggcacatat aaccccaaag agatggctct    16620 ggggaggggtt gtgttgtatt acattgttgg cattgtatta ccaggtgag agatgctgga    16680 ggctgggcgg tgccagtggt gatgaaaagg agagatggat ttgaaacata ggaataatct    16740
ctcagattgt ttcttggcat cacttaccta aaatgcttct ttcaaatata gatgtacaca    16800 cccctcccctt taggatactt gggacaatgt gccacttaga catagggat ggaacaaatt    16860 ggagagtctg tcaatgcccc ctgcaatctt ttctcttgat gttatctcat aatgccccac    16920
aattctctaa aaacagagaa cataaatgag tcattggtcc attccactga cgtttgttga    16980
gtgcttgtta tgaatgtggc attattctag ctccttgtaag gttaccaatt ttttaaaaaa    17040
caaaagtaat gcaagactgc tgatgaaaat ttggaatatg agaaaagcat aaagaagaaa    17100
atacatatct ttaagcacac cacccactgt taacattctg atctatgtac ttctaatatt    17160
ttctccattt tcatatgtac acatacattt atttacatgc atatataaat atcaaagtgt    17220
atatatataa ttttctctgc catttaaatt tttactgtgt aacaatcatg gattgtaaaa    17280
aaagtgaata aaatgtacgc agtcagttta aagactaaca aaatatgcat taaatcacca    17340
gccaggttaa gaagaaatac tattacttat accctggcat ctccctccca cctttacata    17400
gccaaatcca gaaaagatcc gttttcctaa ccttgttcgc ctatttatt atttaaattg    17460 cagcaggagg gaagcatgtc tactttatcc aatttcacac agacgctgga agacgtcttc    17520
cgaaggattt ttattactta tatggacaat tggcgccaga acacaacagc tgagcaagag    17580
gccctccaag ccaaagttga tgctgagaac ttctactatg tcatcctgta cctcatggtg    17640
atgattggaa tgttctcttt catcatcgtg gccatcctgg tgagcactgt gaaatccaag    17700
agacgggaac actccaatga cccctaccac cagtacattg tagaggactg gcaggaaaag    17760
tacaagagcc aaatcttgaa tctagaagaa tcgaaggcca ccatccatga gaacattggt    17820
gcggctgggt tcaaaatgtc cccctgataa gggagaaagg caccaagcta acatctgacg    17880
tccagacatg aagagatgcc agtgccacga ggcaaatcca aattgtcttt gcttagaaga    17940
aagtgagttc cttgctctct gttgagaatt ttcatggaga ttatgtggtt ggccaataaa    18000
gatagatgac atttcaatct cagtgattta tgcttgcttg ttggagcaat attttgtgct    18060
gaagacctct tttacttttcc gggcaagtga atgtcatttt aatcaatatc aatgatgaaa    18120
ataaagccaa atttgaagta aagtgtctgg gcagtggctg tggggataga aaggagagat    18180
ttacaaatca ttgaatcttc tttctcatga acatcattt gtgtgtgaca aattcaattt    18240
ataaataacc cagatgtatt atgtagaagc tgaggctcaa aagctatcac ttgcttacca    18300
gacggacata ggagcattta tctgtaatat taattcatga gtgtggagtc tgaagagatg    18360
aataaacaaa ccataagatt actttacatt tattgttttc ctggcctttta acctatttag    18420 aagtcttaag acagaacaaa cattttttctt tttcttttttc tttttctttt gagacatggt    18480
```

```
ctctctctgt cacccagcct ggagtgcagt ggtgcaatct cagctcactg cagcctcaac    18540
ctcccgggct caagtgatcc tcccacctca gcctccctag tagctgggac tacaggcacg    18600
tgtgccacca cacccagcta acttttgtat ttttttgtaa aaacagggtc tcactatgtt    18660
gcccaggctg gtctcgaacc tgaacaaaca tttcaaagga caaataatcc ataccagaga    18720
agtagagtat ttaagaagta cccagtataa caaaacatat tttaaaacta acatttaaag    18780
ttttgcagaa aactaatctt aaaaagttct cattatttaa gaaaaaaaaa taaaaagtta    18840
taatgtcgct ttaaaaatgt attcttttaa cttgatttag ttttcctcta tttataatta    18900
gttgttagca tttatgttta agaaactaaa ggatacagaa agggtctaaa ttgctgatgc    18960
cctctgaaga cctagacagg aactacttaa tatcttgcac catgtggtgc aggatatcat    19020
agaatgtcag ggctgatcat tctactgttg cagagacca cttcacttac agatgagaga     19080
agggcagtcc actgagagga gacaatttca ttcactaatt cggtcaggca acattgacct    19140
acttggtcca ctggcctaga ccccaagagt ataaagatga gcaaggccgg gcacagtggc    19200
tcacacctgt aatcctagca ctttgagagg ctgaggtggg cagatcacct gaggtcagga    19260
gttcaagacc agcctggcca acatggtgaa actccatctc tactaaaaat ataaaaatta    19320
accgcgtgtg gtggcaggag cctgtaatcc cagctactgg ggagactgag gcatgagaat    19380
cacttgaacc cggagggggg agattgcagt gagccgagat tgcatcattg cactccagcc    19440
tgagtgacag atgctaaaca tcatagtaca atgtgacaag gtcctaacag agatcaatgc    19500
aaagggaca cagccagcca gcacaaggac aggagggcat gcctaatgca ggtcaaggtc      19560
ttctctctca gagcagctga gagtagcagg tcaatggcag cagagagatg tggggcctca    19620
gcatcccatg gcttcatgcc tcctagttta ccctgttctc ctccccatgc cccagccaag    19680
gcacagcaac gatgggcaag gcctcaagcc tcagggtgct aggacaaaat ttagaaaaag    19740
aggctcttct tcagagaatg cttgtagaac tcgttattcc aatcacaagg tttgtctctt    19800
taaaattaca gagtgagata tgtacaaggt atctacttcc taataacaga tttgcaatta    19860
tgccaactga agcattcagt acagttagag aaaaccatcc atattccaag agcagatgta    19920
ggaagagtgg cttccctcct cagatcagaa acccagaaat gttgtcccac ccagaaacat    19980
ccatctcaga gaggccagag cagccatcag gctttaaatc ccagccctct gctctgcatc    20040
cagacagaaa tccgaggttt ccatcaggtg acaaagaccc tctccttaac caaactgtca    20100
agctcctctg agccctcttc ttgactagag cccaaccatg gcctataaa aactgcagac     20160
tctcagcaca catgatttcg cccaccttg cacactaaga gacataaacg ctagcatagg      20220
ttctaagagc tgaaagctaa agcgcctgcc cgagaaagt gaatgcggcc tgaagaattt      20280
actaattgtt ccaaccaaaa cctggtgaca ggcagatagt cccctgatcc ctctcttaag    20340
gcagttactt tagaaagttt gcaattataa atcctttctc tctcccttga gatgtatatc    20400
ttctaccatt cagaactgta ttgtctctct gaaatgcaaa cattcaaact ctccttgctg    20460
gatgggtgcc ttgctctaac ttactgctcc ccatcacaga cagaagtttg tttctactct    20520
agataggagc caattaacaa acccagatca cactgaccaa cccctcccca ctttctatgc    20580
atttccactt cctggactct gctcaagccc catccccact cagttacctt tgcacaaagg    20640
gaagttgagc tgggcctctt ccctctggca atagctaatg atttcagtca atccttactg    20700
ctttaactgg cttctcttac ctttgacaca ggtaaacaca tggagagcaa aatcgaggtt    20760
tttctggccg ggtgcagtag ctcatgcctg taatcccagc actttgggag gccaaggtgg    20820
gaggatcact tgagctcagg agtttgagac cagcctggcc aacatgatga aaccccatct    20880
```

```
ctactaaaaa tacaaaaatt agctgggtgt ggtggtgggt gcctgtaatc ccagctactt   20940
gggaggctga ggcaggagaa ttgcttgaac ctggaggca gaggttgcag tgaaccgaga    21000
ttgcatcact gcactctagc cttggcgact gagtgagact ccatctcaaa aaaaaaaaa   21060
aaaaaatcg aggttttcct aattaagtac attttattat catcactgaa agtacaggtg   21120
gtaacataga gggttatcag ccaacttcac ttttggggaa tgggagaaat gctgactctc   21180
tccaagcatg ttgggtgtct agtggttgaa gccatttgcc aagattgtca ccctaggatc   21240
cactcccacc aaacctgggc ttttcacttt caacccagca actgaaaatg ccagttcaaa   21300
caacttgctg ttttttttcta ccccacttgc ttttagagtt ccttctgcct gttttattgg  21360
ctccatataa cctgaatacc acttatttct taaagcatag ctcagatgct attttaaaag   21420
gagcccagga tagtggctga tttgatagaa tctatacca gattacccag ggtcaagtcc    21480
cagctctggt acctgcggcc tttaaaacca cgaaaaaatt actttaatct ctgtgtctcc   21540
atttcctcat ttgtgaaatg gttatcatta tagcacgtcc cttacagcct tgttatgaga   21600
cttaggcaat agccactagt gcttagaaca aagctatttt tgtaactttc tccaggaaca   21660
cttcccttaa cagaaccaac ccctccaccc ctcagtttgt tcttccctcc acaccctcta   21720
acattctaac ataaccacaa agagtcctga tgggatttgg agttacactg cctgggttcg   21780
aatctcaatt ccgccactgc cattcgcgcg ttttctattg ccagccacct tactctccc    21840
tggcctcagt ttcctcatcc ttagaagggg agcagagcac atggtggtaa ctccctgcac   21900
attcctctct ttccttgtat tgggtgccca gtttgtgccc tcacatggcg ctagcactga   21960
gtgggctcaa actctgtacg cgtttactaa gcatattgac tgaagaaatc tggaaaccta   22020
gtaccgcggc accatatcgt taccccaaag gaaaatgcat gcacgctgtc agagatgacg   22080
aacactgcgt ctggaaactt cttaagggca cccacgtgtc ctcagctgca gacagcagcg   22140
aggagacacc cagggaattc gagacagcgg aaggcggaag ggtcccgcaa caacccaccc   22200
tccagctcag gtgagttcag agtgagaacg caccgccagg cttggacaaa ggcacccggc   22260
ctacacccca gcggctcccc gccgggggcct acgtggactt cagcctccag ccacagggac   22320
aagagctgct ggccagggct gcccgcctgg gctcactgcg cctgcgcagt gagcagcgcg   22380
ccccaggtct tctgcccggg cccactgcgc ctgcgcacgg agtagtgcac tctcgtcggc   22440
ggcaccggcc cactgcgcct gagcacgtag cggtgcattt cgggacctgt agttttcccc   22500
ggcaggacgg tagaagtcgt ggtttgtgcg cggccaggcg ctggagcctc cgctgccggg   22560
agcagtaagt gtgtgacgtc ggggtagaag ggagtgaccc aaattccaaa agctctttgg   22620
gatgctgcga tgtcgcggcc ggcccgcgc tcgggttttc cctcctagac aaaagtctgc   22680
cggctcccgg tcgcgccggg tcggggatcc ggaaggtgaa ggccgccagg ccccacctgc   22740
ggggcgcccc tgctggacct ggccgtcggg cgccgtcaac ccgttgagca gcgtgttccg   22800
gctggcacgt ggcccgggcg gggcccagga ttggttcaag cctacggtgt tggtccccgg   22860
agagtctagg gagacaagca atccctggga atggtggggg aagcgatgac agccctggt   22920
cctcatccgc agctctgggg gaagtcgggg ggtggggagg gcgggtgttg ctccctgagt   22980
gttgggggaa gggtatgggg agaggaccct gaactagccc ccaggttacc caggaggagc   23040
tgaggcccag agaggttcag cgactcgccc agggttgcac agcgagcaca ggcaccgacg   23100
tcgccctccg aggcctgggc ttccagcagg gagagacccg gacacctgtc atcgcttctc   23160
ggtggatccc tgaaatgttg agttgtggag tctgggcagc tgagatcggg cagggctggt  23220
```

```
ttcttgtagg cccaggcttc cgtgtagagg gccaagtgat gcccaaggtt caccetggcag    23280 cccectctct ggacctaccc ctccttatga ttgggtgaag ggttgggtga aaagggtaga    23340
ggccgggaat gagaacagct tcagaaagct cagacaaagg gcgcagcatg attcgtggct    23400
ggaaggagac agcaagcgat agactgatcc ttgaatttgt tagtgtgcca agaagaaaaa    23460
gtattaatag attgtggacg acacattatc catattgctt tagttggtct aaccaaaata    23520
agcgaatagc tttttgttt ctaagagaaa cctgacaaag gaagacaggg tatttttgcg    23580
gtgaaggaaa tagaaatatt tggagttgta tctaagccac ttgttacttt tgtgttttaa    23640
gctaagatca tggataggtc cagggaaagt taaaaatttc ccgcacttct tagattttat    23700 gccectcaaa aacatcccca ccttgttggc ttttgcagtt caaccttcag ataccagctc    23760
cctcgtttct aatattgcat taggtgtaca tatggcagca gagcaaatag cttactgata    23820
cttttagctt ttttcttctc atttgcaaaa gactctatga aaatggctgg cttgggcatg    23880
taattgaagg gaggtgggga aaagtggtaa ttcagaggcg gtgggtggga atgagcaaag    23940
catgtcagtg tggttcaccc tcttgactcc cacctcacca cagcccttct gctacaattg    24000
cagattgact ctaaatatgt ttcttteccta aagagcttga attttatcac tccaggtatg    24060
aagttgaggc agctgccagt atattttggc agtcaggttc tgtgatatca gagaggatgg    24120
tgaattgtga attccagagt tgcagaattg ttctttagat tctgattttt taaatgacag    24180
cactttggtt tggagggtta atgacttacc ccaggtcata tgccacacca tgggtaacac    24240
caagagtaga gctcagatct ccagttgtcc tggtcctcag gctactgatc tttattccct    24300
gccctgctat cttggaatga ctgcatttg ccctggatgt cgctagcctg tatccttcag    24360
gttggcatgt ccagtcatgg aaggagagag atttaacata caacaatgg ctgacattca    24420 gtgctttctg tgtgctggcc atggtgctta gtgtttacag tctaatctgc aagagaattt    24480
acagatgggc aagttgaggc tgagagaggc caagtaactt gtccaaggtc acactgctag    24540
tgaacatagc acatgttttc cagagggcca gaccactgga tgtttttcca ttcatttcct    24600
cctgtaggat cgttggacct atttctcgtt cttgactttg ggaatcaata ttctacgtac    24660
atcaattcac tgggtatgca gttttgcctc tgaaaatttt gagggaacag ccagactcat    24720
ctactgtatt tgtatacaac tcaattaaag caggaattgt aaaaataaaa tttgtaagat    24780
ctttaacatt ttaatataca acattagcta atcactaaga ttactagaga tactcaaagt    24840
gaaaattgta gcaacaggtt ataacatgtt aggagcatat ttctttaggg cagtcagaat    24900
ctgctgcttc ttaaagacaa gtgggccatt tacacatgaa ggtaacaagc acattcagcc    24960
accatcatta tagttaaaca gatctatgat ttaaattcct atcgctacct tatctgactt    25020
tgaaaaagtc atggggaaaa cttggctacc ttgtgccaac tgctagcttg ttttcaagat    25080
attataatct tgaatagatg gaggatgaac ttttttatact tagatagctt tgtaattgaa    25140
agtttgtata aaaacatctt gcctgaagtt catcttatcc ccattctatc taaaggcctt    25200
tgaaattttc agccactttt cttaattatg acggtaagta catttcaaga gaagtgtttc    25260
cctgactttt gaatgcaaag ctctctgcct gtgtcaggat ggtgccgagg ttaaagccct    25320
ggagccagac tggatgggtt cgaatcccag gcccacctgc gagaccctcg atgtgttact    25380 taaatttat ttcctcctct ctaaagtgga ggcagtaagc tgttttatgg ggtagttgtg    25440
agggctaaat gtcttaactc atctaagcac tttagccact ttttccatc tgacacaaaa    25500 aagttaagct atgattattg tgctataaag cattggattt cagaagaagt aggggcacta    25560
aacaccatct gcttgacacc tttcttcact tacagatggg actgaagctc tagagggaag    25620
```

```
tcacttacca gagggtgtag gttcttcatc cagagctgaa gtcttcttgg gggtatgtgt    25680
catattctaa gagtagggac ctacaaggcc ttggagcgaa tcccaaggct cgggctgcca    25740
gccctgcctt ctcatttcca tatgccatgg tgtggcatat gacctggggt aatatcctct    25800
gaaccaaagt gctgtcattt aaaaaatcag aatctaaaga acaattctgc aactctggaa    25860
ttcacaattc accatcctct ctgatatcac ttccttccct accttctact aggtctccct    25920
caagctttag agaaaattyt gcctctgaat tattgcatct gacaattttt ctgccctgtc    25980
acttattccc ttgctcccag ataatcttcg aaaaaccaag atgagtttaa ttaacactca    26040
gaggacttga caaagacact cactcccaaa ccagcttgcg tttaggtctg gaggcaggtg    26100
gagggacaga ttttagactt gggcccttag gttcacagat gaatgggatg ggagcccatg    26160 tccctcaga agcggcgctg tgctgctggc ggctacagac agctggtgag gagagctttc    26220
tgcttagcaa gggccaggcc cgtctgggcc ctcgcccagc ccatccactt cccaccagtc    26280
tctcaatcgc cttgtcagga cacagcccac ctctctgtgg agctcacttt ctgttcacat    26340
tccctctctc catcaaagag acatctttct aaggtggtct gccctaggaa ctccaaattg    26400
acctgcttct ttcttcctgc ccagatcaga ccttccagct gcctctcatg tacttgtctg    26460
ttggggcctt gtgttgatca ggagtgaatt cacagtctac catgaattgg aaggtgagta    26520
tcgttttaaa tatttatggc ttggggtttt ttcttcctcc tgattgtgaa aattcagaat    26580
aacagttcta caccagtagc ttgattaaaa agaaaaagta ggtgaaagca taatatttat    26640
gtttcatttt aagttaaaac ataaatgtac atttattcgc tggacttctg gaagaaggcc    26700 aggcctttc ttcgagtgtg cattcactaa cttcaaatct tcctcacttt tcttacaaaa    26760
actataccct taaagcttta cctgcaattt tgcattgtgc tttctttttt tacacatttt    26820
ttttgtagag atagggctcc actatgttgc ccaggctggt cttgaactcc tgggctcaag    26880
cagtcctcct gcctgagcct cccaaagtgt cgggattaca agaatgaacc actgtgctca    26940
ggccgttttg gttcctttaa agtagatgca gtggactgaa tgtttgtgtt tccccaagtt    27000
catatgttgc aaccgtagtg cccagtgtga tgatatttgg agttggagct tgtaagaggt    27060
aattaggtga tgaggctgga gccctaatgt ttggaatagt gagcttatta aaagggctcc    27120
agggagctct cttaccctct ttctgccatg ttgggggtac aacaagaagc cagccgtcag    27180
cagcctggaa gaggactccg ctagaacccc cctgtactgc gccctgatcc tcagctttca    27240
gcctttcgaa ctgtgacaag tacctcttta ataagtcacc cagtctgtgg tcctttgttc    27300
taggagctga attgactaag acagtggatt aagatcttat gagcagtgca tacacaaaat    27360 cttttccagtg tttcatactc tttcctaatc ttttacagtt gacttgccaa cagcattttt    27420
tttccaacgc aaacttgagt cttcaaagt attcaactta gttttcataa aaactttgc     27480 tttacacagt catatttcac aagcgtaatg tttaaataag ttatgaaaca tagtatcaag    27540
tacaacttaa ataaactgct tggcgagtaa acacacctga cccctgtgaa acattagatt    27600
cagctggtgg gagcagaagt tcaagggcag ccagagagta ggtcagcaat caggttccac    27660
cgagggaaag gagaatgtca tcttaagtcc cggaagtcaa taaggtgagg tggaggttgt    27720
ttaagagagc agccactaaa atatattata gtcactttgc aaagtctaat atcaagcaaa    27780
aatcatacat tgtctcacca tctagaaatg gctactatta acaatctcgg tatattcatc    27840
tttttctgta tatatgtgtg gcgtgttttc atgcatagga tcttatttta cgtgtttttt    27900
caattattat aagcatttc ttcaaaacat ccagtggttt ctattgcaa ggagaaactg      27960
```

```
gaaaggtctg gaagcaggat cagggagcca ggaaggtagc tttcccatct tccccagctg   28020
tgtggggtga ggggctcggc aggccctgca ggagggctga gggcccagga acttgtgtaa   28080
gttaaagatg gcagagtgag tgagctgtga agggtgggaa gatatagaac agtttgttta   28140
gcatgccttg aggatcagag ctcacagtgg aaaggttggg aaggaaagaa gaggcagtga   28200
gaggatggag aggggaagga gcggaaagca gtgtggggtg aggtttaggg aggtcattcg   28260
cccactgcag tggctaagtc agtagaggag agaggcagta actggtacta agggccaggg   28320
ttcaaagcat taaacctcat gcctcaaggt ggtgtttctc actcctgagc actagttaag   28380
gcaaggattt cgagccccac tcccagagtt tctgattggg tagatctggc tggggcctga   28440
gaatttgcac ttcttataag ttccaggcgg tgctggtgca cactggtcga aggcaatgcg   28500
tgggaagttt tcctctttaa ttgtagagtg acaccaaccc atgtgaccac tcgggccagt   28560
cttgcttgtg acagttttt ctgccatcag gaacaaagtc tgcccaaacc ttcccagctt   28620
ctgcaccagg gaagtggcta ccagggagca gcttcgtgtt taaacacagc cccatctcgt   28680
gtagtgttag aaaggaatgg ccgcaggccg ggcgtggtgg ctcatgcctg taatcccagc   28740
actttgggag gccgaggcag gcagatcact ttgagctcag gagtttgaga ccagcctgga   28800
caatgtggcg aaaccccgtc tctacaaaaa aatacaaaga ttagctgggc atggagatgc   28860
gtacgtgtag tccagctac tcgggaagct gaggctggaa aattgcttga gcctgggaag   28920
tggaggttgc agtgagccga gatcatgccc ctgcactcca gcctgggcga cagagtgaga   28980
ccctgtctca aagaaaaaa aaagaaaga cagtcatggc cctgattgca gagagctgca   29040
gaaggtggaa ggttcagtag cccccagtgc gtctggtggc cttccccctc tggctcagtg   29100
ggccatggcc rgcagcgaca gtcaacagtg ctacctgtgc gttagcaaca agtatggcct   29160
cattatttaa aaacttagtt attcccattt cacagatatt ggggttttgt ttttaaaaat   29220
tgatgtagat ctaggccagg catggtggct caccctgta atcctagcac tttgggaggc   29280
tgaggtgggc agatcacatg aacccaggag ttcagcacca gcctgggcaa catagtggga   29340
ccccagctct acaaaaaatc agaaaaaatt agctgggcgt ggtgtcatgt gtctgtagtc   29400
ccgtctactc gggaggctga ggtgggagga ttgcttgagc ctgggaggtc agggctgtgg   29460
gaagccgtga tcatgccact gtactccagc ctagttggag tctcaaaaaa atattcatat   29520
agatccagtc caccctrgca gcattcattt tcctccctga aggtctgtat gtttcaagag   29580
atgtaagggg tttgttaaaa ggaaattgga ggaagggtt cataccactg aaggttagtg   29640
cctaagagag gggcaggaag ggggccctgg agctcttcgc tttaccctgt gaatgttctt   29700
gacctctgct gcccttgtgc tgcgtccttc tcagtccaca cttctgcctc ttgccgtgcg   29760
tctccactgc ctgtaaaaca aagtgaacac tgaagcctcc cactagggtc cattggctga   29820
tgcgtttcca tttccatggg ttttctaact tctggatgag agagtacatt cctgcaattg   29880
ctaaagctaa gtttcctatc tggattgtag acagctatgg gcagtaacat gggctttgtt   29940
atrttagtaa tagggccccg gccaggtgca gtggctcaca cctgtaatcc tagcactttg   30000
ggaggccgag gtggcggat cacgaggtcg ggagttggag accagccggc caacatggtg   30060
aaaccctgtc tctactaaaa atacaaaaaa ttagctgggc atgatgccgc atgcctgtaa   30120
tcccagctac ttgggaggct gaggcaggag aattgcttga acccaggagg tggaggttgc   30180
agtgagctga gatggtgcca ttgcactcca gcctgggtga cagagcaaga ctctgtctcg   30240
agaaaaataa taataataat agggccccat aggtttattc agagagactg agaaagctgg   30300
aagagattag cttttcccag tgtgagtcat tgcctcaggt agcctggaaa atcctagcaa   30360
```

-continued

```
acaaaaagaa gtttatacaa caacattctt ttcatagctg gtttgtatgc atggcgtcaa    30420
accttcacct ctaaaatgtg aaccttcaag aaaacaggat ttcagggttt actggaggga    30480
ggggattagc ctaggtctga gggaagaaga acctggaaat gaagtcagtg tttaaagctc    30540
cttatattta ccagagtaaa aagttgaaaa gtttcacttt tggaactttt tagtcttttg    30600
tactgatgcc agagtgatct ttctgaagtg tatgtgttgt gcttattctt tactgttaaa    30660
acgatatcat ggttgaaaac tattagctaa ttactgagtg ttcttgtgtt cttactgttt    30720
tagtaaaatt aaaacgattt aagtatttgc gtccctgcct cctcccatga ttttcattgt    30780
atttctatca tatcatgcta tatccttctg caaatatcca tacataacca gttaaatgat    30840
ttcagaggta gcgagtctag ttgcctctgg aaaattcagt agccaagcca tagtgtattt    30900
gcatattgta aatgtgaagt ggatgggtgt gaggaatgaa tcatatatag tacaggacag    30960
cgtgatgcta cagagttggg ctttggagca tttggagctg ggtcagcccct gcctcgctga    31020 ctgctggcct ccccgcctct gcattttctc ggctccaccg cagtcagggc gagccatctg    31080
ctcatggagg tggctaaggg cagaagggaa agccgcataa ggcactttgc atgccgtgag    31140
ttcccagtct acagcagctg atgctacagc ttctaagcgt gaaatccaca tctagttctg    31200
agtcataaag agtttygata caatcatagg aacattcatc tacatacact gtgatttcat    31260
gaatttcagt ttgttgaaaa tcaggcatca gtggaaggga gactggcccc ggggttagaa    31320
tgtccttcca actggctcct catgagggag ctgtgggacc ttcaacctct caacctccag    31380
gagctcttct ttccttgctc atataaccag ggggttgagt aggtcccctt gaaagttatt    31440
tccagccccc cggttctgtg agcatattgt acacactaac taggttcaga tcaacttcgg    31500
ttagactatt agagggaggt gcacatgtat cccccacagt ggaatctcat tggtatttca    31560
tataataagt gattgacaga aataaggatt tcattgggat aaaatcctac ctggtcctct    31620
aaaataatga ttgctcaacc agagcatacc ttttcactat ttgggaggga attttttaatc    31680 acacaaaaag cacatacata tcattcaggt catgctaacc atgtgtatgg aactaatatt    31740
gctttgaagt actatttgca atatatagaa tttcacacaa aaaacctact agtgcaaaga    31800
gtgagtaatt caaatgcata gtgtttccct agactttatt ttagtgaatg gggttgcaag    31860
agcagttagt aagtagccat gttttaatgt tttgagttct gtcgtgtttt attttaccag    31920
caagtgccag tgctagtgag tctctagaaa caagagaaaa tcccagagta ctaaagctgc    31980
agtttccaga agcaaggtct gattcaccct tactttgtag atgaagggc aggagctcag    32040 aaagaaagga gctcattgcc tgacccaggt cacacggtca gtcggtggta aagtagagct    32100
ctgacccagg cctccgggct ccagctcctt tcactggatc tggctgctgc ctcagaagca    32160
agggcctggg tgatcagcag gttgcacggt tgagctgtga gagaccagag tccccacgcc    32220
tgtggatgac cggtggtccc ctccatgaag ccagccgcaa gcaagcagca aagagcagag    32280
ctgtaacttg actgttggcc ccatggggat agagacctttt tctgcttggt ctccagtgta    32340
gctccagccc cctatcctcg tgcctgttgc agaataggtg ctaagtaaat atttgttgac    32400
tgaaggatca taaaagaaac ctcccatatc ggtgatggaa catttagtta gcatggcttc    32460
tttcttcttg aaggttcttg agcaygtgcc cctgctgctg tatatcttgg cagcaaaaac    32520
attaattctc tgcctgacat ttgctggggt gaaaatgtat caaagaaaaa ggttggaggc    32580
aaaacaacaa aaactggagg ctgaaaggaa gaagcaatca gagaaaaaag ataactgaag    32640
gtgagtccac agtacccaac cttgcaaatg ggagctggcc agtgggttgg ggtgaccaat    32700
```

```
caatgaacaa gagaggtctg agacctccct gtccgtcggg tctgaagggc tgcgtggggg   32760
catgtggcct cacctgttct ctaaggtaga actgctccat aaagggccag gtgtgcagat   32820
cctggtcctg ggatgtgagt gctgctgagc caaggtgcac ggagcattag ttcatccttc   32880
ttgaaacctg cggtggcaat ggttcttgac aggtattggg ttaagaattg aggactcagt   32940
gacagctgtg gaccttcttc ccagagaagc acacatactg aaaccatctg catttgtgtg   33000
tggggagaag tttgcagatg tggggagtca caggtcattt gaaattccaa gattaagaaa   33060
ccctgttacc tttaagataa agtctgactc catggtatga caaataaatc ccttcccagt   33120
ctggtcttaa cccagacctc atttgccaca tgtgcccact ccccatcccc ctgcaggcca   33180
ttcctcagcc accatggcct ttggccttgc ttattaggtt cttcccaagg acctcctcac   33240
caggcctgag ggtacactca tcgttgtcac ccagtgccta tcacagtgca cactggtggg   33300
cttagaacac acttggggag ttacaataca tcaaggcacc agaaagttcc tgttaagccc   33360
ctgttacaga tttaacacat gacaattcac agttaccttg attccagtgt gttgatgcag   33420
tttcttcact ttgcaggttg agttctgtac tttaaaaatc aggggattca gccaggtgtg   33480
gtgactcatg cctgtaatcc cagtgctttg ggaggcaaag gtgggaggat cacttgagcc   33540
aatgagttca agaccagcct gggcaacata gtgaaaccct gtctctacaa aaattaaaaa   33600 aaaaaacaa aaaaaaccaa aaaaaaaaac caaaaaaaaa cttagctgca cacttactgg   33660
gtgtgtagtc ccaactactc aggagactga ggtggaggat tgcttgaggc ccagaagttc   33720
aaggctgcag tgaggcatga tcacaccact gcactccagc ctgagtgaca gagcgagacc   33780
ctgtctaaaa aaaaaaaagg attcaaatat ggtggcggtg gggttctaga tctgtggttc   33840
ccaaacctag ctaatgatca gaattgccca ggtgtttgtt taaatgaaga ttcccagctt   33900
cagcccagag agattccata atggctctgg ttaggtttgg gtgttggttt tgttgttgt   33960 ttttaagata ggggatccta ctctgtcatc taggctagag cggtgcagtg gcacaatctc   34020
ggctcactgc agcctcagcc tcctgggctc aagcagtcct cccaactcag cctcccgagt   34080
aggtaggact acaggagcac gccaccacac ccggctaggt ttttaaaaca atttttagta   34140 gagaagggt cttgctgtgt tgcccaggct ggtcttgtac tcctgggctc aagcgatact   34200
ttcgcctcag cctcctgaag tgctgaggtt acaggtgtga gccactgtgc ccagcctctg   34260
ttcttttgaa aacccattag ataatcctta ggttgtcttc tcagcaacag gtcattgtag   34320
gaaccactgg gctaggtggc ctcccaaacc cagcccactc tgagattcca tgctgaattc   34380
ccttgcagtg ccgtcaggct tgttgaggct aaagacctac tgatgaggaa tagtagcaac   34440
acctactaag tggttattct gtgctgggga cttttgctaag cattcatgca caactgtgtt   34500
attcagccct gatgactctg tgaggcatgt tcagattgaa agaatggctc tctctacatg   34560
gtgaagaaca gagtcagaaa ttgatcccag gtcaaatgca ttcgatcagc atggccaagc   34620
ccaagctgtg ctaccttcct gaatacaggc aagtgagctc gtagggatgc ttcactctgt   34680
tactcaccac ttccggcagc tgcccactcg ctggtcccca gtgaactgta ggcttttgct   34740
agatagaaga agttactttc tttctttctt tctttctttc ttttttttt tttttttaag   34800 gtgtttgatt gactgaaatt taggagtagg cattacgatg gggaggagag aaattaaaaa   34860
gggtgaggga aggcagttta aattaaaatg ttgctgattg aatttatatt cctgacaatc   34920
ccattttgtg tgctaaactg atcaaaggaa gaaagatga gatggaagat cataaaggct   34980
ttgttcctcc cacaaacatc agcagagacc tgcatttaag tcaggcctgg atggcttaga   35040
agcaactcag ggagttggtc ttcctctcta ggctggcagc ttcttaaaga ctagagactt   35100
```

```
gcttcaaaca aaaagcgttt tcaggccggg cgcggtggct cacgcctgta atcccagcac   35160
tttgggaggc cgaggcgggt ggatcacttg aggtcaggag ttcaaggcca gcctggccaa   35220
catggcgaaa ccccatctct actaaaaata caaaacttag ctgggcgtgg tggcacgtgc   35280
cagtaatccc agttacttgg gaggccgagg cacgagaatc acttgaacct gggaaacaga   35340
ggttgcagtg agctgagatt gtgccactgc actccaggct gggtgacaga gtgagactgt   35400
ttcaaaaaat aaataaataa ataaaagggg ggtggggtgt ttcagatgga agggaaactg   35460
atgctaaaaa tacattggtt aataaataga cttgagtgat agacttgagt ggtgtccgct   35520
tgttaagttt aaatggctga gcatacgtct ttatgctgag cagtaaacat cgggtatact   35580
cttatcaaac atttcctact catcccttg gtattcccctt ctagattctg ccatgtaaat   35640
gtcagcttga gtggactcca gctgagaaga aagagaagaa agacttaatt attgaataat   35700
ttgtcagagg ataaactccc aacctagacc tttcacttaa aatagtgtga atttgtatat   35760 gttttttaaaa gaaccagtac tggccgggta tgctggcttt tacctgaaat cccagcactt   35820
tgggaggccg aggcgagtgg atcgcctgag atcgggagtt tgagaccagc ctggccaaca   35880
tggtaaaatc ctgtctctac taaaaatata aaaattagcc aggtgtagtg gcgcgcgtct   35940
gtaatcccag ctactcggga ggctgaggca ggagaattgc ttgaatccgg gaggtggagg   36000
ttgcagtgag cctaggtcgt gccactgccc tccagcctgg gtgacagagc gactgcgtct   36060
ccaaaaaaaa aaaggtaaaa ttaaaattaa aaaaataat aataaccagt attttgttta   36120
ctaaaataaa atgcctttgt aaaaaagga gtcgtggcct ttggaataag tcaaattgtg   36180
tatctctttc tctttctctt acacagcacc ctctacccccg tgttgtaaag cgggggggttt   36240 tgtaaactta cacctccccc accatctcaa gctgggggt cccaggtgag aggcttccat   36300
agaggacaag gtggtgcaga acatctgct gtgggagtgg ggtccccagc actgggtgct   36360
tcggccagct acccccgacc ccaggccccc tcataggctg ccctcccata ccctcctttc   36420
tcgtcttttc ctcctacagg tgctacaccc ctgtgagagt gttttggagt gttttcattg   36480
ttagggtgga gggaggctgt gtgtgtccag gaaaggtgac tcctgtgtta accatgaggg   36540
tcctcgcagg gaggaatcgt tgggagccct agggtgtgtt ttgtcctctc ctcacctgtt   36600
tgctccttgg gatttgctga tgagaaatga agggtagggc accctagtag ccactggaac   36660
caagggcagg gaggatggga agatgttttta ctcagcacct aacacacgca gatccctgtg   36720
acaagagctc atgctctccc acttcttcgc aagaccccag agtggatggg gagtgaggtg   36780
gcagcagctg gcactggaag cagtgcggag tgtttggtct ggttgctgat ggctgcatgg   36840
gaaacttgca ggagtgtgtg ttagtaaacg tctccccgtc ctggcccagt ttgtgtcgaa   36900
catgcgtttt ccatgtgggg agtcagggga gttccatctt aaattgcact gtgcttgctg   36960
gatgctcttc agnacaattt aggaagcagg aaagaattta caaagttctg aggacagaca   37020
gaccctgctc ctacaagctg cagtgctcac catagtcaaa gtggactttc acgtaagccc   37080
agacctcatt ctctctgaag gaggccgctc cagcctttgc caggagccct ggtgacttta   37140
ttctgcctaa tcctgctgcg gcctggggtc ctgttagaac gtgaatggaa gaccacagca   37200
gaggtgggat gcccttggat ttctgccatc cccacgcttt cgtgwcatgc tcagatgggg   37260
cctagaactg accctgggcc gtggcctacc atcctccctt tgtcagggcc tccttgcacc   37320
ctggcaggtt accccacccca ccctggccca tgttcctgcc ccaggggcct ggcctctctg   37380
ctgcccaccc tgcaggtgta gggtatcacc tgctcctgcc ttgcctggca tcagacctgc   37440
```

```
taccttggca ccacttcctc cctcatgccc acccgcctgt gtgcctcata agtccaaggc    37500
gggggatctg ctgaccagta gacactcatg tgctaaacac aagcgctttt ctaggctttg    37560
ggatttaaag ctacactttg gaatttgtgg aagatctggc catcttggaa aattaggtag    37620
aaggtgacat aaggactgga ctaaaccact gatcatccca acagtgcccg tggcttttct    37680
gttttttgtt tttgcttttg ttttttttaga gatgaggacg tgctgtgtcc ctcaggttgg    37740
agtgcaatgg tacaatcata gcttattgca gccttgaact cctgggctca agcgatcttc    37800
ccacctcagc ctcccgagta gctgggacta ggccctgcta atttatttat cttttgttta    37860
gagacaaggg tcacgctgta ctgcccaggc tgggtgtagg ttttttctga agagcatttg    37920
ggagttttgt ttttgcttgg ttacttttcc tatgcaccct tctaccacta gggggagatg    37980
attaatcact aattgaaggg attttgttcg ttttttatgt tttgggtttt tttgtttgtt    38040
tgtttgtttg tttcaataaa gaaagagttt aattgcagta aggcaggccg cgcaggagat    38100
ggcgttctta ttcaaatcgg tctctctgaa ggctcagagg ttaggggttt tcaaggcgga    38160
gttcttgcta tcattccact ccttaggtac atgaagttgg tagatgtgta gtttgatgtt    38220
aaattattgg gtggatgcat gcaccgctgg ttgtagagac tggtaaagcc cactagcagg    38280
accccacctg gaccaaagca atccctcaac ccgctggrcc atgaccgaga acaaacacaa    38340
aggacctgaa atgcgttgtg aaggccagaa gccgacatcc acattctcca cccacggaga    38400
gccccagagt ccctcatgca catcctgctt gatctattac acacattcac acattcgcaa    38460
cacatttgtt tggttttcaa gcttacaaca tattagaaac agaaaggaag aaaggctgtc    38520
agcagcagaa atacctttga gcaagaggga cggtctttga gaagcagact tgagaactca    38580
ccgtgtgctc ttcatgcgcc agacactgcg gcagccacag cgtcccacat gggatgccac    38640
acgtgatgat gttatgttca tggtgatgac ctcaggcgtg aagaagaggt tcagccgttt    38700
cacacagtct gtttaacaag cacatacata acacagacat acgtgaggaa tctcagaaac    38760
caaataattc aaacaaagag tctgggattc tttcaaaagc gttgcctctg cccaagcttt    38820
cttcaaattc tgtctatagg gaaacgtagc tgtcaatgtc tcattcccga agacttccag    38880
atgcctggat ctttagagtt ctccacctca ccccgagttg attacacaaa tgttcctggg    38940
gctttgctta gtgccctgct ctgtgccagg ccccacaggc agagatggca gggacccagg    39000
cctgacgttg gagagctcct gacccactgc cggaaacaca cgcaccatca caccatgagg    39060 gagctcccc atgcagatct catctgtgtc agagtgaagc cagaggatgg acggtggaga    39120
gtctagaagg agaagagaaa ggaggatgag ttctcataca tgagcaagca ggagaggcca    39180
tttaaaatgc acactctggc ctggtgcagt ggctcatgcc tgtaatccta gtggaggccg    39240
agacaggagg atcacctgag gtcaggagtt tgagaccagc ctggccaaca tggtgaaacc    39300
ctgtctctac taaagaaaa ccaaaaatta gctgggcgtg gtggtgcatg cctgtaatcc    39360
cagctcctcc ggaggctgag gcaggagaat tgcttgaacc cggagggtgg aggttgcagt    39420
gagcagacat cgcaccactg cactccagcc tgggtaaaag agtgagactc tgtgtcaaaa    39480
aaaaaaaaaa aaccaaccta aaaataaaa ataaaaataa aatgcagact cctgggctgg    39540
attccaggtc cactgcatca gaacctgcag gagaaggacc aggaatttgt gatacgaaca    39600
tccccaggca attcttgacc ctcctttga gacctacact gtagaagatg ggcagaggga    39660
gaggcagcag gagcccaacc tgggaaggag ccatcgggaa aggtgggagg agggcagga    39720 gacagcgcac gcgaggcagc aaatccttca gcccttactc cccaagagct cacagctgcc    39780
tccacagagg gtaacggtat cattatcccc ttttcgcaga taaggaaact gaggcagaga    39840
```

```
ggccctgcct aaggtccccc agctggtggg aggcagagac aggaaccagc cctcatggtc    39900
tcactgtgag actggacttt tcacagctgt gcggtcgagt ctgagccaag taaagtaaag    39960 cgagttttg tacttcgaag tctgggacat aaaatcttca agacgtcagc atcagtgaca    40020
cgatggtgac agaggccagc attgcttgtt gtatctttt ccatcctgtt cctatctaca    40080
cttccattct tctgttcatt ctgcttgcat ttcccaccca gatggctttc acggacacac    40140
acacacacac acacaccgca cacacacaca tcactcacag acgcaccctg tgcccaatgt    40200
caaaagacaa aactgcaaca cgtttagtca tagacctcat tgtcttttat tcttgattca    40260
tgaatggggc agcctcctt ctataaaaca gagcaagagc tcccaccgga caattgcaga    40320
acagtgggct ttgtaaggtg gggacaagga acagaacaa tagaaaagaa gctgatgggt    40380
taacatcagg ttacttcagg acctcctaat cacgctgact caggtagacc agaagctcct    40440
gttttcagga aaactaatc tgtttgggga catacctgct tccttattaa agttttgggt    40500
tgattatatg gctcttagca tgactgactc catttggtt tggtttgatc tggtctgttg    40560
gggcctagtg caggatctca gtccaaaaca atagcctccc ataatttttg tttaatgctg    40620
ggtcagcggt aggcttggtc cacttgcgct tctgcctggg tgggccttcc tcttttcctc    40680
cttttctctc tgtggtgaaa tccccattct tctttctgtc ctccacttca gtttcacctc    40740
ttcctgcaac cctgcccaca gctcttcagc gccaggccct ggactcagct ctcactacgc    40800
aaacctccaa catctcactg agtgggaggt ggccccacc tccacaccag acctggacct    40860
tgagggtcca ggcttgtttt ccttggtact cctggccctg acgcacccag ccaggcacac    40920
agaaggtgct ccagtatttg atgagtgaat gactggtagc accagaggaa agggagcagg    40980
gagtatggcc aagaccatta gctgccttcc tcagtgttcc ttctcccctt ctccctagta    41040 atagaacct gacttttacc tggccgtatg gtcactcaaa ataaaggact acatttccca    41100
ccttctctcg caaccaagcc tggccaatca ggtttaagtg gaagtgtagt gtgggacttc    41160
ctggaaggat cttaaaagg acaggatgg gcccctcttc ctcccttct cctttttggc    41220 tgcctggaat actaatgcaa tcgcttgttc cgcagccact ttggactaag aggtgagttt    41280
gagacctgaa ccaaatctag gacaatggag taaaagata ggatcttggg ctctcagtga    41340
ccatggatcc atcatttcac ccctgaactg acaccttgac acttcttatt tttggtggtg    41400
gtggtggggt agcttctatt ttgttggcat ctctgtggtc tattcatagt tcacctgttt    41460
tagctgacac atggagccag ttagagatgg gcgcaagggc ttcctgatat gaagacttgg    41520
attctggtcc tgaccctcct gttactactg ttacgtacgt ggctaggtga gtcggtcacc    41580
accctagcct ggcctttgta aaatgagctc aatgatcact gccctcccta ctgtacagtg    41640
tttgtctgaa ctgaatgagg tcaagcatgt aaagatggtt tgcatgtggc aggacaatca    41700
caaatggaag gagtgtatac tacctcggtg ggcaactcag ccaccagttg gccaggcagg    41760
ggctccatcc aacccaattg gattgagcca atggccaacg aaccccattt gctaatttac    41820
ctcttaggtc cttgtagggg cagcaccatt tcctaatgca ccccccactt gaaagccacc    41880
ttgatccgtg ggagggagag gggctgtggg tattagtgat ggggaaggcc agagaggctg    41940
ggatgttcca tcagccaacc actcagaagg agaatagtgc caccaacatc aggagctcac    42000
ttctagtgga catgtctaga gatatgtggc tcagccctgc gttgctgcgt gtggtcaccc    42060
gctcttaact aaatacagtg ctctaaatat ggctgctccc aaagagactg tgggctgtcc    42120
tcaccagcca tcctgtccca ccccaccag aagaaacctc ttcttattat taattccta    42180
```

```
accgattgca gatattgcag atggtcttaa aggaaatgcc agagaacaaa gtttcctctg    42240
atcaaagtat cttaagatgt gtccaccctc attagatgcc agcgataaaa aggaacaaaa    42300 attttttctca aagagtgaaa aggaaatgag atcagtgatg gcaggtctaa ttgtggacat    42360
gtttgcttcg accttaccat ggaccactca ctcagtgggt gccagacaca atgcagtggc    42420
ttggcgcagg ttatgtgatt ttttttttttt tttgagatg gagtcttgcc ctgtcaccca    42480
gtctggagtg cagtggcatg atctcggctc actgcaacct ccgcctccca ggttcaagcg    42540
attcttctgc ctcagcctcc tgagtagctg ggattacagg catgtgccac catgccaggc    42600
taatttttgt attttttagta gagatgggtt tttgccatgt tggccaggct ggtctcgaac    42660
tcccaacctc aaatgatccg cccaccttgg cctcctaaag tgttgggatt acaggcatga    42720
gccactgctc ctggccaggt tatgtgattt taaagtccca ctgtatttta ttaaggagtt    42780
gattgagcct caaggaagta aagcaactta ccagaacat atagctacga agctagaaac    42840
tcaagattcc aactaggtcc atccaattcc aaaagcccgg tgaactttct gttactttct    42900
atgggaagtt ttcaggttta gtataaagca acatttctta attatgaata caatcttatg    42960
taaccaaatt gcacattaaa gggtattcct tttgatcctt ctttcctctt ttctaataat    43020
ttttacaagg cctcaaagga atagaactct aaatctgttt tattaaattg ctttagtttt    43080
caaacaaaaa tagctcctgt tggtttatct ttagctgata acctaaaaac attccttttt    43140
tatcgctgta aaataatgtg tctttaaagg atattctgtc tcctctttaa ttttatgttg    43200
aaataaaatt ttttggtgtc caggggagtt ggccatttta gcggctggtg tctcatctga    43260
ggtcagaggt gagtcttgcg acatagaaat gatgggggtg aaaaaggaaa agctcagctt    43320
caataactaa gctaagcacg gtggtgagga gcatgggctt cagaatctct tggccccagt    43380
gccttgccag tgcctcagtt tcctcatctg taaaacaact gacaggatta agagaattaa    43440
attataatag ctatgcgtta gtggcatcat gaagaatggc tctaagcatg aattctgggt    43500
tgaatctctc tgggcctcag ttttccacat ttatttattt atttatttat ttatttattt    43560
attttgagag ggagtcttgc tctgtcaccc aggctggagt gcagtggcac aatctcggct    43620
cactgcaacc tccacctcca ggattccagt gattctgctg cctcagcccc ctgagtagct    43680
gagattacaa gtgcccgcca tcacacctgt ctaattttcg tattttagta gagatggggt    43740
ttcaccatgt tggttgggct ggtctcgaac cccttacctc aaatgatccg cccacctcgg    43800 cctccccaaag ttctgggatt acaggagtga gccacggtgc ccagcacgtg tagctgttgg    43860
tgcctattat tccagaaccg cagaggcatg gaataaacgg gatgtagggc aaaacccact    43920
catctcccaa aactcaggcc acccacacgt gggcctgcac aatgacagca cactgaagtg    43980
accaaggaag tttgagtacc atggtttgct ctcaaggaac ttaaatccta aaacgtacat    44040
gaaatcctga gggaaaaaga cctcacaaat atactacaca ataggagtta tttcaccagg    44100
ttaattgcca atgagaaatg caatgtttct attggcagag caagacttcc tttagcaccct    44160 gtggctggct gaatagtggc caccaaagat atcaaggtcc tattccctgg aacctatgaa    44220
tgtcgcttta gatggaaaaa gttctgccta tgtgaccaag ttaaggattt tgagatgtga    44280
agatggtttt agattactca ggtgggccct gaatgcaatc tcaggtgtcc ttgtaagagg    44340
gaggcagagg gagatttgac acaggatgag aaagtggtgt ggccacaagc ccaggaatgc    44400
cggtggccac cagaagctgg aagaggcaag aaacaggtcc tccctggagc ctctggagag    44460
agtgctgccc tgccaacagc ttgcctttgg ctgtcttctc tgtcctgtcc tgtcctatcc    44520
tttttctttt ctttctctct cttttttttt gttttttttgg agatggagtc ttgctctgtt    44580
```

```
gcccgggcag gaatgtgatg gtgtgatctc ggttcactac aacctctgcc tcccaggttc   44640
aagtgattct ccttcctcag ccacccaaga ggtggaatta caggcgccca ccaccatgcc   44700
cagcaaattt ttgtattttt agtagagatg gagtttcacc atgttggcca ggctggtctc   44760
caactcctga cctcaagtgc tcctccgacc tcaggctccc aaagtgctgg gattacaggc   44820
atgagccact gagccaccgt gcctggcctc tttcccttcc cgtcccccct cctctttccc   44880 ttcccttttcc ctcccctgcc cccttccccc cgccccctcc ctctcccctg ccccctcccc   44940
ctccctctcc cctctcctcc ctccccctctt tccttcctcc ctcccttccc tccctccctt   45000
ccttccttct ctctttcttt cttctttctt tctctctctc tctcccctcc ctctcctcct   45060
tagcccccct cctttctccc ttctctctct ttcttttttga cagggtctc cactctatca   45120 cccaggctgg catgcagtgg tgcgatcaga gctcactgta gcctcaagct cctaggctca   45180
agcggtcctc ctgcctcagc ctcccgagta gctgcaacca cagccactac atctggctta   45240
atttctgttg ttttaagcca ccaagcctgt ggtaatttgt ttcaacagcc acaacaaatt   45300
aatatagcac tgttgactgt caagtgaggc ctgcaacagt ggaaacttta tagttctgag   45360
tggtcagctg tttgaggtgt gattaatctc caggaaaaat gttaccagga ttcccttttgt  45420 aaccatgaca aaatgctgag aagtggtgga cacttagttg ctgaaaagca ctgaacgttc   45480
gctttcatct gacaaagtct ttctgaataa tacaggggag ttcgggaggg aaagaaggca   45540
agcaaacgat gggatgcttt ctgcacgtgt ctgtcaggaa attctgggta gaaattcttt   45600 cttttctcctt ttcttttctt tttgagacag agtctgactc tgttacccag gttggagcgc   45660
agtgatacaa tctctgctca atacaacctc cgcctcccag ggctcaagtg attctcccac   45720
ctcagcctcc ctagcagctg ggaacatagg tgtgcgccac catgcccagc gaattttggt   45780 atttttttgta gagacgaggt ttcaccatgt tgctggcctc gaacttctga gctcaagcaa   45840
tcctttcacc ttggccttcc aaattgctcg tacaggcata agccactgtg cccagtccag   45900
aaatgttcat aaattgtttt ttttcataga ccttattttt tagagccatt tttagattc    45960 atgcagaatt gagtgaattg agtgggtgcc ccaccaccca ccaccgctac caacatccca   46020
tgtaagtgta caaatttttt tttttctttt acaggcaggg tttcactttg tcacccaggc   46080
tggagtgtag tggacaacca tagctcactg tagtctcaaa cttctggctc aagtgatcct   46140
cctccctcag cctcccaagt agctaggact atagatgtat gccactcagc ccagctattt   46200
ttaaatattt ttgtagagat gaggtcttgc tgtgtttccc aggctggtct tgaactcgtg   46260
acctcaagca gtcctcctgc ctcggcctcc caaagtgctg ggattacagg tgtgagccat   46320
tgtgcccagc cataaattat tcttttttgca ctcctcggaa tgattacctc tgaaatgact   46380
gtctgaatgt acataaccaa cagtgaattt tatgatatgt ttaatagggg tagtcttttt   46440
ctataaaaat gaaaagaca accacagatt cttacaacag acatcggcag cagccccaaa    46500
cctaaatagg gaggtgttgt cccagctgca agtggctcag ctacagggtc tcgagatgaa   46560
actccacggc acagtctaat gacctgctgg aattcctgga gttggcgggg agattggctg   46620
gataagtggt ctctgcagac ccccatgcgt gccaccccett tgcccaccat agcccacttg   46680 aaccaccac tgtcataact ttccaggtcc taactgggac cacctactcc ccttggaggg   46740
tccggatgga gtttcccctc tgcggctgcc tctcactcat cctccaccac tttgccgaca   46800
aggaaggaag gacaatcggg aggagggagt cttgcttggc gaccatctgg acaatatctc   46860
gcccatggca agctggatcc ctgtggatta ctttggtggg tggaaacttg gcacactatt   46920
```

```
taatttgggc ttttttggggg atgactgcac actggttctc ttttttttctc agacctaaat    46980
ttcgaccact caactttcag cctgctcacc cctgcttatt gccatccacc tttgggctgg     47040
gttagaccta atcctcccct tgacaaagcc ctcaaagtag ccttcacaag ataagagtcg     47100
agacccctaa cttaccaaca aattttaatg aaacttctag taaactcaaa gcgctttgcc     47160
aacatcctta ggagcaaccc agttctcgca gcaccccatg tgaggtcgct gttgaagtat     47220
ctttggctgc agtggtgtgg aattcatctc aacagagttg acggtaaaga ccagacatgt     47280
agcagcctca ctgcttgttg gaggaaccac ccttaagaaa atttcccaag atagtagttt     47340
tcccatctcc gtactttgct agttaatgtt ctccacttgc ttgcgtttat cctttcaatt     47400
cctttgctaa ttaaattgct gaaaagtata cattggtaag aatagccact gtcaatggac     47460
tgcaaacaaa actcgtttct gttattgatg ataaaccatt tcagagaaga ccaggctgag     47520
tctaaagggt tcagataatt acaaggggaa ggcagagaga gtagttcatg ccacaggac      47580
ttggccacct ctgggcaaca cataatgctt gctaagctaa tgactgtagg gatatagaac     47640
tggccctcag cctctctgtc ttcctttggc ctctgctctt cctgctgcct tctctctttg     47700
accacgatga cacactttcc ataggccttc ctcaccacat cacagaactc agagaagagg     47760
ctgtcttctt gtttgataca cagctcgtct cttaggaaca cccgatattt ccaaggcacc     47820
catccttgac taccygcagc atgcacaata caccaagttg gggtttgtat gaaatatcca     47880
tcactaatat cttccccagt tacgagactt tctgggatat tggtttcccc aaaatatacg     47940
gtcttaaatc catcatattg cagtgttctc agggttttca gatattggag gcattgcttc     48000
ctcttgatgc catcaaattg acttctgata atgacatttc ttaaaagagg gcttgcaaag     48060
cgaggcatgg tggcttctca agtgttttta aaagcttgca catctgcatc tggggagaga     48120
tggcaagtgg gggatgatga cctcataaag ggctttctta cagtggtgcc agtcccacac     48180
atacacttca gatttcaagc atcatggaat aaatactcag aacaactccc tgctgaccca     48240
taaaatatgg gaattgcaga tgctacccat aaaaatgcta ctttgacatc acttctgcaa     48300
taggtctgag acagaggttg gcaatctttt aatagtaatg agcctaccca tttggcttaa     48360
gatggggaga aatgtttaca ttcattcatc catttcaaaa atatgtactg atcacctgct     48420
gtacaccagg cattgtgcca ggcaccaggg gtatagtcat gacacaccca gggagtcctg     48480
gacttacgtg ttgtgtgtct gtgtatgcat agaatttgtg ccagttgcct tcccatttgc     48540
acaactaaga gtgattttttt ccaggtggca gaaggaaggt atggcaaatt gcaaagaaa     48600
gtcagtctgc acacctagct tccactggmg cttgcaggtc tttttttttt tttttttttt    48660
tttttttttc tgagagggag tctctctctg ttgcccaggc tggagtgcag tggcacgatc     48720
tcggctcact gcaacttccg cctcccgggt tcaagtgatt ctcctgcctc agcctcccga     48780
gtagctggga ctacaggcac cttccaccat ggccggctaa ttatttgtat ttttagtaga     48840
gatggggttt caccgtgtta gtcaggatgg tctcgatctc ctgaccttgt gatccgcccg     48900
cctcggcctc ccaaagtgct gggattacag atgtgagcca ctgcgcccac ccggagcttg     48960
cagttattga actaattcaa tacctcatct tgaaagcact tttaattta tatactcagg      49020
caaaatgaca gtttgcttca aactctaacc atctcttcct ttgtatttc ttgcctcttt      49080
aatcagagct aaagacattt cataaaatgg gcatgaagga ttccttcaaa tgaagacgtg     49140
gacaaaatga ttggtcaggt cctttgctct actgttgaat ggaggaggat tttttttttt    49200
tttccctcac acaggggttt tcttggagct caagtttgga tgaccccaga cagtaagata    49260
atctcatcat ggtaaagtta atatgaaata tgtggtctcc aaacagcctc tcccagaggc    49320
```

```
caggatcagc aggtttgagt ggataattgg cttgtggtca ttttctcata ggattttct   49380 tttagtagtg gaaactgttt ttcaaatcaa atttggatgc caactatgtg aacagaagt   49440 gtggctgctc tggtggaagt ggcaatggta gtcctagagt ctccctgtca gccacaccct   49500
ttgtctcccc ctacccaagg gaccctgtgg cctggaaccg cagtgtgaaa tgctatatag   49560
tgcaatgaag tcaattcgaa gacaagagtt cttttgccttt ctcatctaat ttttagttat   49620
ggatatgaga ygcttgttca gaagtatgga aaagtatata taatatgtta tcttttagat   49680
gtgggtgtaa atatgcttat gtatgcaata tgcttatatt ttaacgcata aacaacatga   49740
ataaagcaaa cactctagac ttctccaaat gtatcttgtt ttacagttttt cattttggaa   49800 aatgtcaaca ttttttacatt aaaaaatatt actcagccat aaaaaagaat gaaatcacgt   49860
ctcttgcagc aacatggaca gaactggagg ccattattct aagtgaaata attcagaaac   49920
agaaagtcag atgccacatg ttctcacctt taagtgggag ctaaataatg tgtacacatg   49980
ggtacagaat gtaaaataat ggacttcgaa agggaggctg agatgggagg accatttgag   50040
gccaggagtt tgagacaagc ctggccaaca tggtgaaact gcttctctac taaaatgcaa   50100
acaaattagc cagacatggt ggctgacacc tgtaatctca gcactttggg aggccaaagt   50160
gggtggatca cttgaggtca ggagttcaag accagcctgg ccaacatagt gaaaccccat   50220
ctcaactgaa aatacaaaaa aattaactgg gcatagtggt gcgtgcctgt aatcccagct   50280
acttgggagg ctgaggcacg agaatcatga gccgagattg caccactgca ctccagcctg   50340
gacaacagag caagactccg tctaaaaaaa gaaaaaaaaa gaggatagga ttagggtgag   50400
ggatgagaaa ttatttaatg agtacgatgt acactactac actcaaagcc cagacatcac   50460
cactgagcaa tcaatccatt tgacaaaact gcacacctgc acttgtaccc cttaaattta   50520
tayacaaaca aaaacaaagg caaatcaaaa ataaaaataa aacaaaatga tctctaaaca   50580
atacaaacag taactgatga acctagctgc ttatcatgtc rgttccaaaa tcacacagag   50640
ttgaatttct ttcaaatgac cctacaacac agtatttga tcatatattc tccagtagag   50700
tataagctaa ggacaaagaa aaacacatga aatcttaaat ggtactcggt agttttattg   50760
ttaataatga tgctggtatt attattttga aactcatgtc catttctcag ctgccayttg   50820
atattaattt tttttttttt tgaggtggaa tttcactatc actcaggctg gagtgcagtg   50880
gtgtgttctc agctcactgc aacctccacc tcctgggttc aagcgattct tctgctttag   50940
actcccaagt agctgggact acaggcacgt gccaccacac ctggctaatt tttgtattttt  51000 tagaagagac agggtttcgc catgttggcc aggctggtct cgagctcctg acttcaggtg   51060
atctgcctgc ctcagccttc caaagtgctg ggattacagg cgcgagccac tgcgcccagc   51120
cagtgatttt taacctttat caatctgata gacaaaaaga tcatttcatt gttttaactt   51180 cttttaattat gagtaaatct ggcaatatat tatgaaaaca atgacaagaa gaacttgata   51240
taaaatgcac aattcagacg tccttgaaga tcattttaga ggcagcatga agtgggggt   51300 ggcactggtg atgggggctg ggtgtggaga aaaccagcca aaggaggact catgggatmc   51360
tggagctttt gactggggtt cacttggakc ccatactcag gctggttctg acagcagcac   51420
ctgccaggcc tcagcttagg ggcacaatgt gggacacatg gactgggggt gtggtcccag   51480
agcctaagag gcaccaacag agaggtctcc gcagagactc atctgtgccc cccacccacc   51540
accccgggac aggccaagcc agcgtctggc caggaactgc ttttgcacaa ggagccagaa   51600
gtagtttgcc ccgataaatg ggggcctgga ctcacgcaaa ccattgcacc atggatggcc   51660
```

```
agagaaactc agagaacctt cctgtgcttg ttaacatact ctctcacgtc ctctgcagcc   51720
tctgccaagc caagcagcca gctcctagga ctcccctccc tccacctgag gctccttgtc   51780
ctcccttcct caggagtctc cagcctcccg ggacttcccc tccccgctgc ccactccagc   51840
agaggctgcc aactgcctgg gagagagaag tgggcttcct ggggccacct ccccaacttt   51900
ggagtgtttg gaaggtgatg gagcgaccac taggaggcag tgtggacagg tctctgtagg   51960
actgctcagg cagacacctt tgcagggacc tcccaggtcg ggagccctcc acttttcc    52020 catgggagct tctccctcca ccccgagtca ctactatctg ctttcctaga aggcacttct   52080
ttacttctaa ttcttctcca ctgcccaggt aactgatatt ctcaagtggg acattgtaat   52140
ttgtttaatt catttaaatt gatttcatat aattgggaga taaagattgt tcagttgcaa   52200
gacaaagtct taacttgaac tctcaggaca cgggtgggtc cctaaactca atacgtgagt   52260
gttgctgccg ggctgttggg ccatcttcca cccgccatag atcacwttct tcatcaaaga   52320
agaaggaata tttagaaact ggtagtacaa aaaacaaac aaacaacaac aacaacaaca    52380
aaaaaccaaa acaacaaaaa acaccaaatc accaaaaaca aacaaacaaa aaacaaataa   52440
aaacccaaag cagttgctcc tataaataga tgtgtgtata catgtggctg gtatgaatct   52500
tatccacaaa ttcagttttg tgggaaacat cacatttatt tatttaaatc aagtcatatg   52560
ggacttgggc atggttggag gttcttaccc caccccactt cccaaggcca gtgcacaggc   52620
agggccttga ggtcaccctt agccgatgct tgggtctagg tgctcagacc caagcccctg   52680
tggtcccatc atgtgggcac tggcatcttt gctgaggctg agaatttcaa gccaggatc    52740 cagcccattt aggtaaaccc aaagtcactc tcccaggtgg cccagtcatc ttcttgagaa   52800
caagagccat gagcctcagt tccctgcctc aagagcctct gttcaaccct aggcttgtag   52860
acaactctgc cccttcttct ctcccttcag tgtcacggtc ccctgtccca tccctctctg   52920
ggacaggtac cacaacctcc ccaccataca cagggaaagg gtcagccctc aggtttttgg   52980
cctggcatct tgaatctcct cccaggcaac aaaccacaga gggcctggca ttctcctgtg   53040
aaaagcaggg cggaaaggaa acacagagaa caaacccaca gacaacaaac ccacagaaaa   53100
caaacccaca gaaaacaaac ccgcagagaa caaacccaca gacaacaaac ccacatcaac   53160
aaacccacaa caacaaatct acaacaacaa acccacagag agcaagccca cagggaacca   53220
gccaaattat gtctgctgtg catctcggca gacgatgctg ccaccgtctg tgtatgagca   53280
tgtgtgtgtc agactttccc atcgtctcca aacttgtttt cagaataatg cttccagtga   53340
aatgagtcgg ccacatgagg tcacaaagcc cctactctgt tcagcacctg gggtaagtaa   53400
taatattttg gagcacttag tgtggggagt agccctgacc cctttacatg tcatgtctta   53460
gttcattctt gttgccatcc ttggaattga ggccaacatc atctgcccat ttgccagaca   53520
agctgctcag gaggagaggg ccacagcccc ttatctcctc gccaaacaag agaagatccc   53580
cagttgcttt ttttttctgt ggaagagatt cttttaaaaa catttttttc atggagaaga   53640
aaatctgaaa aaaagaatg aaaccgaacc aatagtccca tagacagtta gttgttgttg    53700
ttgttgtttt gtttgtttgt ttgtttttga tgaatacaga aattgaccct tctggtctta   53760
aagcttgaaa attaaatttg ttttatctga gttgcttcct caggaaagga gcccaagtcc   53820
tctccaaaag tatcagagaa ctgaaactca ccagatcatc ttgtctagac aatgagacgt   53880
caggccctcc attcatcatg actgcttcct tacccctccc gagttcctgt tacatttctt   53940
ccctgctata taaaccccta attttagtgg gtccagaaga tggatttgag actgagctcc   54000
atctcctggg cagcagcacc caattaaagc cttcttccct ggcaatactg attgtctcaa   54060
```

```
tgattgcctt ccttccttcc tttcttttg  agatagagtc tcactctgtc acccaagctg    54120
gagcacagtc gctctatctt ggctcactgc aacctctgcc tcccaggttc aagcacttct    54180
cctgcctcag cctcctgagt agctgggatt ataggtaccc gctactacag ctggctaatt    54240
tttgtatttt ttttttttta tagagatggg gtttcactat gttggccagg ctggtctcaa    54300
actcctgacc tcaggtgatc cacctgcctc ggcctcccaa agttctggga tgagaggtgt    54360
gagccatcac gcccagctga gtatgtgtgt gtgtgtgtat gcttatgggg atgtgcaaat    54420
gtgtgtgtga atgtgtgcac gtgtccttgt gaattgtgaa tacccaggac ttgagcacac    54480
tcagttcctg atgcacttcc tgttttctca gcagctgagc tcaggcctgg aactgagtga    54540
cagcacaccc gggcacctgt ctccctgggc acccctccca cgcctgcttc ccacggcatt    54600
cccagctccc accactggga aggagctgga atcatgagtc gggataatca ccraattctc    54660
ttcgaccttc ctcagctcct ggtttgttaa ggcaaacccc catctctggc ttctcctgga    54720
acctcacctg ggaaagaaag aggcagcccc ggagctggaa gctgcttcag ggctcacccg    54780
gaacagcaga ctcaacctgg acccatccag gcatctcctg ggagtttcac ccaattgctt    54840
ctgcctggca ccagctcaga ggttctgaca gaattggcct ggggtgagac ctggcatcca    54900
tgggattttt acaagcttcc aggtgattct acagggaagc caaggtgaga accctgtcc    54960
tagaaccagg tctgatcagg ggccggtggg gaactgtggg tggagaacat tagtgcttcc    55020
agagcctcag ggttggtttt gaaggaacg  taacacattt ttttttctca caaagacata    55080
tagagagaga cttttaaaaa tagacatata tatagagaga tgttttaata aagagaggtt    55140
tgggtttata taagtaaaaa agatgataga aaatagagaa tgagattagg cttcccttg    55200
ctctcaaaaa atggtttgag agtcttggaa ctggttccac tctatgatag ccatgagtac    55260
tgttcgccca acttttggtt ctcagccttc caggccccgg tgggatgaga cttccctgcc    55320
cccacggttg agaggagcca tgggcttatt ctagccaatg aatggtggat ggacgtgact    55380
cgtgtctctt ccaggctgga gcatttaatt gtccaggtga gatactcagg gactcgtccc    55440
tccagagctg agaatggcca tgtttccaga gggtctgcag gagcaacctg agtctcagag    55500
cacagccacc agcagacctg ctgcacgcat gtggcggggg aaagaaagaa agccagctgt    55560
ctgcagccac tgagagtttg gggtggttgt ttctcatgac aaaaccagct caccctgact    55620
tatacaaagt ctttgagtta tatagatgga gaatgaggct cttgggtccc tctattctca    55680
caaagcaata gcctagctaa atccatctaa ctagggagca gaaaagggga tgtgctggct    55740
tgcacaccct agacagttgt tcaagaagtc aggacaccag gcctggagtg atacttcagc    55800
catccttcta ggtgagggtc ttgaggccac acagacagaa gtggcagaga tgggacacac    55860
attcgtcttc tcactcacag tctggcactg agctgtgggc tgctgggaca ccatgccccc    55920
atacgagtag ccttcccact ccttaccttg aaggaaaagt gttttttgga caaatacctg    55980
atggaaacat tacatgggcc ttggaatctg ttagatctag cttcctgaaa ctcttgctag    56040
ctgtgtgaca atatacaagt ttcttaacct ctctgagcct cagtgctcta attacactcc    56100
cctcatagag tttctaagag catcctgggg ctggcacgtg tcaacgcacc cagtatttga    56160
tagagtttgt taaacgttgg ttatcctctc tccctatcgc acctcaaatg gtaagggctg    56220
cctgccagct tccatatccc cagcagtgcc ctgagttgtt cagatgttca tccatctccc    56280
acagaactca ggttcctttg gaggaagcca catcaagtcc tgctccaagc ttaagccagt    56340
cagcacattc catgctctgc cccattgcca gggttcagga gtatgctcgt gatctaagca    56400
```

-continued

| | | |
|---|---|---|
| cccccactcc cagatacagc tcaagattct tgcttggact tctgggcact caggctcctc | 56460 |
| cgagagggaa tcaaacttac ttctctccat gtcctttcct ctaggagatg cgtctttcat | 56520 |
| aaaactctca tcaacactgt tcagacatgt cccaccccag caggggacag cctgggctca | 56580 |
| agctgggatc cctactttat ttattttctg ctaattaaac ttcctaatat actccacact | 56640 |
| aagtgtgctt gcaaggcagg gggtgtggga taagcggccc tgcctggctg ggagaggggg | 56700 |
| cagctccctg ctgtactatg tattaataaa kagacacatg catggcaggg cttgtctggg | 56760 |
| ccttggtggc agcttaggac agaaggcacg tgacagtcag gggttcaaac aacccaggga | 56820 |
| gaacactgct tcagggaaga cagctcagca tcttcctggc aaagataatg acattgataa | 56880 |
| tactctccaa agaatttcag gattttgagc aatcagaaaa gcaacacaga aattcatgtc | 56940 |
| atcaaaacga tatggctcta ttggacactt aagacattta ttggaggctc acaacataa | 57000 |
| tcctgctggt tggttttact tcattgattt tccgttgtgt ctgattacat tgctaatgct | 57060 |
| gatggtggat gagctacggc tcttttcctg cctgtcctga ggtttatcca ccaatgtttc | 57120 |
| agttctgttt taagatattg tcctaagccc ccagcatcgc atgcatgctg ttttttttgtt | 57180 |
| ttgttttgtt ttgttttttta caaagagttc atagcccgtg gaagactctc ctccatcaca | 57240 |
| cacttaggtt ccctccacac caggcctgga aggagtctag cttctgggga ctgtacatat | 57300 |
| gctgtggacc atgcagaacc tggagaggcg gtgacccctt ctagaagtga tctgcctgaa | 57360 |
| tccttccctc tggaggaggc atttattaaa tgccaggttc ctgaaaggct ctgagatggg | 57420 |
| cactccctct cctgagtcgt cccttccatt actgctttcc tatttctggc cagggttccc | 57480 |
| tggcccctcc tccctgctcc catgggaccc cagttcatcc ccatctttgc tcaattgccc | 57540 |
| tgcactgtag taatccattg gcactcttgt cttctccagg agaaatagtt ggaggagaag | 57600 |
| tttatagggt ttcctgggcc agggctggtc tacagtcact ggacagcagg aaacgaccct | 57660 |
| tcggggccta ggagggccaa ggctggtggg caggtacagg gggagccagc actgctgtcc | 57720 |
| accactgtgc agcctggagg ctgtttccca tgaccctgct gatgggaccc aaggcacccc | 57780 |
| aggccaccca ctcccctgcc cccagcaggg tgtcagctcc ccggcttccc tgcatgcctg | 57840 |
| cctgacatgg acagtgcacc ttcgggccac acttgccctg ctagcgagcc tccagtgaac | 57900 |
| tgggaattcc acagagygta gaggactcgc cccagcactg tgctgagagg cttcaccaaa | 57960 |
| ctgtagcctg gcttccacct gcactaagct gcatccccag aggcgacccc agccctggct | 58020 |
| gagtcttggc tcaagacttt gcaatgcagc caaatcacaa aatgcacctc gtccagccca | 58080 |
| ccccgctaaa ccattttcag tagttctccc ctcaccgttc tggaactttc catttccacg | 58140 |
| tggcccccac gttctgtttt catttctcct tcagtccctt tttgttccct ttctgttctc | 58200 |
| tctttgaaga cctcagtcac cgttttctga gttgggttg agcttggtcg gtactggaat | 58260 |
| ctctttccgc tgctgcagga gtctgaagga atcagtcttg ccgcctgtaa cacatgtcca | 58320 |
| gcgctgcttt ttctctgatg agtgtcttag tcagtttggg ctgttaaaac aaatggctta | 58380 |
| ggcaacacac gtttctgtct cacagttctg gaagctggaa gtctgagatc aaggtgttgg | 58440 |
| cagattcggt acccggtgag gacctgcttc ctggttcgcg ggtagaacac ttcttgctgt | 58500 |
| gtcctcacaa ggtgcagaga gagaggggg tctggtgtct cttcctgtaa gggcactgat | 58560 |
| cccatcatgg gggccttaca atcgcgacct catctaaacc tcccgaaacc tcatctaaat | 58620 |
| ctcacctcca tactatcaca ttggggatta aggctttaac atgtggattt caggggacaa | 58680 |
| aggacaaaag cattcagtcc atggcacatg ctcagtgcct cgactcttgc aagtgccaca | 58740 |
| ccacagcctc tctggggctg tgtcctggag gcgtgtgcca tgggccctgt gtgccatggg | 58800 |

```
caaggcgcac agcatcctcc cggccacccc accagcgagt gagctcctgg caccctggct    58860
ctctctggtc acccatctac cagtcttggt gctcctgtgc actagaggac cagctgcctg    58920
gggactgtgg gccaactgtg gccccggcca cccacgaact tcccctccgg ccagtggctg    58980
caatcacatc ttctctaaag acgtctgaag cccagccttg gggagccgag ttggtccttc    59040
cctgggtact gagccctagg gaacccttga gagttctctt tgtatctttg tagtttcttc    59100
ctcaccactt aatcatttcc ttacaggaaa cttcctgtgt tcaagtgact gtatggtttc    59160
tgcctccagc ttcatttgtg ggtgccataa gagaggcaag catggagcac taggcgcagg    59220
ggatgggcaa ctggcaagcg gggagatgca tgcagcgcac ttagtgcctg gtacatacca    59280
agtccttta gtctggattt cattatttt aaatgggtat tgctattttt aaaagaatag      59340
ttacaaatat ttattgtgtg ttttgaaata agtgggtcaa gatcaataag atattgttga    59400
tcaattgatc aataagatat cttttattct taaaaatcat attcttctgg ttcagtgggg    59460
aagagactgc cgacctgtat ttacagcatt atgtgataag tgttctcctt ttcaggtatg    59520
tattagtctg ttctcatgct gtcaataaag acatacctga gactgggtaa tttataaagg    59580
aaagatgctt aattgactca caattcctca tggctgagga ggcctcagga aacttacaat    59640
catggcagaa aaggaagcaa gcatatcctt cttcgcatga tggcaggaag gagaaataca    59700
gagcaaagtg gggaaagccc cttataaaac catcagatct tgtgagaacg caatcactat    59760
caagagaaca gcatggaggt aattacccac cggctccctc ccatgacgca tggggattat    59820
gggaactata gttcaagatg agatttgagt ggggacacag gcaaaccata tcaaggtgac    59880
tcctgcaagc acctacctcc accccctcctt catccttgcc ctcattctac aatgatttgg    59940
tgaaatctgg tccctgcctc agttttacag cctccccatg actctggtta cttcctgatt    60000
agcttaaacg aaacctaact aggttgccct aggaaagcat ttctgttcct gacaccccc     60060
atctgcctgc tgcttccgtt ccacctgtat gtgtctgggc acatccctgc atcccctttgc   60120
tggcttctag cctactcact tcaagcattt atcccatgag tttcataaaa tcgtagaaga    60180
aaagggcttg aggcagtggt ggggaaatga taggaaagtc attctggat gcattctgcc     60240
atcctgcaga tccctaaacc acctctccct ctccattccc tccctccaga gaacagcttc    60300
tccttgtctc ctgtggaata gttccgccca cattcatggg cccttcctgt accaaaactg    60360
tacaggtctc tcttgcttac caaacacttg gcaaacaaat gtgccgtcct tggaaaaatt    60420
ctgttgaata aaattttctc tctttgatcc atccaaatgt tttacaaagt gctacagaag    60480
ccatggagga acaagcaatt ctgccttagg gatcaaggtt tcacacaggg ggtgatatct    60540
gagcaacagt gctttttgg tttgtttgtt ttgttttgag atggagtctc gatctgttgc     60600
ccaggctgga gtgtggtggc acaatctcgg ctcactgcaa cctccgcctc ccaggtttaa    60660
gtgattctcc tgcttcagcc tcctgagtag ttgggattac aggtgcccgc caccataccc    60720
agctaatttt tgtatttta gtagagacgg ggtttcacca tgttggccag gctggtctcg    60780
aactcctgac ctcaagtgat ctgcccacct cggcctccca aagtgctagg attataggca    60840
tgagccacag tgcccagcca acagtgcttt taattggcat tttcttcaaa gactttgatg    60900
tcctatagga gggggcctat gactcagcct cagccaatca gagcgctcca ttccctgggt    60960
cacctgcaca cctgctcttc cctgatccac tgcagtgccc tcaccctgag atctgaaact    61020
tgagcagagg cactaaaagg cagacatggg agctgagctg tcttttggga gaatcctagt    61080
gagaaggttc tccaactggg gccgccaagt aagggcctca tggcagacta accctctccc    61140
```

-continued

```
ttcctaaggc tgggaggagc tgctgtcctt ttgattctgt gagctacctc agttaccttc   61200
ctcaaaatca cacacacgcg cacacacaca cacacacaca cacacacaca cacacacatt   61260
tgcatgcgct aggtagagct gttttccata attgccaaca gaagactaac tgtatttgaa   61320
gaatgagctg gcattcttct gctccggtag aagtcaaggc aatcagttat gagaatcaga   61380
gcccacctgt gactccagaa agaggtgcat aaataccaag aatttagtct ctaaagtctt   61440
tctttaagtc cttttttaaa aaatgtgatg agtacatcac ccaggaaaat caaattgtaa   61500
tgcaaccgag tcgatgcaag ttttatttag gagatgggtt acaatcacct ggggaggctc   61560
tagttacctt gatttggtct ggtacaaacc ctagcaccat catccacaga tccccagagg   61620
aagtcattcc tggatgactt cctcatcgat tttaaataat ttccatttca gaggaaggcc   61680
tttatctgac ctgatcccct aaatattggg ggaaacctac atagggacaa agacagcagg   61740
tgtctgcaat gttgagaatc agtgtgttct gtcactgtct ctatcagggc tggtggcaca   61800
tgcaaatctc tttcccactc tccagttgaa cactaacgcc atggtgccca caccttcctt   61860
attagtccat gtacatgggg tttgtcaaga cagtggttca tggctctgac cctgagcatg   61920
tcagatttca ggggctttat gcaaaatatc ataccagtt ggggtcattt ccatcagta   61980 ttgctcacaa tggagcctac aaaccccctag ttcccatcca acacatctcc aaggcagact   62040
ctcagaccag ctcccagaaa tgaggtgagt ttagatcagg cagcagagag gtggcctagg   62100
aaggagtcct tggagctcat gcacctgtgt ctgggcacca acaggaagat ggtggctttt   62160
gctctttggg agatatcttt ggagccagtc tctgaccaca tgtccaacag acaggcatc   62220 cttggggttt ccatggcagt ctactgacag tcaggggtga ggattaaatg gtacagagtc   62280
tcactgagtg ctctttgaga ggtcaagcaa tgagaagtcc tgcaaatgat tattgagctg   62340
aagtaagaag tgtaccgaat ctgttttttcc cctataaata taaaagccta taaatataaa   62400
aatcttggtg aaaaaaaatg atcccagcct cccacacagc acatcacaca tcttctcttt   62460
tcaaatttga ctccaaggcc cacttccttc gggaaatcat ttatccagtg gtatcattta   62520
ggatattttt ggttgtgagg aacaaaagcc tagctccaaa agacttaata aaaggatctc   62580
attggttcac aaactgaaaa actccagtgg taaatgaagg ctctgggtac agttggtaca   62640
ggctctggtc tctgtaattt cctagttctt ctcccttcta gatgctgggt ttttgccttc   62700
aagttggctt tcttcatggt ggcaaaatgg atccagcaat tctgtcagag gttttcgaag   62760
cagagtgact ccatcttgat taaaggctgt gtaaaatgag gatgagactt gctggactgc   62820
attccaggag ggtaggcatt cttagtcaca gggtgagaca ggaggccagc aggattgata   62880
tcacaagaca caggtcacaa agaccctgct gataaaacaa gatgcaataa agaagccagc   62940
caaaacccac caaaaccaag atggtgatta atgtgacctc tggtcttcct cactgctcat   63000
tatatggtaa ttgtaatgca ttagtgtggt aaaagacact tctactaact ccatgacagc   63060
ttacaaatgc catggcaatg tccagaagtt accctatatg gtctaaaagg agaacctata   63120
tagtctaaaa gaactgaggg ttctgagaaa tccctgaccc tttcctggaa aatttatgaa   63180
taatccactc cttgtttagc atacaatcaa gaaataacca tagtgtactc agtcaagcag   63240
tccctgctgc tgctctgcct atggagtagc cattctttg ttctttactt tcttaataaa   63300
cttgctttca ttttactta tggacttgcc ctcaattctt tcttgtgcaa gattcaagaa   63360
ccctcccttg gggtctggat caggatccca ttcccgtaac aatttcaggc tcagatcggc   63420
ttttaacacc atccagagca agagaaagct ttttgttcc agaattcccc attaaagttc   63480
tcctggtcac tcttattggg ttgtttcgct tagggtcagg tgtccatcct ggtcccaagc   63540
```

```
aatgaggcca ggagatggga tgcaacgact ggatcaatct aggcctctta ttcccacttt    63600
ttaaaacact tattattatt attttttaaa aattattttt cattcagctt tttcatttga    63660
aacttattcc aattcttgaa ctgggggtag tttcaacttt cctagagctg tatgggtcct    63720
caaatgaaaa ttcggggcag ctggattaga aaggggggaa atgcatgctg cagggcaac    63780 caacaagggg agattgtgcc aattcactct tcctatcctc agattcacct aagttctgac    63840
cattcagccc catttgaatg cattctgtat tcctatgact gtggattaca ttttttgtcta   63900 cctttgtgtc ttctgttttg tcctgcccta taagcatctc aaacatatgc ataaagccta   63960
tataaacttt ataaataaac taacacttct gttttcaacc tgtaggatga tgacaatgat   64020
gatgacgaca atgatgatgg taatgatgtg gaaatgtga aaagagaaag aaatacttgg    64080
aaatatatct caccctccat aaacaaagct cggggtttaa ttctgacctg tatgagttca   64140
tggggtgaac tgcagaccgc tgtctgtgga caggaaaacg atatttcatc tctagcccca   64200
gggacatctc caaaagctga gctagatgaa ctttatataa attggtacaa aatataattt   64260
tctctttgcc tgctgaaagc catttctaga aattctgtta atcagaatct ccctaagtta   64320
atcagtcatc tagacagatc ttatttcttt tttagacaaa gaaagtata taagtaacag    64380 gtattggtaa accacttgag tgaagcatat gatatctaat gtaaggaaat ctaaaagtgt   64440
ccacaggcaa aatctcatgg attcaattga tagcacaggt catcaactga catgcagacg   64500
gaattctctt gtggaacaag acaatacagc cattgcttag agactaattg tcaaggaatt   64560
agtcatttcc tgtttcagaa tagcatcatc accaccacca ttaatgccaa catcaaccac   64620
caccacctac gccaccaccg ttagcatcat aaccaccacc aataacatca ccaacagcaa   64680
cactgccatc aacataaacc atcaccacca ccaaaaccat tagcatcacc tagaaccacc   64740
agtcaccacc atcaccactt accacaacaa ggcttatatt tacatactta ttttactttt   64800
cgaaatacat tcacatgcat ggtttcatta gatcttatct acttggtaag gttggcagat   64860
ctgacatcat tagcctcatt ttatctgtat ggaaactaag ttctagagaa gcgaagtgat   64920
gtgtgaaagg acaccagagt gattgataat caaatccaga ctagagtttg gttcttctga   64980
ctccaaaatt aatacatttt tcttaaaaga aaaaatttt ttttgagaca gggtctcact    65040
ctgtcaccca gcttgagtg cagtggcatg atcacagctt actgcagcct cgacttccca    65100
agctcaagca atcctcccac ctcagcctct caagtacctg ggaccatagg cacatgcctg   65160
gctaatgtgt tttaaacatt ttttggctgg gcacggtggc tcatgcttgt aatcccagca   65220 cttttggtagg ccaaggcagg cggaccacaa ggtcaggata tcgagaccag actggccaaa   65280
atggtgaaac ctcatctcta ctaaaaatac aaaaaaatta gccaggcgtg gtggcacatg   65340
cctgtagtcc cagctactca ggaggctgag gtaggagaat tgcttgaacc caggaggcag   65400
aggttgcagt gagctgagat tgtgacattg cactccagcc tgggcgacaa gagcaaactc   65460
cgtctcaaaa caaacaaaa caaacaaaa caaacaaaa caaacaaaa caaaactttt       65520 tttttttttt ttttgtagaa acggggtctc cctaggttgc ccaggctgga ctcaatcttc   65580
tgggctcaag tgatcctact gcctcagggt ctctaaatgc tgggattcag gcatgagcca   65640
ccacacccag ctccaatgct ttttttgtcg tacctaattc tttcaatgaa aatgaagaat   65700
ttccaacttc tgatattaac aactttggtc ctatattcaa gctagagtct ttcaaataaa   65760
atagactttt aaaaccatct gtctccaaac cctaaatgtc tcaggtgagc aactaagctg   65820
ctcagtttat gtgactcccc agaagttgaa ttttaaccca gaactgactc caagttcatt   65880
```

```
cttctttcca cgacaaggag tcacctcctt gtatgccccc aggagtctcc cggattcctc   65940
cgagaacagt ggaatagtgc tcctcccag agcacaggtt ttgccagtga agattgaatt   66000
tggctagaaa ccgctgccct gctctctctt ctcgaagcac ctggaagtct gagaaggaac   66060
tgggtggctg gctctggtca caaactagca gmcagaagca ccccttgtca gtgatgcacc   66120
cccagtcccc ctcaagggct ccaagtaaac ccaaagctgc tccctccaa gaagtctggg   66180 gccaccctag ggaaggcctc ctggccttga ctctcagggg gtctctgggg ttgcggtttg   66240
gggcccgctg cttccgccct ttgccccag gtgggcctgg cagggctgca gcacagctct   66300
gttgctgata gacagggtgg agcacttggc gaccttgccc tgcagccctg tcattttgag   66360
ttcagaggtc anatttgagt aataaacatc ttctaaggac ttgtcattct ttctgaggat   66420
gttgctggcc agccggaaga cgaaaatcac cgcgtagatg ccratgatgg tgagtatata   66480
ccaggcagcg ctggttccgt ctggcacctt cagagccctg gtggagttgg tgtcattcct   66540
cccctctgtg tggtcaccca gcaggagccc caggagggtg ctggcctggg tctggttgga   66600
ggcttcatgg ggagtccact tggcccctga gaaacagaga ggtccggatg mgatccagcg   66660
tcctgggctg agggctgcct ggccacacca aggagaatgg agccctcata tccgtgaaaa   66720
cgtgtcgctg ctcaaagagg ccttctctga ggcatgagca ggagtgtaac aacaggtatg   66780
tcaatatatt tttaaaaatc aaagagtcc aaaacactat tttgttgttg ttttgttttg    66840
ttttttgttt tgtttgtttt agagagacag agtctctgtc acccaggctg gagtgcagtg   66900
gcatgatcat aacttactac agcctcaacc tcctgggctc aattgatcct cctgcctcag   66960
cctcacaaat agacatgcag caccatgccg ggctaatttt tttcttttt ctctctcttt    67020 ttttttttgt agagataggg tcttgccatg ttgaccaggc tggttttgaa ttcctggtct   67080
caagagctcc tctcaccta gcctcccaag ccctgggatt acaggcagga gccactgtgc    67140
ccagaaaaac actaagttct tgaataggag acacaacatc ataaagatgt cagttatccc   67200
tcaaataatt tatacaacaa acataattgc aataaaaaca gcataggat ttctttgtga    67260 aatcaataaa ctattcattt agaaaaatca actgttggcc gggcatggtg tctcatgcct   67320
gtaatcccag cactttggga ggctaaggtg ggaagattgc ttgagcccag gaggttgaga   67380
ccagcctggc caacatgaca agaccctgtc tctacaagaa ataaaaaaac tagccaggtg   67440
tggtgtgcaa gcctatggtc ctaactactc aggaggctga ggccggagga tcacttgagc   67500
ccaggaggtt gaggctgcag tgagctgtgt tcacaccact gcattccagc atgggaccct   67560
atttaaaaaa aacaaaaaaa gaaagaaaga aaaagaaaaa gaaaaatcaa ctgtcaagac   67620
taattagaaa aaaaaatctg aataaaaaga atgactaatg aattagccta gccacaaatt   67680
ttaawtcagc cagctataaa aactaattta cattttttc aatgaatgaa agctttatat    67740
gcacaaagcc cagctgggac ttgctgggct ttgcagagtg tgtgggctgg gggttcttca   67800
gaaccaggta caactctccc tataaaacta caacagtgct gggcatggtg gctcacacct   67860
gtaatcccag cactttggga ggctgaggca ggtggatcac ctgaggtcag gagttcgaga   67920
ccagccctgc caaatggag aaaccccgtc tttactaaaa atacaaaaat taaccaggcg    67980
tggtggcaca cacctgtagt tccagctact agggaggctg aggcaggaga atcgcttgag   68040
tccaggaggt ggaggttgca gtgagccaag tgatgcctgt agttccagca agacagagca   68100
agactctatc ttaaaagta aaaaataa aaataaaact acaacagcta aaatagtgtg      68160
atgcctgtag ttccagctac tagggaggcc gaggcaggag aatcgcttga gtccaggagg   68220
tggaggttgc agtgagccaa gatcgggcca ctgcactcca gcctgggtga cagagcaaga   68280
```

```
ctctgtctta aaaataaaa aaaataaaaa ataaaactac aacagctaaa atagtgtggt    68340
gctgaaaaca caggcaagca gaccaatgaa acagagtaaa aacagcatca atagttagca    68400
attagaattt gatagctagc taataaagga gcatttctga tcggtgggaa aagatgaatt    68460
attcaatatg tagcattggg ggaaatagca ttagatccac atctctccac catatgacca    68520
gataaatcgg tccagattaa aaaaaaaaca gcccagataa atcaaatatt ttaacataaa    68580
aagtgaaata atttatagta ctagagtaca gcatggcaga ttttttcttt atcatctcag    68640
agtggaatat tcttttaagc ataacaaaaa ttcagaagaa acaagaaata gaaatcaaat    68700
tcaactacat aaaaaaaatt aagctatttc ataccataaa accaacaggc agatgacaaa    68760
gtgcaattta tatcactgat tttctaaata gccttcggtt ctgtaagaaa aagtttaaaa    68820
ctgcagtaga aaaatgtgca aaagatatgg acaaatagtt cacagggaaa aaatgaacat    68880
tcaacataag aagagcttct caatatcact catataagaa aaatgcaaat taagataata    68940
actagatacc attttgttac ctattggact tgcaaattca tgatgtttca gaataaacta    69000
acaaaaaaat ggcttttttt tgttcttttg tccagcttag aagaaaggtg tctaaattgg    69060
gagcaaaggt ggcaatgacg tggacttgac accaaaaaaa aattttttta aagaaaagaa    69120
acaagtgcct ctgcatttca ggggtttagg attggcattt ttaaaatgtc aacaaataaa    69180
tgttcatatc cacacttgac attttttcca aggagaattt taattgtata attgctggta    69240
aattcatgca gccaacatgg agggcacacg gacaagatct atgagcatta caagtgcact    69300
tacctttgac ccagcaattc tatctctagg aatctatcct aaagatgctc cagaacatct    69360
agagacaaca tatgctgaag gttagtcatt gcagtcctcc ttgtgatgac gaatgcctgg    69420
gaacagcctg aatagcacca actgagggat ggtgaaatac attttggaac ctccatgcag    69480
tggagtacta cacagtcata aaaagcaatg agttttttat ggtactgaat gttaataagt    69540
gaaaaaataa gctaatggtg acatgctctg caatgccact tgtaaagaag ggggaagtta    69600
tatgttattt gcttgtactt tttttatgta tagaacatct ctggaagaat gaataagaaa    69660
ttagtatctg caattgcctc tggggaagaa acctggggga agaagatata ttttttactg    69720
tttgcccttt tgtacactta gtaccgtgta tacttatttt tgaaaagcaa gagtgtacca    69780
gttggtactt ttctggtctc cctggtgagg tgccctgggg taaagccgtt gtatgccctt    69840
gtaagaccag aagattaaga tctcaattgc tgttcaattc aaaactgttt tctctgcttg    69900
gagagctggt ggagaaaatg aaacaatgaa accagagct gtagagtgca atcctgtgag    69960
acatttccca gtgggccctt actggctcaa ccccccattt cttgctctaa tgtgaacaca    70020
gatgtattta aaaacacatc ataggatcaa tcttgcagcc tgctgtgyag aacaaaggtg    70080
ctccaaaatg cttcccattt gatcgttgtt tgttgctaat tcattttgcg aacgcaagac    70140
tcagagaggc cagtattttt tattatagtt agttgccaga atgtgtgaat gagcttatta    70200
cttttagatg aaggaagaaa ctatttaaaa attacttttc aaactacatg tgacaaagcc    70260
caggacaaat gaacagattt aattacataa aattagtcac tcgcaagaaa caacaccaca    70320
agcataaatt tacaccattg tttggtagaa tggtttgaga cattaaagta aggaaggtga    70380
aaaattcccg taattattgc aacaaacaaa cagacagcaa atcaacccaa caagaacaca    70440
atatccttat attagggcaa gagaacttat tgaaactcag aacacatgta taaactcata    70500
gaactttcta gaaattgtca tagaatgatg caacacattc aaatacaaat aaaatatccc    70560
caactaagag ctacacacag aacattaaat tatttaaaaa ccagtccatt ttctacacga    70620
```

```
aagaaactca ctatattaat tactgcaata cattacattt tacctttctt acaaaggtaa   70680
aagtaagtta ggttgtatct taatggacaa acatatcctg tagaagagag aaacttttte   70740 ctctgtgcta ttttgtactt gtaatttaat gacgtgaaat atgtaaaatc tcaacctgcc   70800
catccttgca ttgtagctga gtactcacat tccatggggt ggtcttgtcc ttgactcttg   70860
gaggggcaag ttcaagcggc taccatgcac agaaggggaa gatgatgaaa ggagaactcc   70920
gtctcctagg gaagaatcag tcctactgca gttgagctgc actgagtttc cagagtgggg   70980
agtaatatga tcttccaaca atcttagggc agcaccaaac agaaacttag taagtggatg   71040
actttgcttt catgcaatta atcagaggat ccgatttgct gtgtcttctg ttgcatcaga   71100
acagaaagca cttcccagct ttgacttgtt aagaagttct caatcaaaac aaatttttaa   71160
aacgtgctgg tattaaggaa tctccatctc tcaggtccca tcatgaactg aggtggccag   71220
aagctccccc tgaggctggc tctccgctta gagcttggat ggctattgaa ttcccctgtg   71280
ttctgcacct gttgcaggtg tggcagatgg ccaggtgtgg cagagatctg tcatcatagg   71340
gccaggaaac tccatggtca agagtcacca gcttcctctg gacagtctcc cagatgagga   71400
aacccagaca ggaagggagt gacaccccaa gggtgacaca cctgagggga cttgggcttt   71460
ccctgagggg tcagtgggca gtggactcct gtgccaggtg gtgagaaatg gctcttctct   71520
ttcccagagt cacagacccc attggagttg aggtaggctt aattggaaag tgttagagta   71580
agtgtctgcg ggtaaagttt ccccaggagc agggagggaa aagttggaag actggcaagt   71640
taaatcatcc agccattgtt tccagttcca tttcttccta atcctcactc taggactcta   71700
acttgccacg tttgtgatgg ttgctggttt ttaagataca atttgatgaa atttccatca   71760
atggggtact gggtaagtaa gttataaaat aagccatatg atccagcaat tctactcctg   71820
ggtatcttcc caggagaaat aaaaatgtaa gtttacacaa aaacttgaac acacatgttc   71880
aaagcagcat tatctgtaat agcaaaaaat ggaaacaacc caaatatcca acaactgact   71940
aatgaataaa taaaatgtgg tttatccata caatggaatg ttattcagca ataaacagga   72000
atgaagtact gatatatgcc ataacacgga tgaaacttgc aaacattgtg ctaaataaaa   72060
gaagtcagtc acaaaggact acatattgta ggatttcatt tatatgaaat gccaagaata   72120
ggcaaatcta caaagataga aaatagatta gtggttcact agcgggaggg attggggtg    72180 ataactaagg gtatatagca ttttggagg ggtaataaaa cttctaaaat tgtggtgctc    72240
actgtacaca atctgtgaat atacaaaaaa attgaatgca tactttaaat ggatgaattt   72300
tatggtatat gaattatatt tcaataaaac tgttaaaaat tataatatac aagctgggtg   72360
cagtggctca cacctgtaat cccagcactt tgggaggccg aggtgggtgg atccctgag    72420 gttgggagtt cgagaccagc ctgaccaaca tggagaaacc ctgtctctac taaaagtaca   72480
aaaaattagc cgggcatagt ggagcatgcc tgtaatccca gttacttggg aggctgaggc   72540
aggagaattg cttgaaccca ggaggcggag gttgcagtga gcagaggttg tgccattgca   72600
ctccagcctg ggcaataaga gtgaaactcc atctcaaaaa aaaattata atatacatat    72660 acaatggagt attacacagc tgtgaaaaag aacgaggaag ctatttatgt actgatgtat   72720
aaagctctct aaggtgtgct gttatgaaaa aggtaaagaa gagagcatgt taacatgtat   72780
ccaaaaattg agaggaagca tatatatata tatctgattt tgccactgta agcatttaaa   72840
acaccagtgg aatatccaag aaattaagaa gaggggttac ctattggagg agagaaccag   72900
gtagatatat ggcaggtgtg ggagggagag ctctcactaa atattttat gctttaaata    72960 tttttaaccg tatgtgtatt acctattcaa taataaatgc acccatttgt tagatatctt   73020
```

```
tgttgaagat tcatttggct cctgctgtct cttgctatgg gatggaccat ggcatccccc   73080
ctctgccaca cagacaaggg atttggacac tgccagtggg acgtgggagg ggagagcacc   73140
tgacccgtga taataagggg ctcgtggcag tgataagggc tgggagtcag ggctctggcc   73200
ccagccacat ccttgctgca tgaccctggg ccagccccct catctttgtg agcctcagtt   73260
tcctcatctg tgaggtgaag gtggtgaagg aggtgaagga tgagcaggat cttatgtcct   73320
tggtcctgag aaggcaggag agaagcctgg ggctctgtgt gggaagagcc gctctctggg   73380
gaggtatctg aatagatgag ggagagcaca ccgggcagcc artgtgccag aggtggaggc   73440
tttggagagt gtttcatttg tgaagtcaac agatttaaca ttcagatcag gaggacgttg   73500
gcatgagatg tggggaatca taagctccaa aacaatcgtg agacagaagg aaagatggcc   73560
ttttgttgag cagccattct cctccacgga gagtcctgtc tagtctgcct gttgaagggg   73620
cactgatgtt aggaataga tctgtgtcaa atgcttccca cctcccagaa tcctgtgagg   73680
caggagtatt atccccattt aaagagagga cactcaggct cagggaagtg actggcccaa   73740
tgtcccatag ctcataggtg ccagaggtgg gtcatccaca ccaaagtcat tctccttcca   73800 tacccctgaat gtcaccttca cgctggaccc aggatcctgt gtggtgaact gtctcgatca   73860
cttccctaaa ggttaaatca taaactctta ctgccaaggc atatccacga ccttaaactc   73920
tccctgttgg gcaaaaacaa tctctgatgt taaaaggcag gatagtggat acttttcagg   73980
gaagggtaaa tgacaagggc atgagggaa ctctgggtgc cggtcatatt ctgttttaca   74040
ggtttgttca atttgagaca cttcatagag ctgtagcctt gtgcacaggc acttttttgc   74100
atgcatcgtc tgcttcaata taaacctctt cctgttgtct tgttttttgtt tttgttttttg   74160 ttttctcttg ttttcttgtc ctgctctgtc acccaggctg gagctcagtg gtgtgatctc   74220
agctcactgc agcccctgcc tcccaggttc aagcgattct tctgctcggc ctcctgagta   74280
gctgggatta cagaggtgtg ctaccacacc tggcttccct gttgtttctt taatgtagaa   74340
agccctgata gatggtggga aaacaaagtt taaggtattc atagaaaaat acaaatacta   74400 ttttttaagga ttctatatct ggccacatgg tgccatctca cgaagagtgt cmccgtccct   74460
tgagggggag tggtcgggat catggtcagt gtggggccct gcagctgcct gcttccctat   74520
gctgtgtgga tgacgcccgc ctccggtcat tccctgtgc ttacataaca gtgaaatrga   74580
acaacctgta tcagcacgag ggccaagaat tttcttctga cttgtggata cctccttcct   74640
taggcctctg atcagtctgg acaaatattg ccctgaacgc aaccaagcaa agccactcac   74700
ctggtaaata tttgtatgag ctacagttct ggaagaacaa attccaatat cctgcagtcc   74760
ccttgacatc aaagacccaa ctctcccaga gggcaatggc ttttttgtcc actgagaagc   74820
cagtcagctt craagaaagg tgtctaaatt gggagcaaag gtggcaatga tgtggacttg   74880
actccaaaag aaattttaaa agaaaaagaa gtgcctttgc atttcagggg gtcagtattg   74940 gcattttttaa aatgtcaaca ataaatgtt catatccaca cttgacattc tttccaagga   75000
gaattttcta gaggagacag acctcatcgg tcagctctga tgccctgcag tgcaaaaaga   75060
cattaaaaat gacggtaaag gaccctgca gagaacaact gagtctcttc cttgccctgc   75120
gtctccagat aaaggatgcc ctgcatccat cccctcctgg ctaagagcac agactccaga   75180 ggcttttttcc tctcctggag gttaaagagg catcacatat gtttaaaatc tttaatttat   75240
atgtcacctt tgtccttcct tttaacttca ttttctctt atccagcatt tagggactca   75300
tctttaggga ggttcaaagg aaagctcatg gcctttagaa ctggaagaac catgttccag   75360
```

```
ttgggacttg atcatttact aattgtggga ttacagccaa gtcacttcat ccctctgctg    75420
taaaaaaaaa aaaaaaaaca aaaaaaaaca tatgatgaca tttgtggaat ggctccccaa    75480
gccaaagagg gcaaatattg tcacagctca tttcttctct cagttaatta cttgcgtcct    75540
cggctgcctg gctggcagga caacctatat tcgcctccct cttaaagcct cctgggttgg    75600
ccaggactcc aagcggcttt gtccagaatg agtagggtgg ttggcctggc ctcctcagcc    75660
aatcagagag gactagcatc tgaacactcc tctgtgctat tgcttctagc tgccacatgg    75720
ggacgctgtt gaaacaccgg cctggtgcag ttggccatat gatgcttcag ggtcttctga    75780
gacttcaaga atgtgctcac agggaaggta ttagctctaa acacttgcct ctgctagttt    75840
acatcacaga acagacagac aagactgttt tgctccctca gctctctcct tttcctagct    75900
tcagtcctgg ggagctcaga agctacagtt tgttttttgt tttttgtttt tgttttttc    75960 ttgagggagt cttgctctgt tgcccaatct ggagttcagt ggtgtgatct tggttcactg    76020
caacctccgt ctcccaggtt caagcaattc tcctgcctca gcctcccgag tagctgggac    76080
tacaggtgcc tgccaccatg ccaatctaat ttctgcattt ttagtagagt caggatttca    76140
ccatgttggc caggctggtc ttgaattcct gacctctggt gatcacccac ctcagcctcc    76200
caaagttctg agattatagg cgtaagccac cgcacccggc cagaagccac agtttacaaa    76260
tctgggggat ttggggcatg ggaacagaaa cagaagagtc ccaatgaaag gaagatacca    76320
gctgagctgc ccactctccc agctgcagtt ctcctgccca cagcaggccc tagctgggac    76380
agggaggagc cccagcctta aatcaaattc agaattttgt ttatgacata agactgcaca    76440
tcttaattac tgaattaaga ctatatttc caacctatca tgactatagg tgcagggcaa    76500
gatcaaactc cagtgtatgt ggggcccgca gaagagattt aaagaaacag tgggggcaga    76560
aataaagctg tgtggttatc agatcccatg agtcttgtct gtaaggatga tggttacagt    76620
cgggatgctc cagagtgcaa agccacatct caaccagagt tagtaacaag ggagagttta    76680
ctggttcatg tgaggaagag agaggaaggg gagggctagc caagggctg gatgcaggaa    76740 ggagggtccc cagggttctc tgtccccctc ctgtcttcca tctctgcctc tctcagcagg    76800
ttggcctaat ttcctccgac tgcagagaag cacacaagct gtggcacctg gtgctcagac    76860
tcacactgca acacttccac cagtagatgg cagagaggta cttttcctgcc tgttcagcca    76920 ngaaaatccc aggggatggc tctgactagc ctaagtcagg aacctgctgt gggcaatcac    76980
tgtagcatta agatgggggc cagtgatgga gccggtctgc agcacatgct cagcaaaaga    77040
caaaacccgc ctgttttaga tcactccggc tgcatcacag agtgtggatt gaacaggcac    77100
agaactggag gcagagaaac aagttaggca gctgcaggca taatccaggc aggagatgac    77160
agtatttgaa agaaggagtg ggagcaagtc tggagagaag tcgatggatc caagagattt    77220
ttagaaggta gaatgtgcag aacttaatta gttggtgcag tgggttgaat ggtgtctccc    77280
taaaagatat gttcacctgg aacctcagca tgtgaccttta tttggaataa gggctcttgc    77340
agaagtaagt aaggtgagaa tcttgaggtg agatcgtcct ggattacagt ggaccttgta    77400
tccaatggca aatgtcctta taagagacag aaaaggaaaa gaaagagaca cagggaagaa    77460
gatgtgaaga tggaggcagg gattggagtg atgcagcctc aagccgcaga atgcctggag    77520
ccaccgagtt tgggagagg caagaaaagg tcctcccccta gagccttcac agggagtagc    77580
gtcctgccaa cgctttgatt ttgagctggt ctccagaact aagagagaat agatatctgt    77640
ttttctaatc caccaagttt gtggttattt tgatgcaggg caggcaagcc cccaaattgg    77700
gttgtagcct gagagggttc ttgggttcat tcaggaagga attcaagggc aagctggtgg    77760
```

-continued

| | |
|---|---|
| tattagacag caacttctgt tgaagcagca gtggacagca gcagcagagg tcctgctctt | 77820 |
| tgcagagcag ggctacccca taggcagtgt gcccagagta gcagctcgaa ggcagttctg | 77880 |
| tagtcctatt tacacccact tttaattata tgcaaattaa ggggcagatt atgcagaaaa | 77940 |
| ttttagaaaa agagtgctaa tttccaggtt gtcgggttgt tgccatggaa aggggccgca | 78000 |
| acttccggtg aactccatag tatgtggcac acactggtgg gcgtgtccca tggaaaggtg | 78060 |
| cttccgccct gtacctgttt tagctagtcc ttaatatggt ccagtatccg cgccctgcct | 78120 |
| ttggagtcaa gttcaacttc ctacctcaat tgatgatagc agtttctgaa aactaacaca | 78180 |
| tgtagatata aatataagtc cttaagtcta tcattattat gcatatccta taggggagtc | 78240 |
| atcgcgaatg aaactgaact tattgtggtt cattcattca gatatttatt taaaaatatt | 78300 |
| tattaaagct tactgtctgc cagtccgata ctgcactagg taagtgctgg ggttacaaac | 78360 |
| agaacaagat agacagatta gttgcccgca tggaacttat atctagtggg aagagaagca | 78420 |
| aaaaaaagt aagcaagcaa taaacagtaa aaaaaaaat actgggattt gagccataaa | 78480 |
| aaagaaata agatgcagaa atcagcaata aggaggttgg ggagaagatc cttctttaga | 78540 |
| aagaattgcc agagaaggtg gttgggatag gcagaaaaaa tagtaatatt cctcttttat | 78600 |
| cttcacctat attagatgat caatagatat ttcctgagaa atgaaggact gagtatatta | 78660 |
| taagaaggta tgattaaaaa caatcaccag aatgaatggc taacaagcac atgaaaagat | 78720 |
| gctcagaatc attagtaatg aaagaaacac aaattaaacc acaatgagat accacttcac | 78780 |
| acataaaaag gaattaacac ttgctggtga ggatgtgggg aaatgtcata tttccccaca | 78840 |
| gcagccatag tacactgctg gtgggaatat aatatgatgc atctgctatg aagagaata | 78900 |
| tagtggctct tcaaaacgtt aatcctagaa agcctggca tggtggctcc cgcctataat | 78960 |
| tccagcactt cgagaggcca aggtgagagg actgtttgag cccaggagtt tgagagcagc | 79020 |
| cttggtaaca tagcaagacc ctgtctctat aaaaatcaaa taaaaataa atagaggaaa | 79080 |
| agcacattaa tcatagaact gccatatcca ccacttccac tccttggtat ataccccaaa | 79140 |
| gaactgaaaa cagctattca aagaaatact tgcacatgag tgttcagatt attaacggaa | 79200 |
| accaaaaggt ggaaataacc cacatgtcta ccaatggatg aatcaataaa caacacatgg | 79260 |
| tctatccata cagtagaata ttgttgagcc ataaaaagga gtgaagtgct ggtacattgc | 79320 |
| cagaacatca aagacccttg aaaacattat gctaagtgaa ataagccaga tgcgaaagga | 79380 |
| catgaattat atgatttcat tgatataaaa tgtccagaaa aggtaaaaaa tatccattga | 79440 |
| gaccaaaagc agattgtggt tgccccggac taaagaaaga gtaattactt aattttcctg | 79500 |
| ggggtttcct cttggcatga tgttctgtat acaggacata caaaaagcct ttatttttta | 79560 |
| ttcttagcaa atacttaatt agtactcacc atgagctggg catgttctaa gtcactttcc | 79620 |
| aattactaac aaatcactta attatattga cacaaaaaga atgggcataa tgcataaagc | 79680 |
| aaatacgaac ataaaaaaga aatctcccta ttaatatcat ttatgttgaa ttcaatgcag | 79740 |
| ggagcattta aataagataa agggagatac ttcataatcc acactggtca gctaacatca | 79800 |
| tgactatcta tgcagaagat aaaccagcat caaaactcat aaagaaaaat ttatagagag | 79860 |
| taagaaaaaa atgaagaaac agtttagagg taggtaattt gaatttactg ttcggtgcat | 79920 |
| aaaagaacaa ataggccaga cgtggtggct caggcctgtg gtcccagcac ttcggggagc | 79980 |
| cgaggcaggc agatctcgag gtcaggagtt cgcgatcagc ctgaccaaca tggtgaaacc | 80040 |
| tgtctctact aaaaatacaa aaaattagct gagtgtggtg gcgtgcactg taatcccagc | 80100 |

```
tactcaggag gctgaggcag gagaatcgct tgaacctggg aggcaggctg ggcgcagtga    80160
ctcacgtccg taatcccagc actttgggag gccgaggcgg gtggatcatg aggtcaggag    80220
atcgagacca tcctggctaa cacggtgaaa cctcgtttct actaaaaaaa tacaaaaaaa    80280
ttaaccaggc atggtggtgg gcacctgtag tcccagctac tcgggaggct gaggcaggag    80340
aatggcgtga acccgggagg aagagcttgc agtgagccga gattgcgcca ctgaactcca    80400
gcctgggtga cagagcaaga ctctgtctca aaaaaaaaa aaaaaaaaa gaaagaaaat     80460 acaggccaca cagatgggga gatgataatt gcaagttata tatttgataa aggactttca    80520
ttcagaatat atgaaatagt cttacaattt aataaaagag gacaaacaac ccagtaaaat    80580
gtaggaaaaa tatttgaaca gatgtttcac caaggaaaaa atacaaatgg ctaatcagca    80640
catgaaaaga tgctcaacat catttagtca ttaaggaaat acgaactaaa accaccataa    80700
tatatcacta cacacctgcc agaatggcta taattttaaa aaatggaca atactgagtg     80760 ctggtaagga tgtggaaaaa cagaaactct catccttgc cagtggcaat gttaaatgat     80820
acagctattc tggaaaacag tttggcattt tcttaaaaat ttaaacttat tatatgaccc    80880
aacaattcca ctcctaggta tctacccaag aaaaataaaa atacatgtcc acacaagggg    80940
acttgtgcat aatgttcata tcagccctat ttgtaataac accaaattgg aaggaatcca    81000
aatgtccatt aactatgaat ggaaaaccaa cattcttaca ataattcaa caataaacct     81060 tcatgaacct tagaaacatt attctgagtg aaagaaacca gacacagaag accacaaggt    81120
gtaggactgt atttatttga catttctaga gaaagcaaaa ctgtagagac agcagatcag    81180
tgactgccag gggctagaga cggaggcaag ggttgataca agcaggcagg aggttgcttt    81240
ctgggctgat ggaaatgttc ttatgctgga ttgtggtaat ggttcacaac tgtataaatt    81300
aacaaaaaat tatcagacta tacccttaca atggtatgta catttcatcc aagtaacgct    81360
gctttaaaat ttgaaattaa gcacctaatg atattaagaa atgaataaca aaataaaccc    81420
aaagaaagca gggggaaaa aaagcaattg gaaaagatga gagcaaaaat aatgaaaaaa     81480
aaaacatcta taatacatct agcggttggt tncttgaaga aaaagaaaga aagaaatgaa    81540
aaaatcatta actatcctaa taaagaaaca aaggagaaag aacaaatata caaaataaga    81600
attgtgaatg aaataattgt agacacagag gatatcaaat gagtgactcc tcaatccctc    81660
tgcaaataga ttcaaaatct tgaccaaatg gatgattttc taggaaaata taattacca     81720 aaactgacca ccaaagagat tttaaaaatc agaaaatatc gtttatcaca gagatggtaa    81780
aaaccttgat aaaaagtcat ttacccagag aagcatctgg ttccaacagc tttgcaagtg    81840
catcctatta aaactttatt gattggcaaa cgctaatttt ttttaatttt tatttttaat    81900
tatactttaa gttctagggt acatgtgtac aacgtgcagt tttgttacat atgtatacgt    81960
gtgccatgtt ggtgtactgc acccattaac tcgtcattta cattaggtat atctcctaat    82020
gctatccctt cccctcccc tctccccacg acaggcccca gtgtgtgatg ttccccactc     82080
tgtgttcaag tgttctcatt gttcaattcc cacctatgag tgagaacatg cggtgtttgg    82140
tcttctgtcc tttcaatagt ttgctcagaa tgatggtttc cagctgcatc catatcccta    82200
caaaggacat gaactcatcc ttttttatgg ctgcttagta ttccacggtg tatatgtgcc    82260
acattttctt aatccagtct atcattgctg gacatttggg ttggtccaa gtctttgcta     82320 ttgttaatag tgccgcaata aacatacatg tgcatgtgtc tttgtaacag catgatttat    82380
aatccttggg gtatataccc tgtaatggga cggctgggtc aaatggtatt tctagttcta    82440
gatccttgag gaattgccac actgtcttcc acaatggttg aactacttta cagtcccacc    82500
```

```
aacagtgtaa aagtgttcct atttctccac atcctctcca acatctgttg tttcctgact    82560
tttaatgatc gcccttctaa ctggtgtgaa atggtatctc attgtggttt tgatttgcat    82620
ttctctgatg gccattgatg atgagcgttt tttcatgtgt ctgttggctg caaaaatgtc    82680
ttcttttgaa aagtgtctgt tcatatcctt tgcccacttt ttgatggggt tgtttgattt    82740
ttttcttgta aatttgttta agttctttgt agattctgga tattagccct ttgtcaggtg    82800
ggtagattgc aaaaattttc acccattctg taggttgcct gttcactctg atggtagttt    82860
cttttgctgt gcagaagctc tttagtttaa ttagatccca tttgtcaatt ttggcttttg    82920
ctgccattgc ttttggtgtt ttagacgtga agtccttgcc catgcctatg tcctgaatgg    82980
tattgcctag gttttcttct aggttttagg tcggacattt aagtctttaa tccgtcttga    83040
attaattttt gtataaggtg taaagaaggg atccaatttc agcttttttac atatggctag   83100 ccagttttcc caacaccatt tattaaatag ggaatccttt ccccatttct tgttttttgtc   83160 aggtttgtca aagatcaggt ggttgtagat gtgtggtatt acttccaagg gctctgttct    83220
gttccattgg ttctgttctg tctctgtttt cgtaccagta ccatgctgtt ttggttactg    83280
tagccttgta gtatagtttg aagtcaggta gcatgatgcc tccagctttg ttcttttggc    83340
ttagaattgt cttggcaatg cgggctcttt tttggttcca tatggacgtt aaagtagttt    83400
tttccaattc tgtgaagaaa gtcattggta gcttgatggg gatgccactg aatctataaa    83460
ttaccttggg cagtatggcc attggcaaac actaatgttt ttaaactgtt ctagagagca    83520
tggagaaagg agaaaacctt ccaaattatt cctgtgaagc ttgcatgtca atgattccat    83580
aacaataact atagaatcaa ataaccacaa taaagaaaa acacagacca actccactta    83640
tggatataga tgtaaatatt ctaaatacaa tattagctga tagatctaac actgcattaa    83700
aagatttgtg gaaggagttg ttcaatatta ggaaatccac tctgtgatta tctcaagtta    83760
gcaattagat gtatattcaa tgctgaaata acagaagcac cccagtttag tcagaaataa    83820
gacccaatta cccattatca ccaccaccat ttagtattgc actggggaat taccaattca    83880
gttagacaag agtgggggaag aggtacaaaa actagaaaga aggtggcaaa aacaatcatt   83940
gactgtatga ttggaaaaaa taagagaatc aattgcaaaa ccattagaaa gagcaggata    84000
attcaggaag ctcaggggggc acaaaataaa tgttttttaca aaacaatatc caagaatcta   84060
tattaacaac aatatctttg agatataatt gaatagaaga ttccatttac aataggaaac    84120
cccaaagata gaacacccaa gagttgcaca aaatttacac aaagaaaatc taaacaacag    84180
agggacaaaa cggaagattt gactacatgc aagtatattt cctagtcttg ggtagaaaga    84240
ctcatctgca taaagatgac aatccttcct gaattaatct ataaatttag tataattcca    84300
atggaaattt cccttgtttt gttgttgttg tgctgttttt gttttgtttt ccagactaca    84360
ctgaatgcca aatattccat ttagtgattt tcttcttccc ttttcctttc taatgacata    84420
ttttgtgctt ttcagacctg cctttctttc tctcggcacc aatgaataaa gttccagctt    84480
taaggcttga aaaatcacag caaagttgca gcaaaattaa aaggaaaaaa atgttctttt    84540
tttttcctgc agctgcagag agtggcagat agcatcctgc gtgataaacg cctattcttg    84600
gctaggcgca gtggctcacg tctgtaatct cagcaacttg ggaggccaag gcaggcaggt    84660
cacctgaggt caggagttcg aggccagcct ggccaacaag gtgaaacccc gtctctacta    84720
aaaatacaaa aattagttgg gtggtggcgc acacctgtaa tcccacctac ttgggaggct    84780
gaggcaggag aattgcttga acctgggacg tggaggttgc agtgagctga gatagtgcca    84840
```

```
ctgcactcca gcctgggtga aaagagtgag actctatctc aaaacaaaca aacaaacaaa   84900
cacctatcct tgcctatgtc attttaacaa aggaggaagt aaatcccctg gatttcagag   84960
gctgatgctc tgcccaagaa aagcaaccct aacttcccca aaggctaaaa ttcagactga   85020
ttggctctgg cagagatatt taaattgata cctctgtttc ctcaaaggta taagcctttg   85080
cgaactttct ttggtttctc tcttctctca caggaggcag gggataaaca aatatgttag   85140
atttcttatt taaacaaaga gcttgagggt tttgcctcat cgaaattaac agagacaagt   85200
tgatgctaat attttttatgg aaaatcgaat atgcaaaaat agccaaggaa attccaggga   85260
aaaagtaatg aaagaaaata tcaccaaaag atgttaaaac attttggaaa gccacagaaa   85320
ttaaaagtgt ttgatcctag catataaaca agcagacaag gggctgggca tggtgactca   85380
tgcctgtaat cccagcactt tgtgaggccg aggctggtgg atcacccgag gtcaggagtt   85440
cgagaccagc ctggccaaca tggtgaaacc tcgtctgtac taaaaataca aaaattagcc   85500
aggcatggtg gcacgcacct gtagtcccag ctacttggca ggccgaggca ggagaattgc   85560
tggaccctgg gaagcagagg ttgcagtaag ccgagattgc accactgcac tccatcctgg   85620
gcgacagagc aagactctat ctcaaaatta aaataaacaa acaaacaaat aaataaataa   85680
acaggcagat agatcagtgg aacagaataa aatccagaaa tagactgaaa acattcagga   85740
aaacagtata aaataaaggg gacatttcaa atcaatggag aaaagattag ttatctcaga   85800
aatgaatggg acgattgagt agactgggaa agagtaaaac tggagctcta cacacaccaa   85860
aatacattcc agatggggct aagatttttat atatctatat atgtttaaat aaagccatga   85920
aagaactaga gcaaacatga gagatttatt tttataatcc cagacggtgg caatctttcc   85980
aagtgtggca caaagtcag aaatcattaa aaaaagactg ataaatccaa ctacacaaag   86040
ttagacattt ctttatggca aaaatgcta tcaaaaagtc aagagatcaa tgataatggg   86100
ggaaacattt gtaacacata caataagctg tccaattttt taatagtcaa agactttaac   86160
attaagaaac agaccagctg gctgggcatg gtggctcgag gctggggat cacttgaggt   86220 caggagttca agatcagtct ggccaacatg gcaaaacccc gtctctacca aaaatacaaa   86280
aattagctgg gcatggtggg gcatggtggt gcatgccagt aatcccagct actcaggagg   86340 ttcttctgc ttctcagctt gcagacagcc tattgtggga ccttatgatt gtgtgagtta   86400
atacttaata aactcctgtt tatattatgt gtgtgtgtgt gtatatatat gtgtgtgtgt   86460
gtgtgtgtgt atacacacat atactggaat atatgtatat acatatatac atatatacac   86520
atacatatat atacacatat acatatatac acatatatat acacatatac atatatacat   86580
atatacacgt atacatatat acatatatac acatatacat aaatacatat atacacatat   86640
atatacatat actatatata tacatataca tatattcatt ccattagttc tgtccctcta   86700
gagaaccctg atgaatacag tgggctacac acctattgga atggccaaaa cccagaacac   86760
tgacaacacc aaatgctggt aaggatgtgg cgttttttat ccgcattcat tgctgatggt   86820
aatgcaaaat agtgcagcca gtttggaaca cagtttggca gctctttaca aaacggcgtg   86880
tactcttacc atacgatcca gaactgtat tcctaggtat ctacccaaag gagttgaaaa   86940
cttgtaacca cacaaaaact tgcacacaga tgctcatagc aagctttatt tattattgcc   87000
caaacttgga agcaaacaag atgtccatca gtaggtgaat ggataaataa actgtggtgt   87060
atccacacag tagaatatta ttcagtgcta aaagaaatg agctatcaag acatgaaaag   87120
acatggagga aactgaaatg catatgactg agtgaaagaa gccctatga aaagctacat   87180 actgtatgac tctaactatg tgacattctg aaaaggcaa aactatggtg aaaacatcag   87240
```

```
tggttgccag cagttgagac gggtgggggg aagataacca ggtagagcat agaggacttt   87300
aagggcagcg aaaatgctct gtatattact acgatggtgg atacatgtca ttatacagca   87360
ggtccttgga tgacactatc tcattcaaca tcattttgct ataaagttga tgagaaaaaa   87420
aagtcaattc ctagccaggc cactgtctct gtggagggtg tgcgttctcc ccatgtctgt   87480
gtgggtttcc tctgggtcct ccagtttcct cccacatccc aaagctatgc acggtaggtg   87540
aactggcatg tctacatggt cccagtgtga gcgagtgtgg aagtgggtga gtgtgcccta   87600
tgatggaaga ggaccctgtc cagggttggt gtctgccttg accctgtgcc tctgggatgg   87660
gctctgccat ccacagctct gaagtggaat aagccagtca ataatattct cgcttgtttt   87720
ttgttgttgt tgttgtttgt ttgttttttgt gacagagtct cactctgttg cccaggctaa   87780
agtgcagtgg cactaactcg gctcactgca acctccacct ccaggttca  agtgattcct   87840 gtgtctcagc ctactgagta gctgggacta caggcatgcg ccaccatgcc cagctaattt   87900 ttgtatttttt agtagaatca ggattttgcc acgttggcca ggctggtctt gaactcttga   87960
cctcaggtga tctgcctgcc tcagcctccc aaagtgctgg gattacaggc gtgagccacc   88020
gtgctcagct ttcacttgtt tgtattaatc tttcctaaat gtatgtatgg ctcacattta   88080
tttcaatgtt tagtattaga agtgtttgag gtctttgtaa gtttggtgat gttttgtgac   88140
cagaaacagg ccataggaac ttaactcttg tttatattaa ttagcttatg gtaaaattgg   88200
ataaatgttt tataagagac atgaaagggc atacagacac acaggagaga aggccacgtg   88260
aagatggagg tggaggagac agtgatgcag ccacaagcca agggatgcaa gcggccacct   88320
gcagttgaga gaggcaggaa ggatcctcag aaggcatgga gcctacgagg aagcctggcc   88380
ctgctggtac cttaattttg gacttccagc ctccagaacc atgagagatt acatttctgt   88440
tgtttgaagc cactgatttt tgtggtcatt ggttatggca gccacaggaa ataagataat   88500
cacccactta attttcmtag aaaagctgtg ttttgaaagt cctcttgaag cctgggttcc   88560
tctctctgca tctcccagtt ttccctcaaa gcttgtggat tctccattcc tcacattaac   88620
tcaggccttt cattgccaag tgaccycgag tcctgccttc gcgggtgctg ggggagcctt   88680
cctgacccac tggaagtgga cctgcccatc tccttgctgt gaaactncat gaggggcttt   88740
gtgtctgagg attgtctggc gtgaggggag agacaccacg tggggacaga ggagtggatg   88800
agcaggccgg ggcatgacgg ggccgtgaca gggacctggc cttccattct gtggaagcct   88860
gagacaagca gcaacttctc tcattcctcc tctctatgac aagacaggaa ctgggacact   88920
caccttacta ccctaattcg ctgagcctcg gaagaaaagc agcttagatt tttaatccca   88980
tccaagatgg aggccctcct gctcctgctg ccttgttctc acccccttc  gtgatgtgcg   89040 aggccatcgg aaggtgtgga atttctccac tgattcctct cattgtccct ttctccctac   89100
tcctggggag gctgcaatgg tgacctcatc caccttcaga ggcaggtgct ggaggaggaa   89160
aggatgtggg agttcaagcc ggctgcagag gcccaagagc ccagatggtg tccttccagc   89220
aaactggaga ggcactcctc ctaccaggca gccactgccc cactccaggg ccctggctc    89280 agctagggaa gtggggctgg gtttcacccc ctgctcatcc cctaaggccc agtgctggac   89340
tcagtgcagc acctgcccag ccatctctag cagcggcata agcataaaa  tcaaggccaa   89400 tgttacgtgc tgccttgaca tgtggtaaaa tgtgaagggc ctcaagtggc ctaaatgcaa   89460
gctcctgtcc cacctctgct cccataaata gggtctccca gctgggcaac ccttctyatc   89520
ccagggacca ggtaccaccc ctgtttgttg ccaagtagca ggcttcagtt ccctgccagt   89580
```

```
ctgcggaatt atttaacaac ctcatgaaga aaccaggggc cactccaccc tctgtattag    89640
cctgttctca ggcagctaat aaagataccc aagactgggg aatttataaa gaaaagaagt    89700
ttaattgact cacagttcca catggcttgg gaggcctcag aaaacctaca atcatggtag    89760
aaggggaggc aaacatgtcc tccttcacgt ggcagcagga aggagaagtg ctgagcaaaa    89820
gggggaaaag tcccttataa atccatcaga tctcatgaga attcactcac tgtcatgaga    89880
acagcatgga ggtaaccccc acatgattca atcacctccc actgggtccc tcccacgaca    89940
tgtgggatt atgggaatta caattcaaga tgagatgtgg aagggggtcac ggccaaacca    90000
tatcactctt gttactacca aacctgctgt ccaacaaccc tgctgttcac tctgctcttg    90060
agcaccacct catgtggccc tgcatagcct gcagtggccc ttcccctggg ctacgagtat    90120
atgtgactag aaaattgccg tgggtctcac ctatccagtg ttgggtgttg tgtgtccagc    90180
cctagagtgg gactccttcc ctcacgaatg gggtgaatag aaggtgataa aaagatctga    90240
gtctagggat acctaggagg tggaatctct tctccatgca tagcatgagt gatcacaggc    90300
ctgaaaccaa aagggactta ggtctggggg agagattatt ttccaggtgc tgaatattcc    90360
tgggataggg gagggagcta aacaggttcc tgcccaaagg aagtgagaag ggggtcctag    90420
caacttctca gggatttaga gctgtgactc cagggccttt gttcagagga gctaccttgc    90480
aaggaacttc tagaagaatg cttctctttc tcagcatcca tcctcccatt tcatagtcgt    90540
gcccacgatg ggccccgtct ccctgaactt gatggctgaa tagaagtgta gcctcccagg    90600
ggcatctaaa ggcactcaga gccccttacc cagccccagc aggcacctgc ctggctgccc    90660
ggtcctcagg gttccctgtg cattgagcaa tatcctcaaa gtgaccacca gggggcagca    90720
gcacccagac tgccttccac tgcacctgca gatcaacaaa ttccagtatt ttgggggaat    90780
atctgtgata acttggctac tgctttactg acctcaggta aatagacaga ccaatgtgct    90840
tgaggagcca attgctttaa atctcctgac tcatttttg tattaagayt tgttttattt    90900
atgcaattat tctgtttact caaagacttt accagaagct gggtgcagtg gctcatgcct    90960
gtaaccccag cactttggga tgccaaggtg agaggatcgt tggagcccag acattggaga    91020
ccagcctggg caacatagtg agaccccatc tctacaaaaa atttaaaaat tagctgggcg    91080
ccactcatgg tggctcaggc ctgtcatccc agaactttgg gaggccaagg caggtggatc    91140
acctgaggac aggagttcga gaccagcctg gtcagcatgg tgaaacccccg tttctactaa    91200
aaatacaaaa attagctggg tgtggcggtg ggcacctgta atcccagcta ctcgggaggc    91260
tgagacagca gaattggttg aatctgggag gcagaggttg cagcgagccg agattacacc    91320
actgcactcc agcctgggca acagagtgaa actcagccct ccatcccgac cccagaaaaa    91380
attacctggg catggtggtt tgagtctata gtcccagcta ctcaggaggc caaggtggga    91440
ggatagcttg agtctgggag ggtgggagtc tggcttgagt ctgggagggc gaggctgcag    91500
tgagctatga ttgcaccact gtactccagc ctgggtgaga gagccagacc ctatctcaaa    91560
aaaaaaaaaa aaaagtacca gcccctatct acccattcat agctttatgt ccatttcttt    91620
tgtcttcaag cactggtakc ctttacttat ctctcctcac ctgatctagt gtttacatct    91680
catttgcgcc catagagaag tcatacactg atgtggattt tagatagggc acgctctcaa    91740
gacagccaca tgtattattc tgtgctcaca cagcctggcc tggagatgca aagattatgg    91800
aatccagaat ctaaatgaga ggatcagatt aatgggatgt tctcacagtg tcaggtgagg    91860
acagcctgat gcagcctttc atcatgaggc tgggacctct gggtcccttg ccccaggac    91920
cacactcgag gacatgcctg ttcctgccaa catggctggg cagagttcct cttttctttc    91980
```

-continued

```
cttttctttt cttttctctt ctcttctctt cttttcttttt ttctttctttt tcctcttttc   92040 cttccttcct tccttcctttt cttctttctt cttctttttct ttttctttctt tttcttttttc   92100 cttctttcta ttttttttttg aaatggagtc ttgctctgtt gcccaggctg gagtgcagtg   92160
gcacactctt ggctcactgc aacctccacc tcccgggttc aagcgattct cccacttcag   92220
gctcccaagt ggctgggatt acaggcaccc accaccacac ccagctaatt tttgtactttt   92280 tagtagaaat ggggtttcgc catgttggcc aggctggtct caaactcctg acctcaggtg   92340
atccacccgc ctaggcctcc caaagtgttg ggattacagg cgtgagccac cacccctag   92400 ccctgagtct gtttatgctt ctgtcaggtg tggcatgggc ctgcctggga gctattctttt   92460 ttctgtaaag cacaggcagt taatcagtgg tctctgggaa gaatccagct cagggttata   92520
tttcgtttga cccactcaag ttttaaaaag taaattagtt gccaatgtgc aaacattaga   92580
agagttcaca gcttctccaa caatacctag aagttcatcc gatggtgccc gcattccctg   92640
ctctgtctag atggtgccca cattccctgc tctgtctaga tggtgccgac atacctgat   92700 ctgtccagac agtgcctaca ttccctgctc catctggatg gtgcccacat tccctgctct   92760
gtccagacgg tgcccacatt ccctgctctg tctggacggt gcccacattc cctgatctgt   92820
ccggacagtg cccacattcc ctcctccgtc cggaaggtgc ccacattccc tgctgtgtct   92880
ggacggtgcc cacatttcct gctccgtcca gacagtgccc acattccctg ctgtgtctag   92940
atggtgccca ttccctgctc tccgtccaga cagtgcccac attccctgct ctgtctagat   93000
ggtgcccaca ttccctgctc cgtccggacg tgcccacat tccctgctcc atccggacg   93060 tgcccacatt ccctgctccg tccggacggt gcccacattc cctgctccgt ccggacggtg   93120
cccacattcc ctgctctgtc cagatggtgc ccacattccc tgctccatct ggacggtgcc   93180
cacattccct cctctgtcta gacagtgccc acattccctg ctccgtccgg acggtgccca   93240
cattccctgc tctgtctgga cggtgctcac attccctgct ctgtctagac agtgcccaca   93300
ttccctgctc catccagacg gtgcccatac tccctgctct gtctagatgg tgtccacatt   93360
ccctgctccg tctagactgt gcccatattc gctgctggct gcaaatgcga ggagttgaca   93420
gcagcctccc ctttacaagg caggaggtgc cactgttcgc cattgtctcc acctagggct   93480
tcacttgctt tctatctgca gacatcagag ggacccacat ctctctgttc tgacacgctg   93540
tgtgttgatg gcagagttta attatccaca tgcaatctta cttttccttat tcccaagtcc   93600 gtggggctgc ctcatcaaag cattgtaaga actgataacc atcttctaga agtatmatag   93660
tgatattaag aacacacatc acagatcata gtaaatggct ttaatttttt arcgaaatct   93720
cactactgca aatgcattgt tgtcctagct aatgaatgca yagagtattg cctgcaaaay   93780
aataattgag attctatttt taagaagctt agaacagtac atggtgcata gcaaagactc   93840
tgtgtatgtg aagccagatt ttaaaatatg gtaacaagtg tctgaaaata tgtggctcaa   93900
tttgtctccc ggttactttt ccctctcccc ctttaaaatg tagaggaagg agaagaagag   93960
ataagaggtt tgtgagtgaa gacaagggcc ctttaaggcc tgggaagact aacgccatag   94020
ggatctccct ctgccttaaa aggcacagga atcttagtgg ggaaaaagaa gtggtgataa   94080
atagccagtc cgtgtgcctg gaatatcaaa gtcagtgcgt gccagggatc acactgcggg   94140
tcacgtgcac tctgggtctc tctctgcaaa cctgccctgc ctcagtctgg gaatatgcaa   94200
ctgcctaaga agggtctggc ttacacaggg gccatgagac gtggcaggca tagctgggct   94260
gctactggtc atgaatcctg gacacggcag gcaaggtgtg gtgtccatat gcattattcg   94320
```

-continued

```
ggtggggcaa agatcacagc tctcactaga cttctcagagg actttgtaac ccaaagaacc    94380
actcatctca aggactgtgg taactcaggg gctgagccat gccagtgttt attatgtgaa     94440
acaaggactg gaacctcaca agaccaagtc tgtccatttg aggatggccc aagatgcaca    94500
cgggctgctt ttatcttatg cgcaggtttt aaaaaaatat gtttcattta aatattccat    94560
actcttcagg aatgcccagg cagctgagct ttcaggatgt cgcattgcag aggactccaa    94620
tgctacatat ggcagctgga gacccttcca aggcaggtgg cagaacggag gccctctcta    94680
tctgctgggg cagccctccg ggtgccccgc tggaaggcag agcagctcca tctctgggtg    94740
ggtgagaggt gctgcatggg ctcactatag tatcccaata ctgtatggca gtaggctgcc    94800
agagtatcct aagctgggtg gcttcaacaa caggtactga ctcacagttc tggaggccaa    94860
aagtttgaat tcaagcaggg ctgtgcttcc tctgaaacct gtgggagagg agccttcctg    94920
gcttcttccc gacttcttgg gatggggatg cgcatccatc ctcggccttc cttggtttgt    94980
ggctgtgtca ctgcaccctc tgcctctgtc acggcatggt gtcctcccta tgcatctgtg    95040
tctgaatttc cctcttccga taaggactcc agtcatattg ggtgagggcc caccccaatg    95100
acctcatctc aactagatca tctgcaaaga ctctatttcc caattaggtc acattgaagg    95160
tacctgtctt tttgggggat acaattcatc tcacaaaacc ggcccatcac ctcaaaagga    95220
cctgccaccc cagtgctatg tgtccctctc tgcccagagc cactccttcc cctggctctc    95280
ggggagtggg ggcacctttc cctgctccca cagtgaccga gcaccttccc cttggtatgc    95340
attctgaagg gggcattttt ttctcctcca tctcagccct gtacaaagca agttctttct    95400
agattgaggt gtgtatgtgt gtctatgtat atgagtgtat gtgcctgtgt gttttcaggg    95460
agatgtgtgc aggatgggtg caagggagga gtggaaggcg gaagggcagg aggaggatag    95520
agccacaaga gtgagcacag aagtgacaag ggcagaatca gtgtgtgctt gtgacaagta    95580
tggaaatgtc atgcctttag gttcagtcct ataaggtagg tgtatcagta agggcattga    95640
ttctgcgacc ttaacagaga tcrgaataac agtggcttaa ggaagagtgg agtggatttc    95700
tctctcctgt aaatctggcc tggtgggtgg taaggaggat ccacgtcgcc caggcccaga    95760
tgtgtgtggc tctttgagtg ccccgttctt tcccagtctc ataactgctc tccacctcct    95820
ccacatccag ccactgggaa gcaggacaaa gttagttaag ggcacgttct tttctttcca    95880
aggattactt ggacattaca gtcttcactt ccatgcctac tggccagggc ttagtcacac    95940
aaccttgcta gctgcaaggg agtctgggaa atgcagctgc tattctcaga ggccatgtcc    96000
tcagggattc tgctaaattt agcaaggcag ggacagatat gggggaacca ctgacagtct    96060
atcacaaaag aacgtgattt tagagaaaca gtgaaacagt gtcattaatc cacccctcac    96120
cccttacaac agcaaaaag aaatccagtg gtatccatca caataaagag tatgagagga     96180
atgtgattag aaaatcaggt tgccaggcag gatgtgtcca gttttagcca gtggtgggt      96240
tcatgggaa ggcttcgtct caggaaggtg tgtgttgggg tgttctatgg ccagatggtt      96300
ttcaacgaca tagcacgacc tgtagctctc caggacccgg gcctggacat aggccttgtc    96360
cttctcttgc caggcatcgg actcgatgta gacgttgaat gggtcgttcg agtgctccag    96420
cttcttggag cggatgtagc tcagcatgat gcccagggtg aagaagccga agaatcccag    96480
taccatgagg acgtagaggg cctccagctt gccgtcactg ctgcgggggg acctgcggc     96540
caggcccgac atgttgccac cctgctgaac tgtctcctgc cacagcttgg tcagaaaggg    96600
cgtcaccgct gtggtgttag acaggatcat cctgggcatt aaggttccac tgctgcagct    96660
caaacttccc aggcacacct cttaaaggaa aaatgcaacc ccaaatcaaa aagtacgtat    96720
```

```
tggccaaaac ccacacgtac gcacacacac gtatacaatt ttaaaatctc aggtgagagg   96780
ggtgagctga cactccacag gccatggcat gtgccatctt gggtctgtgc aatgccttct   96840
cttgatagat gaatggatac attgattccc ttctatttcc atccaccact ccaatctcca   96900
cccctatagg tgaccatcag aatgagcttc tttaatatgc attgctgcat attgtggcgt   96960
atggggttgc atgtgtgcat tttggtttac ctaaatggta tcaggtcatc caactcattc   97020
agtctccttc ttttttcctca tgactgtgct tttgtggctc acttgcggtg ctgggtgtgt   97080
gcattccctt gcttccaatg tttgtataca acccatggtg aacacccact tcttttctct   97140
gccttctccc ccagagatgg acactgctgt ggctgctgac tccataaaca aggggagac   97200 aaatatcccc atccttgacc tcctatggac ctaaaaaaaa tcacgcatct catacaacta   97260
gttcctggcr gcttatgcaa gactagtcag actggttgcc cttggaagca acgtgcaatt   97320
ggtggtctgt ttcaccacag agcatctctc tatgaacagt tacattcatc tgaatgaaaa   97380
atctatgctg tcacgtggtg gacttcagaa tgtctaggga gatttcacag agagctcccc   97440
tcgaagaggc cagtgttgta gcttgtgcta tgttttttccc tccctgccca cacacaggca   97500
cacacacgta cacaatctta aaacctcagg tgagagggt gagctcacat gctccctagt   97560
ccatggtatg tgccgtcttg ggtctacaca atgccctctc ttgattgagc aatggtacat   97620
ggattgcctt ttatttccat tcactactct ctggctatgc agaaagtgac atttttcccta   97680 tcgtttaatc ttgatatcac tgtccctgta tactcagagt gggcctggga attggaaaaa   97740
ttgtctccaa gtagctgtaa gattctgtca gggggtttggt ttgctgtgga aaccccatct   97800
aggtgacctt gagatcattg gtaagctgaa aaaaaacagg tcttgttttt atttatttat   97860
ttatttattt atttaggttt gagcaaatgc cagcctctac ccccagttcc tgctgggaaa   97920
caaaagctcc gaggccaagt tgttgatgtc acattccaaa ctcaagccag aggggccac   97980 tgggagctta tcacacgtaa gtgctcccac tcagttcttt cttttttctgt tttattgaga   98040 cagggtctca ctcttgtcac tcaggctgga gtacagtggc acaatcttgg ctcactgcag   98100
cctcaacctc ctggactcag gtgatcctcc taccctaccc tccagagtag atgggactat   98160
aggtatgcac caccatgact ggctaatttt cgtattttt gcagaggtga ggttgcccta   98220
tgttgccgag gctggtcttg aactcctggg cttacaggat ccgcccacct cggcccccca   98280
aattgctggg attacaggca tgagccaccc tgcttgtccc ctgctcactt cttaggagct   98340
taaagtagct gagtagaaca tggcctggag tagaacatgg cctcgggggg actgttgtaa   98400
ctacaggtga aggatgtatt tgggaagaca gtttatggcc agaatcrcta tggaaagaca   98460
aattccaaca cttgccggga cggcgctgtc tttcccagcc aggatgggga ctgtgacatt   98520
gcacatcatc ttgtgtagga caaataacct cagaaaccta gctcctctcc agcttagacc   98580
cagagctatt tcttcattga attggttttaa ttgtaaaaca taccctgaac ccagcaccag   98640
ctgaagacat ctggcacctt tccgaggccc ctcttcctct acccatctct gaactctggc   98700
tgtgtctcag agttctgtta cctgctctct tctcttccta ctctcctctc tcccagggtg   98760
actgcacctg ctccaggctc acctgcatgg ccatgaccca gggctctctt taagctccag   98820
agccatgcgt ccagtgacct gctaaggaga tggttcccctt tggccatccc caggctcctt   98880
aaagttaaca ctccacccctg tcctgtcaga gactggcccc tgcctcattg agctgagtgg   98940
caacaccact cactccaaaa tctgcatcac tctcactgat gactgcaatc tcatcatggc   99000
agttcccatc ttgaaggcct tccttggctc ctccctgcct tcagggtgaa actcctggtc   99060
```

```
ttctgcatgg atacaggccc taaatttgag agtctatgca tccctctcca attccactgt    99120
tgccactgtg cccagaccct atgctccatg gtccctgctg gccccggagc ctctacacat    99180
tgtgcgtctc cagctcagac tgcgccttct tcttggccca tgaaacttct cagcaatgcc    99240
tactcatgct taaaattcag cccagctctc acctccttcc cgaagcctgc tctgatacay    99300
ggggctggat cagcactgtg cacaccatga cccctgctaa cctcatcatg gtcaggatct    99360
ccaggcccct tatcccatcc ctgccctgcc atccagcctg gtgctgggca cgcaaccaca    99420
caggagctgc ccatgaatgt ttatcgaata gatgccacca gaacttaata ccttttgacc    99480
agtgggcctt gactctttat aacctgctta ctccaatgaa cagatgccaa tgagctgtct    99540
ccgaagctct aactgactcc cttttccaga agggcagtca tctcccaccc tgaaccacag    99600
tctcagaagg caggagtgag gagcagaaag agctcagatt ttgggattcc actgccgcca    99660
caggtttgga ttctagcttt gctacttcct ggccacatga tcctggacag tttccttaga    99720
attgttcagt caagttttttt ttttttttct ttccaaagta gcgagaaaca ccactgacat    99780
ttgcgggctg ttgaatcact gagcaggtgt gtagagtggc tgacagcatg tggcacatgg    99840
caggtgcaca ctcagtggtc ctgggtagga gtttattggt ttttctacct cattaagaaa    99900
ttgctgccca aggatttggg gctttggggg tttaggcttg gctttcctgt ggctgaccat    99960
ggcagctgtc ttctctacgt tgtggagaga tcagacatga atgagaatca aagattgttt   100020
gtggcctttc ctggtttcta ggcttttgag tctgtgcaga gatctgtcag gggttaagct   100080
gcctgggctc aagagattca ggtccttgtt cttgtacaaa actagcattt agccccattc   100140
taaccatcgg ggtaggcagg aattgtttgg taacagatcc aaactcaacg ctcaaccatt   100200
tcttttttaaa tgacccgaaa ccacttatga atgcataaaa ccctgcccca gaaaacagac   100260
agacctggac ctgatactat gatgtaattt ccaaaaaccc agaatgatca caattggcaa   100320
ataattctgc caccaatcac tgttagagag tcttttccaac ttcatgacca tgtgaaggta   100380
gaattatggc aggcgacatt tgaagatcca caagttaatt ggtttaaaac tgataaatcc   100440
atacagcaaa ttaagagtta catctgcaat taattcataa tagtgagttc actgagaagg   100500
cttgttactt agatccagat ggactttctt atgtccaaag aagcaaccaa aaacatctgc   100560
tttgaaaacc tcccaagccc aaaccatcct cagccttgtt ctttagaatg ctttagaatg   100620
accttgttaa aatgcagatt gctcctgtaa tcccagcact ttgggaggcc aaagcaggtg   100680
gatcacttga tgtcaggagt ttgacaccag cctggccaac atactgaaac cccgtctcta   100740
ctaaaaatac aaaaataaga caggcgtggt ggcgggcacc tgtattccca gctatttggg   100800
aggctgaggc aggagaatca cttgaaccca ggaggtggag gttgcagtga gccaagattg   100860
tgccattgca ctcctgcctg ggtgacacag cgagactctg tctcaaaaaa aaatgcagat   100920
tgctgggctc tattttcaga gtttctgatt tggtagaact ggagcgggcc tgggaatctg   100980
cattcctaac acattcccac gtggtgctaa tactgctggt ctgaggccc tgcttggtga   101040
tctattggaa tcaccggggg agcttttaga aaataatggt tcctggatct caccccctaga   101100
gattttaatg tctttggtct gggttcctgc ctgactcaga acttttttag aaaccctccca   101160
aatgatccta atttgtagcc aagattgaga accactgggc tgtggtgtgg gaccctagga   101220
aaatgaccaa tggcctttg tgctgcaggg tacctggaag aattttgcaa aaatatagaa   101280
atatgatctc actgactgtt tttcaaatct tgtttgtttt ttacatttttc tttttttggcc   101340
ttgtttgcct ctgatacagt ctgaaaagaa attgcagaaa gaaactctcc agtcttcagt   101400
gtaacctcag ctgtccccag tctccacacac gctggtgcct tcaattacaa ttctcctgtc   101460
```

```
agagcttaag tccagctaat taactgcctt tcaaatgaca accctatatt tttaaagaat   101520
ttttttaaaa cttcacatgt aatttattgc attgcttttg ctaaatgtcc tccacacccc   101580
caatgcctgc taggctgggt cgccatggta ttttgtgta acgagtctca aaatgagttt    101640
ggcaatgtct ccgtaatagt cagcatggtg taaatgacag tctggatctg catgtcattt   101700
gggattttat atcagattct ctaggttcat ttctatgata cgtgatgcca aagcacccac   101760 atgcccgtg gctgcacttt cagacagttg gactcaaaca gagtgggaga gcaactgatc    101820
caacaatctg aattttcaga aaacggggct ccttagagat gagatggctt gccaaaagta   101880
atctctccta tcagaagtac atatcctcag caaactaacg caggagcaga aaaccaaaca   101940
ccgcatattc tcacttataa gtgggagctg aacagtgaga acacatggac acagggaggg   102000
gaacaacaca cactggggct tgtcggggaa aggtgggtgg ggaagagcat tagggaaaag   102060
agctaatgca cgctgggctt aacacctaga tgatgggttg acaggtgccg caaaccatca   102120
tggcacatat ttatgtctgt aacaaacctg cacatcctgc acatgttccc tggaacttaa   102180
aaaaaaaaaa aaagaaacaa aaacaaccaa ccaaaaatat atctaaaatg tcatctgtta   102240
gcaattgact cacatattat tagtatagaa aagagcaatt cccaggacct tgtacagagg   102300
aagcaggctc aaaacagctg aggaataggc cacttttatc agatagcatt ggatccatgc   102360 acatggggt tggcttctta cctaaatatg ccatcagaaa tcatccttgt tcctgtcccc    102420
tcagcttttg tagcttgcac agtgagtaaa gggatggtgg aggcagaaat ggtaggagcc   102480
agagatgttc aaaatccatc tgatgcttgg cctgtgctga acgttctcaa actgtggcct   102540
tgtcaggccc agaaagtggg gtggattcct ggccgtttct gcttctgcct gggtgtgaga   102600
tgtgaatgct gcccctactg aagggtagtg caatttttt tttttcttaa aagcttagac    102660
ccagagctgc taatctactg gaaatcactc aggacacagg gctctgggca gctgcgctga   102720
gcgagacacc tgcaaatgga gaccaacggg gcctccagca ccctggagtt ccgtaaggcc   102780
cccagctgaa cccaggggag aagagggcag tgggtggcgc ctcgctgctc tgggcacaca   102840
ccacctcttc tgacttctcc cacgtgctcc ggctgtgtcg cctatcagca ctgataacag   102900
cctggaagct ttcagaacag aagctttccc agcatgggaa actctcattc tttcttttt    102960 ttaattttcc aaagccttta tttctaagac caactgtggc ctaccgtgc ataaactggg    103020 caggctgtag acagcaggct tgccaagtaa atactacagc cttcctccca atattgagcc   103080
ctgtcccatt gatcctgcag gggagatgtg tagggcattt gttcacgggg aggccacaag   103140
tttgggcctc tcatcactgt gacctcacac ccctgttgag tgtgtcgtaa acagaggagc   103200
cgttcttcaa gccccctgcc ctgagtgcac ccctctcatt cttttgttat tattagcaaa   103260
tccccccagt tcctgatcat tctttcttaa gcctttagtg actgggtaag gttcttgtgg   103320
ctgactccaa gctttcttct aaaggaata gattctaggg gtgagtagag gagacaggaa    103380
tgtcggagtc agagctcagg aatctggggtt ccagccccag gtcaatccta gataaactag  103440
agggctcctt aacttacttc cctaggttga ctctgggttt ttttatcacg ctcgacagga   103500
ctccttatgc atttcttcga aagagcatcc agtcttaaca tcatcatttg gcctcatttg   103560
gtttaagaag cagaattagg gtaaaagcaa tgatggataa gcctcatttt ggtgaatatg   103620
atcttattga gacaagaatt ctgagtcaat tgtccttgga accaactgtc tattgttttc   103680
atctttatca caacactatg tccaaatttt ggaaacatgt ttccctccta gcagaaaaga   103740
agccacccag ggccaccaga tgcttcccga cacttggctg gctttgtctg gtcttctatc   103800
```

```
cttcccctat ccccagagtc agtgggtact aaggtggcca gggtcgctca aggaatcaga 103860
atgcaaccgt ccagaggccc agaatcagac tgtcctctct gattaggaaa gtgtttcctg 103920
ccacctccca gggggatgtg gggtgtggct tgagtctggt gcttttacca ggagcttccc 103980
agacctctct atgggtgatg gagagagagt ctggggtgtg aaggatggaa atataaacac 104040
tgaatactca gagagtcagg ccagcgagct ggtgaggaga ctccatcaaa ctcaatatga 104100
aaacatgggt gggcgtttgg ggatggataa tgaatgacag ctgaagtcac acatcaggag 104160
ggaaggaagg actctcatct tcagcaaatg acataaatct ggggagcctc agtttcctca 104220
cctgaacagt gagaatgatg gaatctaccc tgagtatata tcccaggtct ttgtgcagca 104280
tggaatcagc ccccagcctt cctagctctt gctttatttt attttatttt agagaccaag 104340
cctcgctctg tcactcaggc tggagtgcag tggcgcgatc ttgacttact acaacctcct 104400
ccgcctcctg ggttcaagtg attctcctgc ctcagcctcc taagtagttg ggtttacagg 104460
tgcatgccac tatgcctggt taattttgt attttagta gagacgggt ttcaccatgt 104520 tgcccaggct caacatgcct gggctgaagc gatccacctg ccttggcctc ccaaagtgct 104580
aggattacag gcgtgagcca ccgtgcctgg cctcttgttt tatgtttgct gttctcgctg 104640
taggtgaggc attcccacca tattcccttg ttaaaatcct actggccctt caaatgccag 104700
ctcatatcca cactgtgtct gaccctgatc cagaatcctc tccccttctt tgacccctg 104760 tatatatctt tcctacagtg ctggtcatat tctaacttct aatcatttgt agacttatct 104820
gggcattttc tcccaggagg tcccaaagga cagagaccat cttgctcacc tttgtcccca 104880
ctccagcacc cagaatgttt caataaggtt ttcctgaatt aagtgggaag caaagtatta 104940
gattcaatac cactacaatg ggaaagtgag tgaataattg ataaagtata ctatgctctg 105000
gaaatagatt attgagtaat cagaggaaaa cctcttgcaa tgtagtatgt ttttatatat 105060
taaattttat attatttatt tatatttata ttattaacat attttgtta ttcattttgt 105120 ttattaagat ttactctata tatatgtg tgtgtgtg cgcgtgtg tgtgtgtaac 105180 ccaccttatt tctaaaaaaa aattttggca gtcagtgact attaatagta gagcacaaac 105240
tcttaacctt tttttcctcc cgctttccca gagtccttat caccttctaa tataataaag 105300
ttttcttaac tgtgatgttg attgttcaac gtttgtcttt cccaccaaaa tgtaagctat 105360
tgcgggcagg gatctttgca tgggttgttc ttcattgcat cccaggccac tagaacagtg 105420
tgtggcatat ggcaggagtg caataaacat tcagcgaatg caggcaggca tgcgtgaacg 105480
catgaataat aagtgttcct ttcaactacc agaaagagcg aaaccacaca ggagctgtct 105540
caccctcaga gatttaagac gacagcaatg agtccctctg atgtcttcta agtgagcttt 105600
attttcaaaa caaatcattt tccaataacc tatcaaaagc aggtcctacc tgaatatcct 105660
tggctatttc ctctggatac agataatgcc ttcctccaat ggatcctcgg ctcacctgat 105720
gattgtgtga aactggccag agaaagcaga gggattttt ctggtgattg gaaatcagag 105780
tcacggctga atttaagcaa ctgtgtgaac tcagcaaagt ccccaccacc tggaccatac 105840
atgacagcta tggttattga caaggtcctt ccttaatgga gctggaacct ccttcttaat 105900
ctaaatgtgg actcaaatga actgtcaatt cacatagagc aatgtgacaa atccgggggg 105960
caaagcatta tgcaatagat tgggcacatg cgcacgtctc tgctacttag tcaacttct 106020 tctaaagttt cccactttc ccattaccac aatcaagatc agatatcagt aatattctcc 106080
gcgtcccatg cccttcctc agggagatgc caaggcccaa gagctggtcc ccccaaaaag 106140
ctgaaggtct ttgaaaaaaa gtggggactc aggtcccgtg agtggttttg attttctttt 106200
```

```
cttttgaaag ttgcatgtaa gtgttttcca aatactatac aagaatgtct ataacttaat   106260
aatggaggaa tgttttcgtt gttctgtgtt ggtgagatgc tttcctatgc gtttgttgta   106320
taagtaagtg agaatggcag aaggaaagga ggggagaggc tgatcatcct atcccgtctc   106380
ccactctggg ggtctcggcg cttccagcct gaagcgcgcc cgctgcgcgt ccggagacgc   106440
aggttccagg agcccccggg ggttgcccga ctaggccact tgcgcccggg aagagggccg   106500
cggaggtggg agaccctaac ttacccgggt ctgagatgcc gagagagccg ggtgtggagc   106560
tgagtgcgcg cctgccgagc gctgaggcca cagacagccc cgccccgggg cggcaccttc   106620
taagggcctg agcgctgcac agggatgggg gcgggcgggg cctcccagag ccgccaggcg   106680
tcccgcccca ctccgcccac acgcacggcc cagcccaggg ttccccggga ccaccccaga   106740
ccagccccgg ccccccgggg tcctccacac tctgcacccc agaccaacac caacgcgcgt   106800
agggaagcgt tttagatcct gtcggagagg ctcaaggccg gcagaaggtt tgcattagga   106860
tcgagaaagc cgaccaacgg acagatctac ctaccttcct gcgggagttt gaggttgcca   106920 gggggaagc cactgcagcc aggagaaagg ccgtctggga accacccac cctcggacgt   106980 gcgggccttc aaatatctct gaacataatc ctccaaagac cgctcaacct ccgctcccga   107040
cgactctttc tagcctcgtc ccgcacccca gctgtggcca cacacctatt aggcaaacat   107100
ttatgaagca cccacttact gggtgtgcag ccctgagctg ggggtgcagc tgtggaccag   107160
acaggagggg gcccgagcg gcagacagtc gctggaggca cccgagcctt ggcgagcaca   107220
ccctaacgtc cttggggcct ttcagcccga gccgtccttg tccagagagc aaaccatgca   107280
atgatgcagg tgacttccca gcaaatttca tagcgttgct caccagcttg gcaggcaaga   107340
ggagaagggg cagtccccaa aagacaatcc catgaacctt ctagggaatg acgtccaggc   107400
tccaggctcc tgctctgcag gcgggtcgca gaggcaggtt cctgacctag gactagaaga   107460
cattctctag ggtcactgcc tccatggtct tccttggcag gtcacttctt cctgggcttc   107520
gacctcggtg ttctcatggg gacgagggtg attggaggcc ctccaagggg tgcaccgatg   107580
tgtcctgtgc accaggcaga accagcattg ccctacagtg tgggtgcaaa atgaacccac   107640
atggccacgt tggaaagtcc tgaaatgttc atagcctatg acatgaaatt gcactgtgtg   107700 aaatctatt attcttttt ttttttctt tttttctga acggagtct caccctgtcg         107760 cccccggctgg agtgcaatgg cacgatctcg gctcactgca acctccacct ccctggttca   107820
agcgattctc ctgcctcagc ctcccgagtt gctgggatta caggcaccgg ccaccatacc   107880
ctgctgattt tttgttatt ttagtagaga cggagtttcg ccatgttggc caggctggtc   107940
tcgaactcct gacttcaggt gatccacccg cctcggcctc ccaaagtgct gggattacag   108000
gtgtgagtca gcgtgcccag actgaaatct atttattcta tggaaaggat cagagctgta   108060 gaaaatcct tatgcatgta aaagttcttt gtgttttac ttgcaataac tagaatctaa       108120
acatccaaaa atagaaaata taggtaatta aattgtagta catatgatat tattctacat   108180
agtagaatat tatgtggagt ccttaaaatg tttacaaata atttataaca acatggggcc   108240
gggcacagtg gcttacacct gtaattccag cactttggga ggccaaggtg ggtgggtcac   108300
ctgaggttag gagttcaaga ccagcctggc caacatggtg aaaccctgtct ctactaaaaa   108360 cacaaaaatt tagctgggcg tggtggtggg cacctgtaat cccagctact tgggagtctg   108420
aggcaagaga ttcacttgaa cccaggaggc ggaggttgca gtgagccaag gtcacgccac   108480
tgcactccag cctgggcgac aagagtgaag ctctgactca aacaaacaa acaaacaaa       108540
```

```
acccaacagg ggagatcttt atattatcat gttacgtgaa aaatacaaaa acagaaaaca   108600
aaacaaaaac cccacaaaac tcaaggcctt aaattgtaaa tatgagatgc caggcattat   108660
tcccaaaatc tataaggaag cacaccaacc accatgttaa cattgtctat tagtggtagg   108720
cctattggag atttattatc ttatttatgc tacttcatgt tttccttcct tttttgtttt   108780
gcaacaactc tgtattagtc tgttctcaca ctgttataaa gaactgcctg aaactgggta   108840
atttataaag gaaaaagtct taattgattc acagttcagc atggctgagg cctcaggaac   108900
ttacaatcat ggccgaaggg gaagcaaaca tgtccttctt tacatggcag caggagagag   108960
aagtgcagag caaagtggaa ggaaaagccc cgtataaaac catcagatct cgtgagaact   109020
cactcattat catgaaaaca gcatggaaga accgcctcca tgatccaatc acttcccaca   109080
aagtccctcc tgcaacatgt ggggattaca atttggatta caattcaaga tgagatttgg   109140
gtggggacac agccaaacca tatcaaactc tatgtacttt aatatttaag gaaaattaca   109200
taaactttat ctgaaaattc cctggattct tctcctcaag gtcatgctgt acatatgcag   109260
gatcctcctg cctacatctc caaatggata atggattgaa gcaaaatgtt tgtcccacca   109320
aacattgatg tgtaaccctt ttagtaacaa ttcatagacc aggtaaacat gtgtggagca   109380
gcccagatca gctggaggga gcattattct catcagagtg tggaacaatg cctacccatc   109440
tgtcagctgg ttatggtgaa gacagtataa atggaagcac tgtcagaaac taaggcttaa   109500
tgtaagtgat gctgttctta tgtctcctct tcctctctat cccacatatg atgaattatt   109560
ttattatgat gatgctgtag ttgttatttt ctatttgaaa tgaaaagaca tgattacaga   109620
tgagaaagag tgtattttgt tatccttgat gcacttgaaa tggtttcctc tttttttttt   109680
cctgttttct tcttcttcct tctctcttca ctctttcatt cttgcctctc tccatttat   109740
aggtatgatt gatcttgaaa taatgatgat aacagaatga tagcccatat agtccttggg   109800
tcacttctgt ctctatttct ctttcttccc tcctcttttt ttcttggtcc ttttgctaga   109860
tgggttgcga gcatggctcc ctgcccctct cagtgggttt atcttcattt tccatgagct   109920
cccacctcac tgcatgtgac atcaaagcca aagctccagc cacttctcat cctttcttag   109980
gaaaatctca agtcttaact tgaaagttga atgtcctgct tttgttccta actctgctca   110040
caggatagtg gaagaagaaa ggctcagcct gttaccagaa agaacagatc tgcagtgtaa   110100
cccatctagg atgaagggtc atgtggacag ttcttcactc ttccctctgg ctgcccttca   110160
gttggtgtcc agatgcccct gtgttagcct gggggcattc cttgcccttt ggccctctt   110220
ttgttgcctt ttttttttctt agacaaggtc taactccgct gcccaggctg gagtgcagtg   110280
gtgcgaccat tgctcattgc aacctcgaac tcctggctca agacattctc ccgctcagc   110340
ctcgtgagta gctggaacta cagttgtaca ccaccatgcc ttggctaatt taaaagtct   110400
ttttgtaggg atgggagtct caggctggtc ttgaacttct ggcctccagt gatcctcctg   110460
ccttggcctc ccaaagtttt gggattacag gcgtgagcca ttgtgccctg cccttgttg   110520
cttttttcact cctttaccct gtggtttcta ctatcctcag ggacaactct cattgccctg   110580
gggcttctgg atcttcagca agacacaccc ctaaaggcaa acaatctttc tttagcagca   110640
gcagagcaca aacggagtgt tgctgtatgc taaaagcata ctatttcccc cccatgagaa   110700
agtctaaggg gtccagggt cctgaagtcc ctatcctgcc cccgccagtg acaggtgatg   110760
gggaacagaa tgctgaaaga gaccccaccc aaccatctgg tgtgtcaaca cccgcccctg   110820
ccggtgctgt ccacaggttg atccccatcc cacatgggtg gcttaacaca ttcatgtctt   110880
ctgagagcca tttgttgctc cccagtctct tctgtcctcc ttctttgacc aacatttccc   110940
```

-continued

```
tgtctgattt gcttggtcac aggtagcctg tgtcagtttc ctcccaggac tctctttgcc 111000
tgggaataag tgctatacat gagaagcatc cctcccaagc gctgtgtgtg gcctcctggc 111060
attctcctaa gacttcctag aggattgctc tggttccaaa aagaaaccag ccacaacctg 111120
tttggagccc tgcaggatgt tccagctcac cgacttcatt ccccactact tgcccctcta 111180
acagagcttc tagaccagca gccaaggtgc ctccattcac tgtacatgac tcacctttcc 111240
cccttctaga cacttcttca cgggtctagc ctctgtttcc agctttacac agcacaggct 111300
gatgcctgcc actgaacggg atccaggact ttttcaaatc tcagatcccc agcaaaggta 111360
tgacaatggg caccctgacc agctctgagc ctctaagcat agggtctatt tgtttaattt 111420
tgaattcact tttaagattt aaaaattgag agctctcatc ttcaacaaaa ttcagggggat 111480 ctagaaacat catgcccact tgtggcagag tagccaactg gcagaaactg atgctgatgc 111540
tgtctgtttc ctacacaaaa tgcaaaccag agtttaccac aggccccgct actccacatt 111600
ctcctccaca aggacactca gcaggctcct gtgctgaacg gcttgcctgg ttctgtaggt 111660
gtagggtttg ttactctgtt ccaggaccta ttttccgcaa agccccttac ctggctgttt 111720
cttcccttgg catacgtgag aactcctttc ctcactgaat tgctttgacc ttgctaatta 111780
gttgtgttgc aagtgctttt tggctgtgtc agacatgtat gttctgttta tcattttaga 111840
gcaatggtta ttaattttt tcagattctt cttgggaatt agagaaaaac ttatgctct 111900 cctccaccat cctgccccca cctaccccaa tgcacacatg tgcaacattt gttctacaat 111960
tcaagagctc tctagacccc tgatatgcta ggcaattcgt ggctgccaca ttaggaaccc 112020
ctgatttagg ggaaggactg ttttctccat tagacaaact caactgtgta gcatcaattt 112080
catgggtcta ctgtgtactg tgcccaaaaa atgccactga atgctgcctg actggtggat 112140
agcaagactg tccattaatg tggtcattta ggttgcctct gcccaggtct tgaggtcatt 112200
ggcactaatt cacaacaccc tcaagtcacc cagggaagat gagacacagt tggctgtaga 112260
cccacagttt gggcattaca gctgcccttg aagttgacaa ataaccacaa ccttcaaatt 112320
gttatgaaaa gagcacaaat ccaattaaga aagcttttcc aaaagaaata acagtgttcc 112380 tacccctct gtcactctcc accccctttt tgtcccagaa taatgttgtg ctgataggaa 112440
catggataaa ttaattacag tctggaatgt tattcatggg taggaaagaa cactaaatct 112500
actcgcacaa tgtttgatat ttaaagataa acattgcctt tatgttttt ttttaaacct 112560 cagtcagcct agtttacgaa gacataggta taatccttt aaatgctgtg gatttttaa 112620 tcgcaaaggt aacaatatgc tgggtgtttt acccagccag agaaccagga gatgcaggaa 112680
tgagattagc atctctttag ttccttgcat atttgatatt attttggtgt acctccaatt 112740
cctgataaca tagaagaact cttgtggttg aagtccctga aatggaagga tattggtaac 112800
cctgaattta aaacaagcac aggcagcctt tgtgggaatg tgtgtgaagg tcaccttcta 112860
gaaacaggac tgtccatagc cattgccatg gtttctgtgt catttcaacc agaaccttag 112920
gcctggaagt ctggatggat gtgggttggc atggtcctct atgggcatta aatgaataaa 112980
tggatatagc agagggagta ccagcatga ctcaaagaag gatgagagga aacatattca 113040
aataaaatct ttgaaaagc aaatttcaaa aaaaatgct taagtataaa atattttgat 113100
gacaaccatg attttcaaat tgaattctta ttctaagtaa tggtctaatc tgaacttaga 113160
cctctttcct taattttttt ctcaataagc ctttggtgtc tagtcagttc aattcagtat 113220
ttactgagtc tctatacaga cagggtataa ggcattaatc aaatgtatgt ccaaaattgc 113280
```

```
ccaccatgca gggcagagct aaaatgccta acacccctcc tctcaccaac acatccccca    113340
cccacatctc caaagacttc ctggcagagg tgatctctgc ctgctgggac agatgtatag    113400
gctccaacag cagcagggtg gcccctctga ccaccacctt gggacccaca ttgctcttag    113460
aactattcct cttttttcat ccttgaagcc cccagcaaag ctcagcctga atcaacttttt    113520 tctaggaatc tgacaagttt ccaggmtgat ttcctgaccc agtcagatcc tcttccatct    113580
ttctttgggt gttcaattttt ctac                                          113604
```

<210> SEQ ID NO 2
<211> LENGTH: 113604
<212> TYPE: DNA
<213> ORGANISM: Human

<400> SEQUENCE: 2

```
tgtcagaaaa agatacaaca tttaataacg atggaatgta aatatcaaat attttttattt     60 acaaacaaat aaaagttttt atatagaact aaaatgattt ctataacacc tgttttcact    120
gttcttcaat atttctcttt taacttttca agatttcct ttttaaaatt ttttttttgta    180 gagatgggat ctcactatgt taacccagtc tggtctcgaa ctcctggcat gtgatcctcc    240
ctccttggcc tcccaaaatg ctgggattac aggcaaaagc caccacgccc agccaagatt    300
ttcttttttt attgtctgta tttaagatat gcaacaagat gttctgacgt acatatgtgg    360
agtgattacc acagacaagc aaattaacat accgttaaca tattcacaca accattaaca    420
tgtccatgtt cgtgtgtgtt ttggggggggg gtatgtgtgg taagagcacc taaaacctac    480
tctcttggca gatttccagt atgcaatgtg tacaatgctt ataaacattt ttctttatta    540
aaacaaaaca aaaaccgcc acatatatgg aaagagctgt gctggatgcc taaggaggaa    600
gcttgatggt tctaagcaaa ggccaaaaag tggtctgatc tatggaaaaa ctggaaagcc    660
ggcaaaattt gctgtgagag cccttttctct gctcccatct gtgctgatct gctttttttcc    720 tacaagagcc cattggcctt ttatagttcc tggggaaaat gaagccccca cggttgtgcc    780
tccttgagtt ccaggacttc cccctctcct tcccatccag ttttaacccc cacacacctg    840
tggcctgcac gctgggggtt cttttctgtt tcttttgatc ctcttcctct ttgaaaatca    900
tctttgtaaa acaaacctaa tacggcacca tttccgtcca gattcatgct ccaggaagaa    960
agggtgctgg aggctacagg ggggcctcac agcccatgtg atctctgtgt tacattcatt   1020
ttccactaac agaaatcaaa gaacatacc tgccattcgg cctgtgacag gggtctttgt   1080
taactttggg tcttgctaaa gttcagtaat gtcagggcaa acagaacaca aggaagctga   1140
gacgttctct ggctttccgt tgcaaactag gcctgttgat gatggtgaca agcttctcaa   1200
tcccagaagc atgaagccag caaggctggg aaagcacctt gggggaaggc tccatcagaa   1260
gagaatcaac tttatcaaaa cttggtttgc tctatcacag cagcggcatt tcagaagcat   1320
cctaccaagt tgcttgtttc attgataaac taaagaaacc ctacatgttt ggagagttct   1380
tggtgaggcc tgttcattgg aagtcgtcat gcttgtgtgt atcttagaga agaagaaaat   1440
tccagtagtt cctcagtcaa atggtgtaat ccactccaga atcattgcca tctcttctaa   1500
tattctgaac caggcacaga gaaagtagaa gctcagtgca tagctaaatg aaattaccag   1560
agattctcaa tgcccccatt tccagctttt cacaaaacca ttgtgctcac attaatagca   1620
tcaaggaaag cttcctactc tgtgagctca attagaaacg tcatgtattg ttaatggttt   1680
tgaaaaggtg aaaactttct tttccagagt cttttttcatc ggaatgataa tcttagtacc   1740
ttgtaaatag atgaggtggt tgatttcatc acagccagaa tctagaatta tcaccattct   1800
```

```
tttgggatac agtgagagct tttttccagc cagacacaga atgggcaata caggtaaggt    1860
ccctgttgtc atggagctca agttctgtta gagacaggaa agaaaaaaac aatcaataaa    1920
acaggaaaac ttcataattc aaagaagcca cgcacagctg tgagactatg cacaggcacc    1980
attcacactg tagactaagt gacagctgcc cccgggttaa gccctgcctt gcctgggcaa    2040
cagtacatgg catccccaca caattcagat aatacaaagt gctatcaggg aaatgtgaag    2100
aaggaagaag ctgtgccaag attgggggaa aagcattaga ggcagagaga gcagcgtatg    2160
caaagatgct gaggcagtcc gtataattgc accatgaaga ggtccctgtc ctaatctctg    2220
gaagctgtga atatgttacc ttacctggta aaatggactt tgcaggtgtg attattaagt    2280
taaggatctt gagatgggaa gatgatcttg gattatccag atgggacaaa tgcaatcaca    2340
aggctcctta taagaagcag gcaggggggct cagggagtgg gagaagatgt gatcacaaaa    2400
gcagaggctg ggccgggtgc ggtggctcat gcctgtaatc ccagcacttt gggaggttga    2460
ggcggacaga tcatttgagg tcacgaattt gagaccagcc tggccaacat agtgaaaccc    2520
catctctact aaaaatatac aaaaattagc ctggcatggt ggcaggcatc tgtagttcca    2580
gctactaggg aggctgaggc aggaggatca cttggaccca ggaggcggag gttgccgtga    2640
gtcaagatcg tgccgctgcg ctccagcctg ggtgacagaa tgagactctg aaaaaaaaaa    2700
agaagaaaga gaaagaagga aagaaagaaa gaaagaagga aggaaggaaa gaaagaagga    2760
aagaaagaaa gaaagagaaa aagaaagaaa aagaaagag aaagaaagaa aaagaaagaa    2820
aagcagaggc tggagggatg ccaggatgcc agggagaggg ccaagagcca agaatgtgg    2880
gtggcctctg gaagctgcaa aaggtaaaga aatggattca cactccctcc tcaacccccca    2940
gagcatccaa aagaaactgg ctctgctgcc atcttgatgt taacccagtg aaatccactt    3000
tggacttctg accccccagaa ctttaagata atattataaa tttgtgttgt ttaagtcact    3060
aagtttgtgg tcatttgtta taacagcaat gggaagctaa tacagattca aagacaaaaa    3120
caaaacaaaa agcagagaag caggatcaga ctatgtgaga agatgagctc gcagaaagga    3180
ccagcggcca gttttccat ggcctggcca gctgcactaa gcattccggg ttttatttc    3240
agggtgaaag gaacccaatg gagagtttca agcagggggaa ttgcgggctg tggtttgtgt    3300
ttccaaaaga tcccactggt ccctcttaga aatatgtgaa tagggacaga gtgcaaagcc    3360
agaggcgtga gcggccagca gtccaggtgt gagctgagaa gtagctgtgc ggggacgtgt    3420
ttggagagtc aaattattac tataataata attattatta tttagagatg gtgtcttgct    3480
ctgtggccca ggctggaatg cagcggcatg atcccggttc acggcaatct ctgcctcccg    3540
ggttcaagcg attctcctgc ctcagccacc caagtagctg ggattacagg cacctgccac    3600
cacacctggc taatttttgt atttttggta gaaacggggt ttcaccatgt tggccaggct    3660
ggtctcgagc tcctgacctc aggtgatcca cctcctcag cctcccaaag tgctgggact    3720
acaggtggga gccactgtgc ccagcctgga gcgtcaaatc aaaacaaaaa aaccaacaga    3780
gcagtaagaa acatatttca atttattacc ttcggggcta ggggaagaga gacaagttct    3840
aagaggcttt tcgtgcaaaa atggaaagaa ctaggtttaa ggcaacagtg agaaatgaca    3900
atgaaaaagg caagcttctg ataacagctg tctgtttggc tggtgagacg gattgtgact    3960
cttcttttgca attggccatt gtactagttt atggcacaaa acccaggca cagttttcaa    4020
agaagttgag atggggtatt aagggtctgg tgggttcgat gtcacccagc acaaactcat    4080
acacccacgt tcaacctgtg cagagtcttt tctttaacag gatgcagagt caacagtatt    4140
```

```
tgctagtgaa ttgggggtgt ggcagggtga ccaaaaaaaa aaaaaaaaaa aagaaatcta    4200
agttaattct ttggttttt ggcttacaca actagaaaga aagtggagtc actttactgt    4260
gataggatag gagtaggttt ggtaggagaa ttgagttatg tttggacatc tgaggttgag    4320
atgcctatta gacatctgag tgaaaatgtc aagtgagcat cttgacattt gattctgaaa    4380
ttcagagaag aggactggac tggagataca catttgcaag tcccctacaa atacatggat    4440
tttaaagaaa tcaactttat tgtggtatag tttcataaa attatacaca cccattttaa    4500
gtgcatggtt caatgagttt tactcaggta accacctaca acaaccaaga tatagaacaa    4560
ttctatcacc ctccaaaatt gtctcttaat cctttgcagt caatcttccc ctcatctggt    4620
catagaaaac tactaatctg ctttctgtca cgagggatgg cttttgtctt tctggaattt    4680
ctagaaatgg aatcaaacag tacaacttct ttgtgtctga cttcttttgc tcatataatc    4740
tttgtgggat tcatccctgt tggtgcatgt atcatttatt tgttcttttt tattgttgag    4800
caatatttca ttgtgtgaat aaaacacaat ttgtttaccc acttatctgt tgagggatat    4860
ttggcttatt tccagttttt agctattttg aataaagctg ctataaacat tcatgagttt    4920
ttgtgtggca tattttgaaa atttctctag gtaaatacct agaaggggca ttgttgggaa    4980
cttttgatct agttaccaaa ctgtttacaa gtggctgtat cattttacat tcctaaggca    5040
atgtatgaaa atccacttag cccacatcct caccaacact tggtgttgtc agtcttttta    5100
aatgtagcca ttctggccag gtatggcggc tcatgcctgt aatcccagca ctttggaagg    5160
ctgaggtggg cagatcaccc tgaggtcagg agtttgagat gagcctggcc aacatggcaa    5220
aaccccgtct ctactaaaaa tacaaaaatt agctgggtat ggtggtgtgc actgtaattc    5280
cagctactct tgttgaggca ggagaatcac ttgaaccctg gacagggagg ttgcagtgag    5340
ccgagatctc accactgcac ttcagtctgg gggacagtga gagattccat ctcaaaaaaa    5400 aaaaaaagt agtcattctg gtgagtgcgt agtggtatct cattgtaatt acaagttata    5460
tttccaatga cgttgagcat ttatgtgctt attgtatata ttttttggta gtgtctgcat    5520
aaacctactg tccattatta ttgagtcaat ttttttcaa atgatgagtt ctttatgtat    5580
tctagatgca aatctgttgt atattctaga tacaaattca tggtggttat tttttcagt    5640 atattacttg ccttttattt ttcttaatta tgttcttcaa ggagtaaaag acttaataa    5700 tgatgaggcc caatatatca atatttcct tttatgatcc atgtgtttca gtctttgttt    5760
cctccatctg cttttaagat tttctcattg cttttgattt taagcatttt atgcaaaggt    5820
gtgactttct ttgaaataat tctctttgag cttttagtt cttgaactca tggcttgatt    5880
tttttaaaaa gcagttttgg aaaaaatctc attcactatt tcttcaaata ttgcttcagc    5940
ttcagccact ttctcctctc tttctgggac tccaactgta cttctgttag tccttttcc    6000 tgtatctctc atacttcntt gggtgtatcc tattattttg ttctgtgctt cactgtagat    6060
attttctgct gactagattt ctaattcact aatcctctct tcagctttgc ctatgctgct    6120
ggtaaatcca tccactaaat tgatacattt aaaaaataga tttctgcgga gattctattt    6180
attcttgggc tgactctgga aatttatatt tttctggcaa attatatatt tcatccaaaa    6240
cttcaaattg tatttccaga gtgacttttt atttagttga ttctatattt atttgttttc    6300
tcttttgttc ctttctgttt ttgttctaaa gtttcattta ttctacattt ttagtttatt    6360
ttttggttct tttgcttttt gagtttaatg agttcctatt attttccttt tatttattt    6420 tatttttag agacagggtt tcactctatc acccagactg gagtgcagtg gcaccataat    6480
agctcagtct aacctagaac tcctgggctc aagcctcttc ccacctcagc ctcctgagta    6540
```

```
gctagggcta cagctatgca ccaccattcc cagataattt taaacaattt cttttttata    6600
gagatagagt ctcagtgtct cactatgtca cccaagctgt tctcaaactc ctggcctcaa    6660
gtgatcctcc tgcctcagcc tcccaaagca gtgggattac aggtataagc caccatgccc    6720
agcctctttt cctttttagtg aattcattta ctgtataaat ttgcctctaa ggttcacatt    6780
gtctgcatcc cagaagtttt caaatatatg gcagttcctt tgtaatttaa tatcttatta    6840
tttatgtgtt ttcctctttta tccatatgtt acgtgatgat atacttattt tttggttttc    6900
agatatatca aggtgtacag actatatttt tgctgattta taattcaact gcattgtagt    6960
aatggaaccc agtctacata aagctgatat ttaaaaattt ggttggactt cttttgtgac    7020
ccagcacatg gtgagttttt aaaaccgttt tatggacact tataaagaat gcacatcatt    7080
tgttggttag gtgtgggttc tctccatcta ttttataaag gtaattaatt ctattactca    7140
attctatatg tttactttttt aaaaaaatct atcagtttct gaaacctaat tcctaccatt    7200
gtgcatgcct caatttcttg taaatctgcc tgtttcactt tgaatatttt gagtccatat    7260
acaagcccat gattttacta tcttcttcgc aggttgtttc ttttatcaaa ttgtagtgac    7320
atttaatatc ctatggatca cctgaaattt cagttttttct tagatgtctg cattttagcc    7380
ttagcttgat atgttttttc atcaccttat tttcaacttt ttatttgttt ttatttttaga   7440
tgtgcatctt tattttgtat tttatttttt gagacagagt cttgctgttt cacccaggct    7500
ggagtgtagc agcgtgatct tggctcactg caacctctgc ctcccaggtt caagtgattc    7560
ttatgcctca gcctcccaag tagctgggat tacaggcata tgccaccatg cctggctgat    7620
tttatatttt ttagtagaga tgaggtttcg ccatgttggc caggtgggtc tcgaactctt    7680
gggttcaagt gatccgcccg tctcgccctc ccgaagtgct gggattacag gtgtgagcca    7740
ccagccccag cctagatgtt tatcttttaa gaagcatata gctagatttt attttgttat    7800
tcagtttaat aatacttctt ttaataggta cttatttttaa aggatattgt gattatagat    7860
atattcagat attatcttag tcattggggc agttatagta aaaattataa actggatgac    7920
ttataaataa caaaaagtta ttgctcatag tttggaggct ggcaggtcca agaccaaggc    7980
actggcagat gcggtgtctg gtgaggtctc cctctttgat tcatagaccg tgccttctag    8040
ctgcgacctc acatggtgga aaggggaagg caacctccct gtagcctctt ttaaagggc    8100
attaatcgca ttcacggggt ctccatcctc ttggcctaac cacctcccaa aagccctacc    8160
ttttagtaat atcacatggg gagttagaat ttcactatat gaattttggg gggacacaaa    8220
catttatgcc acagcagata tctttctacc accttatttg gtgatttctg ggttttgttt    8280
gtttgtttaa gacagagtct cgctctgtcg gccaggctgg agtgcagtgg caccatctcg    8340
gctcaatgca accttcgcct ccccggttca gcgattctc ctgcctcagc tcccaagta     8400
gctgggatta cggacgtgtg ccaccacgcc tggctaattt ttgtattttt agtagagact    8460
gggtttcacc attttggcca ggctggtccc gaactgctga gttcaggtga tccacccgcc    8520
tcggcctccc aaagtctgg gattacaggc gtgagccacc atgtccggct ggtgatttct   8580
gtttaaaagt ttttttcttaa agtgtttttt cccacctagt ttttcattga atgggtaaaa    8640
cattctacat ttgctttttat taaaacaaga atgaatttt gctgcatttc aatttataga   8700
ttttactatc ctacctcgtg ccaggttctg tgctaagtgc tgtatatatc tgtgatcaca    8760
tttaactttt ataacaagcc aaatgagcag gaactcttat ctctatctta cagacgaaga    8820
atccaaagac cagggacagt aagtaatttg ctcacctggt ttgccagcct ccatgacaca    8880
```

```
tcgccgtcca gttctgcctt taattaccaa agcacaacac gctgctttga ttccctctc      8940
ctcggcgcca gaattcaaga gtgaagttaa accgcaaggg ctgagttaga agattggcct    9000
cagttccctg ttcccaccag caggtggcac cgtctcctag cggaattctt acttgaacgt    9060
tttgcttcca tttctgcaga ggcatggtga acacagttac accaccaaag tgttcctcct    9120
ggctgagttt gcctatcttg ttcagtgaag caaacccatg aggacaaatg gtgttaatga    9180
gaagcttttg cggagttaca gagatcctcg tatttcttta aaatacacct aataacgtta    9240
actctgcaat aatttgtaga tcatgttaaa tcttagctat cttcctcttg ccacccagtg    9300
tgcttcaagc cacatggttc agagcaccat ttaatgtgaa actccaattt taaaacaaag    9360
tgaaccttcc ttttacaaaa ccatgagaca agttacagag taatgaccac ccacatgacc    9420
ttgaagtgat tttgagtgag tgagtgtaac ttccgtggct gccatttaaa ttggattcaa    9480
atccaaatgg ctccacctcc atgtcatcag acctcttgtg ccctgattcc cttggctaag    9540
ttcacagtac cttccacatc aggttgtggc aatgattacc tgaggttaat acgataaaag    9600
cacatggtaa gcactcctaa atgatagcca atataaagac tcagttctcc caattccaag    9660
ggtccccacc atgatagaaa aggatctttt ggtaaataga gtatgtttag ctcttgctag    9720
gtctttaaat actttgctgg gggccaggca ccatggctca cacctgtaat cccaccgcct    9780
taggagactg aggctggagg atcctttgcg gccaagagtt tgagaccagc ctgggcaaca    9840
cagcaagacc ctatttctac aaaaataaaa ataaaaatta accaggcttt gtacacactt    9900
gtagtcccat tacttgggag gctgaggcag gaggatccct caagcccaag agttcaaagc    9960
tgtagtgagc tatgattgcg ccactgcact ccagcctggg tgacagagta agactctgtt    10020
tcaaaacaac aacaacaaac aaaaacctca aaacctcttt gttggactta acttccagct    10080
cctccatgta gtaccttagt acccttgcag cccgtttctc ttttacaaga caacaatgtt    10140
gttataaact catttggatg tggtcccgtg gaggagtatt taccagaatc tagcttattt    10200
agcgtcttca gaacacggca cttgcctgga attatactga ccccctcaac ccataccaac    10260
cacccagaga tggctgttct tggctcctct ccctggggcc ctgtccttcc cacatcgtct    10320
tcttcttctt tcttcttctt tcttcttcct tcttcttcct tcttcttcct tcttcttcct    10380
tcttcttcct tcttcctctt cctcttcctc ttcttcttc ttctttcatt gagacagagt    10440
ctcactctgt cacccagcct ggagtgccgt ggtatgattt cagctcactg taacttctgc    10500
cttgtggatt caagtgattc tcctgcctca gcctccagag tagcagggac tacaggtgtg    10560
tgccaccaca cctggctaat ttttacattt ttaagtagag acggggtttc accatgttgg    10620
caaggctggt cttgaactcc tgatctcagg tgatctgccc gcctcagcct cccaaagtgc    10680
tgggattaca ggcgtgagcc accccaccca gcccttccca cgtattctgg cagggaatgc    10740
tgttgtcccc caagcctacc ctaagaggaa gacttcttct ggggaaagat gttcactgta    10800
cccaggcccct gccctggctg gagctggcag gaagggtccc agagcaggaa cttgtgccac    10860
tctgcccaaa gccagagtcc ctgaggcaca caccccatca ggcaccaagg tgaattccaa    10920
ctgccagtta gtatttaact ttccacatac gattagatta aacatgtggg ttcataaaag    10980
cataggattg cagactgcag ttgcaagggc ttagatggtt gtaaggtgaa ggtgcccagc    11040
aggctgaggc ttgtgtgcaa cccagaagag agctcgctaa cgccagcaag aaggttcaga    11100
acagcctggc tttggaaagg aatttcatcc tgcccacaca ctgcataggt aagtcttagc    11160
acacattctt tatttttga ggaattaagt aacaaagtta tctatgtgcc ttttccagaa    11220
aatgataaaa ggaatgattt tcctggtaca tggcctggct cctcatccac tcttccttct    11280
```

```
ttccttcttg tgttttcctt actcatttct ttgttaattg ccttagaatg aaaattttga    11340
gagtttttaa aatggaggat tcatggtaaa cgtaggtaat catattgttt tctcttcttg    11400
atataaaaat gaaagacttt gctgccttt ataggcccag gtgatgtgag cgatctacca    11460
tgtttcaaga aagaaaact ttggggctgg gcgcggtggc tcacgcctgt aatcccagca    11520
ctttgagagg ctgaggcagg cggatcacct gaggtcagga gatcgagacc agcctggcca    11580
acatagtgaa accccatctc tactaaaaat acaaaaaaaa ttagcctggc gtggtggctg    11640
gcgcctgtag tcccagctac tcaggaagct gaggcaggag aacggcatga acccgggagg    11700
tggagcttgc agtgagccga gatcacgcca ctgcactcca gcctgggcga cagagtgaga    11760
ctccatctca aaaaaaaaa aagaaagaa agaaaactc tggactttgg ggtcaaatga    11820
gtgttacttt cctaatagtg tcctgattgc tgttgtcatg aataacacac attcatgaca    11880
ggaatggctg gaattagggg atcattctgt agcctggaga cagggcacaa ctaatgacat    11940
gtgtaagctc aaatcatggt cttgatctta tgtcttgtac ccagttgagc caactggtca    12000
cagcaatgaa aacagtgagt tattggaatg tgtgacctct gctaggacag tcagtgctgg    12060
acactggctt gggtgatgtg agttctagtc caggcactgt ggccaacttg agaggcttgt    12120
gatcttggac aggtgactta agccctctag gctatagtta ttccacctat cagagagcaa    12180
accagcctaa atgatctcca ggggcccagc ctgtgctagg actcagcaag aagcattcac    12240
tggaaatgta ggtcctccta ggttgataca catgaattgc ccatatttga ccatttctaa    12300
cctatataaa tggctatttc atataattcc agagaacata aatggtagtt gtcttagcat    12360
tactaaagta aatgcctatt atgatattct acttaggggt aggataagta tgtataccaa    12420
atatggtttg tttcgatttg attttgaga cagggtctca ctgtcactgc tgagtgcagt    12480
ggtgtgatca tggcttactg cagccttgac ctcccaggtt caagctatcc tcccacctca    12540
gcctcctgag tagctgggac tataggagtg tgccatcaca tccagctatt tttttatgtt    12600
ttgtagaggt ggtgtctcgc tatgttgtcc aggctgatct cgaactcctg ggttcaagcg    12660
atcctcccac ctcggcctcc cgaagtgctg ggattacagg tgtgaaccac tgtgcctggc    12720
ctccaaatat ggttgatgtc tatcagtcag ttaaacagta attctgggaa taaaaaattg    12780
aaatcaaccc acttataatt ggaatgtctt agcataatgt ccttcaacga agctgctttc    12840
acacactgtg atttgttttt ttcctgtggt catggagcag gcatgggcca ctcggccaca    12900
tctcatgcat ccgtattcaa aagccaaatc ccttttggat cctgtttatt tggcctggcc    12960
acgggtgagc acttagacat ttaatcccta taggcccttt catccctgtg attaagtctt    13020
atcaaaaagc acctcctgac cggcttagca gtggggcctt tgttcacatt agaagggttg    13080
aacaaataat gggcagttgg ggctgcttag ctctaaaagg ctggtgaacg ctgccatgcc    13140
tgcacctgga aacaaaccca aatgactcca gtggaattca gcactgaagt ccctcatctc    13200
aaagaccttt tgtggcagag actcttggat gggccttagg ggtcccagga gtcccctgaa    13260
attgaatgta gagcttccta cgtgcatagg tatactttct tggggaaaaa ttaagtcaca    13320
tcattttatt ttacttttcg agggatcttt aacaccgccc ctccccacc cccaattccc    13380
acaccccctta agaataaatt aagaatcact gttctggtag tttccagttg aattccacag    13440
aggaactgtc attcattcac accttcattc aacagatttt tagtaaagat ttgctacgta    13500
cccatcgctg tgtagggtcc cgggattcag agatgagtaa agcaatccct gccttccggg    13560
ggctcaagct ctcctgtcat cgggactcag ttactgaatc tcactaaaca tcctgaaggt    13620
```

```
aggagtttat agagtggttt tgaggatcac atgaataagc acacaataca tgggtaattc    13680
aaaaacgaaa acaaggccgg gcacggtggc tcacgcctgt aatcccagca ctttgggagg    13740
ccaaggtggg cggatcacga ggtcaggaga tcgagaccat cctggctaac atggtgaaac    13800
cccgtctgta ctaaaaatac aaaaaattag ccgggcttcg tggcgggtgc ctgtagaccc    13860
agctactcag gaggctgagg caggagaatg gcgtaaaccc gggaggcaga gcttgcagta    13920
agccgagatc gcgccactgc actccagcct gggcaaaaga gactccatct caaaaaaaaa    13980
aaaaaaaaaa aaaaaaaagg aaaaaaacaa aactaacatg gtcatttgca gaaggggcag    14040
aaaaagggtc tctgcctaga cctggggagg tcagggaaag tactatggat tggtaacaac    14100
cggctgggct tcctacaaga gaaaagact atactcacag agccagaccc catctcaaaa    14160
aaaaaaaaaa aaaaaagtct ggcatggtgg ctcaaacctg taatcccagc accttgggag    14220
gctgaagcag gggatcact tgagcctagg agtttaacaa catagtgaga cctcatcact    14280
acttttttat tttaaaaaag agttaataaa aaataaaatg aaaataaaag ggtaaaagag    14340
ccagtggcaa agtcttgagt ggattaaagc cagctcagct aactttcaca gcagactata    14400
tcattttaaa ggggaaaaag cacatctctg ttacattgct taggaaatat gcttggtata    14460
taccctgggg caatcttatc tatttgttaa gtttccttcc aacccactag cctgtgtggc    14520
caggagaggg agacaaagat cttagagctc tctaaataat agaacttaaa acatcagaca    14580
gagaagagta tattatcttg gtgatggtaa ttctcaatga ggaaaatcct ggggagggat    14640
gttctgtggg agaatgcctg caagtttatt tgtttagtag gtttgattat tcagctgatt    14700
gaaattcctt tcccagatgg ggagatctga ttctcttttc atgaaggaaa gaaaagtcac    14760
atgctaaaga gacgggcatg tctttagaac ggcagcaggc aaacccactg ctgggatcct    14820
ggggctttta ctagtggcta gtcacaggtt tacctcctgc ctgtgctcct tctagctgtg    14880
ttgaaaccca cttgccccat ctatgaaccg tgttcagctc cattttctga gccccttat    14940 cttttttgtcc atacctgttg caactctttg cacgttgcat tgtcattgat ttggtctctc    15000
ccattcaact gagcctctca cagagttcct gtcacctctg cagtttcatc gcctagcata    15060
gtacctggca ctttaattca tgcatcaaat gtccattgag tgccttctat gtgttagaca    15120
tctgctatac cgagctagac aaagttggca gacatgacag ccgagtggaa agatgagcc    15180 cctaaaccaa taatcacaca cacacacaca cacacacaca cacacaatat atatatatat    15240
atatatatat atatatatgt atgttatata tatgtatgtt atatatatgt atgtatgtat    15300
gtattaaaaa atcttggccg ggagcggtgg ctcacacctg taatctcagc actttgggag    15360
gccgaggcag gtggatcacg aggtcacgag atcgagacca tcctggctaa catggcgaaa    15420
ccccgtctct actaaaaata caaaacatta gccaggcgta gtggcggttg cctgtagtcc    15480
cagctacttg ggaggctgag acaggagaat cacttgaacc tgggaggcag aggttgcagt    15540
gagccaagat cgcgccactg cactccagcc tgggtgacag agcgagactc cgtctcaaaa    15600
aaacaaaaaa ttttgccctt gcaatcgttt gccttgatgt tatgtctaaa gccccacaat    15660
tctctaaaaa cagagatgta taaaaaagca cacgtatata attctctgaa aacagaatat    15720
aaatgagtca ttgctccatt taactgacat ttgttgagtg cttgttataa atatggcatt    15780
attctagctg gtgtgaggtt accaattttt tttaaacaaa agtaatatga atatatacac    15840
acacatttag tgactgcata tgtgatgtgt gcttttgaag aaaaaggaga tgctgttgga    15900
ggaaaatggt ggtggtggtg ggaagtgatt tagagtagaa ccagggaagt ctcagaagtg    15960
acaactagct ggaacctaaa gaacgaggag gtagcaggtg gaagagaaag gcaaaggcat    16020
```

```
tctaggttga gagaatagga tgtgataatg tcccgaggaa agagagctta ctgacaggga    16080
gggaagatgt caggtgtgac cgaactgtag tgagcaaagg gtaactgagg aggtggtcag    16140
gagcctgctc agccaatggg gtaaatactg ttaaggaatt aggacttgat tttaagaaca    16200
accatcgcat cattttaaaa gcaaacaaat tgcactataa tttccctctt caaaaggca     16260
cattggctgt gcacggtggc tgacacatgt aatcccagca cttttgggagg ctgaggcggg   16320
tggatcacct gaagtcagga gttcgagacc agcctggcca atgtgttgaa acccgtctc     16380
taccaaaaat acaaaagtta gccaggcgtg gtgacatgtg cctgtaatcc cagctacttg    16440
ggaggctgag gcatgagaat tgcttgaact ggggaggcgg aggtttcagt gagcagagat    16500
cgtgccaccc cactccagcc tggacgacag agcaagattc cgtcttaaga aaaaaaaag     16560
ggcacattga tggctattca aggcagagag gggcacatat aaccccaaag agatggctct    16620
ggggagggtt gtgttgtatt acattgttgg cattgtatta tccaggtgag agatgctgga    16680
ggctgggcgg tgccagtggt gatgaaaagg agagatggat ttgaaacata ggaataatct    16740
ctcagattgt ttcttggcat cacttaccta aaatgcttct ttcaaatata gatgtacaca    16800
cccctccctt taggatactt gggacaatgt gccacttaga catagggat ggaacaaatt     16860
ggagagtctg tcaatgcccc ctgcaatctt ttctcttgat gttatctcat aatgccccac    16920
aattctctaa aaacagagaa cataaatgag tcattggtcc attccactga cgtttgttga    16980
gtgcttgtta tgaatgtggc attattctag ctcttgtaag gttaccaatt ttttaaaaaa    17040
caaaagtaat gcaagactgc tgatgaaaat ttggaatatg agaaaagcat aaagaagaaa    17100
atacatatct ttaagcacac cacccactgt taacattctg atctatgtac ttctaatatt    17160
ttctccatt  tcatatgtac acatacattt atttacatgc atatataaat atcaaagtgt    17220
atatatataa ttttctctgc catttaaatt tttactgtgt aacaatcatg gattgtaaaa    17280
aaagtgaata aaatgtacgc agtcagttta aagactaaca aaatatgcat taaatcacca    17340
gccaggttaa gaagaaatac tattacttat accctggcat ctccctccca cctttacata    17400
gccaaatcca gaaaagatcc gttttcctaa ccttgttcgc ctattttatt atttaaattg    17460
cagcaggagg gaagcatgtc tactttatcc aatttcacac agacgctgga agacgtcttc    17520
cgaaggattt ttattactta tatggacaat tggcgccaga acacaacagc tgagcaagag    17580
gccctccaag ccaaagttga tgctgagaac ttctactatg tcatcctgta cctcatggtg    17640
atgattggaa tgttctcttt catcatcgtg gccatcctgg tgagcactgt gaaatccaag    17700
agacgggaac actccaatga cccctaccac cagtacattg tagaggactg gcaggaaaag    17760
tacaagagcc aaatcttgaa tctagaagaa tcgaaggcca ccatccatga gaacattggt    17820
gcggctgggt tcaaaatgtc ccctgataaa gggagaaagg caccaagcta acatctgacg    17880
tccagacatg aagagatgcc agtgccacga ggcaaatcca aattgtcttt gcttagaaga    17940
aagtgagttc cttgctctct gttgagaatt ttcatggaga ttatgtggtt ggccaataaa    18000
gatagatgac atttcaatct cagtgattta tgcttgcttg ttggagcaat attttgtgct    18060
gaagacctct tttacttcc  gggcaagtga atgtcatttt aatcaatatc aatgatgaaa    18120
ataaagccaa atttgaagta aagtgtctgg gcagtggctg tggggataga aggagagat     18180
ttacaaatca ttgaatcttc tttctcatga aacatcattt gtgtgtgaca aattcaattt    18240
ataaataacc cagatgtatt atgtagaagc tgaggctcaa aagctatcac ttgcttacca    18300
gacggacata ggagcattta tctgtaatat taattcatga gtgtggagtc tgaagagatg    18360
```

```
aataaacaaa ccataagatt actttacatt tattgttttc ctggcccttta acctatttag    18420
aagtcttaag acagaacaaa cattttttctt tttcttttc tttttctttt gagacatggt    18480
ctctctctgt cacccagcct ggagtgcagt ggtgcaatct cagctcactg cagcctcaac    18540
ctcccgggct caagtgatcc tcccacctca gcctccctag tagctgggac tacaggcacg    18600
tgtgccacca cacccagcta acttttgtat tttttgtaa aaacagggtc tcactatgtt    18660
gcccaggctg gtctcgaacc tgaacaaaca tttcaaagga caaataatcc ataccagaga    18720
agtagagtat ttaagaagta cccagtataa caaaacatat tttaaaacta acatttaaag    18780
ttttgcagaa aactaatctt aaaaagttct cattatttaa gaaaaaaaaa taaaagtta    18840
taatgtcgct ttaaaaatgt attcttttaa cttgatttag ttttcctcta tttataatta    18900
gttgttagca tttatgttta agaaactaaa ggatacagaa agggtctaaa ttgctgatgc    18960
cctctgaaga cctagacagg aactacttaa tatcttgcac catgtggtgc aggatatcat    19020
agaatgtcag ggctgatcat tctactgttg gcagagacca cttcacttac agatgagaga    19080
agggcagtcc actgagagga gacaatttca ttcactaatt cggtcaggca acattgacct    19140
acttggtcca ctggcctaga ccccaagagt ataaagatga gcaaggccgg gcacagtggc    19200
tcacacctgt aatcctagca ctttgagagg ctgaggtggg cagatcacct gaggtcagga    19260
gttcaagacc agcctggcca acatggtgaa actccatctc tactaaaaat ataaaaatta    19320
accgcgtgtg gtggcaggag cctgtaatcc cagctactgg ggagactgag gcatgagaat    19380
cacttgaacc cggggagggg agattgcagt gagccgagat tgcatcattg cactccagcc    19440
tgagtgacag atgctaaaca tcatagtaca atgtgacaag gtcctaacag agatcaatgc    19500
aaagggaca cagccagcca gcacaaggac aggagggcat gcctaatgca ggtcaaggtc    19560
ttctctctca gagcagctga gagtagcagg tcaatggcag cagagagatg tggggcctca    19620
gcatcccatg gcttcatgcc tcctagttta ccctgttctc ctccccatgc cccagccaag    19680
gcacagcaac gatgggcaag gcctcaagcc tcaggtgct aggacaaaat ttagaaaaag    19740
aggctcttct tcagagaatg cttgtagaac tcgttattcc aatcacaagg tttgtctctt    19800
taaaattaca gagtgagata tgtacaaggt atctacttcc taataacaga tttgcaatta    19860
tgccaactga agcattcagt acagttagag aaaaccatcc atattccaag agcagatgta    19920
ggaagagtgg cttccctcct cagatcagaa acccagaaat gttgtcccac ccagaaacat    19980
ccatctcaga gaggccagag cagccatcag gctttaaatc ccagccctct gctctgcatc    20040
cagacagaaa tccgaggttt ccatcaggtg acaaagaccc tctccttaac caaactgtca    20100
agctcctctg agccctcttc ttgactagag cccaaccatg gccctataaa aactgcagac    20160
tctcagcaca catgatttcg cccaccttg cacactaaga gacataaacg ctagcatagg    20220
ttctaagagc tgaaagctaa agcgcctgcc cgagaaaagt gaatgcggcc tgaagaattt    20280
actaattgtt ccaaccaaaa cctggtgaca ggcagatagt cccctgatcc ctctcttaag    20340
gcagttactt tagaaagttt gcaattataa atcctttctc tctcccttga gatgtatatc    20400
ttctaccatt cagaactgta ttgtctctct gaaatgcaaa cattcaaact ctccttgctg    20460
gatgggtgcc ttgctctaac ttactgctcc ccatcacaga cagaagtttg tttctactct    20520
agataggagc caattaacaa acccagatca cactgaccaa ccccttccca ctttctatgc    20580
atttccactt cctggactct gctcaagccc catccccact cagttacctt tgcacaaagg    20640
gaagttgagc tgggcctctt ccctctggca atagctaatg atttcagtca atccttactg    20700
cttttaactgg cttttctttac ctttgacaca ggtaaacaca tggagagcaa aatcgaggtt    20760
```

```
tttctggccg ggtgcagtag ctcatgcctg taatcccagc actttgggag gccaaggtgg    20820
gaggatcact tgagctcagg agtttgagac cagcctggcc aacatgatga aaccccatct    20880
ctactaaaaa tacaaaaatt agctgggtgt ggtggtgggt gcctgtaatc ccagctactt    20940
gggaggctga ggcaggagaa ttgcttgaac ctgggaggca gaggttgcag tgaaccgaga    21000
ttgcatcact gcactctagc cttggcgact gagtgagact ccatctcaaa aaaaaaaaa    21060 aaaaaatcg aggttttcct aattaagtac attttattat catcactgaa agtacaggtg    21120
gtaacataga gggttatcag ccaacttcac ttttggggaa tgggagaaat gctgactctc    21180
tccaagcatg ttgggtgtct agtggttgaa gccatttgcc aagattgtca ccctaggatc    21240
cactcccacc aaacctgggc ttttcacttt caacccagca actgaaaatg ccagttcaaa    21300
caacttgctg ttttttttcta ccccacttgc ttttagagtt ccttctgcct gttttattgg    21360
ctccatataa cctgaatacc acttatttct taaagcatag ctcagatgct attttaaaag    21420
gagcccagga tagtggctga tttgatagaa tctataccca gattacccag ggtcaagtcc    21480
cagctctggt acctgcggcc tttaaaacca cgaaaaaatt actttaatct ctgtgtctcc    21540
atttcctcat tgtgaaatg gttatcatta tagcacgtcc cttacagcct tgttatgaga    21600
cttaggcaat agccactagt gcttagaaca aagctatttt tgtaactttc tccaggaaca    21660
cttcccttaa cagaaccaac ccctccaccc ctcagtttgt tcttccctcc acccctcta    21720 acattctaac ataaccacaa agagtcctga tgggatttgg agttacactg cctgggttcg    21780
aatctcaatt ccgccactgc cattcgcgcg ttttctattg ccagccacct tactctcccc    21840
tggcctcagt ttcctcatcc ttagaagggg agcagagcac atggtggtaa ctccctgcac    21900
attcctctct ttccttgtat tgggtgccca gtttgtgccc tcacatggcg ctagcactga    21960
gtgggctcaa actctgtacg cgtttactaa gcatattgac tgaagaaatc tggaaaccta    22020
gtaccgcggc accatatcgt taccccaaag gaaaatgcat gcacgctgtc agagatgacg    22080
aacactgcgt ctggaaactt cttaagggca cccacgtgtc ctcagctgca gacagcagcg    22140
aggagacacc cagggaattc gagacagcgg aaggcggaag ggtcccgcaa caacccaccc    22200
tccagctcag gtgagttcag agtgagaacg caccgccagg cttggacaaa ggcacccggc    22260
ctacacccca gcggctcccc gccggggcct acgtggactt cagcctccag ccacagggac    22320
aagagctgct ggccagggct gcccgcctgg gctcactgcg cctgcgcagt gagcagcgcg    22380
ccccaggtct tctgcccggg cccactgcgc ctgcgcacgg agtagtgcac tctcgtcggc    22440
ggcaccggcc cactgcgcct gagcacgtag cggtgcattt cgggacctgt agttttcccc    22500
ggcaggacgg tagaagtcgt ggtttgtgcg cggccaggcg ctggagcctc cgctgccggg    22560
agcagtaagt gtgtgacgtc ggggtagaag ggagtgaccc aaattccaaa agctctttgg    22620
gatgctgcga tgtcgcggcc ggcccgcgc tcgggttttc cctcctagac aaaagtctgc    22680
cggctcccgg tcgcgccggg tcggggatcc ggaaggtgaa ggccgccagg ccccacctgc    22740
ggggcgcccc tgctggacct ggccgtcggg cgccgtcaac ccgttgagca gcgtgttccg    22800
gctggcacgt ggcccgggcg gggcccagga ttggttcaag cctacggtgt tggtccccgg    22860
agagtctagg gagacaagca atccctggaa atggtggggg aagcgatgac agccctggt    22920 cctcatccgc agctctgggg gaagtcgggg ggtgggagg gcgggtgttg ctccctgagt    22980
gttgggggaa gggtatgggg agaggaccct gaactagccc ccaggttacc caggaggagc    23040
tgaggcccag agaggttcag cgactcgccc agggttgcac agcgagcaca ggcaccgacg    23100
```

```
tcgccctccg aggcctgggc ttccagcagg gagagacccg gacacctgtc atcgcttctc    23160
ggtggatccc tgaaatgttg agttgtggag tctgggcagc tgagatcggg cagggctggt    23220
ttcttgtagg cccaggcttc cgtgtagagg gccaagtgat gcccaaggtt cacctggcag    23280 cccctctct ggacctaccc ctccttatga ttgggtgaag ggttgggtga aaagggtaga    23340
ggccgggaat gagaacagct tcagaaagct cagacaaagg gcgcagcatg attcgtggct    23400
ggaaggagac agcaagcgat agactgatcc ttgaatttgt tagtgtgcca agaagaaaaa    23460
gtattaatag attgtggacg acacattatc catattgctt tagttggtct aaccaaaata    23520
agcgaatagc ttttttgttt ctaagagaaa cctgacaaag gaagacaggg tattttttgcg    23580 gtgaaggaaa tagaaatatt tggagttgta tctaagccac ttgttacttt tgtgttttaa    23640
gctaagatca tggataggtc caggaaagt taaaaatttc ccgcacttct tagattttat    23700
gcccctcaaa aacatcccca ccttgttggc ttttgcagtt caaccttcag ataccagctc    23760
cctcgtttct aatattgcat taggtgtaca tatggcagca gagcaaatag cttactgata    23820
cttttagctt ttttcttctc atttgcaaaa gactctatga aaatggctgg cttgggcatg    23880
taattgaagg gaggtgggga aaagtggtaa ttcagaggca gtgggtggga atgagcaaag    23940
catgtcagtg tggttcaccc tcttgactcc cacctcacca cagcccttct gctacaattg    24000
cagattgact ctaaatatgt ttcttttccta aagagcttga atttttatcac tccaggtatg    24060 aagttgaggc agctgccagt atattttggc agtcaggttc tgtgatatca gagaggatgg    24120
tgaattgtga attccagagt tgcagaattg ttctttagat tctgatttttt taaatgacag    24180 cactttggtt tggagggtta atgacttacc ccaggtcata tgccacacca tgggtaacac    24240
caagagtaga gctcagatct ccagttgtcc tggtcctcag gctactgatc tttattccct    24300
gccctgctat cttggaatga ctgcattttg ccctggatgt cgctagcctg tatccttcag    24360
gttggcatgt ccagtcatgg aaggagagag atttaacata caacaatgg ctgacattca    24420 gtgctttctg tgtgctggcc atggtgctta gtgtttacag tctaatctgc aagagaattt    24480
acagatgggc aagttgaggc tgagagaggc caagtaactt gtccaaggtc acactgctag    24540
tgaacatagc acatgttttc cagagggcca gaccactgga tgttttttca ttcatttcct    24600
cctgtaggat cgttggacct atttctcgtt cttgactttg ggaatcaata ttctacgtac    24660
atcaattcac tgggtatgca gttttgcctc tgaaaatttt gagggaacag ccagactcat    24720
ctactgtatt tgtatacaac tcaattaaag caggaattgt aaaaataaaa tttgtaagat    24780
ctttaacatt ttaatataca acattagcta atcactaaga ttactagaga tactcaaagt    24840
gaaaattgta gcaacaggtt ataacatgtt aggagcatat ttctttaggg cagtcagaat    24900
ctgctgcttc ttaaagacaa gtgggccatt tacacatgaa ggtaacaagc acattcagcc    24960
accatcatta tagttaaaca gatctatgat ttaaattcct atcgctacct tatctgactt    25020
tgaaaaagtc atggggaaaa cttggctacc ttgtgccaac tgctagcttg tttttcaagat    25080 attataatct tgaatagatg gaggatgaac ttttatact tagatagctt tgtaattgaa    25140
agtttgtata aaaacatctt gcctgaagtt catcttatcc ccattctatc taaaggcctt    25200
tgaaattttc agccactttt cttaattatg acggtaagta catttcaaga gaagtgtttc    25260
cctgactttt gaatgcaaag ctctctgcct gtgtcaggat ggtgccgagg ttaaagcccc t    25320 ggagccagac tggatgggtt cgaatcccag gcccacctgc gagaccctcg atgtgttact    25380 taaatttat ttcctcctct ctaaagtgga ggcagtaagc tgttttatgg ggtagttgtg    25440
agggctaaat gtcttaactc atctaagcac tttagccact ttttccatc tgacacaaaa    25500
```

```
aagttaagct atgattattg tgctataaag cattggattt cagaagaagt agggqcacta   25560 aacaccatct gcttgacacc tttcttcact tacagatggg actgaagctc tagagggaag   25620
tcacttacca gagggtgtag gttcttcatc cagagctgaa gtcttcttgg gggtatgtgt   25680
catattctaa gagtagggac ctacaaggcc ttggagcgaa tcccaaggct cgggctgcca   25740
gccctgcctt ctcatttcca tatgccatgg tgtggcatat gacctggggt aatatcctct   25800
gaaccaaagt gctgtcattt aaaaaatcag aatctaaaga acaattctgc aactctggaa   25860
ttcacaattc accatcctct ctgatatcac ttccttccct accttctact aggtctccct   25920
caagctttag agaaaattct gcctctgaat tattgcatct gacaattttt ctgccctgtc   25980
acttattccc ttgctcccag ataatcttcg aaaaaccaag atgagtttaa ttaacactca   26040
gaggacttga caaagacact cactcccaaa ccagcttgcg tttaggtctg gaggcaggtg   26100
gagggacaga ttttagactt gggcccttag gttcacagat gaatgggatg ggagcccatg   26160
tcccctcaga agcggcgctg tgctgctggc ggctacagac agctggtgag gagagctttc   26220
tgcttagcaa gggccaggcc cgtctgggcc ctcgcccagc ccatccactt cccaccagtc   26280
tctcaatcgc cttgtcagga cacagcccac ctctctgtgg agctcacttt ctgttcacat   26340
tccctctctc catcaaagag acatctttct aaggtggtct gccctaggaa ctccaaattg   26400
acctgcttct ttcttcctgc ccagatcaga ccttccagct gcctctcatg tacttgtctg   26460 ttggggcett gtgttgatca ggagtgaatt cacagtctac catgaattgg aaggtgagta   26520
tcgttttaaa tatttatggc ttggggtttt ttcttcctcc tgattgtgaa aattcagaat   26580
aacagttcta caccagtagc ttgattaaaa agaaaaagta ggtgaaagca taatatttat   26640 gtttcattt aagttaaaac ataaatgtac atttattcgc tggacttctg gaagaaggcc    26700 aggcctttc ttcgagtgtg cattcactaa cttcaaatct tcctcacttt tcttacaaaa    26760 actataccctt taaagcttta cctgcaattt tgcattgtgc tttctttttt tacacatttt   26820
ttttgtagag atagggctcc actatgttgc ccaggctggt cttgaactcc tgggctcaag   26880
cagtcctcct gcctgagcct cccaaagtgt cgggattaca agaatgaacc actgtgctca   26940
ggccgttttg gttcctttaa agtagatgca gtggactgaa tgtttgtgtt tccccaagtt   27000
catatgttgc aaccgtagtg cccagtgtga tgatatttgg agttggagct tgtaagaggt   27060
aattaggtga tgaggctgga gccctaatgt ttggaatagt gagcttatta aaagggctcc   27120
agggagctct cttaccctct ttctgccatg ttggggtac aacaagaagc cagccgtcag    27180
cagcctggaa gaggactccg ctagaaccc cctgtactgc gccctgatcc tcagctttca    27240
gcctttcgaa ctgtgacaag tacctcttta ataagtcacc cagtctgtgg tcctttgttc   27300
taggagctga attgactaag acagtggatt aagatcttat gagcagtgca tacacaaaat   27360
ctttccagtg tttcatactc tttcctaatc ttttacagtt gacttgccaa cagcattttt   27420
tttccaacgc aaacttgagt ctttcaaagt attcaactta gttttcataa aaacttttgc   27480
tttacacagt catatttcac aagcgtaatg tttaaataag ttatggaaca tagtatcaag   27540
tacaacttaa ataaactgct tggcgagtaa acacacctga cccctgtgaa acattagatt   27600
cagctggtgg gagcagaagt tcaagggcag ccagagagta ggtcagcaat caggttccac   27660
cgagggaaag gagaatgtca tcttaagtcc cggaagtcaa taaggtgagg tggaggttgt   27720
ttaagagagc agccactaaa atatattata gtcactttgc aaagtctaat atcaagcaaa   27780
aatcatacat tgtctcacca tctagaaatg gctactatta acaatctcgg tatattcatc   27840
```

```
tttttctgta tatatgtgtg gcgtgttttc atgcatagga tcttatttta cgtgtttttt    27900
caattattat aagcattttc ttcaaaacat ccagtggttt tctattgcaa ggagaaactg    27960
gaaaggtctg gaagcaggat cagggagcca ggaaggtagc tttcccatct tccccagctg    28020
tgtgggtga ggggctcggc aggccctgca ggagggctga gggcccagga acttgtgtaa    28080
gttaaagatg gcagagtgag tgagctgtga agggtgggaa gatatagaac agtttgttta    28140
gcatgccttg aggatcagag ctcacagtgg aaaggttggg aaggaaagaa gaggcagtga    28200
gaggatggag aggggaagga gcggaaagca gtgtggggtg aggtttaggg aggtcattcg    28260
cccactgcag tggctaagtc agtagaggag agaggcagta actggtacta agggccaggg    28320
ttcaaagcat taaacctcat gcctcaaggt ggtgtttctc actcctgagc actagttaag    28380
gcaaggattt cgagccccac tcccagagtt tctgattggg tagatctggc tggggcctga    28440
gaatttgcac ttcttataag ttccaggcgg tgctggtgca cactggtcga aggcaatgcg    28500
tgggaagttt tcctctttaa ttgtagagtg acaccaaccc atgtgaccac tcgggccagt    28560
cttgcttgtg acagtttttt ctgccatcag gaacaaagtc tgcccaaacc ttcccagctt    28620
ctgcaccagg gaagtggcta ccagggagca gcttcgtgtt taaacacagc ccatctcgt     28680
gtagtgttag aaaggaatgg ccgcaggccg ggcgtggtgg ctcatgcctg taatcccagc    28740
actttgggag gccgaggcag gcagatcact ttgagctcag gagtttgaga ccagcctgga    28800
caatgtggcg aaaccccgtc tctacaaaaa aatacaaaga ttagctgggc atggagatgc    28860
gtacgtgtag tccagctac tcgggaagct gaggctggaa aattgcttga gcctgggaag     28920
tggaggttgc agtgagccga gatcatgccc ctgcactcca gcctgggcga cagagtgaga    28980
ccctgtctca aaagaaaaaa aaagaaaga cagtcatggc cctgattgca gagagctgca     29040
gaaggtggaa ggttcagtag cccccagtgc gtctggtggc cttcccctc tggctcagtg     29100
ggccatggcc ggcagcgaca gtcaacagtg ctacctgtgc gttagcaaca agtatggcct    29160
cattatttaa aaacttagtt attcccattt cacagatatt ggggttttgt ttttaaaaat    29220
tgatgtagat ctaggccagg catggtggct caccctgta atcctagcac tttgggaggc      29280
tgaggtgggc agatcacatg aacccaggag ttcagcacca gcctgggcaa catagtggga    29340
ccccagctct acaaaaaatc agaaaaaatt agctgggcgt ggtgtcatgt gtctgtagtc    29400
ccgtctactc gggaggctga ggtgggagga ttgcttgagc ctgggaggtc agggctgtgg    29460
gaagccgtga tcatgccact gtactccagc ctagttggag tctcaaaaaa atattcatat    29520
agatccagtc caccctggca gcattcattt tcctccctga aggtctgtat gtttcaagag    29580
atgtaagggg tttgttaaaa ggaaattgga ggaagggtt cataccactg aaggttagtg      29640
cctaagagag gggcaggaag ggggccctgg agctcttcgc tttaccctgt gaatgttctt    29700
gacctctgct gcccttgtgc tgcgtccttc tcagtccaca cttctgcctc ttgccgtgcg    29760
tctccactgc ctgtaaaaca aagtgaacac tgaagcctcc cactagggtc cattggctga    29820
tgcgtttcca tttccatggg ttttctaact tctggatgag agagtacatt cctgcaattg    29880
ctaaagctaa gtttcctatc tggattgtag acagctatgg gcagtaacat gggctttgtt    29940
atattagtaa tagggccccg gccaggtgca gtggctcaca cctgtaatcc tagcactttg    30000
ggaggccgag gtgggcggat cacgaggtcg ggagttggag accagccggc caacatggtg    30060
aaaccctgtc tctactaaaa atacaaaaaa ttagctgggc atgatgccgc atgcctgtaa    30120
tcccagctac ttgggaggct gaggcaggag aattgcttga acccaggagg tggaggttgc    30180
agtgagctga gatggtgcca ttgcactcca gcctgggtga cagagcaaga ctctgtctcg    30240
```

```
agaaaaataa taataataat agggccccat aggtttattc agagagactg agaaagctgg   30300
aagagattag cttttcccag tgtgagtcat tgcctcaggt agcctggaaa atcctagcaa   30360
acaaaaagaa gttatacaa caacattctt ttcatagctg gtttgtatgc atggcgtcaa    30420
accttcacct ctaaaatgtg aaccttcaag aaaacaggat ttcagggttt actggaggga   30480
ggggattagc ctaggtctga gggaagaaga acctggaaat gaagtcagtg tttaaagctc   30540
cttatattta ccagagtaaa aagttgaaaa gtttcacttt tggaactttt tagtcttttg   30600
tactgatgcc agagtgatct ttctgaagtg tatgtgttgt gcttattctt tactgttaaa   30660
acgatatcat ggttgaaaac tattagctaa ttactgagtg ttcttgtgtt cttactgttt    30720
tagtaaaatt aaaacgattt aagtatttgc gtccctgcct cctcccatga ttttcattgt    30780
atttctatca tatcatgcta tatccttctg caaatatcca tacataacca gttaaatgat    30840
ttcagaggta gcgagtctag ttgcctctgg aaaattcagt agccaagcca tagtgtattt    30900
gcatattgta aatgtgaagt ggatgggtgt gaggaatgaa tcatatatag tacaggacag   30960
cgtgatgcta cagagttggg ctttggagca tttggagctg ggtcagcccct gcctcgctga  31020
ctgctggcct ccccgcctct gcattttctc ggctccaccg cagtcagggc gagccatctg    31080
ctcatggagg tggctaaggg cagaagggaa agccgcataa ggcactttgc atgccgtgag   31140
ttcccagtct acagcagctg atgctacagc ttctaagcgt gaaatccaca tctagttctg   31200
agtcataaag agtttcgata caatcatagg aacattcatc tacatacact gtgatttcat    31260
gaatttcagt ttgttgaaaa tcaggcatca gtggaaggga gactggcccc ggggttagaa   31320
tgtccttcca actggctcct catgagggag ctgtgggacc ttcaacctct caacctccag   31380
gagctcttct ttccttgctc atataaccag ggggttgagt aggtcccctt gaaagttatt    31440
tccagccccc cggttctgtg agcatattgt acacactaac taggttcaga tcaacttcgg    31500
ttagactatt agagggaggt gcacatgtat cccccacagt ggaatctcat tggtatttca    31560
tataataagt gattgacaga aataaggatt tcattgggat aaaatcctac ctggtcctct    31620
aaaataatga ttgctcaacc agagcatacc ttttcactat ttgggaggga attttttaatc   31680
acacaaaaag cacatacata tcattcaggt catgctaacc atgtgtatgg aactaatatt    31740
gctttgaagt actatttgca atatatagaa tttcacacaa aaaacctact agtgcaaaga   31800
gtgagtaatt caaatgcata gtgtttccct agactttatt ttagtgaatg gggttgcaag   31860
agcagttagt aagtagccat gttttaatgt tttgagttct gtcgtgtttt attttaccag    31920
caagtgccag tgctagtgag tctctagaaa caagagaaaa tcccagagta ctaaagctgc    31980
agtttccaga agcaaggtct gattcaccct tactttgtag atgaaggggc aggagctcag   32040
aaagaaagga gctcattgcc tgacccaggt cacacggtca gtcggtggta aagtagagct    32100
ctgacccagg cctccgggct ccagctcctt tcactggatc tggctgctgc ctcagaagca    32160
agggcctggg tgatcagcag gttgcacggt tgagctgtga gagaccagag tccccacgcc   32220
tgtggatgac cggtggtccc ctccatgaag ccagccgcaa gcaagcagca aagagcagag    32280
ctgtaacttg actgttggcc ccatggggat agagacctt tctgcttggt ctccagtgta     32340
gctccagccc cctatcctcg tgcctgttgc agaataggtg ctaagtaaat atttgttgac    32400
tgaaggatca taaagaaac ctcccatatc ggtgatggaa catttagtta gcatggcttc      32460
tttcttcttg aaggttcttg agcacgtgcc cctgctgctg tatatcttgg cagcaaaaac    32520
attaattctc tgcctgacat ttgctggggt gaaaatgtat caaagaaaaa ggttggaggc   32580
```

-continued

```
aaaacaacaa aaactggagg ctgaaaggaa gaagcaatca gagaaaaaag ataactgaag   32640
gtgagtccac agtacccaac cttgcaaatg ggagctggcc agtgggttgg ggtgaccaat   32700
caatgaacaa gagaggtctg agacctccct gtccgtcggg tctgaagggc tgcgtggggg   32760
catgtggcct cacctgttct ctaaggtaga actgctccat aaagggccag gtgtgcagat   32820
cctggtcctg ggatgtgagt gctgctgagc caaggtgcac ggagcattag ttcatccttc   32880
ttgaaacctg cggtggcaat ggttcttgac aggtattggg ttaagaattg aggactcagt   32940
gacagctgtg gaccttcttc ccagagaagc acacatactg aaaccatctg catttgtgtg   33000
tggggagaag tttgcagatg tggggagtca caggtcattt gaaattccaa gattaagaaa   33060
ccctgttacc tttaagataa agtctgactc catggtatga caaataaatc ccttcccagt   33120
ctggtcttaa cccagacctc atttgccaca tgtgcccact ccccatcccc ctgcaggcca   33180
ttcctcagcc accatggcct ttggccttgc ttattaggtt cttcccaagg acctcctcac   33240
caggcctgag ggtacactca tcgttgtcac ccagtgccta tcacagtgca cactggtggg   33300
cttagaacac acttggggag ttacaataca tcaaggcacc agaaagttcc tgttaagccc   33360
ctgttacaga tttaacacat gacaattcac agttaccttg attccagtgt gttgatgcag   33420
tttcttcact ttgcaggttg agttctgtac tttaaaaatc aggggattca gccaggtgtg   33480
gtgactcatg cctgtaatcc cagtgctttg ggaggcaaag gtgggaggat cacttgagcc   33540
aatgagttca agaccagcct gggcaacata gtgaaaccct gtctctacaa aaattaaaaa   33600
aaaaaaacaa aaaaaccaa aaaaaaaaac caaaaaaaaa cttagctgca cacttactgg   33660
gtgtgtagtc ccaactactc aggagactga ggtggaggat tgcttgaggc ccagaagttc   33720
aaggctgcag tgaggcatga tcacaccact gcactccagc ctgagtgaca gagcgagacc   33780
ctgtctaaaa aaaaaaaagg attcaaatat ggtggcggtg gggttctaga tctgtggttc   33840
ccaaacctag ctaatgatca gaattgccca ggtgtttgtt taaatgaaga ttcccagctt   33900
cagcccagag agattccata atggctctgg ttaggtttgg gtgttggttt tgttgttgt   33960 ttttaagata ggggatccta ctctgtcatc taggctagag cggtgcagtg gcacaatctc   34020
ggctcactgc agcctcagcc tcctgggctc aagcagtcct cccaactcag cctcccgagt   34080
aggtaggact acaggagcac gccaccacac ccggctaggt tttaaaaca attttttagta   34140 gagaagggt cttgctgtgt tgcccaggct ggtcttgtac tcctgggctc aagcgatact   34200
ttcgcctcag cctcctgaag tgctgaggtt acaggtgtga gccactgtgc ccagcctctg   34260
ttcttttgaa aacccattag ataatcctta ggttgtcttc tcagcaacag gtcattgtag   34320
gaaccactgg gctaggtggc ctcccaaacc cagcccactc tgagattcca tgctgaattc   34380
ccttgcagtg ccgtcaggct tgttgaggct aaagacctac tgatgaggaa tagtagcaac   34440
acctactaag tggttattct gtgctgggga cttttgctaag cattcatgca caactgtgtt   34500 attcagcct gatgactctg tgaggcatgt tcagattgaa agaatggctc tctctacatg   34560
gtgaagaaca gagtcagaaa ttgatcccag gtcaaatgca ttcgatcagc atggccaagc   34620
ccaagctgtg ctaccttcct gaatacaggc aagtgagctc gtagggatgc ttcactctgt   34680
tactcaccac ttccggcagc tgcccactcg ctggtcccca gtgaactgta ggcttttgct   34740
agatagaaga agttactttc tttctttctt tcttttcttc tttttttttt tttttttaag   34800
gtgtttgatt gactgaaatt taggagtagg cattacgatg gggaggagag aaattaaaaa   34860
gggtgaggga aggcagttta aattaaaatg ttgctgattg aatttatatt cctgacaatc   34920
ccattttgtg tgctaaactg atcaaaggaa gaaaagatga gatggaagat cataaaggct   34980
```

```
ttgttcctcc cacaaacatc agcagagacc tgcatttaag tcaggcctgg atggcttaga    35040
agcaactcag ggagttggtc ttcctctcta ggctggcagc ttcttaaaga ctagagactt    35100
gcttcaaaca aaaagcgttt tcaggccggg cgcggtggct cacgcctgta atcccagcac    35160
tttgggaggc cgaggcgggt ggatcacttg aggtcaggag ttcaaggcca gcctggccaa    35220
catggcgaaa ccccatctct actaaaaata caaaacttag ctgggcgtgg tggcacgtgc    35280
cagtaatccc agttacttgg gaggccgagg cacgagaatc acttgaacct gggaaacaga    35340
ggttgcagtg agctgagatt gtgccactgc actccaggct gggtgacaga gtgagactgt    35400
ttcaaaaaat aaataaataa ataaaagggg ggtggggtgt ttcagatgga agggaaactg    35460
atgctaaaaa tacattggtt aataaataga cttgagtgat agacttgagt ggtgtccgct    35520
tgttaagttt aaatggctga gcatacgtct ttatgctgag cagtaaacat cgggtatact    35580
cttatcaaac atttcctact catcccttg tattccctt ctagattctg ccatgtaaat    35640
gtcagcttga gtggactcca gctgagaaga aagagaagaa agacttaatt attgaataat    35700
ttgtcagagg ataaactccc aacctagacc tttcacttaa aatagtgtga atttgtatat    35760 gttttaaaa gaaccagtac tggccgggta tgctggcttt tacctgaaat cccagcactt    35820
tgggaggccg aggcgagtgg atcgcctgag atcgggagtt tgagaccagc ctggccaaca    35880
tggtaaaatc ctgtctctac taaaaatata aaaattagcc aggtgtagtg gcgcgcgtct    35940
gtaatcccag ctactcggga ggctgaggca ggagaattgc ttgaatccgg gaggtggagg    36000
ttgcagtgag cctaggtcgt gccactgccc tccagcctgg gtgacagagc gactgcgtct    36060
ccaaaaaaaa aaaggtaaaa ttaaaattaa aaaaataat aataaccagt attttgttta    36120
ctaaaataaa atgcctttgt aaaaaaagga gtcgtggcct ttggaataag tcaaattgtg    36180
tatctctttc tctttctctt acacagcacc ctctacccg tgttgtaaag cggggggttt    36240
tgtaaactta cacctccccc accatctcaa gctgggggt cccaggtgag aggcttccat    36300
agaggacaag gtggtgcaga acatctgct gtgggagtgg ggtccccagc actgggtgct    36360
tcggccagct acccccgacc ccaggccccc tcataggctg ccctcccata ccctccttc    36420 tcgtctttc ctcctacagg tgctacaccc ctgtgagagt gttttggagt gttttcattg    36480
ttagggtgga gggaggctgt gtgtgtccag gaaaggtgac tcctgtgtta accatgaggg    36540
tcctcgcagg gaggaatcgt tgggagccct agggtgtgtt ttgtcctctc ctcacctgtt    36600
tgctccttgg gatttgctga tgagaaatga agggtagggc accctagtag ccactggaac    36660
caagggcagg gaggatggga agatgtttta ctcagcacct aacacacgca gatccctgtg    36720
acaagagctc atgctctccc acttcttcgc aagaccccag agtggatggg gagtgaggtg    36780
gcagcagctg gcactggaag cagtgcggag tgtttggtct ggttgctgat ggctgcatgg    36840
gaaacttgca ggagtgtgtg ttagtaaacg tctccccgtc ctggcccagt ttgtgtcgaa    36900
catgcgtttt ccatgtgggg agtcagggga gttccatctt aaattgcact gtgcttgctg    36960
gatgctcttc aggacaattt aggaagcagg aaagaattta caaagttctg aggacagaca    37020
gaccctgctc ctacaagctg cagtgctcac catagtcaaa gtggactttc acgtaagccc    37080
agacctcatt ctctctgaag gaggccgctc cagcctttgc caggagccct ggtgacttta    37140
ttctgcctaa tcctgctgcg gcctggggtc ctgttagaac gtgaatggaa gaccacagca    37200
gaggtgggat gcccttggat ttctgccatc cccacgcttt cgtgacatgc tcagatgggg    37260
cctagaactg accctgggcc gtggcctacc atcctccctt tgtcagggcc tccttgcacc    37320
```

```
ctggcaggtt accccaccca ccctggccca tgttcctgcc ccaggggcct ggcctctctg    37380
ctgcccaccc tgcaggtgta gggtatcacc tgctcctgcc ttgcctggca tcagacctgc    37440
taccttggca ccacttcctc cctcatgccc acccgcctgt gtgcctcata agtccaaggc    37500
gggggatctg ctgaccagta gacactcatg tgctaaacac aagcgctttt ctaggctttg    37560
ggatttaaag ctacactttg gaatttgtgg aagatctggc catcttggaa aattaggtag    37620
aaggtgacat aaggactgga ctaaaccact gatcatccca acagtgcccg tggcttttct    37680
gttttttgtt tttgcttttg ttttttaga gatgaggacg tgctgtgtcc ctcaggttgg    37740
agtgcaatgg tacaatcata gcttattgca gccttgaact cctgggctca agcgatcttc    37800
ccacctcagc ctcccgagta gctgggacta ggccctgcta atttatttat cttttgttta    37860
gagacaaggg tcacgctgta ctgcccaggc tgggtgtagg ttttttctga agagcatttg    37920
ggagttttgt ttttgcttgg ttacttttcc tatgcaccct tctaccacta gggggagatg    37980
attaatcact aattgaaggg attttgttcg tttttatgt tttgggtttt tttgtttgtt    38040
tgtttgtttg tttcaataaa gaaagagttt aattgcagta aggcaggccg cgcaggagat    38100
ggcgttctta ttcaaatcgg tctctctgaa ggctcagagg ttaggggttt tcaaggcgga    38160
gttcttgcta tcattccact ccttaggtac atgaagttgg tagatgtgta gtttgatgtt    38220
aaattattgg gtggatgcat gcaccgctgg ttgtagagac tggtaaagcc cactagcagg    38280
accccacctg gaccaaagca atccctcaac ccgctggacc atgaccgaga acaaacacaa    38340
aggacctgaa atgcgttgtg aaggccagaa gccgacatcc acattctcca cccacggaga    38400
gccccagagt ccctcatgca catcctgctt gatctattac acacattcac acattcgcaa    38460
cacatttgtt tggttttcaa gcttacaaca tattagaaac agaaaggaag aaaggctgtc    38520
agcagcagaa ataccttgga gcaagaggga cggtctttga gaagcagact tgagaactca    38580
ccgtgtgctc ttcatgcgcc agacactgcg gcagccacag cgtccacat gggatgccac    38640 acgtgatgat gttatgttca tggtgatgac ctcaggcgtg aagaagaggt tcagccgttt    38700
cacacagtct gtttaacaag cacatacata acacagacat acgtgaggaa tctcagaaac    38760
caaataattc aaacaaagag tctgggattc tttcaaaagc gttgcctctg cccaagcttt    38820
cttcaaattc tgtctatagg gaaacgtagc tgtcaatgtc tcattcccga agacttccag    38880
atgcctggat ctttagagtt ctccacctca ccccgagttg attacacaaa tgttcctggg    38940
gctttgctta gtgccctgct ctgtgccagg ccccacaggc agagatggca gggacccagg    39000
cctgacgttg gagagctcct gacccactgc cggaaacaca cgcaccatca caccatgagg    39060
gagctccccc atgcagatct catctgtgtc agagtgaagc cagaggatgg acggtggaga    39120
gtctagaagg agaagagaaa ggaggatgag ttctcataca tgagcaagca ggagaggcca    39180
tttaaaatgc acactctggc ctggtgcagt ggctcatgcc tgtaatccta gtggaggccg    39240
agacaggagg atcacctgag gtcaggagtt tgagaccagc ctggccaaca tggtgaaacc    39300
ctgtctctac taaaagaaaa ccaaaaatta gctgggcgtg gtggtgcatg cctgtaatcc    39360
cagctcctcc ggaggctgag gcaggagaat tgcttgaacc cggagggtgg aggttgcagt    39420
gagcagacat cgcaccactg cactccagcc tgggtaaaag agtgagactc tgtgtcaaaa    39480
aaaaaaaaaa aaccaaccta aaaataaaa ataaaaataa aatgcagact cctgggctgg    39540
attccaggtc cactgcatca gaacctgcag gagaaggacc aggaatttgt gatacgaaca    39600
tccccaggca attcttgacc ctcctttga gacctacact gtagaagatg ggcagaggga    39660
gaggcagcag gagcccaacc tgggaaggag ccatcgggaa aggtgggagg aggggcagga    39720
```

-continued

```
gacagcgcac gcgaggcagc aaatccttca gcccttactc cccaagagct cacagctgcc    39780
tccacagagg gtaacggtat cattatcccc ttttcgcaga taaggaaact gaggcagaga    39840
ggccctgcct aaggtccccc agctggtggg aggcagagac aggaaccagc cctcatggtc    39900
tcactgtgag actggacttt tcacagctgt gcggtcgagt ctgagccaag taaagtaaag    39960 cgagttttg tacttcgaag tctgggacat aaaatcttca agacgtcagc atcagtgaca     40020
cgatggtgac agaggccagc attgcttgtt gtatctttt ccatcctgtt cctatctaca     40080
cttccattct tctgttcatt ctgcttgcat ttcccaccca gatggctttc acggacacac    40140
acacacacac acacaccgca cacacacaca tcactcacag acgcaccctg tgcccaatgt    40200
caaaagacaa aactgcaaca cgtttagtca tagacctcat tgtctttat tcttgattca     40260 tgaatgggc agcctcccct ctataaaaca gagcaagagc tcccaccgga caattgcaga     40320
acagtgggct ttgtaaggtg gggacaagga aacagaacaa tagaaaagaa gctgatgggt    40380
taacatcagg ttacttcagg acctcctaat cacgctgact caggtagacc agaagctcct    40440
gttttcagga aaactaatc tgtttgggga catacctgct tccttattaa agttttgggt     40500
tgattatatg gctcttagca tgactgactc cattttggtt tggtttgatc tggtctgttg    40560
gggcctagtg caggatctca gtccaaaaca atagcctccc ataatttttg tttaatgctg    40620
ggtcagcggt aggcttggtc cacttgcgct tctgcctggg tgggccttcc tcttttcctc    40680
cttttctctc tgtggtgaaa tccccattct tctttctgtc ctccacttca gtttcacctc    40740
ttcctgcaac cctgcccaca gctcttcagc gccaggccct ggactcagct ctcactacgc    40800
aaacctccaa catctcactg agtgggaggt ggcccccacc tccacaccag acctggacct    40860
tgagggtcca ggcttgtttt ccttggtact cctggccctg acgcacccag ccaggcacac    40920
agaaggtgct ccagtatttg atgagtgaat gactggtagc accagaggaa agggagcagg    40980 gagtatggc aagaccatta gctgccttcc tcagtgttcc ttctcccctt ctccctagta     41040
atagaaccct gacttttacc tggccgtatg gtcactcaaa ataaaggact acatttccca    41100
ccttctctcg caaccaagcc tggccaatca ggtttaagtg gaagtgtagt gtgggacttc    41160
ctggaaggat ctttaaaagg gacaggatgg gcccctcttc ctcccttcct cctttttggc    41220
tgcctggaat actaatgcaa tcgcttgttc cgcagccact ttggactaag aggtgagttt    41280
gagacctgaa ccaaatctag gacaatggag taaaaagata ggatcttggg ctctcagtga    41340
ccatggatcc atcatttcac ccctgaactg acaccttgac acttcttatt tttggtggtg    41400 gtggtgggt agcttctatt ttgttggcat ctctgtggtc tattcatagt tcacctgttt     41460
tagctgacac atggagccag ttagagatgg gcgcaagggc ttcctgatat gaagacttgg    41520
attctggtcc tgaccctcct gttactactg ttacgtacgt ggctaggtga gtcggtcacc    41580 acccctagcct ggcctttgta aaatgagctc aatgatcact gccctcccta ctgtacagtg    41640
tttgtctgaa ctgaatgagg tcaagcatgt aaagatggtt tgcatgtggc aggacaatca    41700
caaatggaag gagtgtatac tacctcggtg ggcaactcag ccaccagttg gccaggcagg    41760
ggctccatcc aacccaattg gattgagcca atggccaacg aacccccattt gctaatttac    41820 ctcttaggtc cttgtagggg cagcaccatt tcctaatgca ccccaccctt gaaagccacc    41880
ttgatccgtg ggagggagag gggctgtggg tattagtgat ggggaaggcc agagaggctg    41940
ggatgttcca tcagccaacc actcagaagg agaatagtgc caccaacatc aggagctcac    42000
ttctagtgga catgtctaga gatatgtggc tcagccctgc gttgctgcgt gtggtcaccc    42060
```

```
gctcttaact aaatacagtg ctctaaatat ggctgctccc aaagagactg tgggctgtcc    42120
tcaccagcca tcctgtccca cccccaccag aagaaacctc ttcttattat taattcccta    42180
accgattgca gatattgcag atggtcttaa aggaaatgcc agagaacaaa gtttcctctg    42240
atcaaagtat cttaagatgt gtccaccctc attagatgcc agcgataaaa aggaacaaaa    42300 attttctca aagagtgaaa aggaaatgag atcagtgatg gcaggtctaa ttgtggacat     42360
gtttgcttcg accttaccat ggaccactca ctcagtgggt gccagacaca atgcagtggc    42420
ttggcgcagg ttatgtgatt tttttttttt ttttgagatg gagtcttgcc ctgtcaccca    42480
gtctggagtg cagtggcatg atctcggctc actgcaacct ccgcctccca ggttcaagcg    42540
attcttctgc ctcagcctcc tgagtagctg ggattacagg catgtgccac catgccaggc    42600
taatttttgt attttagta gagatgggtt tttgccatgt tggccaggct ggtctcgaac     42660
tcccaacctc aaatgatccg cccaccttgg cctcctaaag tgttgggatt acaggcatga    42720
gccactgctc ctggccaggt tatgtgattt taaagtccca ctgtatttta ttaaggagtt    42780
gattgagcct caaggaagta aagcaactta ccagaacat atagctacga agctagaaac     42840
tcaagattcc aactaggtcc atccaattcc aaaagcccgg tgaactttct gttactttct    42900
atgggaagtt ttcaggttta gtataaagca acatttctta attatgaata caatcttatg    42960
taaccaaatt gcacattaaa gggtattcct tttgatcctt cttttcctctt ttctaataat   43020 ttttacaagg cctcaaagga atagaactct aaatctgttt tattaaattg ctttagtttt    43080
caaacaaaaa tagctcctgt tggtttatct ttagctgata acctaaaaac attccttttt    43140
tatcgctgta aaataatgtg tctttaaagg atattctgtc tcctctttaa ttttatgttg    43200
aaataaaatt ttttggtgtc caggggagtt ggccatttta gcggctggtg tctcatctga    43260
ggtcagaggt gagtcttgcg acatagaaat gatgggggtg aaaaaggaaa agctcagctt    43320
caataactaa gctaagcacg gtggtgagga gcatgggctt cagaatctct ggccccagt     43380 gccttgccag tgcctcagtt tcctcatctg taaaacaact gacaggatta agagaattaa    43440
attataatag ctatgcgtta gtggcatcat gaagaatggc tctaagcatg aattctgggt    43500
tgaatctctc tgggcctcag ttttccacat ttatttattt atttatttat ttatttattt    43560
attttgagag ggagtcttgc tctgtcaccc aggctggagt gcagtggcac aatctcggct    43620
cactgcaacc tccacctcca ggattccagt gattctgctg cctcagcccc ctgagtagct    43680
gagattacaa gtgcccgcca tcacacctgt ctaattttcg tatttagta gagatggggt    43740 ttcaccatgt tggttgggct ggtctcgaac cccttacctc aaatgatccg cccacctcgg    43800 cccccaaag ttctgggatt acaggagtga gccacggtgc ccagcacgtg tagctgttgg     43860
tgcctattat tccagaaccg cagaggcatg gaataaacgg gatgtagggc aaaacccact    43920
catctcccaa aactcaggcc acccacacgt gggcctgcac aatgacagca cactgaagtg    43980
accaaggaag tttgagtacc atggtttgct ctcaaggaac ttaaatccta aaacgtacat    44040
gaaatcctga gggaaaaaga cctcacaaat atactacaca ataggagtta tttcaccagg    44100
ttaattgcca atgagaaatg caatgtttct attggcagag caagacttcc tttagcaccct  44160 gtggctggct gaatagtggc caccaaagat atcaaggtcc tattccctgg aacctatgaa    44220
tgtcgcttta gatggaaaaa gttctgccta tgtgaccaag ttaaggattt tgagatgtga    44280
agatggtttt agattactca ggtgggccct gaatgcaatc tcaggtgtcc ttgtaagagg    44340
gaggcagagg gagatttgac acaggatgag aaagtggtgt ggccacaagc ccaggaatgc    44400
cggtggccac cagaagctgg aagaggcaag aaacaggtcc tccctggagc ctctggagag    44460
```

```
agtgctgccc tgccaacagc ttgcctttgg ctgtcttctc tgtcctgtcc tgtcctatcc    44520
tttttctttt ctttctctct cttttttttt gttttttttgg agatggagtc ttgctctgtt    44580
gcccgggcag gaatgtgatg gtgtgatctc ggttcactac aacctctgcc tcccaggttc    44640
aagtgattct ccttcctcag ccacccaaga ggtggaatta caggcgccca ccaccatgcc    44700
cagcaaattt ttgtattttt agtagagatg gagtttcacc atgttggcca ggctggtctc    44760
caactcctga cctcaagtgc tcctccgacc tcaggctccc aaagtgctgg gattacaggc    44820
atgagccact gagccaccgt gcctggcctc tttcccttcc cgtccccctt cctctttccc    44880
ttccctttcc ctcccctgcc ccttccccc cgcccctcc ctctcccctg cccctcccc    44940 ctccctctcc cctctcctcc ctcccctctt tccttcctcc ctcccttccc tccctccctt    45000
ccttccttct ctctttcttt cttctttctt tctctctctc tctccctcc ctctcctcct    45060 tagccccct cctttctccc ttctctctct ttctttttga cagggtct cactctatca    45120 cccaggctgg catgcagtgg tgcgatcaga gctcactgta gcctcaagct cctaggctca    45180
agcggtcctc ctgcctcagc ctcccgagta gctgcaacca cagccactac atctggctta    45240
atttctgttg ttttaagcca ccaagcctgt ggtaatttgt ttcaacagcc acaacaaatt    45300
aatatagcac tgttgactgt caagtgaggc ctgcaacagt ggaaacttta tagttctgag    45360
tggtcagctg tttgaggtgt gattaatctc caggaaaaat gttaccagga ttcccttgt    45420 aaccatgaca aaatgctgag aagtggtgga cacttagttg ctgaaaagca ctgaacgttc    45480
gctttcatct gacaaagtct ttctgaataa tacaggggag ttcgggaggg aaagaaggca    45540
agcaaacgat gggatgcttt ctgcacgtgg ctgtcaggaa attctgggta gaaattcttt    45600 cttttctcctt ttcttttctt tttgagacag agtctgactc tgttacccag gttggagcgc    45660
agtgatacaa tctctgctca atacaacctc cgcctcccag ggctcaagtg attctcccac    45720
ctcagcctcc ctagcagctg ggaacatagg tgtgcgccac catgcccagc gaattttggt    45780
attttttgta gagacgaggt ttcaccatgt tgctggcctc gaacttctga gctcaagcaa    45840 tccttttcacc ttggccttcc aaattgctcg tacaggcata agccactgtg cccagtccag    45900
aaatgttcat aaattgtttt ttttcataga ccttattttt tagagccatt ttttagattc    45960
atgcagaatt gagtgaattg agtgggtgcc ccaccaccca ccaccgctac caacatccca    46020
tgtaagtgta caaaattttt tttttctttt acaggcaggg tttcactttg tcacccaggc    46080
tggagtgtag tggacaacca tagctcactg tagtctcaaa cttctggctc aagtgatcct    46140
cctccctcag cctcccaagt agctaggact atagatgtat gccactcagc ccagctattt    46200
ttaaatattt ttgtagagat gaggtcttgc tgtgtttccc aggctggtct tgaactcgtg    46260
acctcaagca gtcctcctgc ctcggcctcc caaagtgctg ggattacagg tgtgagccat    46320
tgtgcccagc cataaattat tcttttttgca ctcctcggaa tgattacctc tgaaatgact    46380
gtctgaatgt acataaccaa cagtgaattt tatgatatgt ttaatagggg tagtctttt    46440 ctataaaaat gaaaagaca accacagatt cttacaacag acatcggcag cagccccaaa    46500
cctaaatagg gaggtgttgt cccagctgca agtggctcag ctacagggtc tcgagatgaa    46560
actccacggc acagtctaat gacctgctgg aattcctgga gttggcgggg agattggctg    46620
gataagtggt ctctgcagac ccccatgcgt gccaccccctt tgcccaccat agcccacttg    46680
aacccaccac tgtcataact ttccaggtcc taactgggac cacctactcc ccttggaggg    46740
tccggatgga gtttcccctc tgcggctgcc tctcactcat cctccaccac tttgccgaca    46800
```

```
aggaaggaag gacaatcggg aggagggagt cttgcttggc gaccatctgg acaatatctc   46860
gcccatggca agctggatcc ctgtggatta ctttggtggg tggaaacttg gcacactatt   46920
taatttgggc tttttggggg atgactgcac actggttctc ttttttttctc agacctaaat  46980 ttcgaccact caactttcag cctgctcacc cctgcttatt gccatccacc tttgggctgg   47040
gttagaccta atcctcccct tgacaaagcc ctcaaagtag ccttcacaag ataagagtcg   47100
agacccctaa cttaccaaca aatttttaatg aaacttctag taaactcaaa gcgctttgcc  47160
aacatcctta ggagcaaccc agttctcgca gcaccccatg tgaggtcgct gttgaagtat   47220 cttttggctgc agtggtgtgg aattcatctc aacagagttg acggtaaaga ccagacatgt  47280
agcagcctca ctgcttgttg gaggaaccac ccttaagaaa atttcccaag atagtagttt   47340
tcccatctcc gtactttgct agttaatgtt ctccacttgc ttgcgtttat cctttcaatt   47400
cctttgctaa ttaaattgct gaaaagtata cattggtaag aatagccact gtcaatggac   47460
tgcaaacaaa actcgtttct gttattgatg ataaaccatt tcagagaaga ccaggctgag   47520
tctaaagggt tcagataatt acaaggggaa ggcagagaga gtagttcatg ccacaggac    47580 ttggccacct ctgggcaaca cataatgctt gctaagctaa tgactgtagg gatatagaac   47640
tggccctcag cctctctgtc ttcctttggc ctctgctctt cctgctgcct tctctctttg   47700
accacgatga cacactttcc ataggccttc ctcaccacat cacagaactc agagaagagg   47760
ctgtcttctt gtttgataca cagctcgtct cttaggaaca cccgatattt ccaaggcacc   47820
catccttgac tacccgcagc atgcacaata caccaagttg gggtttgtat gaaatatcca   47880
tcactaatat cttccccagt tacgagactt tctgggatat tggtttcccc aaaatatacg   47940
gtcttaaatc catcatattg cagtgttctc agggttttca gatattggag gcattgcttc   48000
ctcttgatgc catcaaattg acttctgata atgacatttc ttaaaagagg gcttgcaaag   48060
cgaggcatgg tggcttctca agtgttttta aaagcttgca catctgcatc tggggagaga   48120
tggcaagtgg gggatgatga cctcataaag ggctttctta cagtggtgcc agtcccacac   48180
atacacttca gatttcaagc atcatggaat aaatactcag aacaactccc tgctgaccca   48240
taaaatatgg gaattgcaga tgctacccat aaaaatgcta ctttgacatc acttctgcaa   48300
taggtctgag acagaggttg gcaatctttt aatagtaatg agcctaccca tttggcttaa   48360
gatggggaga atgtttaca ttcattcatc catttcaaaa atatgtactg atcacctgct    48420
gtacaccagg cattgtgcca ggcaccaggg gtatagtcat gacacaccca gggagtcctg   48480
gacttacgtg ttgtgtgtct gtgtatgcat agaatttgtg ccagttgcct tcccatttgc   48540
acaactaaga gtgattttttt ccaggtggca gaaggaaggt atggcaaatt gcaaagaaa   48600 gtcagtctgc acacctagct tccactggcg cttgcaggtc ttttttttttt ttttttttt   48660 tttttttttc tgagagggag tctctctctg ttgcccaggc tggagtgcag tggcacgatc   48720
tcggctcact gcaacttccg cctcccgggt tcaagtgatt ctcctgcctc agcctcccga   48780
gtagctggga ctacaggcac cttccaccat ggccggctaa ttatttgtat tttttagtaga  48840 gatgggtttt ccaccgtgtta gtcaggatgg tctcgatctc ctgaccttgt gatccgcccg   48900
cctcggcctc ccaaagtgct gggattacag atgtgagcca ctgcgcccac ccggagcttg   48960
cagttattga actaattcaa tacctcatct tgaaagcact tttaatttta tatactcagg   49020
caaaatgaca gtttgcttca aactctaacc atctcttcct ttgtattttc ttgcctcttt   49080
aatcagagct aaagacattt cataaaatgg gcatgaagga ttccttcaaa tgaagacgtg   49140
gacaaaatga ttggtcaggt cctttgctct actgttgaat ggaggaggat tttttttttt   49200
```

```
tttccctcac acaggggttt tcttggagct caagtttgga tgaccccaga cagtaagata    49260
atctcatcat ggtaaagtta atatgaaata tgtggtctcc aaacagcctc tcccagaggc    49320
caggatcagc aggtttgagt ggataattgg cttgtggtca ttttctcata ggattttttct   49380 tttagtagtg gaaactgttt ttcaaatcaa atttggatgc caactatgtg aacagaagt    49440 gtggctgctc tggtggaagt ggcaatggta gtcctagagt ctccctgtca gccacaccct    49500
ttgtctcccc ctacccaagg gaccctgtgg cctggaaccg cagtgtgaaa tgctatatag    49560
tgcaatgaag tcaattcgaa gacaagagtt cttttgccttt ctcatctaat ttttagttat   49620
ggatatgaga cgcttgttca gaagtatgga aaagtatata taatatgtta tcttttagat    49680
gtgggtgtaa atatgcttat gtatgcaata tgcttatatt ttaacgcata acaacatga     49740 ataaagcaaa cactctagac ttctccaaat gtatcttgtt ttacagttttt cattttggaa   49800 aatgtcaaca tttttacatt aaaaaatatt actcagccat aaaaaagaat gaaatcacgt    49860
ctcttgcagc aacatggaca gaactggagg ccattattct aagtgaaata attcagaaac    49920
agaaagtcag atgccacatg ttctcaccttt aagtgggag ctaaataatg tgtacacatg    49980
ggtacagaat gtaaaataat ggacttcgaa agggaggctg agatgggagg accatttgag    50040
gccaggagtt tgagacaagc ctggccaaca tggtgaaact gcttctctac taaaatgcaa    50100
acaaattagc cagacatggt ggctgacacc tgtaatctca gcactttggg aggccaaagt    50160
gggtggatca cttgaggtca ggagttcaag accagcctgg ccaacatagt gaaaccccat    50220
ctcaactgaa aatacaaaaa aattaactgg gcatagtggt gcgtgcctgt aatcccagct    50280
acttgggagg ctgaggcacg agaatcatga gccgagattg caccactgca ctccagcctg    50340
gacaacagag caagactccg tctaaaaaaa gaaaaaaaaa gaggatagga ttagggtgag    50400
ggatgagaaa ttatttaatg agtacgatgt acactactac actcaaagcc cagacatcac    50460
cactgagcaa tcaatccatt tgacaaaact gcacacctgc acttgtaccc cttaaattta    50520
tatacaaaca aaaacaaagg caaatcaaaa ataaaaataa aacaaatga tctctaaaca     50580 atacaaacag taactgatga acctagctgc ttatcatgtc agttccaaaa tcacacagag    50640
ttgaatttct ttcaaatgac cctacaacac agtattttga tcatatattc tccagtagag    50700
tataagctaa ggacaaagaa aaacacatga atcttaaat ggtactcggt agttttattg     50760
ttaataatga tgctggtatt attatttga aactcatgtc catttctcag ctgccatttg     50820
atattaattt ttttttttt tgaggtggaa tttcactatc actcaggctg gagtgcagtg     50880
gtgtgttctc agctcactgc aacctccacc tcctgggttc aagcgattct tctgctttag    50940
actcccaagt agctgggact acaggcacgt gccaccacac ctggctaatt tttgtatttt    51000
tagaagagac agggtttcgc catgttggcc aggctggtct cgagctcctg acttcaggtg    51060
atctgcctgc ctcagccttc caaagtgctg ggattacagg cgcgagccac tgcgcccagc    51120
cagtgatttt taacctttat caatctgata gacaaaaga tcatttcatt gttttaactt     51180
ctttaattat gagtaaatct ggcaatatat tatgaaaaca atgacaagaa gaacttgata    51240
taaaatgcac aattcagacg tccttgaaga tcatttttaga ggcagcatga agtgggggt    51300 ggcactggtg atgggggctg ggtgtggaga aaaccagcca aaggaggact catgggatcc    51360
tggagctttt gactggggtt cacttggagc ccatactcag gctggttctg acagcagcac    51420
ctgccaggcc tcagcttagg ggcacaatgt gggacacatg gactgggggt gtggtcccag    51480
agcctaagag gcaccaacag agaggtctcc gcagagactc atctgtgccc cccacccacc    51540
```

```
accccgggac aggccaagcc agcgtctggc caggaactgc ttttgcacaa ggagccagaa   51600
gtagtttgcc ccgataaatg ggggcctgga ctcacgcaaa ccattgcacc atggatggcc   51660
agagaaactc agagaacctt cctgtgcttg ttaacatact ctctcacgtc ctctgcagcc   51720
tctgccaagc caagcagcca gctcctagga ctcccctccc tccacctgag gctccttgtc   51780
ctcccttcct caggagtctc cagcctcccg ggacttcccc tccccgctgc ccactccagc   51840
agaggctgcc aactgcctgg gagagagaag tgggcttcct ggggccacct ccccaacttt   51900
ggagtgtttg gaaggtgatg gagcgaccac taggaggcag tgtggacagg tctctgtagg   51960
actgctcagg cagacacctt tgcagggacc tcccaggtcg ggagccctcc acactttttcc  52020 catgggagct tctccctcca ccccgagtca ctactatctg ctttcctaga aggcacttct   52080
ttacttctaa ttcttctcca ctgcccaggt aactgatatt ctcaagtggg acattgtaat   52140
ttgtttaatt catttaaatt gatttcatat aattgggaga taaagattgt tcagttgcaa   52200
gacaaagtct taacttgaac tctcaggaca cgggtgggtc cctaaactca atacgtgagt   52260
gttgctgccg ggctgttggg ccatcttcca cccgccatag atcactttct tcatcaaaga   52320
agaaggaata tttagaaact ggtagtacaa aaaaacaaac aaacaacaac aacaacaaca   52380
aaaaaccaaa acaacaaaaa acaccaaatc accaaaaaca aacaaacaaa aaacaaataa   52440
aaacccaaag cagttgctcc tataaataga tgtgtgtata catgtggctg gtatgaatct   52500
tatccacaaa ttcagttttg tgggaaacat cacatttatt tatttaaatc aagtcatatg   52560
ggacttgggc atggttggag gttcttaccc caccccactt cccaaggcca gtgcacaggc   52620
agggccttga ggtcacccctt agccgatgct tgggtctagg tgctcagacc caagcccctg   52680
tggtcccatc atgtgggcac tggcatcttt gctgaggctg agaatttcaa agccaggatc   52740
cagcccattt aggtaaaccc aaagtcactc tcccaggtgg cccagtcatc ttcttgagaa   52800
caagagccat gagcctcagt tccctgcctc aagagcctct gttcaaccct aggcttgtag   52860
acaactctgc cccttcttct ctcccttcag tgtcacggtc ccctgtccca tccctctctg   52920
ggacaggtac cacaacctcc ccaccataca cagggaaagg gtcagccctc aggttttttgg  52980 cctggcatct tgaatctcct cccaggcaac aaaccacaga gggcctggca ttctcctgtg   53040
aaaagcaggg cggaaaggaa acacagagaa caaacccaca gacaacaaac ccacagaaaa   53100
caaacccaca gaaaacaaac ccgcagagaa caaacccaca gacaacaaac ccacatcaac   53160
aaacccacaa caacaaatct acaacaacaa acccacagag agcaagccca cagggaacca   53220
gccaaattat gtctgctgtg catctcggca gacgatgctg ccaccgtctg tgtatgagca   53280
tgtgtgtgtc agactttccc atcgtctcca aacttgtttt cagaataatg cttccagtga   53340
aatgagtcgg ccacatgagg tcacaaagcc cctactctgt tcagcacctg gggtaagtaa   53400
taatattttg gagcacttag tgtggggagt agccctgacc cctttacatg tcatgtctta   53460
gttcattctt gttgccatcc ttggaattga ggccaacatc atctgcccat ttgccagaca   53520
agctgctcag gaggagaggg ccacagcccc ttatctcctc gccaaacaag agaagatccc   53580
cagttgcttt ttttttctgt ggaagagatt ctttttaaaa catttttttc atggagaaga   53640
aaatctgaaa aaaagaatg aaaccgaacc aatagtccca tagacagtta gttgttgttg   53700
ttgttgtttt gtttgtttgt ttgttttttga tgaatacgaa aattgaccct tctggtcttaa  53760 aagcttgaaa attaaatttg ttttatctga gttgcttcct caggaaagga gcccaagtcc   53820
tctccaaaag tatcagagaa ctgaaactca ccagatcatc ttgtctagac aatgagacgt   53880
caggccctcc attcatcatg actgcttcct tacccctccc gagttcctgt tacatttctt   53940
```

-continued

```
ccctgctata taaacccta attttagtgg gtccagaaga tggatttgag actgagctcc    54000
atctcctggg cagcagcacc caattaaagc cttcttccct ggcaatactg attgtctcaa    54060
tgattgcctt ccttccttcc tttcttttttg agatagagtc tcactctgtc acccaagctg    54120
gagcacagtc gctctatctt ggctcactgc aacctctgcc tcccaggttc aagcacttct    54180
cctgcctcag cctcctgagt agctgggatt ataggtaccc gctactacag ctggctaatt    54240
tttgtatttt ttttttttta tagagatggg gtttcactat gttggccagg ctggtctcaa    54300
actcctgacc tcaggtgatc cacctgcctc ggcctcccaa agttctggga tgagaggtgt    54360
gagccatcac gcccagctga gtatgtgtgt gtgtgtgtat gcttatgggg atgtgcaaat    54420
gtgtgtgtga atgtgtgcac gtgtccttgt gaattgtgaa tacccaggac ttgagcacac    54480
tcagttcctg atgcacttcc tgtttctca gcagctgagc tcaggcctgg aactgagtga    54540
cagcacaccc gggcacctgt ctccctgggc acccctccca cgcctgcttc ccacggcatt    54600
cccagctccc accactggga aggagctgga atcatgagtc gggataatca ccgaattctc    54660
ttcgaccttc ctcagctcct ggtttgttaa ggcaaacccc catctctggc ttctcctgga    54720
acctcacctg ggaaagaaag aggcagcccc ggagctggaa gctgcttcag ggctcacccg    54780
gaacagcaga ctcaacctgg acccatccag gcatctcctg ggagtttcac ccaattgctt    54840
ctgcctggca ccagctcaga ggttctgaca gaattggcct ggggtgagac ctggcatcca    54900
tgggattttt acaagcttcc aggtgattct acagggaagc caaggtgaga acccctgtcc    54960
tagaaccagg tctgatcagg ggccggtggg gaactgtggg tggagaacat tagtgcttcc    55020
agagcctcag ggttggtttt gaaaggaacg taacacattt ttttttctca caaagacata    55080
tagagagaga cttttaaaa tagacatata tatagagaga tgttttaata aagagaggtt    55140
tgggtttata taagtaaaaa agatgataga aaatagagaa tgagattagg cttccccttg    55200
ctctcaaaaa atggtttgag agtcttggaa ctggttccac tctatgatag ccatgagtac    55260
tgttcgccca acttttggtt ctcagccttc caggccccgg tgggatgaga cttccctgcc    55320
cccacggttg agaggagcca tgggcttatt ctagccaatg aatggtggat ggacgtgact    55380
cgtgtctctt ccaggctgga gcatttaatt gtccaggtga gatactcagg gactcgtccc    55440
tccagagctg agaatggcca tgtttccaga gggtctgcag gagcaacctg agtctcagag    55500
cacagccacc agcagacctg ctgcacgcat gtggcggggg aaagaaagaa agccagctgt    55560
ctgcagccac tgagagtttg gggtggttgt ttctcatgac aaaaccagct cacccctgact    55620
tatacaaagt ctttgagtta tatagatgga gaatgaggct cttgggtccc tctattctca    55680
caaagcaata gcctagctaa atccatctaa ctagggagca gaaaaggga tgtgctggct    55740
tgcacaccct agacagttgt tcaagaagtc aggacaccag gcctggagtg atacttcagc    55800
catccttcta ggtgagggtc ttgaggccac acagacagaa gtggcagaga tgggacacac    55860
attcgtcttc tcactcacag tctggcactg agctgtgggc tgctgggaca ccatgccccc    55920
atacgagtag ccttcccact ccttaccttg aaggaaaagt gttttttgga caaatacctg    55980
atggaaacat tacatgggcc ttggaatctg ttagatctag cttcctgaaa ctcttgctag    56040
ctgtgtgaca atatacaagt ttcttaacct ctctgagcct cagtgctcta attcactcc    56100
cctcatagag tttctaagag catcctgggg ctggcacgtg tcaacgcacc cagtatttga    56160
tagagtttgt taaacgttgg ttatcctctc tccctatcgc acctcaaatg gtaagggctg    56220
cctgccagct tccatatccc cagcagtgcc ctgagttgtt cagatgttca tccatctccc    56280
```

```
acagaactca ggttcctttg gaggaagcca catcaagtcc tgctccaagc ttaagccagt    56340
cagcacattc catgctctgc cccattgcca gggttcagga gtatgctcgt gatctaagca    56400
cccccactcc cagatacagc tcaagattct tgcttggact tctgggcact caggctcctc    56460
cgagagggaa tcaaacttac ttctctccat gtcctttcct ctaggagatg cgtctttcat    56520
aaaactctca tcaacactgt tcagacatgt cccaccccag caggggacag cctgggctca    56580
agctgggatc cctactttat ttattttctg ctaattaaac ttcctaatat actccacact    56640
aagtgtgctt gcaaggcagg gggtgtggga taagcggccc tgcctggctg ggagaggggg    56700
cagctccctg ctgtactatg tattaataaa gagacacatg catggcaggg cttgtctggg    56760
ccttggtggc agcttaggac agaaggcacg tgacagtcag gggttcaaac aacccaggga    56820
gaacactgct tcaggaaga cagctcagca tcttcctggc aaagataatg acattgataa    56880
tactctccaa agaatttcag gattttgagc aatcagaaaa gcaacacaga aattcatgtc    56940
atcaaaacga tatggctcta ttggacactt aagacattta ttggaggctc aacaacataa    57000
tcctgctggt tggttttact tcattgattt tccgttgtgt ctgattacat tgctaatgct    57060
gatggtggat gagctacggc tcttttcctg cctgtcctga ggtttatcca ccaatgtttc    57120
agttctgttt taagatattg tcctaagccc ccagcatcgc atgcatgctg ttttttttgtt    57180 ttgtttgtt ttgtttttta caaagagttc atagcccgtg gaagactctc ctccatcaca    57240
cacttaggtt ccctccacac caggcctgga aggagtctag cttctgggga ctgtacatat    57300
gctgtggacc atgcagaacc tggagaggcg gtgaccccctt ctagaagtga tctgcctgaa    57360
tccttccctc tggaggaggc atttattaaa tgccaggttc ctgaaaggct ctgagatggg    57420
cactccctct cctgagtcgt cccttccatt actgctttcc tatttctggc cagggttccc    57480
tggcccctcc tccctgctcc catgggaccc cagttcatcc ccatctttgc tcaattgccc    57540
tgcactgtag taatccattg gcactcttgt cttctccagg agaaatagtt ggaggagaag    57600
tttatagggt ttcctgggcc agggctggtc tacagtcact ggacagcagg aaacgaccct    57660
tcggggccta ggagggccaa ggctggtggg caggtacagg gggagccagc actgctgtcc    57720
accactgtgc agcctggagg ctgtttccca tgaccctgct gatgggaccc aaggcacccc    57780
aggccaccca ctcccctgcc cccagcaggg tgtcagctcc ccggcttccc tgcatgcctg    57840
cctgacatgg acagtgcacc ttcgggccac acttgccctg ctagcgagcc tccagtgaac    57900
tgggaattcc acagagtgta gaggactcgc cccagcactg tgctgagagg cttcaccaaa    57960
ctgtagcctg gcttccacct gcactaagct gcatccccag aggcgacccc agccctggct    58020
gagtcttggc tcaagacttt gcaatgcagc caaatcacaa aatgcacctc gtccagccca    58080
ccccgctaaa ccattttcag tagttctccc ctcaccgttc tggaactttc catttccacg    58140
tggcccccac gttctgtttt catttctcct tcagtccctt tttgttccct ttctgttctc    58200
tctttgaaga cctcagtcac cgttttctga gttgggttg agcttggtcg gtactggaat    58260
ctctttccgc tgctgcagga gtctgaagga atcagtcttg ccgcctgtaa cacatgtcca    58320
gcgctgcttt ttctctgatg agtgtcttag tcagtttggg ctgttaaaac aaatggctta    58380
ggcaacacac gtttctgtct cacagttctg gaagctggaa gtctgagatc aagtgttgg    58440 cagattcggt acccggtgag gacctgcttc ctggttcgcg ggtagaacac ttcttgctgt    58500
gtcctcacaa ggtgcagaga gagaggggg tctggtgtct cttcctgtaa gggcactgat    58560
cccatcatgg gggccttaca atcgcgacct catctaaacc tcccgaaacc tcatctaaat    58620
ctcacctcca tactatcaca ttggggatta aggctttaac atgtggattt caggggacaa    58680
```

```
aggacaaaag cattcagtcc atggcacatg ctcagtgcct cgactcttgc aagtgccaca   58740
ccacagcctc tctggggctg tgtcctggag gcgtgtgcca tgggccctgt gtgccatggg   58800
caaggcgcac agcatcctcc cggccacccc accagcgagt gagctcctgg cacccctggct  58860 ctctctggtc acccatctac cagtcttggt gctcctgtgc actagaggac cagctgcctg   58920
gggactgtgg gccaactgtg gccccggcca cccacgaact tcccctccgg ccagtggctg   58980
caatcacatc ttctctaaag acgtctgaag cccagccttg gggagccgag ttggtccttc   59040
cctgggtact gagccctagg gaaccttga gagttctctt tgtatctttg tagtttcttc    59100
ctcaccactt aatcatttcc ttacaggaaa cttcctgtgt tcaagtgact gtatggtttc   59160
tgcctccagc ttcatttgtg ggtgccataa gagaggcaag catggagcac taggcgcagg   59220
ggatgggcaa ctggcaagcg gggagatgca tgcagcgcac ttagtgcctg gtacatacca   59280 agtccttta gtctggattt cattattttt aaatgggtat tgctatttt aaaagaatag     59340 ttacaaatat ttattgtgtg ttttgaaata agtgggtcaa gatcaataag atattgttga   59400
tcaattgatc aataagatat cttttattct taaaaatcat attcttctgg ttcagtgggg   59460
aagagactgc cgacctgtat ttacagcatt atgtgataag tgttctcctt ttcaggtatg   59520
tattagtctg ttctcatgct gtcaataaag acatacctga gactgggtaa tttataaagg   59580
aaagatgctt aattgactca caattcctca tggctgagga ggcctcagga aacttacaat   59640
catggcagaa aaggaagcaa gcatatcctt cttcgcatga tggcaggaag gagaaataca   59700
gagcaaagtg gggaaagccc cttataaaac catcagatct tgtgagaacg caatcactat   59760
caagagaaca gcatggaggt aattacccac cggctccctc ccatgacgca tggggattat   59820
gggaactata gttcaagatg agatttgagt ggggacacag gcaaaccata tcaaggtgac   59880
tcctgcaagc acctacctcc acccctcctt catccttgcc ctcattctac aatgatttgg   59940
tgaaatctgg tccctgcctc agttttacag cctccccatg actctggtta cttcctgatt   60000
agcttaaacg aaacctaact aggttgccct aggaaagcat ttctgttcct gacaccccc    60060 atctgcctgc tgcttccgtt ccacctgtat gtgtctgggc acatccctgc atcccttgc    60120 tggcttctag cctactcact tcaagcattt atcccatgag tttcataaaa tcgtagaaga   60180
aaagggcttg aggcagtggt ggggaaatga taggaaagtc atttctggat gcattctgcc   60240
atcctgcaga tccctaaacc acctctccct ctccattccc tccctccaga gaacagcttc   60300
tccttgtctc ctgtggaata gttccgccca cattcatggg cccttcctgt accaaaactg   60360
tacaggtctc tcttgcttac caaacacttg gcaaacaaat gtgccgtcct tggaaaaatt   60420
ctgttgaata aaattttctc tctttgatcc atccaaatgt tttacaaagt gctacagaag   60480
ccatggagga acaagcaatt ctgccttagg gatcaaggtt tcacacaggg ggtgatatct   60540
gagcaacagt gcttttttgg tttgtttgtt ttgttttgag atggagtctc gatctgttgc   60600
ccaggctgga gtgtggtggc acaatctcgg ctcactgcaa cctccgcctc ccaggtttaa   60660
gtgattctcc tgcttcagcc tcctgagtag ttgggattac aggtgcccgc caccataccc   60720
agctaatttt tgtattttta gtagagacgg ggtttcacca tgttggccag gctggtctcg   60780
aactcctgac ctcaagtgat ctgcccacct cggcctccca aagtgctagg attataggca   60840
tgagccacag tgcccagcca acagtgcttt taattggcat tttcttcaaa gactttgatg   60900
tcctatagga gggggcctat gactcagcct cagccaatca gagcgctcca ttccctgggt   60960
cacctgcaca cctgctcttc cctgatccac tgcagtgccc tcaccctgag atctgaaact   61020
```

-continued

```
tgagcagagg cactaaaagg cagacatggg agctgagctg tcttttggga gaatcctagt    61080
gagaaggttc tccaactggg gccgccaagt aagggcctca tggcagacta acccctctcc    61140
ttcctaaggc tgggaggagc tgctgtcctt ttgattctgt gagctacctc agttaccttc    61200
ctcaaaatca cacacacgcg cacacacaca cacacacaca cacacacaca cacacacatt    61260
tgcatgcgct aggtagagct gttttccata attgccaaca gaagactaac tgtatttgaa    61320
gaatgagctg gcattcttct gctccggtag aagtcaaggc aatcagttat gagaatcaga    61380
gcccacctgt gactccagaa agaggtgcat aaataccaag aatttagtct ctaaagtctt    61440
tctttaagtc cttttttaaa aaatgtgatg agtacatcac ccaggaaaat caaattgtaa    61500
tgcaaccgag tcgatgcaag ttttatttag gagatgggtt acaatcacct ggggaggctc    61560
tagttacctt gatttggtct ggtacaaacc ctagcaccat catccacaga tccccagagg    61620
aagtcattcc tggatgactt cctcatcgat tttaaataat ttccatttca gaggaaggcc    61680
tttatctgac ctgatcccct aaatattggg ggaaacctac atagggacaa agacagcagg    61740
tgtctgcaat gttgagaatc agtgtgttct gtcactgtct ctatcagggc tggtggcaca    61800
tgcaaatctc tttcccactc tccagttgaa cactaacgcc atggtgccca caccttcctt    61860
attagtccat gtacatgggg tttgtcaaga cagtggttca tggctctgac cctgagcatg    61920
tcagatttca ggggctttat gcaaaatatc cataccagtt ggggtcattt cccatcagta    61980
ttgctcacaa tggagcctac aaaccccctag ttcccatcca acacatctcc aaggcagact    62040
ctcagaccag ctcccagaaa tgaggtgagt ttagatcagg cagcagagag gtggcctagg    62100
aaggagtcct tggagctcat gcacctgtgt ctgggcacca acaggaagat ggtggctttt    62160
gctctttggg agatatcttt ggagccagtc tctgaccaca tgtccaacag acaggcatc    62220 cttggggttt ccatggcagt ctactgacag tcaggggtga ggattaaatg gtacagagtc    62280
tcactgagtg ctctttgaga ggtcaagcaa tgagaagtcc tgcaaatgat tattgagctg    62340
aagtaagaag tgtaccgaat ctgttttttcc cctataaata taaaagccta taaatataaa    62400
aatcttggtg aaaaaaaatg atcccagcct cccacacagc acatcacaca tcttctcttt    62460
tcaaatttga ctccaaggcc cacttccttc gggaaatcat ttatccagtg gtatcattta    62520 ggatatttt ggttgtgagg aacaaaagcc tagctccaaa agacttaata aaaggatctc    62580
attggttcac aaactgaaaa actccagtgg taaatgaagg ctctgggtac agttggtaca    62640
ggctctggtc tctgtaattt cctagttctt ctcccttcta gatgctgggt ttttgccttc    62700
aagttggctt tcttcatggt ggcaaaatgg atccagcaat tctgtcagag gttttcgaag    62760
cagagtgact ccatcttgat taaaggctgt gtaaaatgag gatgagactt gctggactgc    62820
attccaggag ggtaggcatt cttagtcaca gggtgagaca ggaggccagc aggattgata    62880
tcacaagaca caggtcacaa agaccctgct gataaaacaa gatgcaataa agaagccagc    62940
caaaacccac caaaaccaag atggtgatta atgtgacctc tggtcttcct cactgctcat    63000
tatatggtaa ttgtaatgca ttagtgtggt aaaagacact tctactaact ccatgacagc    63060
ttacaaatgc catggcaatg tccagaagtt accctatatg gtctaaaagg agaacctata    63120
tagtctaaaa gaactgaggg ttctgagaaa tccctgaccc tttcctggaa aatttatgaa    63180
taatccactc cttgtttagc atacaatcaa gaaataacca tagtgtactc agtcaagcag    63240
tccctgctgc tgctctgcct atggagtagc cattctttg ttctttactt tcttaataaa    63300
cttgctttca ttttacttta tggacttgcc ctcaattctt tcttgtgcaa gattcaagaa    63360
ccctcccttg gggtctggat caggatccca ttcccgtaac aatttcaggc tcagatcggc    63420
```

```
ttttaacacc atccagagca agagaaagct tttttgttcc agaattcccc attaaagttc    63480
tcctggtcac tcttattggg ttgtttcgct tagggtcagg tgtccatcct ggtcccaagc    63540
aatgaggcca ggagatggga tgcaacgact ggatcaatct aggcctctta ttcccacttt    63600
ttaaaacact tattattatt attttttaaa aattatttt cattcagctt tttcatttga     63660
aacttattcc aattcttgaa ctggggtag tttcaacttt cctagagctg tatgggtcct     63720
caaatgaaaa ttcggggcag ctggattaga aaggggaa atgcatgctg cagggcaac      63780
caacaagggg agattgtgcc aattcactct tcctatcctc agattcacct aagttctgac    63840
cattcagccc catttgaatg cattctgtat tcctatgact gtggattaca tttttgtcta    63900
cctttgtgtc ttctgttttg tcctgcccta taagcatctc aaacatatgc ataaagccta   63960
tataaacttt ataaataaac taacacttct gtttcaacc tgtaggatga tgacaatgat    64020
gatgacgaca atgatgatgg taatgatgtg gaaaatgtga aaagagaaag aaatacttgg   64080
aaatatatct caccctccat aaacaaagct cggggtttaa ttctgacctg tatgagttca   64140
tggggtgaac tgcagaccgc tgtctgtgga caggaaaacg atatttcatc tctagcccca   64200
gggacatctc caaaagctga gctagatgaa ctttatataa attggtacaa aatataattt   64260
tctctttgcc tgctgaaagc catttctaga aattctgtta atcagaatct ccctaagtta   64320
atcagtcatc tagacagatc ttatttcttt tttagacaaa gaaagtata taagtaacag    64380
gtattggtaa accacttgag tgaagcatat gatatctaat gtaaggaaat ctaaaagtgt   64440
ccacaggcaa aatctcatgg attcaattga tagcacaggt catcaactga catgcagacg   64500
gaattctctt gtggaacaag acaatacagc cattgcttag agactaattg tcaaggaatt   64560
agtcatttcc tgtttcagaa tagcatcatc accaccacca ttaatgccaa catcaaccac   64620
caccacctac gccaccaccg ttagcatcat aaccaccacc aataacatca ccaacagcaa   64680
cactgccatc aacataaacc atcaccacca ccaaaaccat tagcatcacc tagaaccacc   64740
agtcaccacc atcaccactt accacaacaa ggcttatatt tacatactta ttttactttt   64800
cgaaatacat tcacatgcat ggtttcatta gatcttatct acttggtaag gttggcagat   64860
ctgacatcat tagcctcatt ttatctgtat ggaaactaag ttctagagaa gcgaagtgat   64920
gtgtgaaagg acaccagagt gattgataat caaatccaga ctagagtttg gttcttctga   64980
ctccaaaatt aatacatttt tcttaaaaga aaaaatttt ttttgagaca gggtctcact    65040
ctgtcaccca agcttgagtg cagtggcatg atcacagctt actgcagcct cgacttccca   65100
agctcaagca atcctcccac ctcagcctct caagtacctg ggaccatagg cacatgcctg   65160
gctaatgtgt tttaaacatt ttttggctgg gcacggtggc tcatgcttgt aatcccagca   65220
ctttggtagg ccaaggcagg cggaccacaa ggtcaggata tcgagaccag actggccaaa   65280
atggtgaaac ctcatctcta ctaaaaatac aaaaaaatta gccaggcgtg gtggcacatg   65340
cctgtagtcc cagctactca ggaggctgag gtaggagaat tgcttgaacc caggaggcag   65400
aggttgcagt gagctgagat tgtgacattg cactccagcc tgggcgacaa gagcaaactc   65460
cgtctcaaaa caaacaaaa caaacaaaa caaacaaaa caaacaaaa caaacttt       65520
ttttttttt tttgtagaa acggggtctc cctaggttgc ccaggctgga ctcaatcttc    65580
tgggctcaag tgatcctact gcctcaggt ctctaaatgc tgggattcag gcatgagcca    65640
ccacacccag ctccaatgct ttttttgtcg tacctaattc tttcaatgaa aatgaagaat   65700
ttccaacttc tgatattaac aactttggtc ctatattcaa gctagagtct ttcaaataaa   65760
```

```
atagactttt aaaaccatct gtctccaaac cctaaatgtc tcaggtgagc aactaagctg    65820
ctcagtttat gtgactcccc agaagttgaa ttttaaccca gaactgactc caagttcatt    65880
cttctttcca cgacaaggag tcacctcctt gtatgccccc aggagtctcc cggattcctc    65940
cgagaacagt ggaatagtgc tcctccccag agcacaggtt ttgccagtga agattgaatt    66000
tggctagaaa ccgctgccct gctctctctt ctcgaagcac ctggaagtct gagaaggaac    66060
tgggtggctg gctctggtca caaactagca gccagaagca ccccttgtca gtgatgcacc    66120
cccagtcccc ctcaagggct ccaagtaaac ccaaagctgc tcccctccaa gaagtctggg    66180
gccaccctag ggaaggcctc ctggccttga ctctcagggg gtctctgggg ttgcggtttg    66240
gggcccgctg cttccgccct ttgccccag gtgggcctgg cagggctgca gcacagctct    66300
gttgctgata gacagggtgg agcacttggc gaccttgccc tgcagccctg tcattttgag    66360
ttcagaggtc agatttgagt aataaacatc ttctaaggac ttgtcattct ttctgaggat    66420
gttgctggcc agccggaaga cgaaaatcac cgcgtagatg ccgatgatgg tgagtatata    66480
ccaggcagcg ctggttccgt ctggcacctt cagagccctg gtggagttgg tgtcattcct    66540
cccctctgtg tggtcaccca gcaggagccc caggagggtg ctggcctggg tctggttgga    66600
ggcttcatgg ggagtccact tggcccctga gaaacagaga ggtccggatg agatccagcg    66660
tcctgggctg agggctgcct ggccacacca aggagaatgg agccctcata tccgtgaaaa    66720
cgtgtcgctg ctcaaagagg ccttctctga ggcatgagca ggagtgtaac aacaggtatg    66780
tcaatatatt tttaaaaatc aaagagtcc aaaacactat tttgttgttg ttttgttttg    66840
tttttttgttt tgtttgtttt agagagacag agtctctgtc acccaggctg gagtgcagtg    66900
gcatgatcat aacttactac agcctcaacc tcctgggctc aattgatcct cctgcctcag    66960
cctcacaaat agacatgcag caccatgccg ggctaatttt tttctttttt ctctctcttt    67020
ttttttttgt agagataggg tcttgccatg ttgaccaggc tggttttgaa ttcctggtct    67080
caagagctcc tctcaccttca gcctcccaag ccctgggatt acaggcagga gccactgtgc    67140
ccagaaaaac actaagttct tgaataggag acacaacatc ataaagatgt cagttatccc    67200
tcaaataatt tatacaacaa acataattgc aataaaaaca gcataggat ttctttgtga    67260
aatcaataaa ctattcattt agaaaaatca actgttggcc gggcatggtg tctcatgcct    67320
gtaatcccag cactttggga ggctaaggtg ggaagattgc ttgagcccag gaggttgaga    67380
ccagcctggc caacatgaca agaccctgtc tctacaagaa ataaaaaac tagccaggtg    67440
tggtgtgcaa gcctatggtc ctaactactc aggaggctga ggccggagga tcacttgagc    67500
ccaggaggtt gaggctgcag tgagctgtgt tcacaccact gcattccagc atgggaccct    67560
atttaaaaaa aacaaaaaaa gaaagaaaga aaagaaaaa gaaaaatcaa ctgtcaagac    67620
taattagaaa aaaaaatctg aataaaaaga atgactaatg aattagccta gccacaaatt    67680
ttaaatcagc cagctataaa aactaattta cattttttc aatgaatgaa agctttatat    67740
gcacaaagcc cagctgggac ttgctgggct ttgcagagtg tgtgggctgg gggttcttca    67800
gaaccaggta caactctccc tataaaacta caacagtgct gggcatggtg gctcacacct    67860
gtaatcccag cactttggga ggctgaggca ggtggatcac ctgaggtcag gagttcgaga    67920
ccagccctgc caaaatggag aaaccccgtc tttactaaaa atacaaaaat taaccaggcg    67980
tggtggcaca cacctgtagt tccagctact agggaggctg aggcaggaga atcgcttgag    68040
tccaggaggt ggaggttgca gtgagccaag tgatgcctgt agttccagca agacagagca    68100
agactctatc ttaaaagta aaaaaataaa aaataaaact acaacagcta aatagtgtg    68160
```

```
atgcctgtag ttccagctac tagggaggcc gaggcaggag aatcgcttga gtccaggagg  68220
tggaggttgc agtgagccaa gatcgggcca ctgcactcca gcctgggtga cagagcaaga  68280
ctctgtctta aaaataaaa aaaataaaaa ataaaactac aacagctaaa atagtgtggt   68340
gctgaaaaca caggcaagca gaccaatgaa acagagtaaa aacagcatca atagttagca  68400
attagaattt gatagctagc taataaagga gcatttctga tcggtgggaa agatgaattt  68460
attcaatatg tagcattggg ggaaatagca ttagatccac atctctccac catatgacca  68520
gataaatcgg tccagattaa aaaaaaaaca gcccagataa atcaaatatt ttaacataaa  68580
aagtgaaata atttatagta ctagagtaca gcatggcaga tttttctttt atcatctcag  68640
agtggaatat tcttttaagc ataacaaaaa ttcagaagaa acaagaaata gaaatcaaat  68700
tcaactacat aaaaaaaatt aagctatttc ataccataaa accaacaggc agatgacaaa  68760
gtgcaattta tatcactgat tttctaaata gccttcggtt ctgtaagaaa agttttaaaa  68820
ctgcagtaga aaaatgtgca aagatatgg acaaatagtt cacagggaaa aaatgaacat   68880
tcaacataag aagagcttct caatatcact catataagaa aaatgcaaat taagataata  68940
actagatacc attttgttac ctattggact tgcaaattca tgatgtttca gaataaacta  69000
acaaaaaaat ggcttttttt tgttcttttg tccagcttag aagaaaggtg tctaaattgg  69060
gagcaaaggt ggcaatgacg tggacttgac accaaaaaaa aattttttta aagaaaagaa  69120
acaagtgcct ctgcatttca ggggtttagg attggcattt ttaaaatgtc aacaaataaa  69180
tgttcatatc cacacttgac atttttccca aggagaattt taattgtata attgctggta  69240
aattcatgca gccaacatgg agggcacacg gacaagatct atgagcatta caagtgcact  69300
tacctttgac ccagcaattc tatctctagg aatctatcct aaagatgctc cagaacatct  69360
agagacaaca tatgctgaag gttagtcatt gcagtcctcc ttgtgatgac gaatgcctgg  69420
gaacagcctg aatagcacca actgagggat ggtgaaatac attttggaac ctccatgcag  69480
tggagtacta cacagtcata aaaagcaatg agttttttat ggtactgaat gttaataagt  69540
gaaaaaataa gctaatggtg acatgctctg caatgccact tgtaaagaag ggggaagtta  69600
tatgttattt gcttgtactt ttttttatgta tagaacatct ctggaagaat gaataagaaa  69660
ttagtatctg caattgcctc tggggaagaa acctggggga agaagatata tttttttactg  69720
tttgcccttt tgtacactta gtaccgtgta tacttatttt tgaaaagcaa gagtgtacca  69780
gttggtactt ttctggtctc cctggtgagg tgcccctggg taaagccgtt gtatgccctt  69840
gtaagaccag aagattaaga tctcaattgc tgttcaattc aaaactgttt tctctgcttg  69900
gagagctggt ggagaaaatg aaacaatgaa accagagct gtagagtgca atcctgtgag    69960
acatttccca gtgggcctt actggctcaa acccccattt cttgctctaa tgtgaacaca  70020
gatgtattta aaaacacatc ataggatcaa tcttgcagcc tgctgtgcag aacaaaggtg  70080
ctccaaaatg cttcccattt gatcgttgtt tgttgctaat tcattttgcg aacgcaagac  70140
tcagagaggc cagtattttt tattatagtt agttgccaga atgtgtgaat gagcttatta  70200
cttttagatg aaggaagaaa ctatttaaaa attacttttc aaactacatg tgacaaagcc  70260
caggacaaat gaacagattt aattacataa aattagtcac tcgcaagaaa caacaccaca  70320
agcataaatt tacaccattg tttggtagaa tggtttgaga cattaaagta aggaaggtga  70380
aaaattcccg taattattgc aacaaacaaa cagacagcaa atcaacccaa caagaacaca  70440
atatccttat attagggcaa gagaacttat tgaaactcag aacacatgta taaactcata  70500
```

-continued

```
gaactttcta gaaattgtca tagaatgatg caacacattc aaatacaaat aaaatatccc    70560
caactaagag ctacacacag aacattaaat tatttaaaaa ccagtccatt ttctacacga    70620
aagaaactca ctatattaat tactgcaata cattacattt tacctttctt acaaaggtaa    70680
aagtaagtta ggttgtatct taatggacaa acatatcctg tagaagagag aaacttttc    70740
ctctgtgcta ttttgtactt gtaatttaat gacgtgaaat atgtaaaatc tcaacctgcc    70800
catccttgca ttgtagctga gtactcacat tccatggggt ggtcttgtcc ttgactcttg    70860
gaggggcaag ttcaagcggc taccatgcac agaaggggaa gatgatgaaa ggagaactcc    70920
gtctcctagg aagaatcag tcctactgca gttgagctgc actgagtttc cagagtgggg    70980
agtaatatga tcttccaaca atcttagggc agcaccaaac agaaacttag taagtggatg    71040
actttgcttt catgcaatta atcagaggat ccgatttgct gtgtcttctg ttgcatcaga    71100
acagaaagca cttcccagct ttgacttgtt aagaagttct caatcaaaac aaattttaa    71160
aacgtgctgg tattaaggaa tctccatctc tcaggtccca tcatgaactg aggtggccag    71220
aagctccccc tgaggctggc tctccgctta gagcttggat ggctattgaa ttcccctgtg    71280
ttctgcacct gttgcaggtg tggcagatgg ccaggtgtgg cagagatctg tcatcatagg    71340
gccaggaaac tccatggtca agagtcacca gcttcctctg gacagtctcc cagatgagga    71400
aacccagaca ggaagggagt gacacccaa gggtgacaca cctgagggga cttgggcttt    71460
ccctgagggg tcagtgggca gtggactcct gtgccaggtg gtgagaaatg gctcttctct    71520
ttcccagagt cacagacccc attggagttg aggtaggctt aattggaaag tgttagagta    71580
agtgtctgcg ggtaaagttt ccccaggagc agggagggaa aagttggaag actggcaagt    71640
taaatcatcc agccattgtt tccagttcca tttcttccta atcctcactc taggactcta    71700
acttgccacg tttgtgatgg ttgctggttt ttaagataca atttgatgaa atttccatca    71760
atggggtact gggtaagtaa gttataaaat aagccatatg atccagcaat tctactcctg    71820
ggtatcttcc caggagaaat aaaaatgtaa gtttacacaa aaacttgaac acacatgttc    71880
aaagcagcat tatctgtaat agcaaaaaat ggaaacaacc caaatatcca acaactgact    71940
aatgaataaa taaaatgtgg tttatccata caatggaatg ttattcagca ataaacagga    72000
atgaagtact gatatatgcc ataacacgga tgaaacttgc aaacattgtg ctaaataaaa    72060
gaagtcagtc acaaaggact acatattgta ggatttcatt tatatgaaat gccaagaata    72120
ggcaaatcta caaagataga aaatagatta gtggttcact agcgggaggg attgggggtg    72180
ataactaagg gtatatagca tttttggagg ggtaataaaa cttctaaaat tgtggtgctc    72240
actgtacaca atctgtgaat atacaaaaaa attgaatgca tactttaaat ggatgaattt    72300
tatggtatat gaattatatt tcaataaaac tgttaaaaat tataatatac aagctgggtg    72360
cagtggctca cacctgtaat cccagcactt tgggaggccg aggtgggtgg atccctgag    72420
gttgggagtt cgagaccagc ctgaccaaca tggagaaacc ctgtctctac taaaagtaca    72480
aaaaattagc cgggcatagt ggagcatgcc tgtaatccca gttacttggg aggctgaggc    72540
aggagaattg cttgaaccca ggaggcgag gttgcagtga gcagaggttg tgccattgca    72600
ctccagcctg ggcaataaga gtgaaactcc atctcaaaaa aaaaattata atatacatat    72660
acaatggagt attacacagc tgtgaaaaag aacgaggaag ctatttatgt actgatgtat    72720
aaagctctct aaggtgtgct gttatgaaaa aggtaaagaa gagagcatgt taacatgtat    72780
ccaaaaattg agaggaagca tatatatata tatctgattt tgccactgta agcatttaaa    72840
acaccagtgg aatatccaag aaattaagaa gaggggttac ctattggagg agagaaccag    72900
```

-continued

```
gtagatatat ggcaggtgtg ggagggagag ctctcactaa atattttat gctttaaata    72960
tttttaaccg tatgtgtatt acctattcaa taataaatgc acccatttgt tagatatctt    73020
tgttgaagat tcatttggct cctgctgtct cttgctatgg gatggaccat ggcatccccc    73080
ctctgccaca cagacaaggg atttggacac tgccagtggg acgtgggagg ggagagcacc    73140
tgacccgtga taataagggg ctcgtggcag tgataagggc tgggagtcag ggctctggcc    73200
ccagccacat ccttgctgca tgaccctggg ccagccccct catctttgtg agcctcagtt    73260
tcctcatctg tgaggtgaag gtggtgaagg aggtgaagga tgagcaggat cttatgtcct    73320
tggtcctgag aaggcaggag agaagcctgg ggctctgtgt gggaagagcc gctctctggg    73380
gaggtatctg aatagatgag ggagagcaca ccgggcagcc aatgtgccag aggtggaggc    73440
tttggagagt gtttcatttg tgaagtcaac agatttaaca ttcagatcag gaggacgttg    73500
gcatgagatg tggggaatca taagctccaa aacaatcgtg agacagaagg aaagatggcc    73560
ttttgttgag cagccattct cctccacgga gagtcctgtc tagtctgcct gttgaagggg    73620
cactgatgtt aggaaataga tctgtgtcaa atgcttccca cctcccagaa tcctgtgagg    73680
caggagtatt atccccattt aaagagagga cactcaggct cagggaagtg actggcccaa    73740
tgtcccatag ctcataggtg ccagaggtgg gtcatccaca ccaaagtcat tctccttcca    73800
taccctgaat gtcaccttca cgctggaccc aggatcctgt gtggtgaact gtctcgatca    73860
cttccctaaa ggttaaatca taaactctta ctgccaaggc atatccacga ccttaaactc    73920
tccctgttgg gcaaaaacaa tctctgatgt taaaaggcag gatagtggat acttttcagg    73980
gaagggtaaa tgacaagggc atgagggaa ctctgggtgc cggtcatatt ctgttttaca    74040
ggtttgttca atttgagaca cttcatagag ctgtagcctt gtgcacaggc acttttttgc    74100
atgcatcgtc tgcttcaata taaacctctt cctgttgtct tgttttttgtt tttgtttttg    74160
ttttctcttg ttttcttgtc ctgctctgtc acccaggctg gagctcagtg gtgtgatctc    74220
agctcactgc agcccctgcc tcccaggttc aagcgattct tctgctcggc ctcctgagta    74280
gctgggatta cagaggtgtg ctaccacacc tggcttccct gttgtttctt taatgtagaa    74340
agccctgata gatggtggga aaacaaagtt taaggtattc atagaaaaat acaaatacta    74400
tttttaagga ttctatatct ggccacatgg tgccatctca cgaagagtgt ccccgtccct    74460
tgaggggggag tggtcgggat catggtcagt gtggggccct gcagctgcct gcttccctat    74520
gctgtgtgga tgacgcccgc ctccggtcat tcccctgtgc ttacataaca gtgaaatgga    74580
acaacctgta tcagcacgag ggccaagaat tttcttctga cttgtggata cctccttcct    74640
taggcctctg atcagtctgg acaaatattg ccctgaacgc aaccaagcaa agccactcac    74700
ctggtaaata tttgtatgag ctacagttct ggaagaacaa attccaatat cctgcagtcc    74760
ccttgacatc aaagacccaa ctctcccaga gggcaatggc ttttttgtcc actgagaagc    74820
cagtcagctt cgaagaaagg tgtctaaatt gggagcaaag gtggcaatga tgtggacttg    74880
actccaaaag aaattttaaa agaaaagaa gtgcctttgc atttcagggg gtcagtattg    74940
gcatttttaa aatgtcaaca aataaatgtt catatccaca cttgacattc tttccaagga    75000
gaattttcta gaggagacag acctcatcgg tcagctctga tgccctgcag tgcaaaagaa    75060
cattaaaaat gacggtaaag gaccctgca gagaacaact gagtctcttc cttgccctgc    75120
gtctccagat aaaggatgcc ctgcatccat ccctcctgg ctaagagcac agactccaga    75180
ggcttttttcc tctcctggag gttaaagagg catcacatat gtttaaaatc tttaatttat    75240
```

-continued

```
atgtcacctt tgtccttcct tttaacttca tttttctctt atccagcatt tagggactca    75300
tctttaggga ggttcaaagg aaagctcatg gcctttagaa ctggaagaac catgttccag    75360
ttgggacttg atcatttact aattgtggga ttacagccaa gtcacttcat ccctctgctg    75420
taaaaaaaaa aaaaaaaaca aaaaaaaaca tatgatgaca tttgtggaat ggctcccaa     75480
gccaaagagg gcaaatattg tcacagctca tttcttctct cagttaatta cttgcgtcct    75540
cggctgcctg gctggcagga caacctatat tcgcctccct cttaaagcct cctgggttgg    75600
ccaggactcc aagcggcttt gtccagaatg agtagggtgg ttggcctggc ctcctcagcc    75660
aatcagagag gactagcatc tgaacactcc tctgtgctat tgcttctagc tgccacatgg    75720
ggacgctgtt gaaacaccgg cctggtgcag ttggccatat gatgcttcag ggtcttctga    75780
gacttcaaga atgtgctcac agggaaggta ttagctctaa acacttgcct ctgctagttt    75840
acatcacaga acagacagac aagactgttt tgctccctca gctctctcct tttcctagct    75900
tcagtcctgg ggagctcaga agctacagtt tgttttttgt tttttgtttt tgttttttc     75960
ttgagggagt cttgctctgt tgcccaatct ggagttcagt ggtgtgatct tggttcactg    76020
caacctccgt ctcccaggtt caagcaattc tcctgcctca gcctcccgag tagctgggac    76080
tacaggtgcc tgccaccatg ccaatctaat ttctgcattt ttagtagagt caggatttca    76140
ccatgttggc caggctggtc ttgaattcct gacctctggt gatcacccac ctcagcctcc    76200
caaagtctg agattatagg cgtaagccac cgcacccggc cagaagccac agtttacaaa     76260
tctgggggat tgggggcatg ggaacagaaa cagaagagtc ccaatgaaag gaagatacca    76320
gctgagctgc ccactctccc agctgcagtt ctcctgccca cagcaggccc tagctgggac    76380
agggaggagc cccagcctta aatcaaattc agaattttgt ttatgacata agactgcaca    76440
tcttaattac tgaattaaga ctatattttc caacctatca tgactatagg tgcagggcaa    76500
gatcaaactc cagtgtatgt ggggcccgca gaagagattt aaagaaacag tgggggcaga    76560
aataaagctg tgtggttatc agatcccatg agtcttgtct gtaaggatga tggttacagt    76620
cgggatgctc cagagtgcaa agccacatct caaccagagt tagtaacaag ggagagttta    76680
ctggttcatg tgaggaagag agaggaaggg gagggctagc caagggctg gatgcaggaa     76740
ggagggtccc cagggttctc tgtccccctc ctgtcttcca tctctgcctc tctcagcagg    76800
ttggcctaat ttcctccgac tgcagagaag cacacaagct gtggcacctg gtgctcagac    76860
tcacactgca acacttccac cagtagatgg cagagaggta ctttcctgcc tgttcagcca    76920
cgaaaatccc agggggatggc tctgactagc ctaagtcagg aacctgctgt gggcaatcac   76980
tgtagcatta agatggggc cagtgatgga gccggtctgc agcacatgct cagcaaaaga    77040
caaaacccgc ctgttttaga tcactccggc tgcatcacag agtgtggatt gaacaggcac    77100
agaactggag gcagagaaac aagttaggca gctgcaggca taatccaggc aggagatgac    77160
agtatttgaa agaaggagtg ggagcaagtc tggagagaag tcgatggatc caagagattt    77220
ttagaaggta gaatgtgcag aacttaatta gttggtgcag tgggttgaat ggtgtctccc    77280
taaaagatat gttcacctgg aacctcagca tgtgaccta tttggaataa gggctcttgc     77340
agaagtaagt aaggtgagaa tcttgaggtg agatcgtcct ggattacagt ggaccttgta    77400
tccaatggca aatgtcctta taagagacag aaaaggaaaa gaaagagaca cagggaagaa    77460
gatgtgaaga tggaggcagg gattggagtg atgcagcctc aagccgcaga atgcctggag    77520
ccaccgagag ttgggagagg caagaaaagg tcctcccccta gagccttcac agggagtagc    77580
gtcctgccaa cgctttgatt ttgagctggt ctccagaact aagagagaat agatatctgt    77640
```

-continued

```
ttttctaatc caccaagttt gtggttattt tgatgcaggg caggcaagcc cccaaattgg    77700
gttgtagcct gagagggttc ttgggttcat tcaggaagga attcaagggc aagctggtgg    77760
tattagacag caacttctgt tgaagcagca gtggacagca gcagcagagg tcctgctctt    77820
tgcagagcag ggctacccca taggcagtgt gcccagagta gcagctcgaa ggcagttctg    77880
tagtcctatt tacacccact tttaattata tgcaaattaa ggggcagatt atgcagaaaa    77940
ttttagaaaa agagtgctaa tttccaggtt gtcgggttgt tgccatggaa aggggccgca    78000
acttccggtg aactccatag tatgtggcac acactggtgg gcgtgtccca tggaaaggtg    78060
cttccgccct gtacctgttt tagctagtcc ttaatatggt ccagtatccg cgccctgcct    78120
ttggagtcaa gttcaacttc ctacctcaat tgatgatagc agtttctgaa aactaacaca    78180
tgtagatata aatataagtc cttaagtcta tcattattat gcatatccta tagggagtc     78240 atcgcgaatg aaactgaact tattgtggtt cattcattca gatatttatt taaaaatatt    78300
tattaaagct tactgtctgc cagtccgata ctgcactagg taagtgctgg ggttacaaac    78360
agaacaagat agacagatta gttgcccgca tggaacttat atctagtggg aagagaagca    78420
aaaaaaaagt aagcaagcaa taaacagtaa aaaaaaaaat actgggattt gagccataaa    78480
aaaagaaata agatgcagaa atcagcaata aggaggttgg ggagaagatc cttcttttaga   78540 aagaattgcc agagaaggtg gttgggatag gcagaaaaaa tagtaatatt cctcttttat    78600
cttcacctat attagatgat caatagatat ttcctgagaa atgaaggact gagtatatta    78660
taagaaggta tgattaaaaa caatcaccag aatgaatggc taacaagcac atgaaaagat    78720
gctcagaatc attagtaatg aaagaaacac aaattaaacc acaatgagat accacttcac    78780
acataaaaag gaattaacac ttgctggtga ggatgtgggg aaatgtcata tttccccaca    78840
gcagccatag tacactgctg gtgggaatat aaatgatgc atctgctatg gaagagaata    78900
tagtggctct tcaaaacgtt aatcctagaa agcctgggca tggtggctcc cgcctataat    78960
tccagcactt cgagaggcca aggtgagagg actgtttgag cccaggagtt tgagagcagc    79020
cttggtaaca tagcaagacc ctgtctctat aaaaatcaaa taaaaaataa atagaggaaa    79080
agcacattaa tcatagaact gccatatcca ccacttccac tccttggtat ataccccaaa    79140
gaactgaaaa cagctattca aagaaatact tgcacatgag tgttcagatt attaacggaa    79200
accaaaaggt ggaaataacc cacatgtcta ccaatggatg aatcaataaa caacacatgg    79260
tctatccata cagtagaata ttgttgagcc ataaaaagga gtgaagtgct ggtacattgc    79320
cagaacatca aagacccttg aaaacattat gctaagtgaa ataagccaga tgcgaaagga    79380
catgaattat atgatttcat tgatataaaa tgtccagaaa aggtaaaaaa tatccattga    79440
gaccaaaagc agattgtggt tgccccggac taaagaaaga gtaattactt aattttcctg    79500
ggggtttcct cttggcatga tgttctgtat acaggacata caaaaagcct ttatttttta    79560
ttcttagcaa atacttaatt agtactcacc atgagctggg catgttctaa gtcactttcc    79620
aattactaac aaatcactta attatattga cacaaaaaga atgggcataa tgcataaagc    79680
aaatacgaac ataaaaaaga aatctcccta ttaatatcat ttatgttgaa ttcaatgcag    79740
ggagcattta aataagataa agggagatac ttcataatcc acactggtca gctaacatca    79800
tgactatcta tgcagaagat aaaccagcat caaaactcat aaagaaaaat ttatagagag    79860
taagaaaaaa atgaagaaac agtttagagg taggtaattt gaatttactg ttcggtgcat    79920
aaaagaacaa ataggccaga cgtggtggct caggcctgtg gtcccagcac ttcgggaggc    79980
```

```
cgaggcaggc agatctcgag gtcaggagtt cgcgatcagc ctgaccaaca tggtgaaacc    80040
tgtctctact aaaaatacaa aaaattagct gagtgtggtg gcgtgcactg taatcccagc    80100
tactcaggag gctgaggcag gagaatcgct tgaacctggg aggcaggctg gcgcagtga     80160 ctcacgtccg taatcccagc actttgggag gccgaggcgg gtggatcatg aggtcaggag    80220
atcgagacca tcctggctaa cacggtgaaa cctcgtttct actaaaaaaa tacaaaaaaa    80280
ttaaccaggc atggtggtgg gcacctgtag tcccagctac tcgggaggct gaggcaggag    80340
aatggcgtga acccgggagg aagagcttgc agtgagccga gattgcgcca ctgaactcca    80400
gcctgggtga cagagcaaga ctctgtctca aaaaaaaaaa aaaaaaaaaa gaaagaaaat    80460
acaggccaca cagatgggga gatgataatt gcaagttata tatttgataa aggactttca    80520
ttcagaatat atgaaatagt cttacaattt aataaaagag gacaaacaac ccagtaaaat    80580
gtaggaaaaa tatttgaaca gatgtttcac caaggaaaaa atacaaatgg ctaatcagca    80640
catgaaagaa tgctcaacat catttagtca ttaaggaaat acgaactaaa accaccataa    80700
tatatcacta cacacctgcc agaatggcta aatttttaaa aaatggaca atactgagtg    80760 ctggtaagga tgtggaaaaa cagaaactct cataccttgc cagtggcaat gttaaatgat    80820
acagctattc tggaaaacag tttggcattt tcttaaaaat ttaaacttat tatatgaccc    80880
aacaattcca ctcctaggta tctacccaag aaaaataaaa atacatgtcc acacaagggg    80940
acttgtgcat aatgttcata tcagccctat ttgtaataac accaaattgg aaggaatcca    81000
aatgtccatt aactatgaat ggaaaaccaa cattcttaca aataattcaa caataaacct    81060
tcatgaacct tagaaacatt attctgagtg aaagaaacca gacacagaag accacaaggt    81120
gtaggactgt atttatttga catttctaga gaaagcaaaa ctgtagagac agcagatcag    81180
tgactgccag gggctagaga cggaggcaag ggttgataca agcaggcagg aggttgcttt    81240
ctgggctgat ggaaatgttc ttatgctgga ttgtggtaat ggttcacaac tgtataaatt    81300
aacaaaaaat tatcagacta tacccttaca atggtatgta catttcatcc aagtaacgct    81360
gcttttaaat ttgaaattaa gcacctaatg atattaagaa atgaataaca aaataaaccc    81420
aaagaaagca gggggggaaaa aaagcaattg gaaaagatga gagcaaaaat aatgaaaaaa    81480
aaaacatcta taatcatctc agcggttggt tccttgaaga aaagaaaga aagaaatgaa     81540 aaaatcatta actatcctaa taaagaaaca aaggagaaag aacaaatata caaaataaga    81600
attgtgaatg aaataattgt agacacagag gatatcaaat gagtgactcc tcaatccctc    81660
tgcaaataga ttcaaaatct tgaccaaatg gatgattttc taggaaaata taaattacca    81720
aaactgacca ccaaagagat tttaaaaatc agaaaatatc gtttatcaca gagatggtaa    81780
aaaccttgat aaaaagtcat ttacccagag aagcatctgg ttccaacagc tttgcaagtg    81840
catcctatta aaactttatt gattggcaaa cgctaatttt ttttaatttt tattttaat    81900 tatactttaa gttctagggt acatgtgtac aacgtgcagt tttgttacat atgtatacgt    81960
gtgccatgtt ggtgtactgc acccattaac tcgtcattta cattaggtat atctcctaat    82020
gctatccctt cccccctcccc tctccccacg acaggcccca gtgtgtgatg ttccccactc    82080
tgtgttcaag tgttctcatt gttcaattcc cacctatgag tgagaacatg cggtgtttgg    82140
tcttctgtcc tttcaatagt ttgctcagaa tgatggtttc cagctgcatc catatcccta    82200
caaaggacat gaactcatcc ttttttatgg ctgcttagta ttccacggtg tatatgtgcc    82260
acattttctt aatccagtct atcattgctg gacatttggg ttggttccaa gtctttgcta    82320
ttgttaatag tgccgcaata aacatacatg tgcatgtgtc tttgtaacag catgatttat    82380
```

```
aatcctttgg gtatataccc tgtaatggga cggctgggtc aaatggtatt tctagttcta   82440
gatccttgag gaattgccac actgtcttcc acaatggttg aactacttta cagtcccacc   82500
aacagtgtaa aagtgttcct atttctccac atcctctcca acatctgttg tttcctgact   82560
tttaatgatc gcccttctaa ctggtgtgaa atggtatctc attgtggttt tgatttgcat   82620
ttctctgatg gccattgatg atgagcgttt tttcatgtgt ctgttggctg caaaaatgtc   82680
ttcttttgaa aagtgtctgt tcatatcctt tgcccacttt ttgatggggt tgtttgattt   82740
ttttcttgta aatttgttta agttctttgt agattctgga tattagccct ttgtcaggtg   82800
ggtagattgc aaaaattttc acccattctg taggttgcct gttcactctg atggtagttt   82860
cttttgctgt gcagaagctc tttagtttaa ttagatccca tttgtcaatt ttggcttttg   82920
ctgccattgc ttttggtgtt ttagacgtga agtccttgcc catgcctatg tcctgaatgg   82980
tattgcctag gttttcttct aggttttagg tcggacattt aagtctttaa tccgtcttga   83040
attaattttt gtataaggtg taaagaaggg atccaatttc agcttttac atatggctag    83100 ccagttttcc caacaccatt tattaaatag ggaatccttt ccccatttct tgttttgtc     83160 aggtttgtca aagatcaggt ggttgtagat gtgtggtatt acttccaagg gctctgttct   83220
gttccattgg ttctgttctg tctctgtttt cgtaccagta ccatgctgtt ttggttactg   83280
tagccttgta gtatagtttg aagtcaggta gcatgatgcc tccagctttg ttcttttggc   83340
ttagaattgt cttggcaatg cgggctcttt tttggttcca tatggacgtt aaagtagttt   83400
tttccaattc tgtgaagaaa gtcattggta gcttgatggg gatgccactg aatctataaa   83460
ttaccttggg cagtatggcc attggcaaac actaatgttt ttaaactgtt ctagagagca   83520
tggagaaagg agaaaacctt ccaaattatt cctgtgaagc ttgcatgtca atgattccat   83580
aacaataact atagaatcaa ataaccacaa taaagaaaa acacagacca actccactta    83640
tggatataga tgtaaatatt ctaaatacaa tattagctga tagatctaac actgcattaa   83700
aagatttgtg gaaggagttg ttcaatatta ggaaatccac tctgtgatta tctcaagtta   83760
gcaattagat gtatattcaa tgctgaaata acagaagcac cccagtttag tcagaaataa   83820
gacccaatta cccattatca ccaccaccat ttagtattgc actggggaat taccaattca   83880
gttagacaag agtggggaag aggtacaaaa actagaaaga aggtggcaaa aacaatcatt   83940
gactgtatga ttggaaaaaa taagagaatc aattgcaaaa ccattagaaa gagcaggata   84000
attcaggaag ctcaggggc acaaaataaa tgttttaca aaacaatatc caagaatcta    84060
tattaacaac aatatctttg agatataatt gaatagaaga ttccatttac aataggaaac   84120
cccaaagata gaacacccaa gagttgcaca aaatttacac aaagaaaatc taaacaacag   84180
agggacaaaa cggaagattt gactacatgc aagtatattt cctagtcttg ggtagaaaga   84240
ctcatctgca taaagatgac aatccttcct gaattaatct ataaatttag tataattcca   84300
atggaaattt cccttgtttt gttgttgttg tgctgttttt gttttgtttt ccagactaca   84360
ctgaatgcca atatttccat ttagtgattt tcttcttccc ttttcctttc taatgacata   84420
ttttgtgctt ttcagacctg cctttctttc tctcggcacc aatgaataaa gttccagctt   84480
taaggcttga aaaatcacag caaagttgca gcaaaattaa aaggaaaaaa atgttctttt   84540 ttttcctgc agctgcagag agtggcagat agcatcctgc gtgataaacg cctattcttg   84600
gctaggcgca gtggctcacg tctgtaatct cagcaacttg ggaggccaag gcaggcaggt   84660
cacctgaggt caggagttcg aggccagcct ggccaacaag gtgaaacccc gtctctacta   84720
```

| | | | | | |
|---|---|---|---|---|---|
| aaaatacaaa | aattagttgg | gtggtggcgc | acacctgtaa | tcccacctac | ttgggaggct | 84780 |
| gaggcaggag | aattgcttga | acctgggacg | tggaggttgc | agtgagctga | gatagtgcca | 84840 |
| ctgcactcca | gcctgggtga | aaagagtgag | actctatctc | aaaacaaaca | aacaaacaaa | 84900 |
| cacctatcct | tgcctatgtc | attttaacaa | aggaggaagt | aaatcccctg | gatttcagag | 84960 |
| gctgatgctc | tgcccaagaa | aagcaaccct | aacttcccca | aaggctaaaa | ttcagactga | 85020 |
| ttggctctgg | cagagatatt | taaattgata | cctctgtttc | ctcaaaggta | taagcctttg | 85080 |
| cgaactttct | ttggtttctc | tcttctctca | caggaggcag | gggataaaca | aatatgttag | 85140 |
| atttcttatt | taaacaaaga | gcttgagggt | tttgcctcat | cgaaattaac | agagacaagt | 85200 |
| tgatgctaat | attttatgg | aaatcgaat | atgcaaaaat | agccaaggaa | attccaggga | 85260 |
| aaaagtaatg | aaagaaaata | tcaccaaaag | atgttaaaac | attttggaaa | gccacagaaa | 85320 |
| ttaaaagtgt | ttgatcctag | catataaaca | agcagacaag | gggctgggca | tggtgactca | 85380 |
| tgcctgtaat | cccagcactt | tgtgaggccg | aggctggtgg | atcacccgag | gtcaggagtt | 85440 |
| cgagaccagc | ctggccaaca | tggtgaaacc | tcgtctgtac | taaaaataca | aaaattagcc | 85500 |
| aggcatggtg | gcacgcacct | gtagtcccag | ctacttggca | ggccgaggca | ggagaattgc | 85560 |
| tggaccctgg | gaagcagagg | ttgcagtaag | ccgagattgc | accactgcac | tccatcctgg | 85620 |
| gcgacagagc | aagactctat | ctcaaaatta | aaataaacaa | acaaacaaat | aaataaataa | 85680 |
| acaggcagat | agatcagtgg | aacagaataa | aatccagaaa | tagactgaaa | acattcagga | 85740 |
| aaacagtata | aaataaaggg | gacatttcaa | atcaatggag | aaaagattag | ttatctcaga | 85800 |
| aatgaatggg | acgattgagt | agactgggaa | agagtaaaac | tggagctcta | cacacaccaa | 85860 |
| aatacattcc | agatggggct | aagattttat | atatctatat | atgttaaat | aaagccatga | 85920 |
| aagaactaga | gcaaacatga | gagatttatt | tttataatcc | cagacggtgg | caatctttcc | 85980 |
| aagtgtggca | caaaagtcag | aaatcattaa | aaaaagactg | ataaatccaa | ctacacaaag | 86040 |
| ttagacattt | ctttatggca | aaaatgcta | tcaaaaagtc | aagagatcaa | tgataatggg | 86100 |
| ggaaacattt | gtaacacata | caataagctg | tccaattttt | taatagtcaa | agactttaac | 86160 |
| attaagaaac | agaccagctg | gctgggcatg | gtggctcgag | gctggggat | cacttgaggt | 86220 |
| caggagttca | agatcagtct | ggccaacatg | gcaaaacccc | gtctctacca | aaaatacaaa | 86280 |
| aattagctgg | gcatggtggg | gcatggtggt | gcatgccagt | aatcccagct | actcaggagg | 86340 |
| ttcttctggc | ttctcagctt | gcagacagcc | tattgtggga | ccttatgatt | gtgtgagtta | 86400 |
| atacttaata | aactcctgtt | tatattatgt | gtgtgtgtgt | gtatatatat | gtgtgtgtgt | 86460 |
| gtgtgtgtgt | atacacacat | atactggaat | atatgtatat | acatatatac | atatatacac | 86520 |
| atacatatat | atacacatat | acatatatac | acatatatat | acacatatac | atatatacat | 86580 |
| atatacacgt | atacatatat | acatatatac | acatatacat | aaatacatat | atacacatat | 86640 |
| atatacatat | actatatata | tacatataca | tatattcatt | ccattagttc | tgtccctcta | 86700 |
| gagaaccctg | atgaatacag | tgggctacac | acctattgga | atggcaaaaa | cccagaacac | 86760 |
| tgacaacacc | aaatgctggt | aaggatgtgg | cgttttttat | ccgcattcat | tgctgatggt | 86820 |
| aatgcaaaat | agtgcagcca | gtttggaaca | cagtttggca | gctctttaca | aaacggcgtg | 86880 |
| tactcttacc | atacgatcca | gaactgtat | tcctaggtat | ctacccaaag | gagttgaaaa | 86940 |
| cttgtaacca | cacaaaaact | tgcacacaga | tgctcatagc | aagctttatt | tattattgcc | 87000 |
| caaacttgga | agcaaacaag | atgtccatca | gtaggtgaat | ggataaataa | actgtgggtgt | 87060 |
| atccacacag | tagaatatta | ttcagtgcta | aaaagaaatg | agctatcaag | acatgaaaag | 87120 |

```
acatggagga aactgaaatg catatgactg agtgaaagaa gcccttatga aaagctacat    87180
actgtatgac tctaactatg tgacattctg aaaaaggcaa aactatggtg aaaacatcag    87240
tggttgccag cagttgagac gggtgggggg aagataacca ggtagagcat agaggacttt    87300
aagggcagcg aaaatgctct gtatattact acgatggtgg atacatgtca ttatacagca    87360
ggtccttgga tgacactatc tcattcaaca tcattttgct ataaagttga tgagaaaaaa    87420
aagtcaattc ctagccaggc cactgtctct gtggagggtg tgcgttctcc ccatgtctgt    87480
gtgggtttcc tctgggtcct ccagtttcct cccacatccc aaagctatgc acggtaggtg    87540
aactggcatg tctacatggt cccagtgtga gcgagtgtgg aagtgggtga gtgtgcccta    87600
tgatggaaga ggaccctgtc cagggttggt gtctgccttg accctgtgcc tctgggatgg    87660
gctctgccat ccacagctct gaagtggaat aagccagtca ataatattct cgcttgtttt    87720
ttgttgttgt tgttgtttgt ttgttttttgt gacagagtct cactctgttg cccaggctaa    87780
agtgcagtgg cactaactcg gctcactgca acctccacct ccaggttca agtgattcct    87840 gtgtctcagc ctactgagta gctgggacta caggcatgcg ccaccatgcc cagctaattt    87900
ttgtattttt agtagaatca ggattttgcc acgttggcca ggctggtctt gaactcttga    87960
cctcaggtga tctgcctgcc tcagcctccc aaagtgctgg gattacaggc gtgagccacc    88020
gtgctcagct ttcacttgtt tgtattaatc tttcctaaat gtatgtatgg ctcacattta    88080
tttcaatgtt tagtattaga agtgtttgag gtctttgtaa gtttggtgat gttttgtgac    88140
cagaaacagg ccataggaac ttaactcttg tttatattaa ttagcttatg gtaaaattgg    88200
ataaatgttt tataagagac atgaaagggc atacagacac acaggagaga aggccacgtg    88260
aagatggagg tggaggagac agtgatgcag ccacaagcca agggatgcaa gcggccacct    88320
gcagttgaga gaggcaggaa ggatcctcag aaggcatgga gcctacgagg aagcctggcc    88380
ctgctggtac cttaattttg gacttccagc ctccagaacc atgagagatt acatttctgt    88440
tgtttgaagc cactgatttt tgtggtcatt ggttatggca gccacaggaa ataagataat    88500
cacccactta attttcctag aaaagctgtg ttttgaaagt cctcttgaag cctgggttcc    88560
tctctctgca tctcccagtt ttccctcaaa gcttgtggat tctccattcc tcacattaac    88620
tcaggccttt cattgccaag tgaccccgag tcctgccttc gcgggtgctg ggggagcctt    88680
cctgacccac tggaagtgga cctgcccatc tccttgctgt gaaactgcat gagggggctt    88740
gtgtctgagg attgtctggc gtgaggggag agacaccacg tggggacaga ggagtggatg    88800
agcaggccgg ggcatgacgg ggccgtgaca gggacctggc cttccattct gtggaagcct    88860
gagacaagca gcaacttctc tcattcctcc tctctatgac aagacaggaa ctgggacact    88920
caccttacta ccctaattcg ctgagcctcg gaagaaaagc agcttagatt tttaatccca    88980
tccaagatgg aggccctcct gctcctgctg ccttgttctc accccctttc gtgatgtgcg    89040
aggccatcgg aaggtgtgga atttctccac tgattcctct cattgtccct ttctccctac    89100
tcctggggag gctgcaatgg tgacctcatc caccttcaga ggcaggtgct ggaggaggaa    89160
aggatgtggg agttcaagcc ggctgcagag gcccaagagc ccagatggtg tccttccagc    89220
aaactgagaa ggcactcctc ctaccaggca gccactgccc cactccaggg cccctggctc    89280
agctagggaa gtgggctgg gtttcacccc ctgctcatcc cctaaggccc agtgctggac    89340
tcagtgcagc acctgcccag ccatctctag cagcggcata agcataaaaa tcaaggccaa    89400
tgttacgtgc tgccttgaca tgtggtaaaa tgtgaagggc ctcaagtggc ctaaatgcaa    89460
```

-continued

```
gctcctgtcc cacctctgct cccataaata gggtctccca gctgggcaac ccttctcatc    89520
ccagggacca ggtaccaccc ctgtttgttg ccaagtagca ggcttcagtt ccctgccagt    89580
ctgcggaatt atttaacaac ctcatgaaga aaccagggc cactccaccc tctgtattag    89640
cctgttctca ggcagctaat aaagataccc aagactgggt aatttataaa gaaaagaagt    89700
ttaattgact cacagttcca catggcttgg gaggcctcag aaaacctaca atcatggtag    89760 aagggaggc aaacatgtcc tccttcacgt ggcagcagga aggagaagtg ctgagcaaaa    89820
gggggaaaag tcccttataa atccatcaga tctcatgaga attcactcac tgtcatgaga    89880
acagcatgga ggtaaccccc acatgattca atcacctccc actgggtccc tcccacgaca    89940 tgtgggatt atgggaatta caattcaaga tgagatgtgg aaggggtcac ggccaaacca    90000
tatcactctt gttactacca aacctgctgt ccaacaaccc tgctgttcac tctgctcttg    90060
agcaccacct catgtggccc tgcatagcct gcagtggccc ttccctgggg ctacgagtat    90120
atgtgactag aaaattgccg tgggtctcac ctatccagtg ttgggtgttg tgtgtccagc    90180
cctagagtgg gactccttcc ctcacgaatg gggtgaatag aaggtgataa aaagatctga    90240
gtctagggat acctaggagg tggaatctct tctccatgca tagcatgagt gatcacaggc    90300
ctgaaaccaa aagggactta ggtctggggg agagattatt ttccaggtgc tgaatattcc    90360 tgggatagg gagggagcta aacaggttcc tgcccaaagg aagtgagaag ggggtcctag    90420
caacttctca gggatttaga gctgtgactc cagggccttt gttcagagga gctaccttgc    90480
aaggaacttc tagaagaatg cttctctttc tcagcatcca tcctcccatt tcatagtcgt    90540
gcccacgatg ggccccgtct ccctgaactt gatggctgaa tagaagtgta gcctcccagg    90600
ggcatctaaa ggcactcaga gccccttacc cagccccagc aggcacctgc ctggctgccc    90660
ggtcctcagg gttccctgtg cattgagcaa tatcctcaaa gtgaccacca gggggcagca    90720
gcacccagac tgccttccac tgcacctgca gatcaacaaa ttccagtatt ttgggggaat    90780
atctgtgata acttggctac tgctttactg acctcaggta aatagacaga ccaatgtgct    90840
tgaggagcca attgctttaa atctcctgac tcattttttg tattaagatt tgttttattt    90900
atgcaattat tctgtttact caaagacttt accagaagct gggtgcagtg gctcatgcct    90960
gtaaccccag cactttggga tgccaaggtg agaggatcgt tggagcccag acattggaga    91020
ccagcctggg caacatagtg agaccccatc tctacaaaaa atttaaaaat tagctgggcg    91080
ccactcatgg tggctcaggc ctgtcatccc agaactttgg gaggccaagg caggtggatc    91140
acctgaggac aggagttcga gaccagcctg gtcagcatgt gaaacccg tttctactaa    91200 aaatacaaaa attagctggg tgtggcggtg ggcacctgta atcccagcta ctcgggaggc    91260
tgagacagca gaattggttg aatctgggag gcagaggttg cagcgagccg agattacacc    91320
actgcactcc agcctgggca acagagtgaa actcagccct ccatcccgac cccagaaaaa    91380
attacctggg catggtggtt tgagtctata gtcccagcta ctcaggaggc caaggtggga    91440
ggatagcttg agtctgggag ggtgggagtc tggcttgagt ctgggagggc gaggctgcag    91500
tgagctatga ttgcaccact gtactccagc ctgggtgaga gagccagacc ctatctcaaa    91560
aaaaaaaaaa aaaagtacca gcccctatct acccattcat agctttatgt ccatttcttt    91620
tgtcttcaag cactggtatc ctttacttat ctctcctcac ctgatctagt gtttacatct    91680
catttgcgcc catagagaag tcatacactg atgtggattt tagatagggc acgctctcaa    91740
gacagccaca tgtattattc tgtgctcaca cagcctggcc tggagatgca aagattatgc    91800
aatccagaat ctaaatgaga ggatcagatt aatgggatgt tctcacagtg tcaggtgagg    91860
```

```
acagcctgat gcagcctttc atcatgaggc tgggacctct gggtcccttg gccccaggac    91920
cacactcgag gacatgcctg ttcctgccaa catggctggg cagagttcct cttttctttc    91980
cttttctttt cttttctctt ctcttctctt cttttctttt ttctttcttt tcctcttttc    92040
cttccttcct tccttccttt cttctttctt ctttctttct tttctttctt tttcttttc    92100 cttctttcta tttttttttg aaatggagtc ttgctctgtt gcccaggctg gagtgcagtg    92160
gcacactctt ggctcactgc aacctccacc tcccgggttc aagcgattct cccacttcag    92220
gctcccaagt ggctgggatt acaggcaccc accaccacac ccagctaatt tttgtacttt    92280
tagtagaaat ggggtttcgc catgttggcc aggctggtct caaactcctg acctcaggtg    92340
atccacccgc ctaggcctcc caaagtgttg ggattacagg cgtgagccac cacccctag    92400 ccctgagtct gtttatgctt ctgtcaggtg tggcatgggc ctgcctggga gctattcttt    92460
ttctgtaaag cacaggcagt taatcagtgg tctctgggaa gaatccagct cagggttata    92520
tttcgtttga cccactcaag ttttaaaaag taaattagtt gccaatgtgc aaacattaga    92580
agagttcaca gcttctccaa caatacctag aagttcatcc gatggtgccc gcattccctg    92640
ctctgtctag atggtgccca cattccctgc tctgtctaga tggtgccgac atacctgat    92700 ctgtccagac agtgcctaca ttccctgctc catctggatg gtgcccacat tccctgctct    92760
gtccagacgg tgcccacatt ccctgctctg tctggacggt gcccacattc cctgatctgt    92820
ccggacagtg cccacattcc ctcctccgtc cggaaggtgc ccacattccc tgctgtgtct    92880
ggacggtgcc cacatttcct gctccgtcca gacagtgccc acattccctg ctgtgtctag    92940
atggtgccca cattccctgc tccgtccaga cagtgcccac attccctgct ctgtctagat    93000
ggtgcccaca ttccctgctc cgtccggacg tgcccacat tccctgctcc atccggacgg    93060
tgcccacatt ccctgctccg tccggacggt gcccacattc cctgctccgt ccggacggtg    93120
cccacattcc ctgctctgtc cagatggtgc ccacattccc tgctccatct ggacggtgcc    93180
cacattccct cctctgtcta gacagtgccc acattccctg ctccgtccgg acggtgccca    93240
cattccctgc tctgtctgga cggtgctcac attccctgct ctgtctagac agtgcccaca    93300
ttccctgctc catccagacg gtgcccatac tccctgctct gtctagatgg tgtccacatt    93360
ccctgctccg tctagactgt gcccatattc gctgctggct gcaaatgcga ggagttgaca    93420
gcagcctccc ctttacaagg caggaggtgc cactgttcgc cattgtctcc acctagggct    93480
tcacttgctt tctatctgca gacatcagag ggacccacat ctctctgttc tgacacgctg    93540
tgtgttgatg gcagagttta attatccaca tgcaatctta cttttccttat tcccaagtcc    93600 gtggggctgc ctcatcaaag cattgtaaga actgataacc atcttctaga agtatcatag    93660
tgatattaag aacacacatc acagatcata gtaaatggct ttaattttt agcgaaatct    93720 cactactgca aatgcattgt tgtcctagct aatgaatgca tagagtattg cctgcaaaat    93780
aataattgag attctattt taagaagctt agaacagtac atggtgcata gcaaagactc    93840
tgtgtatgtg aagccagatt ttaaaatatg gtaacaagtg tctgaaaata tgtggctcaa    93900
tttgtctccc ggttactttt ccctctcccc ctttaaaatg tagaggaagg agaagaagag    93960
ataagaggtt tgtgagtgaa gacaagggcc ctttaaggcc tgggaagact aacgccatag    94020
ggatctccct ctgccttaaa aggcacagga atcttagtgg ggaaaaagaa gtggtgataa    94080
atagccagtc cgtgtgcctg gaatatcaaa gtcagtgcgt gccagggatc acactgcggg    94140
tcacgtgcac tctgggtctc tctctgcaaa cctgccctgc ctcagtctgg gaatatgcaa    94200
```

```
ctgcctaaga agggtctggc ttacacaggg gccatgagac gtggcaggca tagctgggct    94260
gctactggtc atgaatcctg gacacggcag gcaaggtgtg tgtccatat gcattattcg    94320
ggtgggcaa agatcacagc tctcactaga cttcagagg actttgtaac ccaaagaacc    94380
actcatctca aggactgtgg taactcaggg gctgagccat gccagtgttt attatgtgaa    94440
acaaggactg gaacctcaca agaccaagtc tgtccatttg aggatggccc aagatgcaca    94500
cgggctgctt ttatcttatg cgcaggtttt aaaaaaatat gtttcattta aatattccat    94560
actcttcagg aatgcccagg cagctgagct ttcaggatgt cgcattgcag aggactccaa    94620
tgctacatat ggcagctgga gacccttca aggcaggtgg cagaacggag gccctctcta    94680
tctgctgggg cagccctccg ggtgccccgc tggaaggcag agcagctcca tctctgggtg    94740
ggtgagaggt gctgcatggg ctcactatag tatcccaata ctgtatggca gtaggctgcc    94800
agagtatcct aagctgggtg gcttcaacaa caggtactga ctcacagttc tggaggccaa    94860
aagtttgaat tcaagcaggg ctgtgcttcc tctgaaacct gtgggagagg agccttcctg    94920
gcttcttccc gacttcttgg gatggggatg cgcatccatc ctcggccttc cttggtttgt    94980
ggctgtgtca ctgcaccctc tgcctctgtc acggcatggt gtcctcccta tgcatctgtg    95040
tctgaatttc cctcttccga taaggactcc agtcatattg ggtgagggcc caccccaatg    95100
acctcatctc aactagatca tctgcaaaga ctctatttcc caattaggtc acattgaagg    95160
tacctgtctt tttgggggat acaattcatc tcacaaaacc ggcccatcac ctcaaaagga    95220
cctgccaccc cagtgctatg tgtccctctc tgcccagagc cactccttcc cctggctctc    95280
ggggagtggg ggcaccttc cctgctccca cagtgaccga gcaccttccc cttggtatgc    95340
attctgaagg gggcattttt ttctcctcca tctcagccct gtacaaagca agttcttct    95400
agattgaggt gtgtatgtgt gtctatgtat atgagtgtat gtgcctgtgt gttttcaggg    95460
agatgtgtgc aggatgggtg caagggagga gtggaaggcg gaagggcagg aggaggatag    95520
agccacaaga gtgagcacag aagtgacaag ggcagaatca gtgtgtgctt gtgacaagta    95580
tggaaatgtc atgccttag gttcagtcct ataaggtagg tgtatcagta agggcattga    95640
ttctgcgacc ttaacagaga tcagaataac agtggcttaa ggaagagtgg agtggatttc    95700
tctctcctgt aaatctggcc tggtgggtgg taaggaggat ccacgtcgcc caggcccaga    95760
tgtgtgtggc tctttgagtg ccccgttctt tcccagtctc ataactgctc tccacctcct    95820
ccacatccag ccactgggaa gcaggacaaa gttagttaag ggcacgttct ttttctttcca    95880
aggattactt ggacattaca gtcttcactt ccatgcctac tggccaggc ttagtcacac    95940
aaccttgcta gctgcaaggg agtctgggaa atgcagctgc tattctcaga ggccatgtcc    96000
tcagggattc tgctaaattt agcaaggcag ggacagatat gggggaacca ctgacagtct    96060
atcacaaaag aacgtgattt tagagaaaca gtgaaacagt gtcattaatc caccctcac    96120
cccttacaac agccaaaaag aaatccagtg gtatccatca caataaagag tatgagagga    96180
atgtgattag aaaatcaggt tgccaggcag gatgtgtcca gttttagcca gtggtgggt    96240
tcatggggaa ggcttcgtct caggaaggtg tgtgttgggt tgttctatgg ccagatggtt    96300
ttcaacgaca tagcacgacc tgtagctctc caggaccgg gcctggacat aggccttgtc    96360
cttctcttgc caggcatcgg actcgatgta gacgttgaat gggtcgttcg agtgctccag    96420
cttcttggag cggatgtagc tcagcatgat gcccagggtg aagaagccga agaatcccag    96480
taccatgagg acgtagaggg cctccagctt gccgtcactg ctgcgggggg acctgcggc    96540
caggcccgac atgttgccac cctgctgaac tgtctcctgc cacagcttgg tcagaaaggg    96600
```

```
cgtcaccgct gtggtgttag acaggatcat cctgggcatt aaggttccac tgctgcagct   96660
caaacttccc aggcacacct cttaaaggaa aaatgcaacc ccaaatcaaa aagtacgtat   96720
tggccaaaac ccacacgtac gcacacacac gtatacaatt ttaaaatctc aggtgagagg   96780
ggtgagctga cactccacag gccatggcat gtgccatctt gggtctgtgc aatgccttct   96840
cttgatagat gaatggatac attgattccc ttctatttcc atccaccact ccaatctcca   96900
cccctatagg tgaccatcag aatgagcttc tttaatatgc attgctgcat attgtggcgt   96960
atggggttgc atgtgtgcat tttggtttac ctaaatggta tcaggtcatc caactcattc   97020
agtctccttc ttttttcctca tgactgtgct tttgtggctc acttgcggtg ctgggtgtgt   97080
gcattccctt gcttccaatg tttgtataca acccatggtg aacacccact tcttttctct   97140
gccttctccc ccagagatgg acactgctgt ggctgctgac tccataaaca aggggagac    97200 aaatatcccc atccttgacc tcctatggac ctaaaaaaaa tcacgcatct catacaacta   97260
gttcctggca gcttatgcaa gactagtcag actggttgcc cttggaagca acgtgcaatt   97320
ggtggtctgt ttcaccacag agcatctctc tatgaacagt tacattcatc tgaatgaaaa   97380
atctatgctg tcacgtggtg gacttcagaa tgtctaggga gatttcacag agagctcccc   97440
tcgaagaggc cagtgttgta gcttgtgcta tgttttttccc tccctgccca cacacaggca   97500
cacacacgta cacaatctta aaacctcagg tgagagggggt gagctcacat gctccctagt   97560
ccatggtatg tgccgtcttg ggtctacaca atgccctctc ttgattgagc aatggtacat   97620
ggattgcctt ttatttccat tcactactct ctggctatgc agaaaagtgac attttcccta   97680 tcgtttaatc ttgatatcac tgtccctgta tactcagagt gggcctggga attggaaaaa   97740
ttgtctccaa gtagctgtaa gattctgtca ggggtttggt ttgctgtgga aaccccatct   97800
aggtgacctt gagatcattg gtaagctgaa aaaaaacagg tcttgttttt atttatttat   97860
ttatttattt atttaggttt gagcaaatgc cagcctctac ccccagttcc tgctgggaaa   97920
caaaagctcc gaggccaagt tgttgatgtc acattccaaa ctcaagccag agggggccac   97980
tgggagctta tcacacgtaa gtgctcccac tcagttcttt cttttttctgt tttattgaga   98040 cagggtctca ctcttgtcac tcaggctgga gtacagtggc acaatcttgg ctcactgcag   98100
cctcaacctc ctggactcag gtgatcctcc taccctaccc tccagagtag atgggactat   98160
aggtatgcac caccatgact ggctaatttt cgtattttttt gcagaggtga ggttgcccta   98220
tgttgccgag gctggtcttg aactcctggg cttacaggat ccgcccacct cggccccccca   98280 aattgctggg attacaggca tgagccaccc tgcttgtccc ctgctcactt cttaggagct   98340
taaagtagct gagtagaaca tggcctggag tagaacatgg cctcgggggg actgttgtaa   98400
ctacaggtga aggatgtatt tgggaagaca gtttatggcc agaatcgcta tggaaagaca   98460
aattccaaca cttgccggga cggcgctgtc tttcccagcc aggatgggga ctgtgacatt   98520
gcacatcatc ttgtgtagga caaataacct cagaaaccta gctcctctcc agcttagacc   98580
cagagctatt tcttcattga attggtttaa ttgtaaaaca taccctgaac ccagcaccag   98640
ctgaagacat ctggcacctt tccgaggccc ctcttcctct acccatctct gaactctggc   98700
tgtgtctcag agttctgtta cctgctctct tctcttccta ctctcctctc tcccagggtg   98760
actgcacctg ctccaggctc acctgcatgg ccatgaccca gggctctctt taagctccag   98820
agccatgcgt ccagtgacct gctaaggaga tggttccctt tggccatccc caggctcctt   98880
aaagttaaca ctccaccctg tcctgtcaga gactggcccc tgcctcattg agctgagtgg   98940
```

```
caacaccact cactccaaaa tctgcatcac tctcactgat gactgcaatc tcatcatggc     99000
agttcccatc ttgaaggcct tccttggctc ctccctgcct tcagggtgaa actcctggtc    99060
ttctgcatgg atacaggccc taaatttgag agtctatgca tccctctcca attccactgt    99120
tgccactgtg cccagaccct atgctccatg gtccctgctg gccccggagc ctctacacat    99180
tgtgcgtctc cagctcagac tgcgccttct tcttggccca tgaaacttct cagcaatgcc    99240
tactcatgct taaaattcag cccagctctc acctccttcc cgaagcctgc tctgatacat    99300
ggggctggat cagcactgtg cacaccatga cccctgctaa cctcatcatg gtcaggatct    99360
ccaggcccct tatcccatcc ctgccctgcc atccagcctg gtgctgggca cgcaaccaca    99420
caggagctgc ccatgaatgt ttatcgaata gatgccacca gaacttaata ccttttgacc    99480
agtgggcttt gactctttat aacctgctta ctccaatgaa cagatgccaa tgagctgtct    99540
ccgaagctct aactgactcc cttttccaga agggcagtca tctcccaccc tgaaccacag    99600
tctcagaagg caggagtgag gagcagaaag agctcagatt ttgggattcc actgccgcca    99660
caggtttgga ttctagcttt gctacttcct ggccacatga tcctggacag tttccttaga    99720
attgttcagt caagtttttt ttttttttct ttccaaagta gcgagaaaca ccactgacat    99780
ttgcgggctg ttgaatcact gagcaggtgt gtagagtggc tgacagcatg tggcacatgg    99840
caggtgcaca ctcagtggtc ctgggtagga gtttattggt ttttctacct cattaagaaa    99900
ttgctgccca aggatttggg gctttggggg tttaggcttg gctttcctgt ggctgaccat    99960
ggcagctgtc ttctctacgt tgtggagaga tcagacatga atgagaatca aagattgttt   100020
gtggcctttc ctggtttcta ggcttttgag tctgtgcaga gatctgtcag gggttaagct   100080
gcctgggctc aagagattca ggtccttgtt cttgtacaaa actagcattt agccccattc   100140
taaccatcgg ggtaggcagg aattgtttgg taacagatcc aaactcaacg ctcaaccatt   100200
tcttttaaa tgacccgaaa ccacttatga atgcataaaa ccctgcccca gaaaacagac   100260
agacctggac ctgatactat gatgtaattt ccaaaaaccc agaatgatca caattggcaa   100320
ataattctgc caccaatcac tgttagagag tctttccaac ttcatgacca tgtgaaggta   100380
gaattatggc aggcgacatt tgaagatcca caagttaatt ggtttaaaac tgataaatcc   100440
atacagcaaa ttaagagtta catctgcaat taattcataa tagtgagttc actgagaagg   100500
cttgttactt agatccagat ggactttctt atgtccaaag aagcaaccaa aaacatctgc   100560
tttgaaaacc tcccaagccc aaaccatcct cagccttgtt ctttagaatg ctttagaatg   100620
accttgttaa aatgcagatt gctcctgtaa tcccagcact ttgggaggcc aaagcaggtg   100680
gatcacttga tgtcaggagt ttgacaccag cctggccaac atactgaaac cccgtctcta   100740
ctaaaaatac aaaaataaga caggcgtggt ggcgggcacc tgtattccca gctatttggg   100800
aggctgaggc aggagaatca cttgaaccca ggaggtggag gttgcagtga gccaagattg   100860
tgccattgca ctcctgcctg ggtgacacag cgagactctg tctcaaaaaa aaatgcagat   100920
tgctgggctc tattttcaga gtttctgatt tggtagaact ggagcgggcc tgggaatctg   100980
cattcctaac acattcccac gtggtgctaa tactgctggt ctggaggccc tgcttggtga   101040
tctattggaa tcaccggggg agcttttaga aaataatggt tcctggatct caccccctaga   101100
gattttaatg tctttggtct gggttcctgc ctgactcaga gacttttag aaacctccca    101160
aatgatccta atttgtagcc aagattgaga accactgggc tgtggtgtgg gaccctagga   101220
aaatgaccaa tggccttttg tgctgcaggg tacctggaag aattttgcaa aaatatagaa   101280
atatgatctc actgactgtt tttcaaatct tgtttgtttt ttacattttc ttttttggcc   101340
```

```
ttgtttgcct ctgatacagt ctgaaaagaa attgcagaaa gaaactctcc agtcttcagt    101400
gtaacctcag ctgtccccag tctcacacac gctggtgcct tcaattacaa ttctcctgtc    101460
agagcttaag tccagctaat taactgcctt tcaaatgaca accctatatt tttaaagaat    101520
tttttttaaaa cttcacatgt aatttattgc attgcttttg ctaaatgtcc tccacacccc   101580
caatgcctgc taggctgggt cgccatggta tttttgtgta acgagtctca aaatgagttt    101640
ggcaatgtct ccgtaatagt cagcatggtg taaatgacag tctggatctg catgtcattt    101700
gggattttat atcagattct ctaggttcat ttctatgata cgtgatgcca aagcacccac    101760
atgcccccgtg gctgcacttt cagacagttg gactcaaaca gagtgggaga gcaactgatc   101820
caacaatctg aattttcaga aaacgggggct ccttagagat gagatggctt gccaaaagta   101880
atctctccta tcagaagtac atatcctcag caaactaacg caggagcaga aaaccaaaca    101940
ccgcatattc tcacttataa gtgggagctg aacagtgaga acacatggac acagggaggg    102000
gaacaacaca cactggggct tgtcggggaa aggtgggtgg ggaagagcat tagggaaaag    102060
agctaatgca cgctgggctt aacacctaga tgatgggttg acaggtgccg caaaccatca    102120
tggcacatat ttatgtctgt aacaaacctg cacatcctgc acatgttccc tggaacttaa    102180
aaaaaaaaaa aaagaaacaa aaacaaccaa ccaaaaatat atctaaaatg tcatctgtta    102240
gcaattgact cacatattat tagtatagaa aagagcaatt cccaggacct tgtacagagg    102300
aagcaggctc aaaacagctg aggaataggc cacttttatc agatagcatt ggatccatgc    102360
acatggggt tggcttctta cctaaatatg ccatcagaaa tcatccttgt tcctgtcccc     102420
tcagcttttg tagcttgcac agtgagtaaa gggatggtgg aggcagaaat ggtaggagcc    102480
agagatgttc aaaatccatc tgatgcttgg cctgtgctga acgttctcaa actgtggcct    102540
tgtcaggccc agaaagtggg gtggattcct ggccgtttct gcttctgcct gggtgtgaga    102600
tgtgaatgct gcccctactg aagggtagtg caatttttt ttttcttaa aagcttagac      102660
ccagagctgc taatctactg gaaatcactc aggacacagg gctctgggca gctgcgctga    102720
gcgagacacc tgcaaatgga gaccaacggg gcctccagca ccctggagtt ccgtaaggcc    102780
cccagctgaa cccaggggag aagagggcag tgggtggcgc ctcgctgctc tgggcacaca    102840
ccacctcttc tgacttctcc cacgtgctcc ggctgtgtcg cctatcagca ctgataacag    102900
cctggaagct ttcagaacag aagctttccc agcatgggaa actctcattc tttctttttt    102960
ttaatttttcc aaagccttta tttctaagac caactgtggc ctacccgtgc ataaactggg   103020
caggctgtag acagcaggct tgccaagtaa atactacagc cttcctccca atattgagcc    103080
ctgtcccatt gatcctgcag gggagatgtg tagggcattt gttcacgggg aggccacaag    103140
tttgggcctc tcatcactgt gacctcacac ccctgttgag tgtgtcgtaa acagaggagc    103200
cgttcttcaa gcccccgtcc ctgagtgcac ccctctcatt cttttgttat tattagcaaa    103260
ttcccccagt tcctgatcat tctttcttaa gcctttagtg actgggtaag gttcttgtgg    103320
ctgactccaa gctttcttct aaaaggaata gattctaggg gtgagtagag gagacaggaa    103380
tgtcggagtc agagctcagg aatctgggtt ccagccccag gtcaatccta gataaactag    103440
agggctcctt aacttacttc cctaggttga ctctgggttt ttttatcacg ctcgacagga    103500
ctccttatgc atttcttcga aagagcatcc agtcttaaca tcatcatttg gcctcatttg    103560
gtttaagaag cagaattagg gtaaaagcaa tgatggataa gcctcatttt ggtgaatatg    103620
atcttattga gacaagaatt ctgagtcaat tgtccttgga accaactgtc tattgttttc    103680
```

```
atctttatca caacactatg tccaaatttt ggaaacatgt ttccctccta gcagaaaaga   103740
agccacccag ggccaccaga tgcttcccga cacttggctg gctttgtctg gtcttctatc   103800
cttcccctat ccccagagtc agtgggtact aaggtggcca gggtcgctca aggaatcaga   103860
atgcaaccgt ccagaggccc agaatcagac tgtcctctct gattaggaaa gtgtttcctg   103920
ccacctccca gggggatgtg gggtgtggct tgagtctggt gcttttacca ggagcttccc   103980
agacctctct atgggtgatg gagagagagt ctggggtgtg aaggatggaa atataaacac   104040
tgaatactca gagagtcagg ccagcgagct ggtgaggaga ctccatcaaa ctcaatatga   104100
aaacatgggt gggcgtttgg ggatggataa tgaatgacag ctgaagtcac acatcaggag   104160
ggaaggaagg actctcatct tcagcaaatg acataaatct ggggagcctc agtttcctca   104220
cctgaacagt gagaatgatg gaatctaccc tgagtatata tcccaggtct ttgtgcagca   104280
tggaatcagc ccccagcctt cctagctctt gctttatttt attttatttt agagaccaag   104340
cctcgctctg tcactcaggc tggagtgcag tggcgcgatc ttgacttact acaacctcct   104400
ccgcctcctg ggttcaagtg attctcctgc ctcagcctcc taagtagttg ggtttacagg   104460
tgcatgccac tatgcctggt taattttgt attttagta gagacggggt ttcaccatgt   104520
tgcccaggct caacatgcct gggctgaagc gatccacctg ccttggcctc ccaaagtgct   104580
aggattacag gcgtgagcca ccgtgcctgg cctcttgttt tatgtttgct gttctcgctg   104640
taggtgaggc attcccacca tattcccttg ttaaaatcct actggcccct caaatgccag   104700
ctcatatcca cactgtgtct gaccctgatc cagaatcctc tccccttctt tgacccctg   104760
tatatatctt tcctacagtg ctggtcatat tctaacttct aatcatttgt agacttatct   104820
gggcattttc tcccaggagg tcccaaagga cagagaccat cttgctcacc tttgtcccca   104880
ctccagcacc cagaatgttt caataaggtt ttcctgaatt aagtgggaag caaagtatta   104940
gattcaatac cactacaatg ggaaagtgag tgaataattg ataaagtata ctatgctctg   105000
gaaatagatt attgagtaat cagaggaaaa cctcttgcaa tgtagtatgt ttttatatat   105060
taaattttat attatttatt tatatttata ttattaacat attttgtta ttcattttgt   105120
ttattaagat ttactctata tatatatgtg tgtgtgtgtg cgcgtgtgtg tgtgtgtaac   105180
ccaccttatt tctaaaaaaa aattttggca gtcagtgact attaatagta gagcacaaac   105240
tcttaacctt tttttcctcc cgctttccca gagtccttat caccttctaa tataataaag   105300
ttttcttaac tgtgatgttg attgttcaac gtttgtcttt cccaccaaaa tgtaagctat   105360
tgcgggcagg gatctttgca tgggttgttc ttcattgcat cccaggccac tagaacagtg   105420
tgtggcatat ggcaggagtg caataaacat tcagcgaatg caggcaggca tgcgtgaacg   105480
catgaataat aagtgttcct ttcaactacc agaaagagcg aaaccacaca ggagctgtct   105540
caccctcaga gatttaagac gacagcaatg agtccctctg atgtcttcta agtgagcttt   105600
attttcaaaa caaatcattt tccaataacc tatcaaaagc aggtcctacc tgaatatcct   105660
tggctatttc ctctggatac agataatgcc ttcctccaat ggatcctcgg ctcacctgat   105720
gattgtgtga aactggccag agaaagcaga gggattttc ctggtgattg gaaatcgag    105780
tcacggctga atttaagcaa ctgtgtgaac tcagcaaagt ccccaccacc tggaccatac   105840
atgacagcta tggttattga caaggtcctt ccttaatgga gctggaacct ccttcttaat   105900
ctaaatgtgg actcaaatga actgtcaatt cacatagagc aatgtgacaa atccgggggg   105960
caaagcatta tgcaatagat tgggcacatg cgcacgtctc tgctacttag tcaacttct   106020
tctaaagttt cccactttc ccattaccac aatcaagatc agatatcagt aatattctcc    106080
```

```
gcgtcccatg cccttttcctc agggagatgc caaggcccaa gagctggtcc ccccaaaaag 106140
ctgaaggtct ttgaaaaaaa gtggggactc aggtcccgtg agtggttttg atttctttt 106200 cttttgaaag ttgcatgtaa gtgttttcca aatactatac aagaatgtct ataacttaat 106260
aatggaggaa tgttttcgtt gttctgtgtt ggtgagatgc tttcctatgc gtttgttgta 106320
taagtaagtg agaatggcag aaggaaagga ggggagaggc tgatcatcct atcccgtctc 106380
ccactctggg ggtctcggcg cttccagcct gaagcgcgcc cgctgcgcgt ccggagacgc 106440
aggttccagg agcccccgg ggttgcccga ctaggccact tgcgcccgg aagagggcc 106500 cggaggtggg agccctaac ttacccgggt ctgagatgcc gagagagccg ggtgtggagc 106560
tgagtgcgcg cctgccgagc gctgaggcca cagacagccc cgccccgggg cggcaccttc 106620
taagggcctg agcgctgcac agggatgggg gcgggcgggg cctcccagag ccgccaggcg 106680
tcccgcccca ctccgcccac acgcacggcc cagcccaggg ttccccggga ccaccccaga 106740 ccagcccgg cccccccggg tcctccacac tctgcacccc agaccaacac caacgcgcgt 106800
agggaagcgt tttagatcct gtcggagagg ctcaaggccg gcagaaggtt tgcattagga 106860
tcgagaaagc cgaccaacgg acagatctac ctaccttcct gcgggagttt gaggttgcca 106920 gggggggaagc cactgcagcc aggagaaagg ccgtctggga accacccac cctcggacgt 106980 gcgggccttc aaatatctct gaacataatc ctccaaagac cgctcaacct ccgctcccga 107040
cgactctttc tagcctcgtc ccgcacccca gctgtggcca cacctatt aggcaaacat 107100 ttatgaagca cccacttact gggtgtgcag ccctgagctg ggggtgcagc tgtgaccag 107160 acaggagggg gcccggagcg gcagacagtc gctggaggca cccgagcctt ggcgagcaca 107220
ccctaacgtc cttggggcct ttcagcccga gccgtccttg tccagagagc aaaccatgca 107280
atgatgcagg tgacttccca gcaaatttca tagcgttgct caccagcttg gcaggcaaga 107340
ggagaagggg cagtccccaa aagacaatcc catgaaacctt ctagggaatg acgtccaggc 107400
tccaggctcc tgctctgcag gcgggtcgca gaggcaggtt cctgacctag gactagaaga 107460
cattctctag ggtcactgcc tccatggtct tccttggcag gtcacttctt cctgggcttc 107520
gacctcggtg ttctcatggg gacgagggtg attggaggcc ctccaagggg tgcaccgatg 107580
tgtcctgtgc accaggcaga accagcattg ccctacagtg tgggtgcaaa atgaaccac 107640 atggccacgt tggaaagtcc tgaaatgttc atagcctatg acatgaaatt gcactgtgtg 107700
aaatctattt attctttttt tttttttctt tttttctga acggagtct caccctgtcg 107760 ccccggctgg agtgcaatgg cacgatctcg gctcactgca acctccacct ccctggttca 107820
agcgattctc ctgcctcagc ctcccgagtt gctgggatta caggcaccgg ccaccatacc 107880 ctgctgatt tttgttattt ttagtagaga cggagtttcg ccatgttggc caggctggtc 107940
tcgaactcct gacttcaggt gatccacccg cctcggcctc ccaaagtgct gggattacag 108000
gtgtgagtca gcgtgcccag actgaaatct atttattcta tggaaaggat cagagctgta 108060
gaaaaatcct tatgcatgta aaagttcttt gtgtttttac ttgcaataac tagaatctaa 108120
acatccaaaa atagaaaata taggtaatta aattgtagta catatgatat tattctacat 108180 agtagaaatat tatgtggagt ccttaaaatg tttacaaata atttataaca acatggggcc 108240
gggcacagtg gcttacacct gtaattccag cactttggga ggccaaggtg ggtgggtcac 108300
ctgaggttag gagttcaaga ccagcctggc caacatggtg aaaccgtctct ctactaaaaa 108360 cacaaaaatt tagctgggcg tggtggtggg cacctgtaat cccagctact tgggagtctg 108420
```

```
aggcaagaga ttcacttgaa cccaggaggc ggaggttgca gtgagccaag gtcacgccac  108480
tgcactccag cctgggcgac aagagtgaag ctctgactca aaacaaacaa acaaacaaaa  108540
acccaacagg ggagatcttt atattatcat gttacgtgaa aaatacaaaa acagaaaaca  108600
aaacaaaaac cccacaaaac tcaaggcctt aaattgtaaa tatgagatgc caggcattat  108660
tcccaaaatc tataaggaag cacaccaacc accatgttaa cattgtctat tagtggtagg  108720
cctattggag atttattatc ttatttatgc tacttcatgt tttccttcct tttttgtttt  108780
gcaacaactc tgtattagtc tgttctcaca ctgttataaa gaactgcctg aaactgggta  108840
atttataaag gaaaaagtct taattgattc acagttcagc atggctgagg cctcaggaac  108900
ttacaatcat ggccgaaggg gaagcaaaca tgtccttctt tacatggcag caggagagag  108960
aagtgcagag caaagtggaa ggaaaagccc cgtataaaac catcagatct cgtgagaact  109020
cactcattat catgaaaaca gcatggaaga accgcctcca tgatccaatc acttcccaca  109080
aagtccctcc tgcaacatgt ggggattaca atttggatta caattcaaga tgagatttgg  109140
gtggggacac agccaaacca tatcaaactc tatgtacttt aatatttaag gaaaattaca  109200
taaactttat ctgaaaattc cctggattct tctcctcaag gtcatgctgt acatatgcag  109260
gatcctcctg cctacatctc caaatggata atggattgaa gcaaaatgtt tgtcccacca  109320
aacattgatg tgtaacccct ttagtaacaa ttcatagacc aggtaaacat gtgtggagca  109380
gcccagatca gctggaggga gcattattct catcagagtg tggaacaatg cctacccatc  109440
tgtcagctgg ttatggtgaa gacagtataa atggaagcac tgtcagaaac taaaggctta  109500
tgtaagtgat gctgttctta tgtctcctct tcctctctat cccacatatg atgaattatt  109560
ttattatgat gatgctgtag ttgttatttt ctatttgaaa tgaaaagaca tgattacaga  109620
tgagaaagag tgtattttgt tatccttgat gcacttgaaa tggtttcctc tttttttttt  109680
cctgttttct tcttcttcct tctctcttca ctctttcatt cttgcctctc tccatttttat  109740
aggtatgatt gatcttgaaa taatgatgat aacagaatga tagcccatat agtccttggg  109800
tcacttctgt ctctatttct ctttcttccc tcctctttt ttcttggtcc ttttgctaga  109860
tgggttgcga gcatggctcc ctgcccctct cagtgggttt atcttcattt tccatgagct  109920
cccacctcac tgcatgtgac atcaaagcca aagctccagc cacttctcat cctttcttag  109980
gaaaatctca agtcttaact tgaaagttga atgtcctgct tttgttccta actctgctca  110040
caggatagtg gaagaagaaa ggctcagcct gttaccagaa agaacagatc tgcagtgtaa  110100
cccatctagg atgaagggtc atgtggacag ttcttcactc ttccctctgg ctgcccttca  110160
gttggtgtcc agatgcccct gtgttagcct ggggcattc cttgcccttt ggcccctctt  110220
ttgttgcctt ttttttttctt agacaaggtc taactccgct gcccaggctg gagtgcagtg  110280
gtgcgaccat tgctcattgc aacctcgaac tcctggctca agacattctc cccgctcagc  110340
ctcgtgagta gctggaacta cagttgtaca ccaccatgcc ttggctaatt taaaaagtct  110400
ttttgtaggg atgggagtct caggctggtc ttgaacttct ggcctccagt gatcctcctg  110460
ccttggcctc ccaaagtttt gggattacag gcgtgagcca ttgtgccctg cccttttgttg  110520
cttttttcact cctttaccct gtggtttcta ctatcctcag ggacaactct cattgccctg  110580
gggcttctgg atcttcagca agacacaccc ctaaaggcaa acaatctttc tttagcagca  110640
gcagagcaca aacggagtgt tgctgtatgc taaaagcata ctatttcccc cccatgagaa  110700
agtctaaggg gtccagggt cctgaagtcc ctatcctgcc cccgccagtg acaggtgatg  110760
gggaacagaa tgctgaaaga gaccccaccc aaccatctgg tgtgtcaaca cccgcccctg  110820
```

```
ccggtgctgt ccacaggttg atccccatcc cacatgggtg gcttaacaca ttcatgtctt    110880
ctgagagcca tttgttgctc cccagtctct tctgtcctcc ttctttgacc aacatttccc    110940
tgtctgattt gcttggtcac aggtagcctg tgtcagtttc ctcccaggac tctctttgcc    111000
tgggaataag tgctatacat gagaagcatc cctcccaagc gctgtgtgtg gcctcctggc    111060
attctcctaa gacttcctag aggattgctc tggttccaaa aagaaaccag ccacaacctg    111120
tttggagccc tgcaggatgt tccagctcac cgacttcatt ccccactact tgcccctcta    111180
acagagcttc tagaccagca gccaaggtgc ctccattcac tgtacatgac tcacctttcc    111240
cccttctaga cacttcttca cgggtctagc ctctgtttcc agctttacac agcacaggct    111300
gatgcctgcc actgaacggg atccaggact ttttcaaatc tcagatcccc agcaaaggta    111360
tgacaatggg caccctgacc agctctgagc ctctaagcat agggtctatt tgtttaattt    111420
tgaattcact tttaagattt aaaaattgag agctctcatc ttcaacaaaa ttcagggggat   111480 ctagaaacat catgcccact tgtggcagag tagccaactg gcagaaactg atgctgatgc    111540
tgtctgtttc ctacacaaaa tgcaaaccag agtttaccac aggcccccgct actccacatt   111600 ctcctccaca aggacactca gcaggctcct gtgctgaacg gcttgcctgg ttctgtaggt    111660
gtagggtttg ttactctgtt ccaggaccta ttttccgcaa agccccttac ctggctgttt    111720
cttcccttgg catacgtgag aactcctttc ctcactgaat tgctttgacc ttgctaatta    111780
gttgtgttgc aagtgctttt tggctgtgtc agacatgtat gttctgttta tcattttaga    111840
gcaatggtta ttaatttttt tcagattctt cttgggaatt agagaaaaac ttatggctct    111900
cctccaccat cctgccccca cctacccaaa tgcacacatg tgcaacattt gttctacaat    111960
tcaagagctc tctagacccc tgatatgcta ggcaattcgt ggctgccaca ttaggaaccc    112020
ctgatttagg ggaaggactg ttttctccat tagacaaact caactgtgta gcatcaattt    112080
catgggtcta ctgtgtactg tgcccaaaaa atgccactga atgctgcctg actggtggat    112140
agcaagactg tccattaatg tggtcattta ggttgcctct gcccaggtct tgaggtcatt    112200
ggcactaatt cacaacaccc tcaagtcacc caggaagat gagacacagt tggctgtaga    112260
cccacagttt gggcattaca gctgcccttg aagttgacaa ataaccacaa ccttcaaatt    112320
gttatgaaaa gagcacaaat ccaattaaga aagcttttcc aaaagaaata acagtgttcc    112380
taccccctct gtcactctcc acccccttt tgtcccagaa taatgttgtg ctgataggaa     112440
catggataaa ttaattacag tctggaatgt tattcatggg taggaaagaa cactaaatct   112500
actcgcacaa tgtttgatat ttaaagataa acattgcctt tatgtttttt tttaaaccct    112560
cagtcagcct agtttacgaa gacataggta taatcctttt aaatgctgtg gatttttaa     112620 tcgcaaaggt aacaatatgc tgggtgtttt acccagccag agaaccagga gatgcaggaa   112680
tgagattagc atctctttag ttccttgcat atttgatatt attttggtgt acctccaatt   112740
cctgataaca tagaagaact cttgtggttg aagtccctga aatggaagga tattggtaac    112800
cctgaattta aaacaagcac aggcagcctt tgtgggaatg tgtgtgaagg tcaccttcta    112860
gaaacaggac tgtccatagc cattgccatg gtttctgtgt catttcaacc agaaccttag    112920
gcctggaagt ctggatggat gtgggttggc atggtcctct atgggcatta aatgaataaa    112980
tggatatagc agagggagta tccagcatga ctcaaagaag gatgagagga aacatattca    113040
aataaaatct ttagaaaagc aaatttcaaa aaaaaatgct taagtataaa atattttgat   113100
gacaaccatg attttcaaat tgaattctta ttctaagtaa tggtctaatc tgaacttaga    113160
```

-continued

```
cctctttcct taatttttt ctcaataagc ctttggtgtc tagtcagttc aattcagtat  113220
ttactgagtc tctatacaga cagggtataa ggcattaatc aaatgtatgt ccaaaattgc  113280
ccaccatgca gggcagagct aaaatgccta acacccctcc tctcaccaac acatccccca  113340
cccacatctc caaagacttc ctggcagagg tgatctctgc ctgctgggac agatgtatag  113400
gctccaacag cagcagggtg gcccctctga ccaccacctt gggacccaca ttgctcttag  113460
aactattcct cttttttcat ccttgaagcc cccagcaaag ctcagcctga atcaactttt  113520
tctaggaatc tgacaagttt ccaggctgat ttcctgaccc agtcagatcc tcttccatct  113580
ttctttgggt gttcaatttt ctac                                         113604
```